US007868006B2

(12) United States Patent
Kim et al.

(10) Patent No.: US 7,868,006 B2
(45) Date of Patent: Jan. 11, 2011

(54) HETEROCYCLIC SUBSTITUTED PIPERAZINES WITH CXCR3 ANTAGONIST ACTIVITY

(75) Inventors: Seong Heon Kim, Livingston, NJ (US); Gopinadhan N. Anilkumar, Edison, NJ (US); Michael K. C. Wong, North Brunswick, NJ (US); Qingbei Zeng, Edison, NJ (US); Stuart B. Rosenblum, West Orange, NJ (US); Joseph A. Kozlowski, Princeton, NJ (US); Yuefei Shao, Princeton, NJ (US); Brian F. McGuinness, Plainsboro, NJ (US); Douglas W. Hobbs, Yardley, PA (US)

(73) Assignees: Schering Corporation, Kenilworth, NJ (US); Pharmacopeia Drug Discovery, Inc., Princeton, NJ (US)

( * ) Notice: Subject to any disclaimer, the term of this patent is extended or adjusted under 35 U.S.C. 154(b) by 444 days.

(21) Appl. No.: 11/353,641

(22) Filed: Feb. 14, 2006

(65) Prior Publication Data

US 2006/0276479 A1  Dec. 7, 2006

Related U.S. Application Data

(60) Provisional application No. 60/653,309, filed on Feb. 16, 2005.

(51) Int. Cl.
*A61K 31/497* (2006.01)
*C07D 241/02* (2006.01)
(52) U.S. Cl. .................. 514/252.12; 544/357
(58) Field of Classification Search .......... None
See application file for complete search history.

(56) References Cited

U.S. PATENT DOCUMENTS

| | | | |
|---|---|---|---|
| 6,124,319 A | 9/2000 | MacCoss et al. | |
| 6,794,379 B2 | 9/2004 | Medina et al. | |
| 7,417,045 B2 | 8/2008 | Anilkumar et al. | |
| 7,566,718 B2 | 7/2009 | Wong et al. | |
| 2002/0018776 A1 | 2/2002 | Hancock | |
| 2003/0055054 A1 | 3/2003 | Medina et al. | |
| 2006/0276448 A1 | 12/2006 | Zeng et al. | |
| 2006/0276457 A1 | 12/2006 | Yu et al. | |
| 2007/0021611 A1 | 1/2007 | McGuinness et al. | |
| 2007/0054919 A1 | 3/2007 | Rosenblum et al. | |
| 2007/0082913 A1* | 4/2007 | Kim et al. ............ | 514/252.11 |
| 2008/0039474 A1 | 2/2008 | Rosenblum et al. | |
| 2008/0058343 A1 | 3/2008 | Rosenblum et al. | |
| 2008/0292589 A1 | 11/2008 | Anilkumar et al. | |

FOREIGN PATENT DOCUMENTS

| WO | WO93/10091 | 5/1993 |
|---|---|---|
| WO | WO 93/14077 | 7/1993 |
| WO | WO99/20606 | 4/1999 |
| WO | WO03/070242 | 8/2001 |
| WO | WO02/085861 | 10/2001 |
| WO | WO03/082335 | 10/2003 |
| WO | WO03/098185 | 11/2003 |
| WO | WO03/101970 | 12/2003 |
| WO | WO2004/074278 | 9/2004 |
| WO | WO2004/074287 | 9/2004 |
| WO | WO 2004/113323 | 12/2004 |
| WO | WO2008/079279 | 7/2008 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
International Search Report, International app. No. PCT/US2006/005123, International filing date: Feb. 14, 2006 (mail date: Aug. 4, 2006).
Qingbei Zeng et al., U.S. Appl. No. 12/519,970; Preliminary Amendment—Mailed Jun. 18, 2009.
Notice of Allowance in U.S. Appl. No. 11/545,201 mailed Nov. 17, 2009.
Notice of Allowance in U.S. Appl. No. 11/353,697 mailed Jan. 7, 2010.
Notice of Allowance in U.S. Appl. No. 11/688,014 mailed Jan. 19, 2010.

* cited by examiner

*Primary Examiner*—James O Wilson
*Assistant Examiner*—Jeffrey H Murray
(74) *Attorney, Agent, or Firm*—Eric A. Meade; Krishna G. Banerjee; Palaiyur Kalyanaraman

(57) ABSTRACT

The present application discloses a compound, or enantiomers, stereoisomers, rotamers, tautomers, racemates or prodrug of said compound, or pharmaceutically acceptable salts, solvates or esters of said compound, or of said prodrug, said compound having the general structure shown in Formula 1:

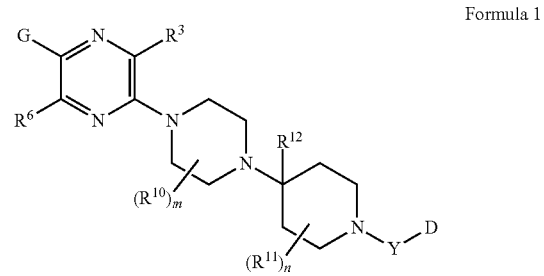

Formula 1 or a pharmaceutically acceptable salt, solvate or ester thereof, wherein the various moieties are defined herein. Also disclosed is a method of treating chemokine mediated diseases, such as, palliative therapy, curative therapy, prophylactic therapy of certain diseases and conditions such as inflammatory diseases (non-limiting example(s) include, psoriasis), autoimmune diseases (non-limiting example(s) include, rheumatoid arthritis, multiple sclerosis), graft rejection (non-limiting example(s) include, allograft rejection, xenograft rejection), infectious diseases (e.g, tuberculoid leprosy), fixed drug eruptions, cutaneous delayed-type hypersensitivity responses, ophthalmic inflammation, type I diabetes, viral meningitis and tumors using a compound of Formula 1.

44 Claims, No Drawings

HETEROCYCLIC SUBSTITUTED PIPERAZINES WITH CXCR3 ANTAGONIST ACTIVITY

REFERENCE TO PRIORITY APPLICATIONS

This Application claims the benefit of U.S. Provisional Application Ser. No. 60/653,309 filed Feb. 16, 2005, which is incorporated herein in its entirety by reference.

FIELD OF THE INVENTION

The present invention relates to novel heterocyclic substituted piperazines with CXCR3 antagonist activity, pharmaceutical compositions containing one or more such antagonists, one or more such antagonists in combination with other compounds with chemokine activity, one or more such antagonists in combination with known immunosuppressive agents, non-limiting example(s) include Methotrexate, interferon, cyclosporin, FK-506 and FTY720, methods of preparing such antagonists and methods of using such antagonists to modulate CXCR3 activity. This invention also discloses methods of using such CXCR3 antagonists for the treatment (non-limiting examples include palliative, curative and prophylactic therapies) of diseases and conditions where CXCR3 has been implicated. Diseases and conditions where CXCR3 has been implicated include but are not limited to inflammatory conditions (psoriasis and inflammatory bowel disease), autoimmune disease (multiple sclerosis, rheumatoid arthritis), fixed drug eruptions, cutaneous delayed-type hypersensitivity responses, type I diabetes, viral meningitis and tuberculoid leprosy. CXCR3 antagonist activity has also been indicated as a therapy for tumor growth suppression as well as graft rejection (allograft and zenograft rejections for example).

BACKGROUND OF THE INVENTION

Chemokines constitute a family of cytokines that are produced in inflammation and regulate leukocyte recruitment (Baggiolini, M. et al., *Adv. Immunol.*, 55: 97-179 (1994); Springer, T. A., *Annual Rev. Physio.*, 57: 827-872 (1995); and Schall, T. J. and K. B. Bacon, *Curr. Opin. Immunol*, 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

Chemokines are related in primary structure and share four conserved cysteines, which form disulfide bonds. Based upon this conserved cysteine motif, the family can be divided into distinct branches, including the C—X—C chemokines (α-chemokines) in which the first two conserved cysteines are separated by an intervening residue (e.g., IL-8, IP-10, Mig, I-TAC, PF4, ENA-78, GCP-2, GROα, GROβ, GROδ, NAP-2, NAP-4), and the C—C chemokines (β-chemokines), in which the first two conserved cysteines are adjacent residues (e.g., MIP-1α, MIP-1β, RANTES, MCP-1, MCP-2, MCP-3, I-309) (Baggiolini, M. and Dahinden, C. A., *Immunology Today*, 15: 127-133 (1994)). Most CXC-chemokines attract neutrophil leukocytes. For example, the CXC-chemokines interleukin-8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes.

CC-chemokines are generally less selective and can attract a variety of leukocyte cell types, including monocytes, eosinophils, basophils, T lymphocytes and natural killer cells. CC-chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

A chemokine receptor that binds the CXC-chemokines IP-10 and Mig has been cloned, characterized (Loetscher, M. et al., *J. Exp. Med.*, 184: 963-969 (1996)) and designated CXCR3. CXCR3 is a G-protein coupled receptor with seven transmembrane-spanning domains and has been shown to be restrictively expressed in activated T cells, preferentially human Th1 cells. On binding of the appropriate ligand, chemokine receptors transduce an intracellular signal through the associated G-protein resulting in a rapid increase in intracellular calcium concentration.

The CXCR3 receptor mediates $Ca^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP4, MIP-Iα, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009-2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Qin, S. et al., *J. Clin. Invest.*, 101: 746-754 (1998)). Additional studies of receptor distribution indicate that it is mostly $CD3^+$ cells that express CXCR3, including cells which are $CD95^+$, $CD45RO^+$, and $CD45RA^{low}$, a phenotype consistent with previous activation, although a proportion of $CD20^+$ (B) cells and $CD56^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J Exp. Med.,* 177: 18090-1814 (1993); Taub, D. D. et al., *J. Immunol.,* 155: 3877-3888 (1995); Cole, K. E. et al., *J. Exp. Med.,* 187: 2009-2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128-23134 (1991); Hebert, C. A. et al., *J. Biol. Chem.,* 266: 18989-18994 (1991); and Clark-Lewis, 1. et al., *Proc. Natl. Acad. Sc. USA,* 90: 3574-3577 (1993)). In addition, both recombinant human Mig and recombinant human IP-10 have been reported to induce calcium flux in tumor infiltrating lymphocytes (TIL) (Liao, F. et al., *J Exp. Med,* 182: 1301-1314 (1995)). While IP-10 has been reported to induce chemotaxis of monocytes in vitro (Taub, D. D. et al., *J. Exp. Med.,* 177: 1809-1814 (1993), the receptor responsible has not been identified), human Mig and I-TAC appear highly selective, and do not show such an effect (Liao, F. et al., *J. Exp. Med.,* 182: 1301-1314 (1995); Cole, K. E. et al., *J. Exp. Med.,* 187: 2009-2021 (1998)). IP-10 expression is induced in a variety of tissues in inflammatory conditions such as psoriasis, fixed drug eruptions, cutaneous delayed-type hypersensitivity responses and tuberculoid leprosy as well as tumors and in animal model studies, for example, experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.,* 178: 1057-1065 (1993); Luster, A. D. et al., *J Exp. Med.* 182: 219-231 (1995); Angiolillo, A. L. et al., *J. Exp. Med.,* 182: 155-162 (1995); Taub, D. D. et al., *J. Immunol.,* 155: 3877-3888 (1995)). The expression patterns of IP-10, Mig and I-TAC are also distinct from that of other CXC chemokines in that expression of each is induced by interferon-gamma (IFNδ), while the expression of IL-8 is down-regulated by IFNδ (Luster, A. D. et al., *Nature,* 315: 672-676 (1985); Farber, J. M., *Proc. Natl. Acad. Sci. USA,* 87: 5238-5242 (1990); Farber, J. M., *Biochem. Biophys. Res. Commun.,* 192 (1): 223-230 (1993), Liao, F. et al., *J. Exp. Med.,* 182: 1301-1314 (1995); Seitz, M. et al., *J. Clin. Invest.,* 87: 463-469 (1991); Galy, A. H. M. and H. Spits, *J. Immunol.,* 147: 3823-3830 (1991); Cole, K. E. et al., *J. Exp. Med.,* 187: 2009-2021 (1998)).

Chemokines are recognized as the long-sought mediators for the recruitment of lymphocytes. Several CC-chemokines were found to elicit lymphocyte chemotaxis (Loetscher, P. et al., *FASEB J.,* 8: 1055-1060 (1994)), however, they are also active on granulocytes and monocytes (Uguccioni, M. et al., *Eur. J. Immunol.,* 25: 64-68 (1995); Baggiolini, M. and C. A. Dahinden, *Immunol. Today,* 15: 127-133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes. Accordingly, activated and effector T cells have been implicated in a number of disease states such as graft-rejection, inflammation, rheumatoid arthritis, multiple sclerosis, inflammatory bowel disease (such as Crohn's disease and ulcerative colitis) and psoriasis. Thus, CXCR3 represents a promising target for the development of novel therapeutics.

Reference is made to PCT Publication No. WO 93/10091 (Applicant: Glaxo Group Limited, Published May 27, 1993) which discloses piperidine acetic acid derivatives as inhibitors of fibrinogen-dependent blood platelet aggregation having the formula:

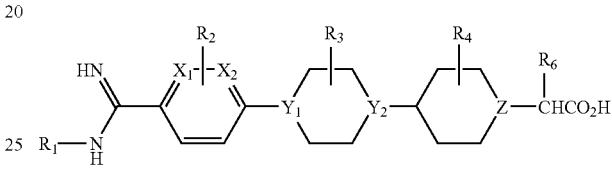

An illustrative compound of that series is:

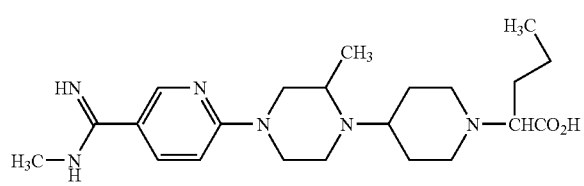

Reference is also made to PCT Publication No. WO 99/20606 (Applicant: J. Uriach & CIA. S. A., Published Apr. 29, 1999) which discloses piperazines as platelet aggregation inhibitors having the formula:

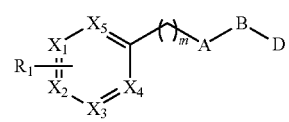

Reference is also made to US Patent Application No. US 2002/0018776 A1 (Applicant: Hancock, et al. Published Feb. 14, 2002) which discloses methods of treating graft rejection.

Reference is also made to PCT Publication No. WO 03/098185 A2 (Applicant: Renovar, Inc., Published Nov. 27, 2003) which discloses methods of diagnosing and predicting organ transplant rejection by detection of chemokines, for example, CXCR3 and CCL chemokines in urine.

Reference is also made to PCT Publication No. WO 03/082335 A1 (Applicant: Sumitomo Pharmaceuticals Co. Ltd., Published Oct. 9, 2003) which discloses methods of screening a CXCR3 ligand and methods of diagnosing type 2 diabetes by detecting the expression dose of a CXCR3 ligand in a biological sample.

Reference is also made to PCT Publication No. WO 02/085861 (Applicant: Millennium Pharmaceuticals, Inc.

Published Oct. 31, 2002) which discloses imidazolidine compounds and their use as CXCR3 antagonists having the formula:

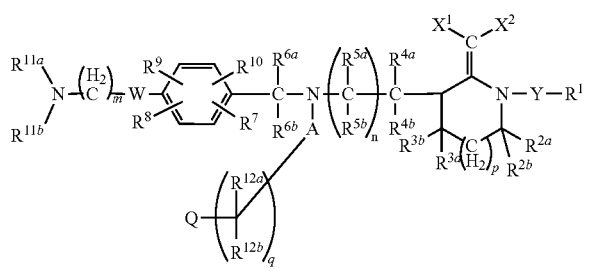

An illustrative compound of that series is:

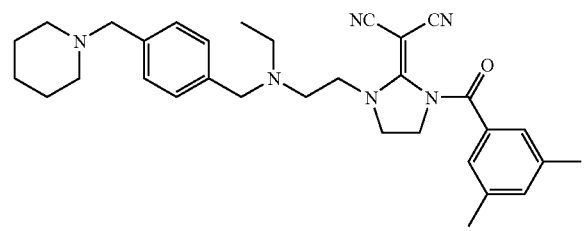

Reference is also made to PCT Publication No. WO 03/101970 (Applicant: Smithkline Beecham Corporation, Published Dec. 11, 2003) which discloses imidazolium compounds and their use as CXCR3 antagonists having the formula:

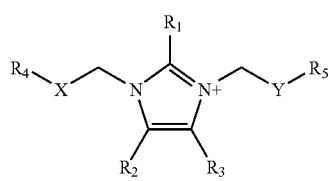

An illustrative example of that series is:

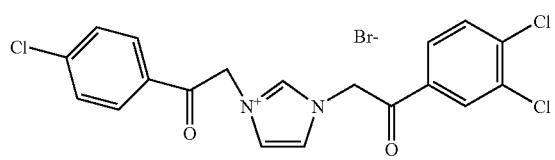

Reference is also made to US Patent Application No. US 2003/0055054 A1 (Applicant: Medina et al, Published Mar. 20, 2003) and related patent U.S. Pat. No. 6,794,379 B2 ((Applicant: Medina et al, Published Sep. 21, 2004) which discloses compounds with CXCR3 activity having the formula:

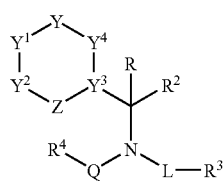

An illustrative compound of that series is:

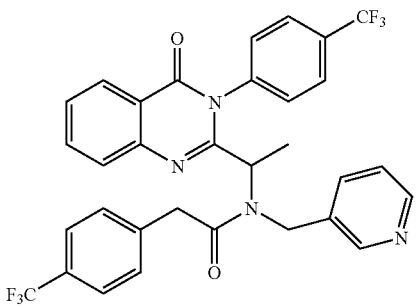

Reference is also made to U.S. Pat. No. 6,124,319 (Applicant: MacCoss et al., issued Sep. 6, 2000) which discloses compounds useful as chemokine receptor modulators having the formula:

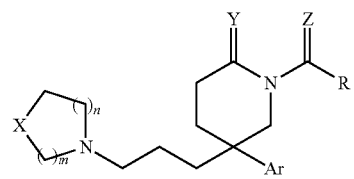

Reference is also made to PCT Publication WO 03/070242 A1 (Applicant: CELLTECH R& D limited, Published Aug. 28, 2003) which discloses compounds useful as "chemokine receptor inhibitors for the treatment of inflammatory diseases" having the formula:

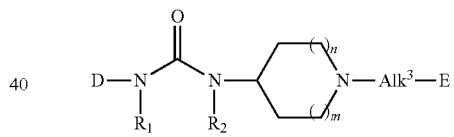

Reference is also made to PCT Publication WO 04/074287 A1, WO 04/074273 A1, WO 04/74278 (Applicant: AstraZeneca R & D Published Feb. 19$^{th}$ 2004) which discloses pyridine derivatives, processes for their preparation and their use in the modulation of autoimmune disease having the formula:

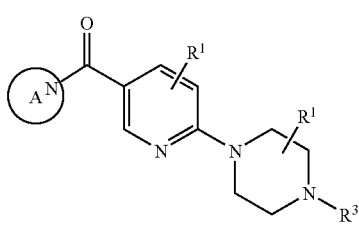

where $R^3$ is phenyl, or a 5- or 6-membered aromatic ring with 1 or more nitrogen atoms.

There is a need for compounds that are capable of modulating CXCR3 activity. For example, there is a need for new treatments and therapies for diseases and conditions associated with CXCR3 such as inflammatory conditions (psoriasis and inflammatory bowel disease), autoimmune disease (multiple sclerosis, rheumatoid arthritis) and graft rejection (allograft and zenograft rejections for example) as well as infectious diseases, cancers and tumors, fixed drug eruptions, cutaneous delayed-type hypersensitivity responses, type I diabetes, viral meningitis and tuberculoid leprosy.

There is a need for methods of treatment or prevention or amelioration of one or more symptoms of diseases and conditions associated with CXCR3. There is a need for methods for modulating CXCR3 activity using the compounds provided herein.

SUMMARY OF THE INVENTION

In its many embodiments, the present invention discloses a compound having the general structure shown in Formula 1:

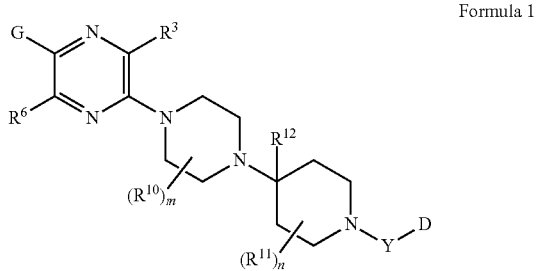

Formula 1 or a pharmaceutically acceptable salt, solvate or ester thereof, wherein:

G represents a 5-membered heteroaryl or heterocyclenyl ring containing at least one —C=N— moiety as part of said heteroaryl or heterocyclenyl ring, said heteroaryl or heterocyclenyl ring optionally additionally containing one or more moieties selected from the group consisting of N, N(→O), O, S, S(O) and S(O$_2$) on the ring, which moieties can be the same or different, each being independently selected, further wherein said heteroaryl or heterocyclenyl ring can be either (i) unsubstituted, or (ii) optionally independently substituted on one or more ring carbon atoms with one or more $R^9$ substituents, or on one or more ring nitrogen atoms with one or more $R^8$ substituents, wherein said $R^8$ and $R^9$ substituents can be the same or different;

$R^3$ and $R^6$ moieties can be the same or different, each being independently selected from the group consisting of H, alkyl, alkylaryl, aralkyl, —CN, CF$_3$, haloalkyl, cycloalkyl, halogen, hydroxyalkyl, —N=CH—(R$^{31}$), —C(=O)N(R$^{30}$)$_2$, —N(R$^{30}$)$_2$, —OR$^{30}$, —SO$_2$(R$^{31}$), —N(R$^{30}$)C(=O)N(R$^{30}$)$_2$ and —N(R$^{30}$)C(=O)R$^{31}$;

the $R^8$ moieties can be the same or different, each being independently selected from the group consisting of H, alkyl, alkenyl, alkylaryl, arylalkyl, cycloalkyl, aryl, heteroaryl, heterocyclyl, —C(=O)-aryl-halogen, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, (CH$_2$)$_q$C(=O)OR$^{31}$, —(CH$_2$)$_q$SO$_2$R$^{31}$, —(CH$_2$)$_q$NSO$_2$R$^{31}$, or —(CH$_2$)$_q$SO$_2$NHR$^{31}$;

the $R^9$ moieties can be the same or different, each being independently selected from the group consisting of H, alkyl, alkenyl, alkylaryl, arylalkyl, alkoxy, amidinyl, aryl, cycloalkyl, cyano, heteroaryl, heterocyclyl, hydroxyl, —C(=O)OR$^{30}$, —C(=O)N(R$^{30}$)$_2$, —C(=S)N(R$^{30}$)$_2$, —C(=O)alkyl, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —N(R$^{30}$)$_2$, —N(R$^{30}$)S(O$_2$)R$^{31}$, —N(R$^{30}$)C(=O)N(R$^{30}$)$_2$, —OR$^{30}$, —SO$_2$(R$^{31}$), —SO$_2$N(R$^{30}$)$_2$, =O and =S;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(=O)N(R$^{30}$)$_2$, —(CH$_2$)$_q$OH, —(CH$_2$)$_q$OR$^{31}$, —OR$^{30}$, halogen, =O, and —C(=O)R$^{31}$;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, carboxamide, CO$_2$H, —(CH$_2$)$_q$OH, —(CH$_2$)$_q$OR$^{31}$, —OR$^{30}$, halogen, =O, and —C(=O)R$^{31}$;

$R^{12}$ moieties can be the same or different, each being independently selected from the group consisting of H, alkyl, —CN, —C(=O)N(R$^{30}$)$_2$, —(CH$_2$)$_q$OH, —(CH$_2$)$_q$OR$^{31}$ and —S(O$_2$)R$^{31}$;

ring D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of a covalent bond, —(CR$^{13}$R$^{13}$)$_r$—, —CHR$^{13}$C(=O)—, —(CHR$^{13}$)$_r$O—, —(CHR$^{13}$)$_r$N(R$^{30}$)—, —C(=O)—, —C(=O)—(CHR$^{13}$)—, —C(=O)—(CHR$^{13}$)$_r$—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)$_r$C(=O)— and —(CHR$^{13}$)$_r$N(H)C(=O)—; or alternatively Y is cycloalkyl, heterocyclenyl, or heterocyclyl wherein the cycloalkyl, heterocyclenyl, or heterocyclyl is fused with ring D;

the R$^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)OR$^{31}$, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CHR$^{30}$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the R$^{30}$ moieties can be the same or different, each being independently selected from the group consisting of H, alkyl, alkylaryl, aryl, aralkyl, cycloalkyl, -cycloalkylalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)O-alkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

the R$^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and hetroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

In another embodiment, the present invention discloses the compound of Formula 1, or a pharmaceutically acceptable salt, solvate or ester thereof, wherein:

G represents a 5-membered heteroaryl or heterocyclenyl ring containing at least one —C=N— moiety as part of said heteroaryl or heterocyclenyl ring, said heteroaryl or heterocyclenyl ring optionally additionally containing one or more moieties selected from the group consisting of N, N(→O), O, S, S(O) and S(O$_2$) on the ring, which moieties can be the same or different, each being independently selected, further wherein said heteroaryl or heterocyclenyl ring can be either (i) unsubstituted, or (ii) optionally independently substituted on one or more ring carbon atoms with one or more R$^9$ substituents, or on one or more ring nitrogen atoms with one or more R$^8$ substituents, wherein said R$^8$ and R$^9$ substituents can be the same or different;

R$^3$ and R$^6$ moieties can be the same or different, each being independently selected from the group consisting of H, alkyl, alkylaryl, aralkyl, —CN, CF$_3$, haloalkyl, cycloalkyl, halogen, hydroxyalkyl, —N=CH—(R$^{31}$), —C(=O)N(R$^{30}$)$_2$, —N(R$^{30}$)$_2$, —OR$^{30}$, —SO$_2$(R$^{31}$), —N(R$^{30}$)C(=O)N(R$^{30}$)$_2$ and —N(R$^{30}$)C(=O)R$^{31}$;

the R$^8$ moieties can be the same or different, each being independently selected from the group consisting of H, alkyl, alkenyl, alkylaryl, arylalkyl, cycloalkyl, aryl, heteroaryl, heterocyclyl, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, CH$_2$)$_q$C(=O)OR$^{31}$, —(CH$_2$)$_q$SO$_2$R$^{31}$, —(CH$_2$)$_q$NSO$_2$R$^{31}$, or —(CH$_2$)$_q$SO$_2$NHR$^{31}$;

the R$^9$ moieties can be the same or different, each being independently selected from the group consisting of H, alkyl, alkenyl, alkylaryl, arylalkyl, alkoxy, amidinyl, aryl, cycloalkyl, cyano, heteroaryl, heterocyclyl, hydroxyl, —C(=O)N(R$^{30}$)$_2$, —C(=S)N(R$^{30}$)$_2$, —C(=O)alkyl, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —N(R$^{30}$)$_2$, —N(R$^{30}$)S(O$_2$)R$^{31}$, —N(R$^{30}$)C(=O)N(R$^{30}$)$_2$, —OR$^{30}$, —SO$_2$(R$^{31}$), —SO$_2$N(R$^{30}$)$_2$, =O and =S;

the R$^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(=O)N(R$^{30}$)$_2$, —(CH$_2$)$_q$OH, —(CH$_2$)$_q$OR$^{31}$, —OR$^{30}$, halogen, =O, and —C(=O)R$^{31}$;

the R$^{11}$ moieties can be the same or different, each being independently selected from the group consisting of H, alkyl, cycloalkyl, aryl, heteroaryl, heterocyclyl, heterocyclenyl, alkylaryl, arylalkyl, carboxamide, CO$_2$H, —(CH$_2$)$_q$OH, —(CH$_2$)$_q$OR$^{31}$, —OR$^{30}$, halogen, =O, and —C(=O)R$^{31}$;

R$^{12}$ moieties can be the same or different, each being independently selected from the group consisting of H, alkyl, —CN, —C(=O)N(R$^{30}$)$_2$, —(CH$_2$)$_q$OH, —(CH$_2$)$_q$OR$^{31}$ and —S(O$_2$)R$^{31}$;

ring D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected R$^{20}$ moieties;

the R$^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$ OR$^{31}$, —C(=O)R$^{30}$, —C(=O)N(R$^{30}$)$_2$, —C(=NR$^{30}$) NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC (=O)N(R$^{30}$)$_2$, —N(R$^{30}$)C(=O)OR$^{31}$, —N(R$^{30}$)C(=NCN) N(R$^{30}$)$_2$, —N(R$^{30}$)C(=O)N(R$^{30}$)SO$_2$(R$^{31}$), —N(R$^{30}$)C (=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$; or alternatively two R$^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 R$^{21}$ moieties;

the R$^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —CHR$^{13}$C(=O)—, —(CHR$^{13}$)$_r$O—, —(CHR$^{13}$)$_r$N(R$^{30}$)—, —C(=O)—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)$_r$C(=O)— and —(CHR$^{13}$)$_r$N(H)C(=O)—; or alternatively Y is cycloalkyl, heterocyclenyl, or heterocyclyl wherein the cycloalkyl, heterocyclenyl, or heterocyclyl is fused with ring D;

the R$^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CH R$^{30}$)$_q$NHR$^{31}$, —(CH$_2$)$_q$C(=O) NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the R$^{30}$ moieties can be the same or different, each being independently selected from the group consisting of H, alkyl, alkylaryl, aryl, aralkyl, cycloalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

the R$^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

The term "G represents a 5-membered heteroaryl or heterocyclenyl ring containing at least one —C=N— moiety" means that G represents, in a non-limiting manner, moieties such as dihydroimidazole, imidazole, dihydrooxazole, oxazole, dihydrooxadiazole, oxadiazole, dihydrothiazole, thiazole, triazole, tetrazole and the like. These moieties may be optionally substituted on the ring carbon(s) with one or more R$^9$ groups as stated above, or on the ring nitrogen(s) with one or more R$^8$ groups as stated above.

The present invention also provides a compound of the formula

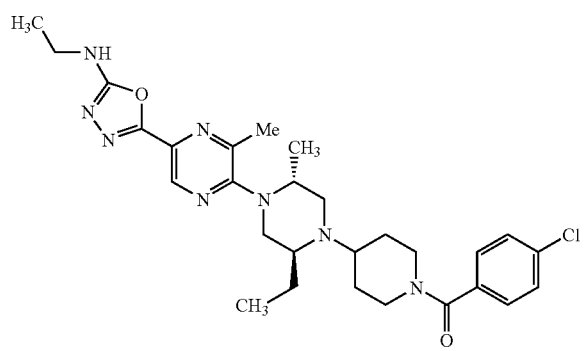

or a pharmaceutically acceptable salt, or solvate thereof. In one embodiment, the pharmaceutically acceptable salt is a mesylate salt of this compound.

A further feature of the invention is a pharmaceutical composition containing as active ingredient at least one compound of Formula 1 together with at least one pharmaceutically acceptable carrier or excipient.

The invention provides methods of preparing compounds of Formula 1, as well as methods for treating diseases, for example, treatment (e.g., palliative therapy, curative therapy, prophylactic therapy) of certain diseases and conditions e.g., inflammatory diseases (e.g., psoriasis, inflammatory bowel disease), autoimmune diseases (e.g., rheumatoid arthritis, multiple sclerosis), graft rejection (e.g., allograft rejection, xenograft rejection), ophthalmic inflammation or dry eye, infectious diseases and tumors. The invention provides a method of treating a CXCR3 chemokine mediated disease in a patient in need of such treatment comprising administering to the patient a therapeutically effective amount of at least one compound of Formula 1, or a pharmaceutically acceptable salt, solvate or ester thereof.

The invention provides methods of treating diseases, for example, treatment (e.g., palliative therapy, curative therapy, prophylactic therapy) of certain diseases and conditions such as inflammatory diseases (e.g., psoriasis, inflammatory bowel disease), autoimmune diseases (e.g., rheumatoid arthritis, multiple sclerosis), graft rejection (e.g., allograft rejection, xenograft rejection), infectious diseases as well as cancers and tumors, fixed drug eruptions, cutaneous delayed-type hypersensitivity responses, ophthalmic inflammation or dry eye, type I diabetes, viral meningitis and tuberculoid leprosy comprising administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics.

The invention also provides a method of modulating (inhibiting or promoting) an inflammatory response in an individual in need of such therapy. The method comprises administering a therapeutically effective amount of a compound (e.g., small organic molecule) which inhibits or promotes mammalian CXCR3 function in an individual in need thereof. Also disclosed is a method of inhibiting or blocking T-cell mediated chemotaxis in a patient in need of such treatment comprising administering to the patient a therapeutically effective amount of a compound of Formula 1 or a pharmaceutically acceptable salt, solvate or ester thereof.

Also disclosed is a method of treating inflammatory bowel disease (such Crohn's disease, ulcerative colitis) in a patient in need of such treatment comprising administering to the patient a therapeutically effective amount of at least one compound of Formula 1, or a pharmaceutically acceptable salt, solvate or ester thereof.

Also disclosed is a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Also disclosed is a method of treating graft rejection in a patient in need of such treatment comprising administering to the patient a therapeutically effective amount of at least one compound of Formula 1, or a pharmaceutically acceptable salt, solvate or ester thereof.

Also disclosed is a method of treating graft rejection in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA4 inhibitors, FTY720, anti-IL-12 inhibitors, and CB2-selective inhibitors.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Also disclosed is a method of treating rheumatoid arthritis in a patient in need of such treatment the method comprising administering to the patient a therapeutically effective amount of: (a) at least one compound of Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Also disclosed is a method of treating psoriasis in a patient in need of such treatment the method comprising administering to the patient a therapeutically effective amount of: a) at least one compound of Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Also disclosed is a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Also disclosed is a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

The invention also provides a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

DETAILED DESCRIPTION OF THE INVENTION

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used above, and throughout the specification, the following terms, unless otherwise indicated, shall be understood to have the following meanings:

"Acyl" means an H—C(=O)—, alkyl-C(=O)—, alkenyl-C(=O)—, alkynyl-C(=O)—, cycloalkyl-C(=O)—, cycloalkenyl-C(=O)—, or cycloalkynyl-C(=O)— group in which the various groups are as previously described. The bond to the parent moiety is through the carbonyl carbon atom. Preferred acyls contain a lower alkyl. Non-limiting examples of suitable acyl groups include formyl, acetyl, propanoyl, 2-methylpropanoyl, butanoyl and cyclohexanoyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The alkenyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, amino, aminosulfonyl, halo, carboxyl, carboxyalkyl (non-limiting example(s) include ester), alkoxycarbonyl, hydroxyalkyl, carbonyl (non-limiting example(s) include ketone), —C(=O)heterocyclyl, formyl (non-limiting example(s) include aldehyde), carboxamido (i.e amido, —C(=O)NH$_2$), —C(=O)N(alkyl)$_2$, —C(=O)NH(alkyl), —C(=O)N(cycloalkyl)$_2$, —C(=O)NH(cycloalkyl), —NHC(=O)alkyl, urea (e.g —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, alkylthiocarboxy, —S(O)$_2$alkyl, —S(O)$_2$aryl, —OS(O)$_2$alkyl, —OS(O)$_2$aryl, sulfonyl urea (non-limiting example(s) include NHC(=S)NHalkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched or a combination thereof, and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), alkoxycarbonyl, hydroxyalkyl, carbonyl (non-limiting example(s) include ketone), —C(=O)heterocyclyl, formyl, carboxamido (i.e amido, —C(=O)NH$_2$, —C(=O)N(alkyl)$_2$, —C(=O)NH(alkyl), —C(=O)N(cycloalkyl)$_2$, —C(=O)NH(cycloalkyl)), —NHC(=O)alkyl, amidinyl, hydrazidyl, hydroxamate, —NHC(=O)H, —NHC(=O)alkyl, urea (e.g —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e —CO$_2$NH$_2$), —NHC(=O)Oalkyl, —CO$_2$N(alkyl)$_2$, —NHC(=O)NH—S(O)$_2$alkyl, —NHC(=O)N(alkyl)-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthio, alkylthiocarboxy, —S(O)alkyl, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylheteroaryl" means an alkyl-heteroaryl-group wherein the alkyl is as previously described and the bond to the parent moiety is through the heteroaryl group.

"Alkylamino" means an —NH$_2$ or —NH$_3$+group in which one or more of the hydrogen atoms on the nitrogen is replaced by an alkyl group as defined above. The bond to the parent is through the nitrogen.

"Alkylaryl" means an alkyl-aryl-group in which the alkyl and aryl are as described herein. Preferred alkylaryls comprise a lower alkyl group. Non-limiting examples of suitable alkylaryl groups include o-tolyl, p-tolyl and xylyl. The bond to the parent moiety is through the aryl.

"Alkylthio" means an alkyl-S— group in which the alkyl group is as described herein. Non-limiting examples of suitable alkylthio groups include methylthio, ethylthio, i-propylthio and heptylthio. The bond to the parent moiety is through the sulfur.

"Alkylthiocarboxy" means an alkyl-S—C(=O)O— group. Preferred groups are those in which the alkyl group is lower alkyl. The bond to the parent moiety is through the carboxy.

"Alkylsulfonyl" means an alkyl-S(O)$_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, alkoxyl, aryl, aryloxy, cycloalkyl, cycloalkenyl, cyano, heteroaryl, heterocyclyl, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, alkoxycarbonyl, hydroxyalkyl, carbonyl (non-limiting example(s) include ketone), —C(=O)heterocyclyl, carboxamido (i.e amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, —NHC(=O)alkyl, urea (e.g —NH(C=O)NH$_2$), —NH(C=O)NH(alkyl), —NH(C=O)NH(alkyl)$_2$, —NH(C=O)NH(heteroaryl), —NH(C=O)NH(heterocyclyl), —S(O)$_2$alkyl, and —S(O)$_2$aryl.

"Alkoxy" means an alkyl-O— group in which the alkyl group is as previously described. Non-limiting examples of suitable alkoxy groups include methoxy, ethoxy, n-propoxy, isopropoxy, n-butoxy, heptoxy and methylhydroxy. The bond to the parent moiety is through the ether oxygen.

"Alkoxycarbonyl" means an alkyl-O—C(=O)— group. Non-limiting examples of suitable alkoxycarbonyl groups include methoxycarbonyl and ethoxycarbonyl. The bond to the parent moiety is through the carbonyl.

"Aminoalkyl" means an amine-alkyl-group in which alkyl is as previously defined. Preferred aminoalkyls contain lower alkyl. Non-limiting examples of suitable aminoalkyl groups include aminomethyl and 2-Dimethlylamino-2-ethyl. The bond to the parent moiety is through the alkyl.

"Amidinyl" means —C(=NR)NHRgroup. The Rgroups are defined as H, alkyl, alkylaryl, heteroaryl, hydroxyl, alkoxy, amino, ester, —NHSO$_2$alkyl, —NHSO$_2$aryl, —NHC(=O)NHalkyl, and —NHalkyl. The bond to the parent moiety is through the carbon.

"Aralkyl" or "arylalkyl" means an aryl-alkyl-group in which the aryl and alkyl are as previously described. Preferred aralkyls comprise a lower alkyl group attached to the aryl group. Non-limiting examples of suitable aralkyl groups include benzyl, 2-phenethyl and naphthalenylmethyl. The bond to the parent moiety is through the alkyl.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aralkoxy" means an aralkyl-O— group in which the aralkyl group is as described above. The bond to the parent moiety is through the oxygen group.

"Aralkoxycarbonyl" means an aralkyl-O—C(=O)— group. Non-limiting example of a suitable aralkoxycarbonyl group is benzyloxycarbonyl. The bond to the parent moiety is through the carbonyl.

"Aroyl" means an aryl-C(=O)— group in which the aryl group is as previously described. The bond to the parent moiety is through the carbonyl. Non-limiting examples of suitable groups include benzoyl and 1- and 2-naphthoyl.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Arylsulfonyl" means an aryl-S(O)$_2$— group. The bond to the parent moiety is through the sulfonyl.

"Arylsulfinyl" means an aryl-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

"Carboxyalkyl" means an alkyl-C(=O)O— group. The bond to the parent moiety is through the carboxy.

Carbamates and urea substituents refer to groups with oxygens and nitrogens respectively adjacent an amide; representative carbamate and urea substituents include the following:

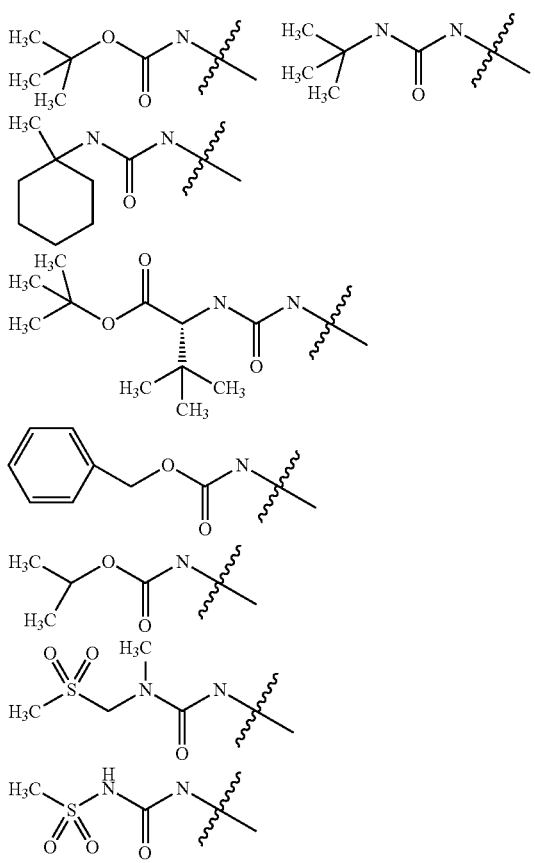

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. The term "cycloalkenyl" additionally means moieties such as cyclobutenedione, cyclopentenone, cyclopentenedione and the like.

"Halogen" (or halo) means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above. Non-limiting examples include trifluoromethyl, 2,2,2-trifluoroethyl, 2-chloropropyl and alike.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclenyl" means a partially unsaturated monocyclic or partially unsaturated multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heterocyclenyls contain about 5 to about 6 ring atoms and 1-3 double bonds. Preferred heterocyclenyls also contain at least one —C=N as part of the ring. The "heterocyclenyl" can be optionally substituted by one or more "ring system substituents" which may be the same or different, and are as defined herein. The prefix aza, oxa or thia before the heterocyclenyl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heterocyclenyls include dihydroimidazole, dihydrooxazole, dihydrooxadiazole, dihydrothiazole, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, oxazolidinyl, imidazolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Also included are ring systems comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Non-limiting examples of suitable monocyclic azaheterocyclic (i.e., azaheterocyclyl) groups include 1,2,3,4-tetrahydropyridine, 1,2-dihydropyridyl, 1,4-dihydropyridyl, 1,2,3,6-tetrahydropyridine, 1,4,5, 6-tetrahydropyrimidine, dihydro-2-pyrrolinyl, dihydro-3-pyrrolinyl, dihydro-2-imidazolinyl, dihydro-2-pyrazolinyl, dihydro-4,5-triazolyl and the like. Non-limiting examples of suitable oxaheterocyclic (i.e., oxaheterocyclyl) groups include 3,4-dihydro-2H-pyran, dihydrofuranyl, fluorodihydrofuranyl, and the like. Non-limiting example of a suitable multicyclic oxaheterocyclic group is 7-oxabicyclo[2.2.1]heptenyl. Non-limiting examples of suitable monocyclic thiaheterocyclic (i.e., thiaheterocyclyl) rings include dihydrothiophenyl, dihydrothiopyranyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-(3-yl)methyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl. The bond to the parent moiety is through the alkyl.

"Hydroxamate" means an alkyl-C(=O)NH—O— group. The bond to the parent moiety is through the oxygen group.

"Ring system substituent" means a substituent attached to an aromatic or non-aromatic ring system which, for example, replaces an available hydrogen on the ring system. Ring system substituents may be the same or different, each being independently selected from the group consisting of H, alkyl, alkenyl, alkynyl, alkoxyl, aryl, aroyl, aryloxy, cycloalkyl, cycloalkenyl, heteroaryl, heterocyclyl, alkylaryl, alkylheteroaryl, aralkyl, aralkenyl, aralkoxy, aralkoxycarbonyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), cyano, alkoxycarbonyl, hydroxyalkyl, carbonyl (non-limiting example(s) include ketone), —C(=O)heterocyclyl, formyl (non-limiting example(s) include aldehyde), carboxamido (i.e amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, -amidino, hydrazido, hydroxamate, —NHC(=O)H, —NHC(=O)alkyl, urea (e.g —NH(C=O)NH$_2$), —NH(C=O)NH(alkyl), —NH(C=O)NH(alkyl)$_2$, —NH(C=O)NH(heteroaryl), —NH(C=O)NH(heterocyclyl), guanidinyl, —NHC(=NCN)NH$_2$, —NHC(=NCN)N(alkyl)$_2$, carbamoyl (i.e —CO$_2$NH$_2$), —NHC(=O)Oalkyl, —CO$_2$N(alkyl)$_2$, —NHC(=O)NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$,thio, alkylthiocarboxy, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$.

"Spiroalkyl" means an alkylene group wherein two carbon atoms of an alkyl group are attached to one carbon atom of a parent molecular group thereby forming a carbocyclic or heterocyclic ring of three to eleven atoms. Representative structures include examples such as:

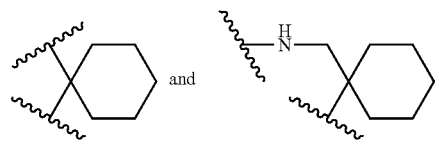

and

The spiroalkyl groups of this invention can be optionally substituted by one or more ring system substituents, wherein "ring system substituent" is as defined herein.

"Ring system substituent" also means a cyclic ring of 3 to 7 ring atoms of which may contain 1 or 2 heteroatoms, attached to an aryl, heteroaryl, or heterocyclyl ring by simultaneously substituting two ring hydrogen atoms on said aryl, heteroaryl, heterocyclyl ring. Non-limiting examples include:

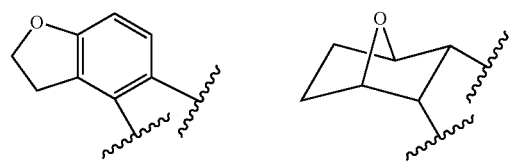

and the like.

The term "optionally substituted" means optional substitution with the specified groups, radicals or moieties, in available position or positions.

With reference to the number of moieties (non-limiting example(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line —— as a bond generally indicates a mixture of, or either of, the possible isomers, non-limiting example(s) include, containing (R)- and (S)-stereochemistry. For example,

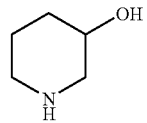

means containing both

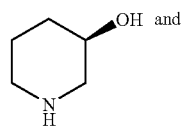 and 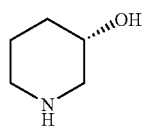

A dashed line (-----) represents an optional bond.

Lines drawn into the ring systems, such as, for example:

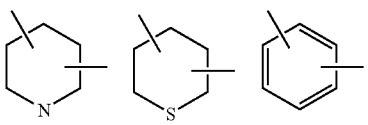

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

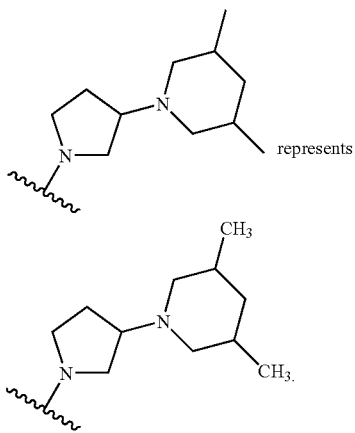

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Metabolic conjugates", for example, glucuronides and sulfates which can undergo reversible conversion to compounds of Formula 1 are contemplated in this application.

"Effective amount" or "therapeutically effective amount" is meant to describe an amount of compound or a composition of the present invention effective to antagonize CXCR3 and thus produce the desired therapeutic effect in a suitable patient.

"Mammal" means humans and other mammalian animals.

"Patient" includes both human and animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$. In general, the solvated forms are equivalent to the unsolvated forms and are intended to be encompassed within the scope of this invention.

The compounds of Formula 1 form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (non-limiting example(s) include, non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (non-limiting example(s) include methyl, ethyl, propyl, and butyl chlorides, bromides and iodides), dialkyl sulfates (non-limiting example(s) include dimethyl, diethyl, dibutyl, and diamyl sulfates), long chain halides (non-limiting example(s) include decyl, lauryl, myristyl and stearyl chlorides, bromides and iodides), aralkyl halides (non-limiting example(s) include benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula 1, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate, ester and prodrug of enantiomers, stereoisomers, rotamers, tautomers, racemates or prodrugs of the inventive compounds.

It should also be noted that throughout the specification and Claims appended hereto any formula, compound, moiety or chemical illustration with unsatisfied valences is assumed to have the hydrogen atom to satisfy the valences unless the context indicates a bond.

In one embodiment, the present invention discloses compounds of Formula 1, having CXCR3 antagonist activity, or a pharmaceutically acceptable derivative thereof, where the various definitions are given above.

In another embodiment of this invention, G represents a dihydroimidazole, imidazole, dihydrooxazole, oxazole, dihydrooxadiazole, oxadiazole, triazole, or tetrazole ring.

In another embodiment of this invention, ring G is selected from the group consisting of:

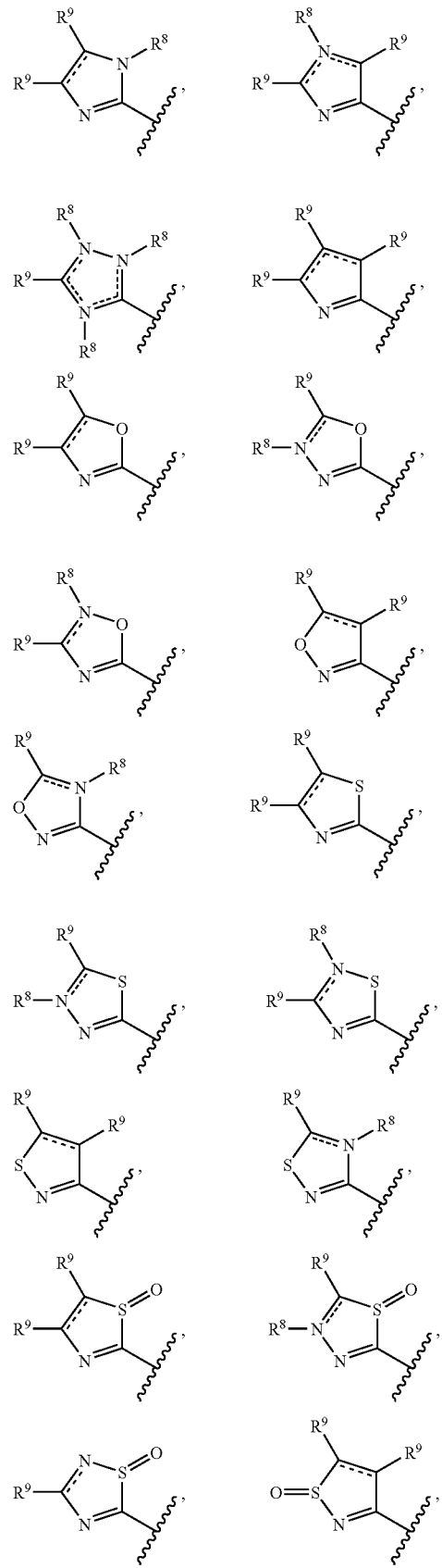

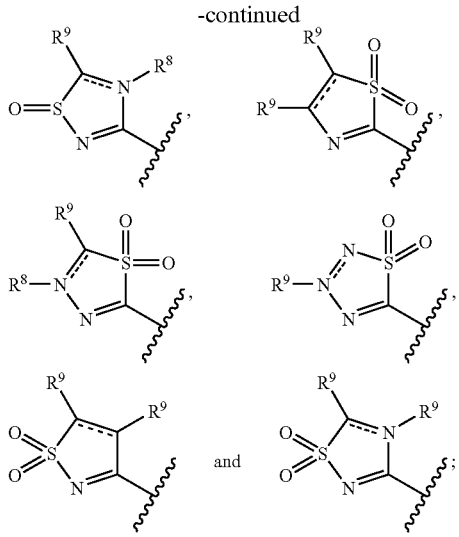

wherein ⸺ is a single bond or double bond.

In another embodiment of this invention, $R^3$ is selected from the group consisting of H, alkyl, haloalkyl, hydroxyalkyl, halogen, —N($R^{30}$)$_2$, —O$R^{30}$ and —CF$_3$.

In another embodiment of this invention, $R^3$ is selected from the group consisting of H, alkyl, haloalkyl, hydroxyalkyl, halogen, —N($R^{30}$)$_2$, —O$R^{30}$ and —CF$_3$.

In another embodiment of this invention, $R^3$ is selected from the group consisting of H, —CH$_3$, —CH$_2$CH$_3$, —CH(CH$_3$)$_2$, cyclopropyl, —F, —Cl, OCH$_3$, OCF$_3$ and CF$_3$.

In another embodiment of this invention, $R^3$ is selected from the group consisting of H, —CH$_3$, —CH$_2$CH$_3$, cyclopropyl, —F, —Cl, OCH$_3$, OCF$_3$ and CF$_3$.

In another embodiment of this invention, $R^6$ is selected from the group consisting of H, alkyl, halogen, hydroxyalkyl, —CN, —N($R^{30}$)$_2$, —O$R^{30}$, —N═CH-alkyl, —N$R^{30}$C(═O)alkyl, and —N$R^{30}$C(═O)N($R^{30}$)$_2$.

In another embodiment of this invention, $R^6$ is selected from the group consisting of H, alkyl, halogen, hydroxyalkyl, —CN, —N($R^{30}$)$_2$, —O$R^{30}$, —N═CH-alkyl, and —N$R^{30}$C(═O)alkyl.

In another embodiment of this invention, $R^6$ is selected from the group consisting of H, alkyl, halogen, hydroxyalkyl, —CN, —N($R^{30}$)$_2$, —O$R^{30}$, —N═CH-alkyl, and —N$R^{30}$C(═O)alkyl.

In another embodiment of this invention, $R^6$ is selected from the group consisting of H, —NH$_2$, —NHC(═O)CH$_3$, —NHC(═O)N(CH$_3$)$_2$, —CH$_3$, —CN and —F.

In another embodiment of this invention, $R^8$ is selected from the group consisting of H, alkyl, alkenyl, arylalkyl, cycloalkyl, —(CH$_2$)$_q$OH, —(CH$_2$)$_q$O$R^{31}$, —(CH$_2$)$_q$NH$_2$, —(CH$_2$)$_q$NH$R^{31}$, —(CH$_2$)$_q$C(═O)NH$R^{31}$, —(CH$_2$)$_q$SO$_2$$R^{31}$, —(CH$_2$)$_q$NSO$_2$$R^{31}$, —(CH$_2$)$_q$SO$_2$NH$R^{31}$, and —C(═O)-aryl-halogen.

In another embodiment of this invention, $R^8$ is selected from the group consisting of H, alkyl, alkenyl, arylalkyl, cycloalkyl, —(CH$_2$)$_q$OH, —(CH$_2$)$_q$O$R^{31}$, —(CH$_2$)$_q$NH$_2$, —(CH$_2$)$_q$NH$R^{31}$, —(CH$_2$)$_q$C(═O)NH$R^{31}$, —(CH$_2$)$_q$SO$_2$$R^{31}$, —(CH$_2$)$_q$NSO$_2$$R^{31}$, or —(CH$_2$)$_q$SO$_2$NH$R^{31}$.

In another embodiment of this invention, the $R^9$ moieties can be the same or different, each being independently selected from the group consisting of H, alkyl, cycloalkyl, —C(═O) N(H)$R^{30}$, —C(═O)O$R^{30}$, —C(═O)alkyl, —(CH$_2$)$_q$OH, —(CH$_2$)$_q$O$R^{31}$, —(CH$_2$)$_q$NH$_2$, —(CH$_2$)$_q$NH$R^{31}$, —N(H)$R^{30}$, —N(H)S(O$_2$)$R^{31}$, —N(H)C(═O)NH($R^{30}$), —O$R^{30}$, —SO$_2$($R^{31}$), and —SO$_2$N(H)$R^{30}$.

In another embodiment of this invention, the $R^9$ moieties can be the same or different, each being independently selected from the group consisting of H, alkyl, cycloalkyl, —C(═O)N(H)$R^{30}$, —C(═O)alkyl, —(CH$_2$)$_q$OH, —(CH$_2$)$_q$O$R^{31}$, —(CH$_2$)$_q$NH$_2$, —(CH$_2$)$_q$NH$R^{31}$, —N(H)$R^{30}$, —N(H)S(O$_2$)$R^{31}$, —N(H)C(═O)NH($R^{30}$), —O$R^{30}$, —SO$_2$($R^{31}$), and —SO$_2$N(H)$R^{30}$.

In another embodiment of this invention, the $R^9$ moieties can be the same or different, each being independently selected from the group consisting of H, —OH, cyclopropyl, —CF$_3$, —CH$_3$, —CH$_2$OH, —CH$_2$CH$_2$OH, —C(CH$_3$)$_2$OH, —CH$_2$CH$_2$OCH$_3$, —C(═O)OCH$_3$, —C(═O)OCH$_2$CH$_3$, —CH$_2$NH$_2$, —CH$_2$CH$_2$NH$_2$, —CH$_2$CH$_2$NHSO$_2$CH$_3$, —CH$_2$CH$_2$SO$_2$CH$_3$, —C(═O)NH$_2$, —C(═O)N(H)CH$_2$CH$_2$OH, —CH$_2$N(H)C(═O)CF$_3$, —C(═O)N(H)-cyclopropyl, —C(═O)N(H)CH$_2$CF$_3$, —NH$_2$, —NHCH$_3$, —N(CH$_3$)$_2$, —N(H)CH$_2$CH$_3$, —N(H)-cyclopropyl-CH$_3$, —N(H)CH(CH$_3$)$_2$, —N(H)CH$_2$CH$_2$CH$_3$, —N(H)CH$_2$C(═O)OCH$_3$, —N(H)CH$_2$C(═O)OCH$_2$CH$_3$, —N(H)CH$_2$C(═O)NH-cyclopropyl, —N(H)CH$_2$CH$_2$OH, —N(H)CH$_2$CH$_2$NH$_2$, —N(H)CH$_2$CH$_2$NHSO$_2$CH$_3$, —N(H)CH$_2$CH$_2$SO$_2$CH$_3$, —N(H)C(═O)N(H)CH$_2$CH$_3$, —N(H)CH$_2$C(═O)NH$_2$, —OCH$_3$, —N(CH$_2$CH$_3$)S(═O)$_2$-phenylalkyl, —N(H)S(═O)$_2$-alkyl, ═S and ═O.

In another embodiment of this invention, the $R^9$ moieties can be the same or different, each being independently selected from the group consisting of H, —OH, —CF$_3$, —CH$_3$, —CH$_2$CH$_3$, —CH(CH$_3$)$_2$, cyclopropyl, —C(═O)OCH$_3$, —C(═O)OCH$_2$CH$_3$, —CH$_2$CH$_2$OH, —CH$_2$CH$_2$NH$_2$, —NH$_2$, —NHCH$_3$, —N(H)CH$_2$CH$_3$, —N(H)CH(CH$_3$)$_2$, —N(H)CH$_2$CH$_2$CH$_3$, —N(H)-cyclopropyl-CH$_3$, —N(H)CH$_2$C(═O)OCH$_3$, —N(H)CH$_2$C(═O)OCH$_3$, —N(H)CH$_2$C(═O)NHCH$_3$, —N(H)CH$_2$C(═O)NH-cyclopropyl, —N(H)CH$_2$CH$_2$OH, —N(CH$_2$CH$_3$)S(═O)$_2$-phenyl-alkyl, and —N(H)S(═O)$_2$-alkyl.

In another embodiment of this invention, the $R^9$ moieties can be the same or different, each being independently selected from the group consisting of H, cyclopropyl, —CF$_3$, —CH$_3$, —CH$_2$OH, —CH$_2$CH$_2$OH, —C(CH$_3$)$_2$OH, —CH$_2$CH$_2$OCH$_3$, —C(═O)OCH$_2$CH$_3$, —CH$_2$NH$_2$, —CH$_2$CH$_2$NH$_2$, —CH$_2$CH$_2$NHSO$_2$CH$_3$, —CH$_2$CH$_2$SO$_2$CH$_3$, —C(═O)NH$_2$, —C(═O)N(H)CH$_2$CH$_2$OH, —CH$_2$N(H)C(═O)CF$_3$, —C(═O)N(H)-cyclopropyl, —C(═O)N(H)CH$_2$CF$_3$, —NH$_2$, —NHCH$_3$, —N(CH$_3$)$_2$, —N(H)CH$_2$CH$_3$, —N(H)CH(CH$_3$)$_2$, —N(H)CH$_2$CH$_2$CH$_3$, —N(H)CH$_2$C(═O)OCH$_3$, —N(H)CH$_2$OH, —N(H)CH$_2$CH$_2$NH$_2$, —N(H)CH$_2$CH$_2$NHSO$_2$CH$_3$, —N(H)CH$_2$CH$_2$SO$_2$CH$_3$, —N(H)C(═O)N(H)CH$_2$CH$_3$, —N(H)CH$_2$C(═O)NH$_2$, —OCH$_3$, ═S and ═O.

In another embodiment of this invention, the $R^9$ moieties can be the same or different, each being independently selected from the group consisting of H, —CF$_3$, —CH$_3$, —CH$_2$CH$_2$OH, —CH$_2$CH$_2$NH$_2$, —NH$_2$, —NHCH$_3$, —N(H)CH$_2$CH$_3$, —N(H)CH(CH$_3$)$_2$, —N(H)CH$_2$CH$_2$CH$_3$, —N(H)CH$_2$C(═O)OCH$_3$, and —N(H)CH$_2$CH$_2$OH.

In another embodiment of this invention, $R^{10}$ is selected from the group consisting of H, alkyl, aralkyl, hydroxyalkyl, and carbonyl.

In another embodiment of this invention, $R^{10}$ is selected from the group consisting of —CH$_3$, —CH$_2$CH$_3$ and —CH$_2$CH$_2$CH$_3$, and m is 0-2.

In another embodiment of this invention, $R^{11}$ is selected from the group consisting of H, alkyl, hydroxyalkyl and carbonyl.

In another embodiment of this invention, $R^{11}$ is H or —$CH_3$.

In another embodiment of this invention, $R^{12}$ is selected from the group consisting of H, CN, —C(=O)N($R^{30}$)$_2$ and alkyl.

In another embodiment of this invention, $R^{12}$ is selected from the group consisting of H, —$CH_3$, CN and —$CH_2CH_3$.

In another embodiment of this invention, the ring atoms of ring D are independently C, N, O and S, and substituted by 0-4 $R^{20}$ moieties.

In another embodiment of this invention, the ring atoms of ring D are independently C or N and substituted by 0-4 $R^{20}$ moieties.

In another embodiment of this invention, ring D is a 5 to 6 membered aryl, heteroaryl, heterocyclenyl, or heterocyclyl ring and substituted by 0-4 $R^{20}$ moieties.

In another embodiment of this invention, the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluromethyl, trifluoromethoxy, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —N(R$^{30}$)SO$_2$(R$^{31}$), —N(R$^{30}$)SO$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$.

In another embodiment of this invention, the $R^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$, and —OSO$_2$(R$^{31}$)).

In another embodiment of this invention, two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties. In another embodiment of this invention, the $R^{20}$ moieties can be the same or different, each being independently selected from the group consisting of H, —CN, —CH$_3$, —CH$_2$CH$_3$, —CH(CH$_3$)$_2$, cyclopropyl, —CF$_3$, —CH$_2$OH, —CH$_2$—S(=O)$_2$CH$_3$, —C(=O)H, —CO$_2$H, —CO$_2$CH$_3$, —NH$_2$, —N(H)CH$_3$, —N(H)S(=O)$_2$CH$_3$, —OCF$_3$, —OH, F, Cl, Br, —C(=NOH)NH$_2$, —OCH$_2$CH$_2$S(O$_2$)CH$_3$, —C(=O)NH$_2$,

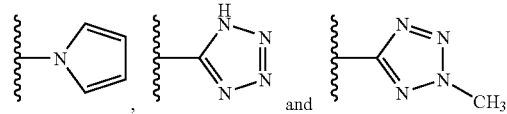

In another embodiment of this invention, the $R^{20}$ moieties can be the same or different, each being independently selected from the group consisting of H, —CN, —CH$_3$, —CF$_3$, —CH$_2$OH, —CO$_2$H, —CO$_2$CH$_3$, —NH$_2$, —NHCH$_3$, —OCF$_3$, —OH, F, Cl, Br, —C(=NOH)NH$_2$, —OCH$_2$CH$_2$S(O$_2$)CH$_3$, —C(=O)NH$_2$,

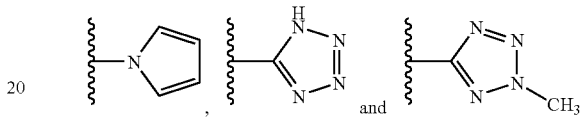

In another embodiment of this invention, the $R^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy.

In another embodiment of this invention, Y is selected from the group consisting of —(CHR$^{13}$)$_r$—, —(CR$^{13}$R$^{13}$)$_r$—, —C(=O)—, —CHR$^{13}$C(=O)—, and —(CHR$^{13}$)$_r$C(=O).

In another embodiment of this invention, Y is selected from the group consisting of: —(CHR$^{13}$)$_r$—, —(CR$^{13}$R$^{13}$)$_r$—, —C(=O)— and —CHR$^{13}$C(=O)—.

In another embodiment of this invention, Y is selected from the group consisting of: —CH$_2$—, —CH$_2$CH$_2$—, —CH(CH$_3$)—, —CH$_2$CH$_2$O—, —CH(CH$_2$OH)—, —CH(CH$_2$OCH$_2$-phenyl)-, —C(=O)—, —C(=O)CH$_2$— and —CH(C=O)O-alkyl-.

In another embodiment of this invention, Y is selected from the group consisting of: —CH$_2$—, —CH(CH$_3$)—, —CH(CH$_2$OH)—, —C(=O)— and —CH(CO$_2$alkyl)-.

In another embodiment of this invention, m is 0-2.

In another embodiment of this invention, n is 0-2.

In another embodiment of this invention, q is 1 or 2.

In another embodiment of this invention, r is 1 or 2.

In another embodiment of this invention, ring G is selected from the group consisting of:

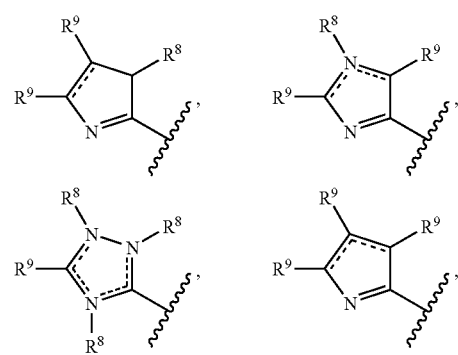

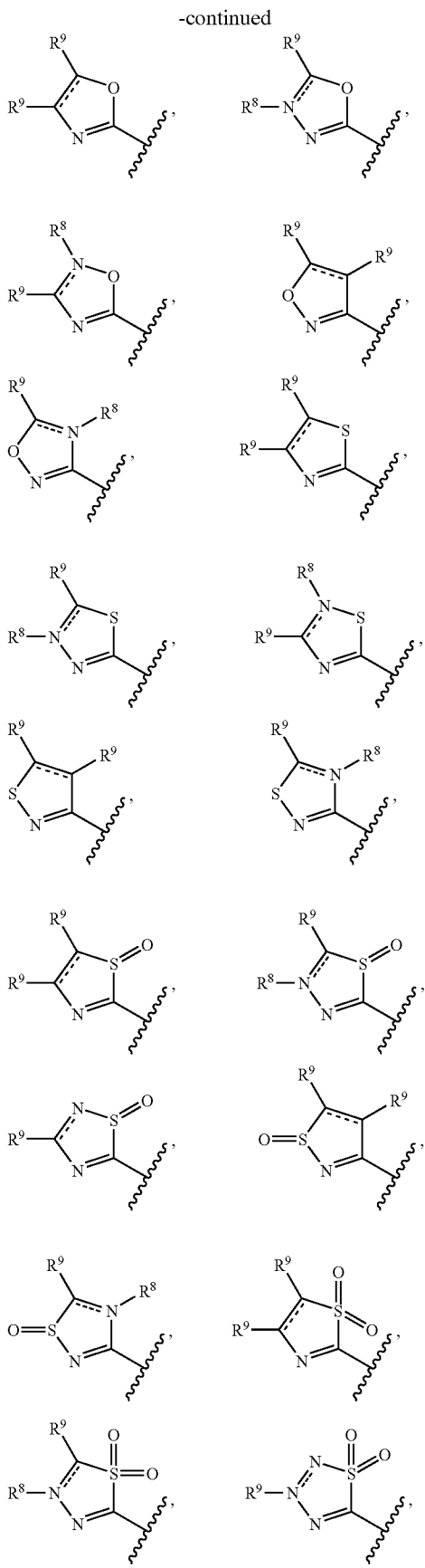

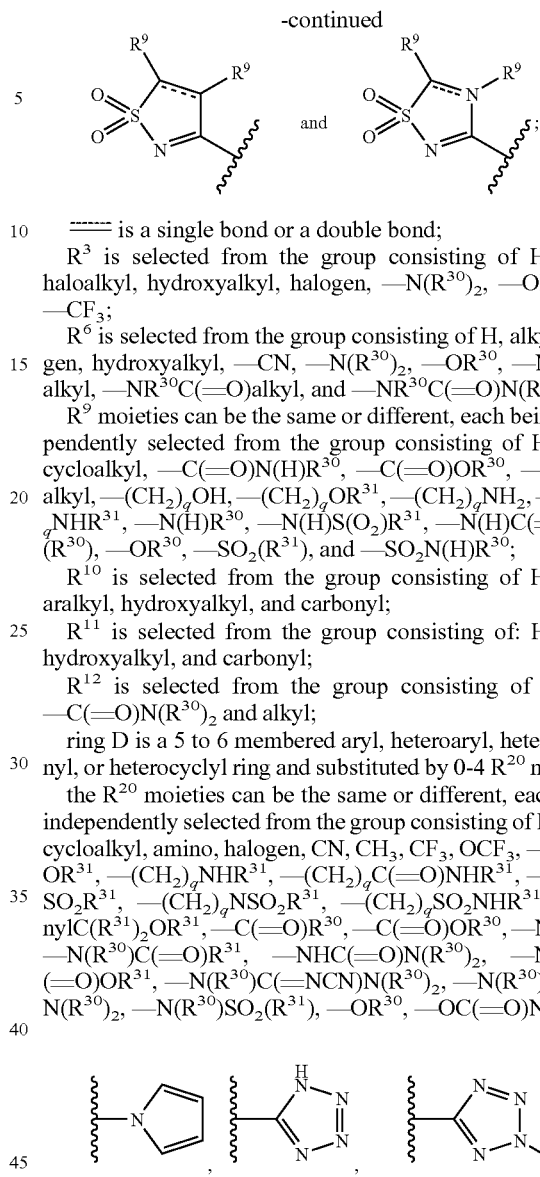

is a single bond or a double bond;

$R^3$ is selected from the group consisting of H, alkyl, haloalkyl, hydroxyalkyl, halogen, $-N(R^{30})_2$, $-OR^{30}$ and $-CF_3$;

$R^6$ is selected from the group consisting of H, alkyl, halogen, hydroxyalkyl, $-CN$, $-N(R^{30})_2$, $-OR^{30}$, $-N=CH$-alkyl, $-NR^{30}C(=O)$alkyl, and $-NR^{30}C(=O)N(R^{30})_2$;

$R^9$ moieties can be the same or different, each being independently selected from the group consisting of H, alkyl, cycloalkyl, $-C(=O)N(H)R^{30}$, $-C(=O)OR^{30}$, $-C(=O)$alkyl, $-(CH_2)_qOH$, $-(CH_2)_qOR^{31}$, $-(CH_2)_qNH_2$, $-(CH_2)_qNHR^{31}$, $-N(H)R^{30}$, $-N(H)S(O_2)R^{31}$, $-N(H)C(=O)NH(R^{30})$, $-OR^{30}$, $-SO_2(R^{31})$, and $-SO_2N(H)R^{30}$;

$R^{10}$ is selected from the group consisting of H, alkyl, aralkyl, hydroxyalkyl, and carbonyl;

$R^{11}$ is selected from the group consisting of: H, alkyl, hydroxyalkyl, and carbonyl;

$R^{12}$ is selected from the group consisting of H, CN, $-C(=O)N(R^{30})_2$ and alkyl;

ring D is a 5 to 6 membered aryl, heteroaryl, heterocyclenyl, or heterocyclyl ring and substituted by 0-4 $R^{20}$ moieties;

the $R^{20}$ moieties can be the same or different, each being independently selected from the group consisting of H, alkyl, cycloalkyl, amino, halogen, CN, $CH_3$, $CF_3$, $OCF_3$, $-(CH_2)_qOR^{31}$, $-(CH_2)_qNHR^{31}$, $-(CH_2)_qC(=O)NHR^{31}$, $-(CH_2)_qSO_2R^{31}$, $-(CH_2)_qNSO_2R^{31}$, $-(CH_2)_qSO_2NHR^{31}$, -alkynylC$(R^{31})_2OR^{31}$, $-C(=O)R^{30}$, $-C(=O)OR^{30}$, $-N(R^{30})_2$, $-N(R^{30})C(=O)R^{31}$, $-NHC(=O)N(R^{30})_2$, $-N(R^{30})C(=O)OR^{31}$, $-N(R^{30})C(=NCN)N(R^{30})_2$, $-N(R^{30})C(=O)N(R^{30})_2$, $-N(R^{30})SO_2(R^{31})$, $-OR^{30}$, $-OC(=O)N(R^{30})_2$, and $-OSO_2(R^{31})$; or alternatively, two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties;

the $R^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy;

Y is selected from the group consisting of $-CH_2-$, $-CH_2CH_2-$, $-CH(CH_3)-$, $-CH_2CH_2O-$, $-CH(CH_2OH)-$, $-CH(CH_2OCH_2$-phenyl)-, $-C(=O)-$, $-C(=O)CH_2-$ and $-CH(C=O)O$-alkyl-;

m is 0-2;
n is 0-2;
q is 1 or 2; and
r is 1 or 2.

In another embodiment of this invention, ring G is selected from the group consisting of:

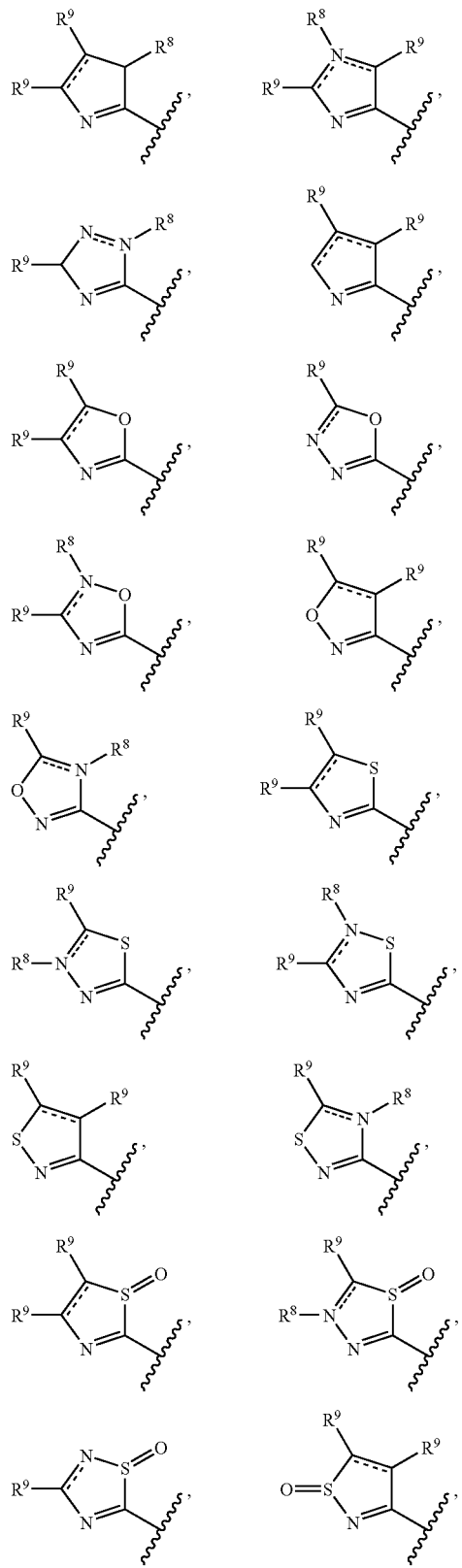

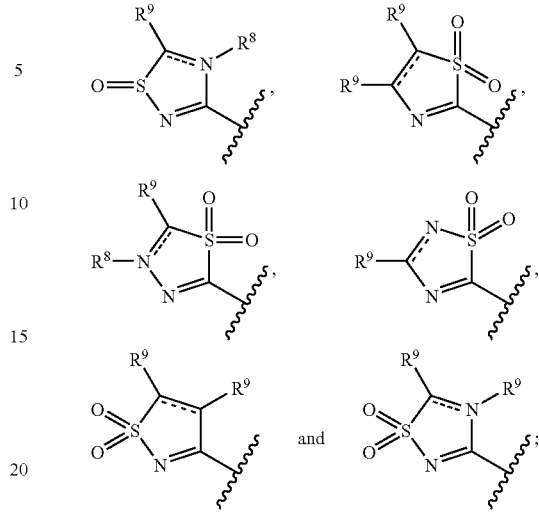

═══ is a single bond or a double bond;

$R^3$ is selected from the group consisting of H, alkyl, haloalkyl, hydroxyalkyl, halogen, —N($R^{30}$)$_2$, —O$R^{30}$ and —CF$_3$;

$R^6$ is selected from the group consisting of H, alkyl, halogen, hydroxyalkyl, —CN, —N($R^{30}$)$_2$, —O$R^{30}$, —N═CH-alkyl, and —N$R^{30}$C(═O)alkyl;

$R^9$ moieties can be the same or different, each being independently selected from the group consisting of H, alkyl, cycloalkyl, —C(═O)N(H)$R^{30}$, —C(═O)alkyl, —(CH$_2$)$_q$OH, —(CH$_2$)$_q$O$R^{31}$, —(CH$_2$)$_q$NH$_2$, —(CH$_2$)$_q$NH$R^{31}$, —N(H)$R^{30}$, —N(H)S(O$_2$)$R^{31}$, —N(H)C(═O)NH($R^{30}$), —O$R^{30}$, —SO$_2$($R^{31}$), and —SO$_2$N(H)$R^{30}$;

$R^{10}$ is selected from the group consisting of H, alkyl, aralkyl, hydroxyalkyl, and carbonyl;

$R^{11}$ is selected from the group consisting of: H, alkyl, hydroxyalkyl, and carbonyl;

$R^{12}$ is selected from the group consisting of H, CN, —C(═O)N($R^{30}$)$_2$ and alkyl;

ring D is a 5 to 6 membered aryl, heteroaryl, heterocyclenyl, or heterocyclyl ring and substituted by 0-4 $R^{20}$ moieties;

the $R^{20}$ moieties can be the same or different, each being independently selected from the group consisting of H, alkyl, amino, halogen, CN, CH$_3$, CF$_3$, OCF$_3$, —(CH$_2$)$_q$O$R^{31}$, —(CH$_2$)$_q$NH$R^{31}$, —(CH$_2$)$_q$C(═O)NH$R^{31}$, —(CH$_2$)$_q$SO$_2$$R^{31}$, —(CH$_2$)$_q$NSO$_2$$R^{31}$, —(CH$_2$)$_q$SO$_2$NH$R^{31}$, -alkynylC($R^{31}$)$_2$O$R^{31}$, —C(═O)$R^{30}$, —C(═O)O$R^{30}$, —N($R^{30}$)$_2$, —N($R^{30}$)C(═O)$R^{31}$, —NHC(═O)N($R^{30}$)$_2$, —N($R^{30}$)C(═O)O$R^{31}$, —N($R^{30}$)C(═NCN)N($R^{30}$)$_2$, —N($R^{30}$)C(═O)N($R^{30}$)$_2$, —O$R^{30}$, —OC(═O)N($R^{30}$)$_2$,

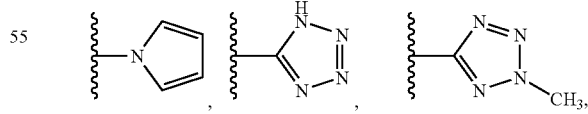

and —OSO$_2$($R^{31}$);

Y is selected from the group consisting of —CH$_2$—, —CH(CH$_3$)—, —CH(CH$_2$OH)—, —C(═O)— and —CH(CO$_2$alkyl)-;

m is 0-2;
n is 0-2;
q is 1 or 2; and
r is 1 or 2.

In another embodiment, the compound of Formula 1 is represented by structural Formulae 2-11:
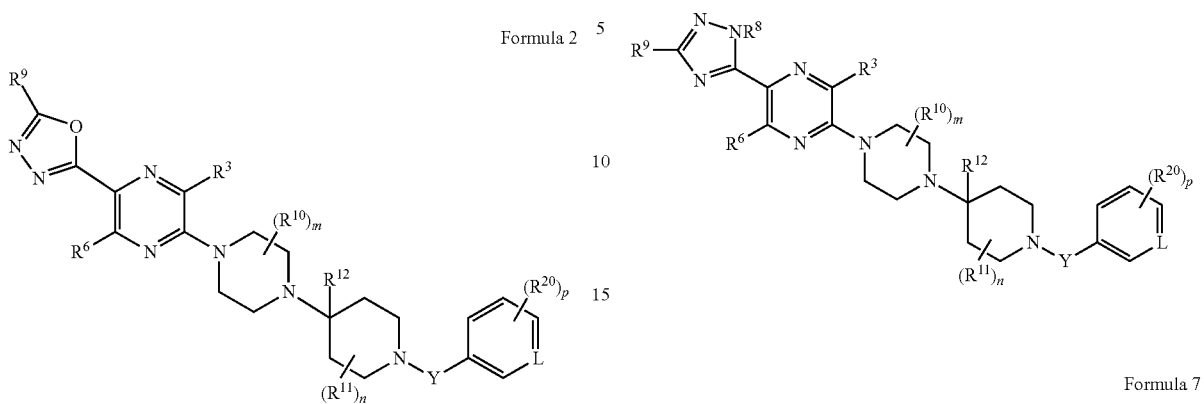
Formula 2
Formula 3
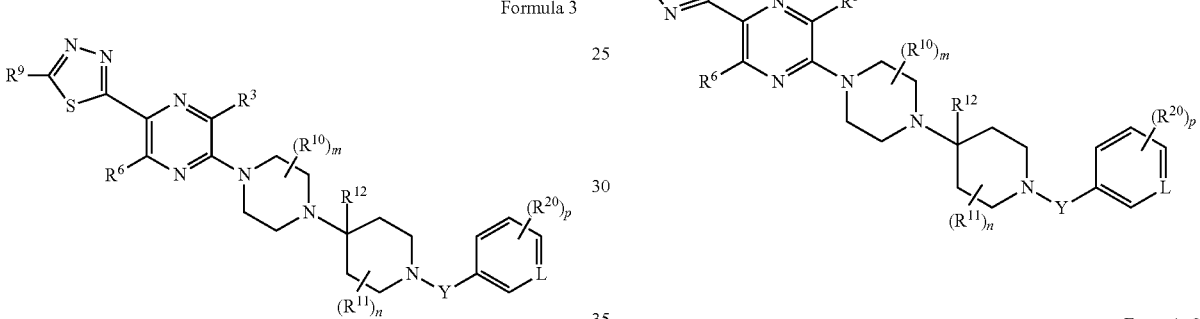
Formula 4
Formula 5
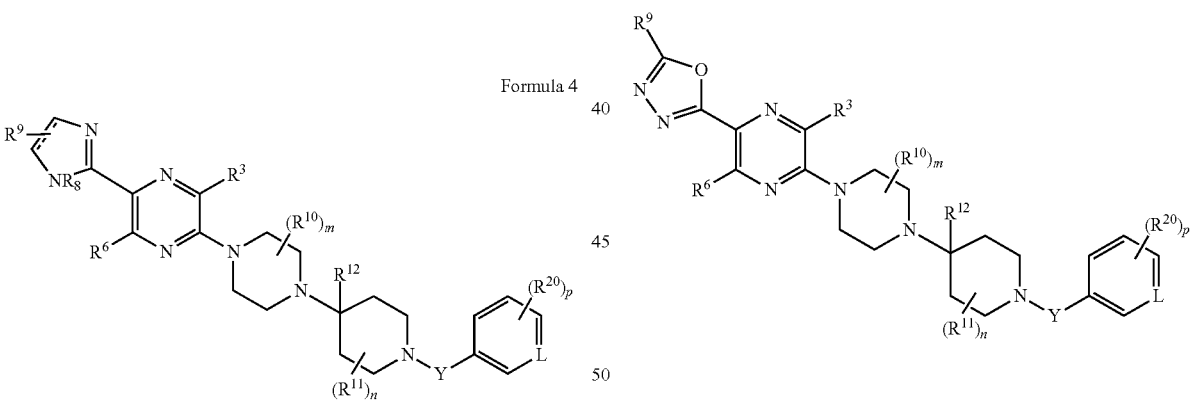
Formula 6
Formula 7
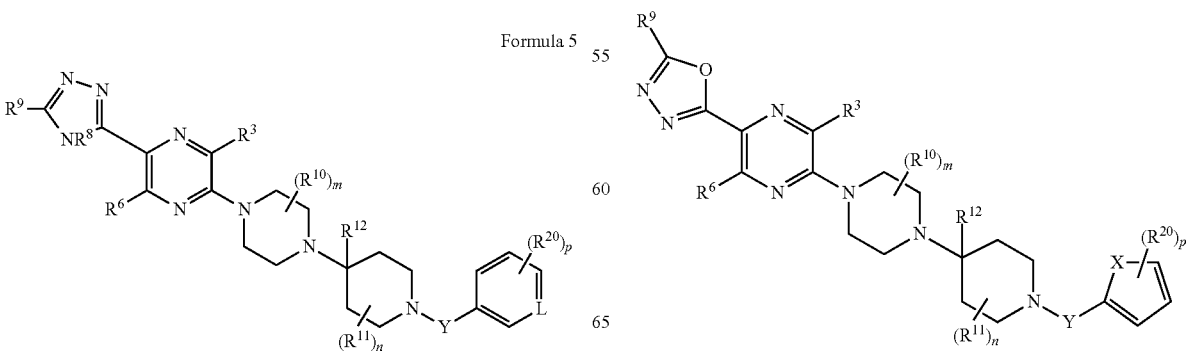
Formula 8
Formula 9

-continued

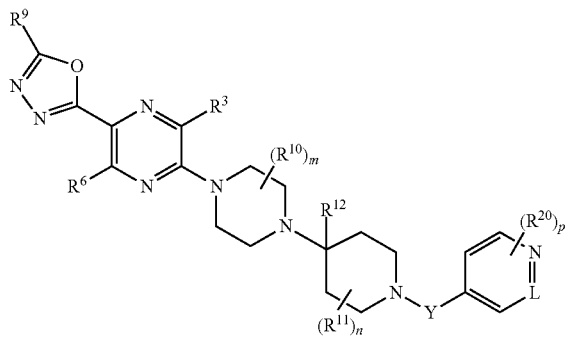

Formula 10

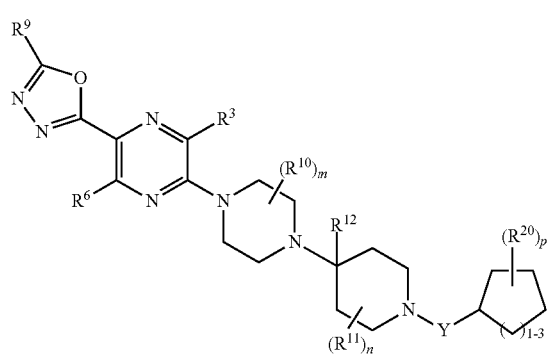

Formula 11 wherein:

the R[8] moieties can be the same or different, each being independently selected from the group consisting of H, alkyl, alkenyl, arylalkyl, cycloalkyl, —(CH$_2$)$_q$OH, —(CH$_2$)$_q$OR[31], —(CH$_2$)$_q$NH$_2$, —(CH$_2$)$_q$NHR[31], —(CH$_2$)$_q$C(=O)NHR[31], —(CH$_2$)$_q$SO$_2$R[31], —(CH$_2$)$_q$NSO$_2$R[31], —(CH$_2$)$_q$SO$_2$NHR[31], and —C(=O)-aryl-halogen;

the R[9] moieties can be the same or different, each being independently selected from the group consisting of of H, alkyl, cycloalkyl, —C(=O)N(H)R[30], —C(=O)OR[30], —C(=O)alkyl, —(CH$_2$)$_q$OH, —(CH$_2$)$_q$OR[31], —(CH$_2$)$_q$NH$_2$, —(CH$_2$)$_q$NHR[31], —N(H)R[30], —N(H)S(O$_2$)R[31], —N(H)C(=O)NH(R[30]), —OR[30], —SO$_2$(R[31]), and —SO$_2$N(H)R[30];

L is C or N;

═══ in Formula 4 is a single bond or a double bond;

X in formula 9 is N, O, or S;

p is 0 to 4; and m, n, q, R[10], R[11], R[12], R[20] and Y are as defined in claim 1.

In another embodiment, in formulae 2-11, R[3] is selected from the group consisting of H, alkyl, haloalkyl, hydroxyalkyl, halogen, —N(R[30])$_2$, —OR[30] and —CF$_3$.

In another embodiment, in formulae 2-11, R[6] is selected from the group consisting of H, alkyl, halogen, hydroxyalkyl, —CN, —N(R[30])$_2$, —OR[30], —N=CH-alkyl, —NR[30]C(=O)alkyl, and —NR[30]C(=O)N(R[30])$_2$.

In another embodiment, in formulae 2-11, R[9] moieties are the same or different, each being independently selected from the group consisting of H, —OH, cyclopropyl, —CF$_3$, —CH$_3$, —CH$_2$OH, —CH$_2$CH$_2$OH, —C(CH$_3$)$_2$OH, —CH$_2$CH$_2$OCH$_3$, —C(=O)OCH$_3$, —C(=O)OCH$_2$CH$_3$, —CH$_2$NH$_2$, —CH$_2$CH$_2$NH$_2$, —CH$_2$CH$_2$NHSO$_2$CH$_3$, —CH$_2$CH$_2$SO$_2$CH$_3$, —C(=O)NH$_2$, —C(=O)N(H) CH$_2$CH$_2$OH, —CH$_2$N(H)C(=O)CF$_3$, —C(=O)N(H)-cyclopropyl, —C(=O)N(H)CH$_2$CF$_3$, —NH$_2$, —NHCH$_3$, —N(CH$_3$)$_2$, —N(H)CH$_2$CH$_3$, —N(H)-cyclopropyl-CH$_3$, —N(H)CH(CH$_3$)$_2$, —N(H)CH$_2$CH$_2$CH$_3$, —N(H)CH$_2$C(=O)OCH$_3$, —N(H)CH$_2$C(=O)OCH$_2$CH$_3$, —N(H)CH$_2$C(=O)NH-cyclopropyl, —N(H)CH$_2$CH$_2$OH, —N(H)CH$_2$CH$_2$NH$_2$, —N(H)CH$_2$CH$_2$NHSO$_2$CH$_3$, —N(H)CH$_2$CH$_2$SO$_2$CH$_3$, —N(H)C(=O)N(H)CH$_2$CH$_3$, —N(H)CH$_2$C(=O)NH$_2$, —OCH$_3$, —N(CH$_2$CH$_3$)S(=O)$_2$-phenyl-alkyl, —N(H)S(=O)$_2$-alkyl, =S and =O.

In another embodiment, in formulae 2-11, R[10] is selected from the group consisting of H, alkyl, aralkyl, hydroxyalkyl, and carbonyl.

In another embodiment, in formulae 2-11, R[11] is selected from the group consisting of: of H, alkyl, hydroxyalkyl and carbonyl.

In another embodiment, in formulae 2-11, R[12] is selected from the group consisting of H, —CH$_3$, CN or —CH$_2$CH$_3$.

In another embodiment, in formulae 2-11, the R[20] moieties can be the same or different, each being independently selected from the group consisting of H, alkyl, cycloalkyl, amino, halogen, CN, CH$_3$, CF$_3$, OCF$_3$, —(CH$_2$)$_q$OR[31], —(CH$_2$)$_q$NHR[31], —(CH$_2$)$_q$C(=O)NHR[31], —(CH$_2$)$_q$SO$_2$R[31], —(CH$_2$)$_q$NSO$_2$R[31], —(CH$_2$)$_q$SO$_2$NHR[31], -alkynylC(R[31])$_2$OR[31], —C(=O)R[30], —C(=O)OR[30], —N(R[30])$_2$, —N(R[30])C(=O)R[31], —NHC(=O)N(R[30])$_2$, —N(R[30])C(=O)OR[31], —N(R[30])C(=NCN)N(R[30])$_2$, —N(R[30])C(=O)N(R[30])$_2$, —N(R[30])SO$_2$(R[31]), —OR[30], —OC(=O)N(R[30])$_2$,

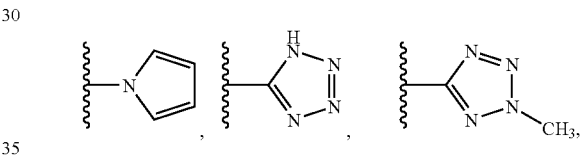

and —OSO$_2$(R[31]); or alternatively, two R[20] moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 R[21] moieties; and the R[21] moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy.

In another embodiment, in formulae 2-11, the R[20] moieties can be the same or different, each being independently selected from the group consisting of H, —CN, —CH$_3$, —CH$_2$CH$_3$, —CH(CH$_3$)$_2$, cyclopropyl, —CF$_3$, —CH$_2$OH, —CH$_2$—S(=O)$_2$CH$_3$, —C(=O)H, —CO$_2$H, —CO$_2$CH$_3$, —NH$_2$, —N(H)CH$_3$, —N(H)S(=O)$_2$CH$_3$, —OCF$_3$, —OH, F, Cl, Br, —C(=NOH)NH$_2$, —OCH$_2$CH$_2$S(O$_2$)CH$_3$, —C(=O)NH$_2$,

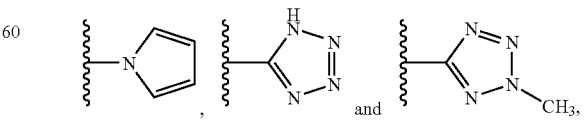

or alternatively, two R[20] moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties;

the $R^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy.

In another embodiment, the compound of Formula 1 is represented by structural Formula 2, Formula 3, Formula 4, Formula 5, Formula 6 or Formula 7:

Formula 2

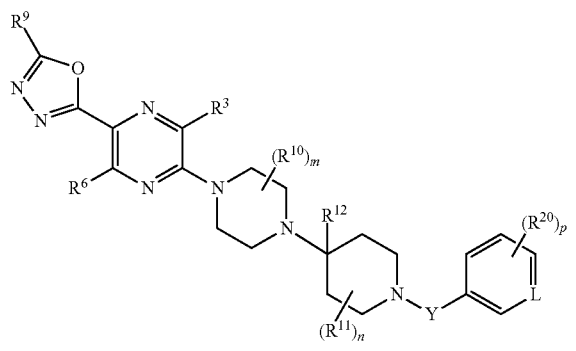

Formula 3

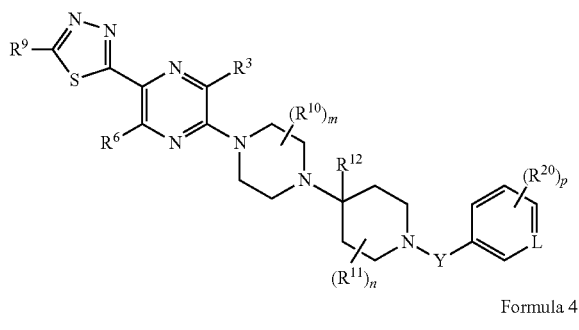

Formula 4

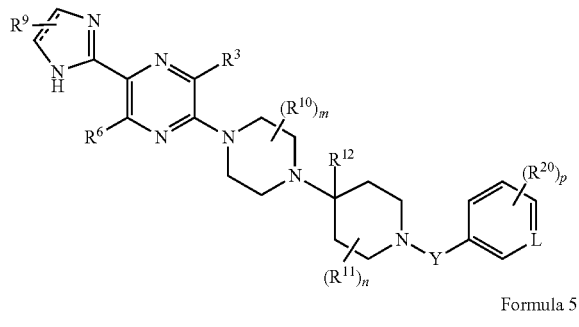

Formula 5

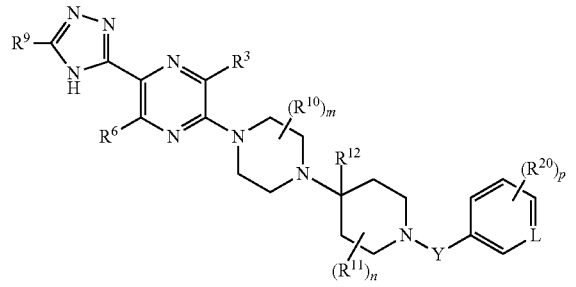

Formula 6

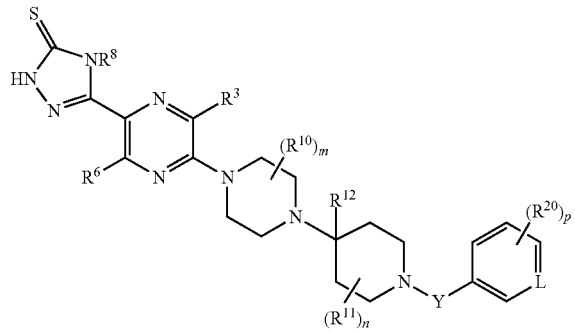

Formula 7 wherein:

the $R^8$ moieties can be the same or different, each being independently selected from the group consisting of H, alkyl, alkenyl, alkylaryl, arylalkyl, cycloalkyl, aryl, heteroaryl, heterocyclenyl, heterocyclyl, —$(CH_2)_qOH$, —$(CH_2)_qOR^{31}$, —$(CH_2)_qNH_2$, —$(CH_2)_qNHR^{31}$, —$(CH_2)_qC(=O)NHR^{31}$, —$(CH_2)_qSO_2R^{31}$, —$(CH_2)_qNSO_2R^{31}$, or —$(CH_2)_qSO_2NHR^{31}$;

the $R^9$ moieties can be the same or different, each being independently selected from the group consisting of H, alkyl, arylalkyl, alkylaryl, cycloalkyl, heteroaryl, heterocyclenyl, heterocyclyl, —$C(=O)N(H)R^{30}$, —$C(=O)$alkyl, —$N(H)R^{30}$, —$N(H)S(O_2)R^{31}$, —$N(H)C(=O)NH(R^{30})$, —$OR^{30}$, —$SO_2(R^{31})$, =O, =S, and —$SO_2N(H)R^{30}$;

L is C or N;

═══ in Formula 4 is a single bond or a double bond; and m, n, p, q, $R^{10}$, $R^{11}$, $R^{12}$, $R^{20}$ and Y are as defined in claim 1.

In yet another embodiment, in the above-shown Formulas 2, 3, 4, 5, 6 and 7, $R^3$ is selected from the group consisting of H, alkyl, haloalkyl, hydroxyalkyl, halogen, —$N(R^{30})_2$, —$OR^{30}$ and —$CF_3$.

In yet another embodiment, in the above-shown Formulas 2, 3, 4, 5, 6 and 7, $R^6$ is selected from the group consisting of H, alkyl, halogen, —$N(R^{30})_2$, —$OR^{30}$ and —$NR^1C(=O)$alkyl.

In yet another embodiment, in the above-shown Formulas 2, 3, 4, 5, 6 and 7, $R^9$ moieties are the same or different, each being independently selected from the group consisting of H, cyclopropyl, —$CF_3$, —$CH_3$, —$CH_2CH_3$, —$CH_2OH$, —$CH_2CH_2OH$, —$C(CH_3)_2OH$, —$CH_2CH_2OCH_3$, —$C(=O)OCH_2CH_3$, —$CH_2NH_2$, —$CH_2CH_2NH_2$, —$CH_2CH_2NHSO_2CH_3$, —$CH_2CH_2SO_2CH_3$, —$C(=O)NH_2$, —$C(=O)N(H)CH_2CH_2OH$, —$CH_2N(H)C(=O)CF_3$, —C(=O)N(H)-cyclopropyl, —C(=O)N(H)CH$_2$CF$_3$, —NH$_2$, —NHCH$_3$, —N(CH$_3$)$_2$, —N(H)CH$_2$CH$_3$, —N(H)CH(CH$_3$)$_2$, —N(H)CH$_2$CH$_2$CH$_3$, —N(H)CH$_2$C(=O)OCH$_3$, —N(H)CH$_2$CH$_2$OH, —N(H)CH$_2$CH$_2$NH$_2$, —N(H)CH$_2$CH$_2$NHSO$_2$CH$_3$, —N(H)CH$_2$CH$_2$SO$_2$CH$_3$, —N(H)C(=O)N(H)CH$_2$CH$_3$, —N(H)CH$_2$C(=O)NH$_2$, =O, =S, and —OCH$_3$.

In yet another embodiment, in the above-shown Formulas 2, 3, 4, 5, 6 and 7, R$^{10}$ is selected from the group consisting of H, alkyl, aralkyl, hydroxyalkyl, and carbonyl.

In yet another embodiment, in the above-shown Formulas 2, 3, 4, 5, 6 and 7, R$^{11}$ is selected from the group consisting of: H, alkyl and carbonyl.

In yet another embodiment, in the above-shown Formulas 2, 3, 4, 5, 6 and 7, R$^{12}$ is selected from the group consisting of H, —CH$_3$, CN or —CH$_2$CH$_3$.

In yet another embodiment, in the above-shown Formulas 2, 3, 4, 5, 6 and 7, the R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$, —OSO$_2$(R$^{31}$),

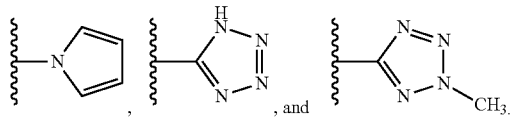
, and

In yet another embodiment, in the above-shown Formulas 2, 3, 4, 5, 6 and 7, the R$^{20}$ moieties can be the same or different, each being independently selected from the group consisting of H, —CN, —CH$_3$, —CF$_3$, —CH$_2$OH, —CO$_2$H, —CO$_2$CH$_3$, —NH$_2$, —NHCH$_3$, —OCF$_3$, —OH, F, Cl, Br, —C(=NOH)NH$_2$, —OCH$_2$CH$_2$S(O$_2$)CH$_3$, —C(=O)NH$_2$,

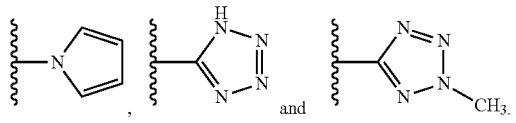
and

In yet another embodiment, in the above-shown Formulae 2-11, L is carbon.

In yet another embodiment, in the above-shown Formulae 2-11, L is nitrogen.

In yet another embodiment, in the above-shown Formulae 2-11, Y is selected from the group consisting of: —CH$_2$—, —CH$_2$CH$_2$—, —CH(CH$_3$)—, —CH$_2$CH$_2$O—, —CH(CH$_2$OH)—, —CH(CH$_2$OCH$_2$-phenyl)-, —C(=O)—, —C(=O)CH$_2$—and —CH(C=O)O-alkyl-.

In another embodiment, in formulae 2-11, R$^3$ is selected from the group consisting of H, alkyl, haloalkyl, hydroxyalkyl, halogen, —N(R$^{30}$)$_2$, —OR$^{30}$ and —CF$_3$;

R$^6$ is selected from the group consisting of H, alkyl, halogen, hydroxyalkyl, —CN, —N(R$^{30}$)$_2$, —OR$^{30}$, —N=CH-alkyl, —NR$^{30}$C(=O)alkyl, and —NR$^{30}$C(=O)N(R$^{30}$)$_2$;

the R$^9$ moieties can be the same or different, each being independently selected from the group consisting of H, alkyl, cycloalkyl, —C(=O)N(H)R$^{30}$, —C(=O)OR$^{30}$, —C(=O)alkyl, —(CH$_2$)$_q$OH, —(CH$_2$)$_q$OR$^{31}$, —(CH$_2$)$_q$NH$_2$, —(CH$_2$)$_q$NHR$^{31}$, —N(H)R$^{30}$, —N(H)S(O$_2$)R$^{31}$, —N(H)C(=O)NH(R$^{30}$), —OR$^{30}$, —SO$_2$(R$^{31}$), and —SO$_2$N(H)R$^{30}$;

R$^{10}$ is selected from the group consisting of H, alkyl, aralkyl, hydroxyalkyl and carbonyl;

the R$^{20}$ moieties can be the same or different, each being independently selected from the group consisting of H, alkyl, cycloalkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —N(R$^{30}$)SO$_2$(R$^{31}$), —OR$^{30}$, —OC(=O)N(R$^{30}$)$_2$,

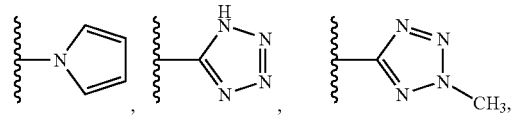
, and —OSO$_2$(R$^{31}$); or alternatively, two R$^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 R$^{21}$ moieties;

the R$^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy;

Y is selected from the group consisting of —CH$_2$—, —CH$_2$CH$_2$—, —CH(CH$_3$)—, —CH$_2$CH$_2$O—, —CH(CH$_2$OH)—, —CH(CH$_2$OCH$_2$-phenyl)-, —C(=O)—, —C(=O)CH$_2$—and —CH(C=O)O-alkyl-;

m is 0-2;
n is 0-2;
q is 1 or 2; and
r is 1 or 2.

In yet another embodiment, in the above-shown Formulas 2, 3, 4, 5, 6 and 7, L is carbon.

In yet another embodiment, in the above-shown Formulas 2, 3, 4, 5, 6 and 7, L is nitrogen.

In yet another embodiment, in the above-shown Formulas 2, 3, 4, 5, 6 and 7, Y is selected from the group consisting of: —CH$_2$—, —C(=O)—, —CH(CH$_2$OH)— and —CH(CO$_2$alkyl)-.

In yet another embodiment, in the above-shown Formulas 2, 3, 4, 5, 6 and 7, R$^3$ is selected from the group consisting of H, alkyl, haloalkyl, hydroxyalkyl, halogen, —N(R$^{30}$)$_2$, —OR$^{30}$ and —CF$_3$;

R$^6$ is selected from the group consisting of H, alkyl, halogen, —N(R$^{30}$)$_2$, —OR$^{30}$, and —NR$^1$C(=O)alkyl;

the R$^9$ moieties can be the same or different, each being independently selected from the group consisting of H, alkyl, cycloalkyl, —C(=O)N(H)R$^{30}$, —C(=O)alkyl, —N(H)R$^{30}$, —N(H)S(O$_2$)R$^{31}$, —N(H)C(=O)NH(R$^{30}$), —OR$^{30}$, —SO$_2$(R$^{31}$), and —SO$_2$N(H)R$^{30}$;

R$^{10}$ is selected from the group consisting of H, alkyl, aralkyl, hydroxyalkyl and carbonyl;

the R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C (=O)OR³¹, —N(R³⁰)C(=NCN)N(R³⁰)₂, —N(R³⁰)C(=O)N(R³⁰)₂, —OR³⁰, —OC(=O)N(R³⁰)₂, and —OSO₂(R³¹),
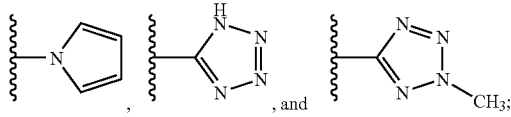
Y is selected from the group consisting of —CH₂—, —C(=O)—, —CH(CH₂OH)— and —CH(CO₂alkyl)-;
m is 0-2;
q is 1 or 2; and
r is 1 or 2.
In still another embodiment of the present invention, a compound is selected from the group consisting of:
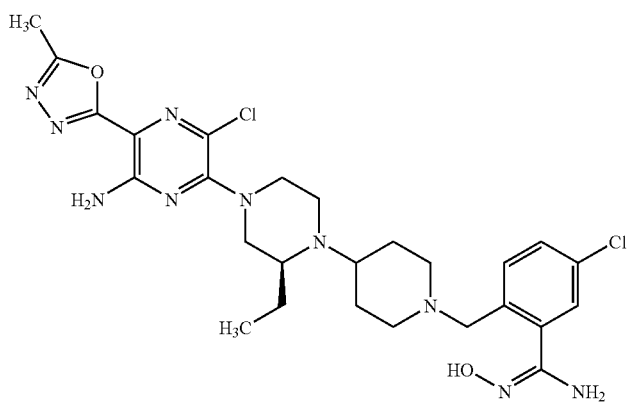
(0.2 nM)
1
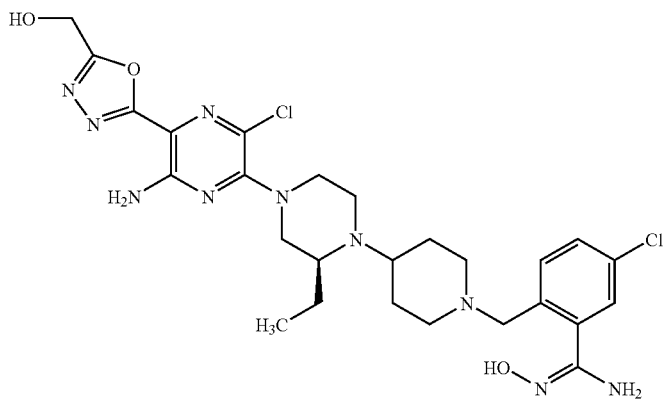
(0.3 nM)
2
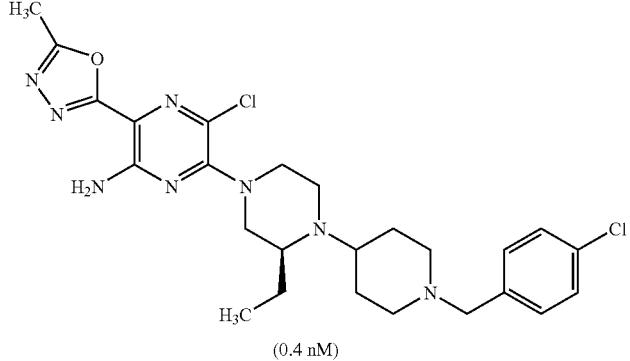
(0.4 nM)
4

-continued
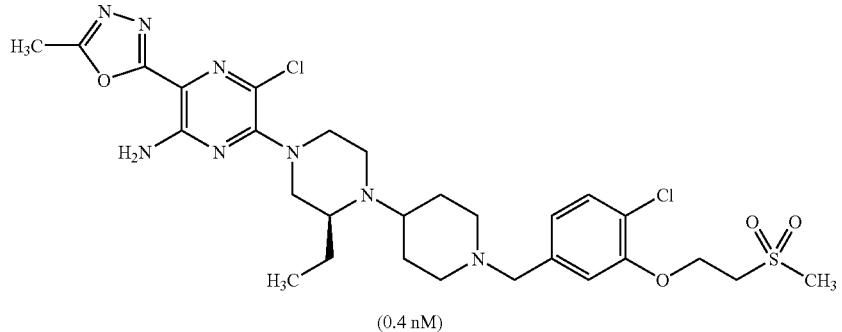
7
(0.4 nM)
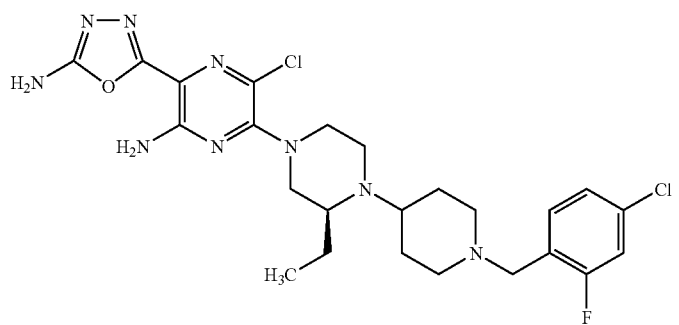
3
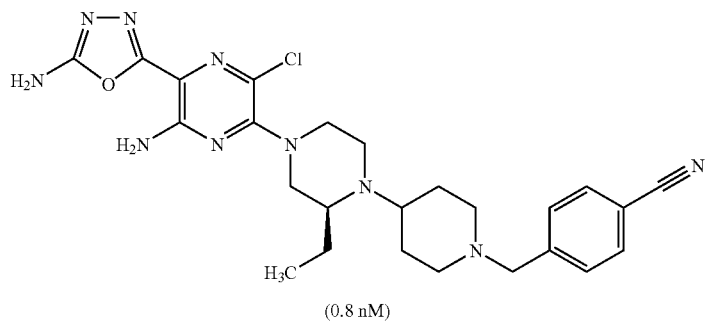
9
(0.8 nM)
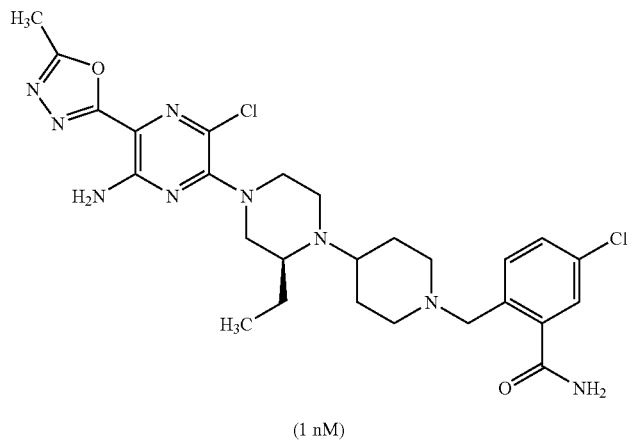
8
(1 nM)

-continued
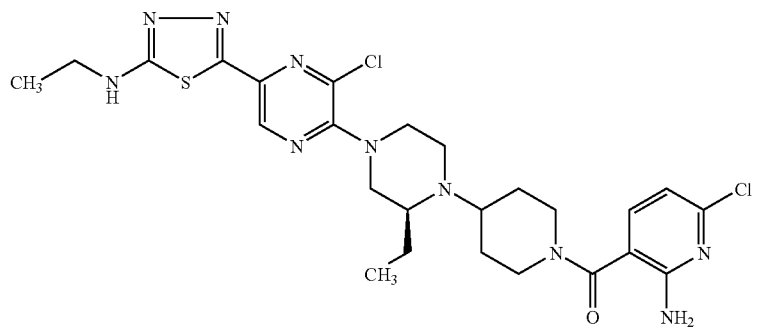
18
(1.3 nM)
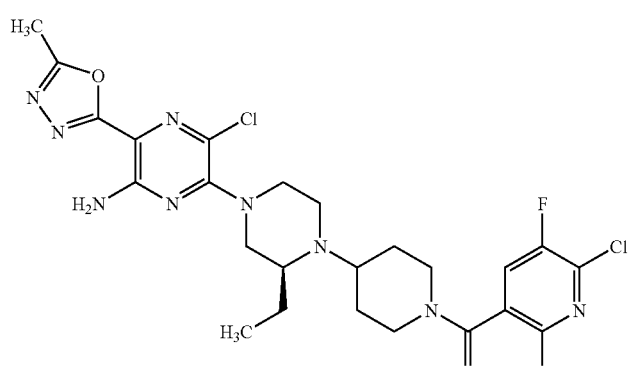
19
(1.4 nM)
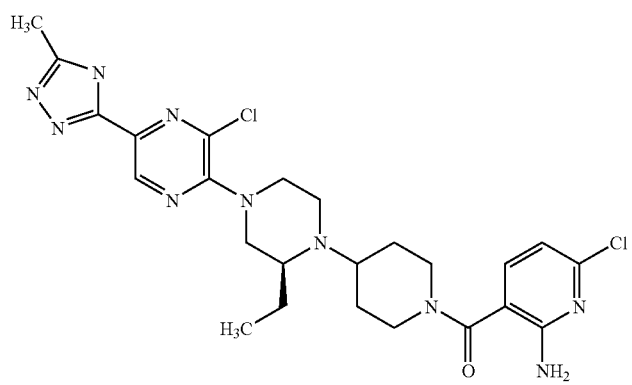
37
(1.9 nM)
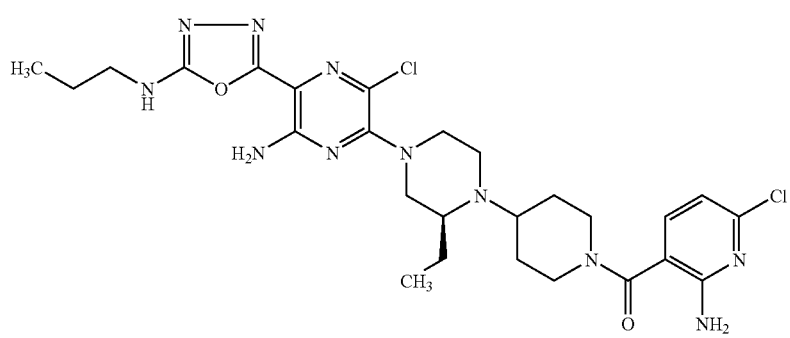
12
(1.7 nM)

-continued
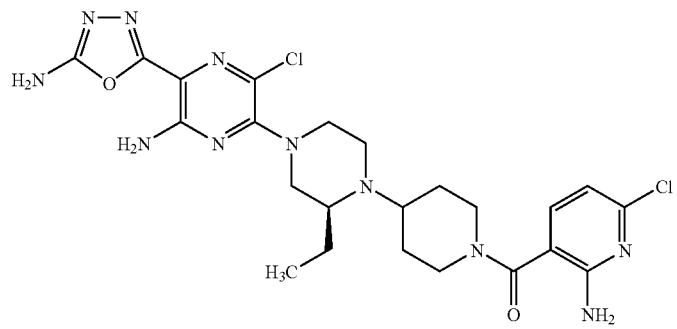
(2.7 nM)
17
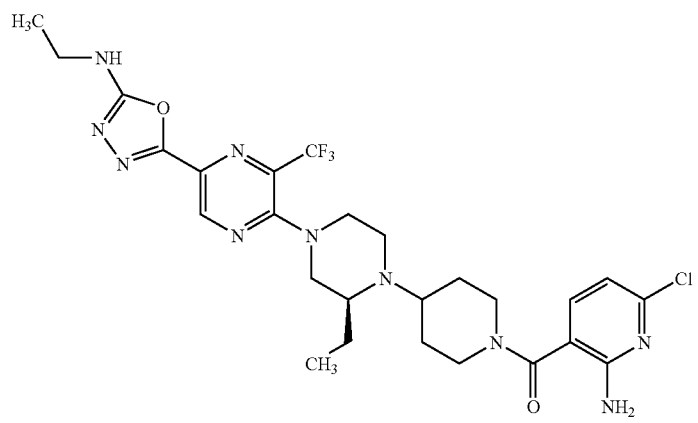
(1 nM)
103
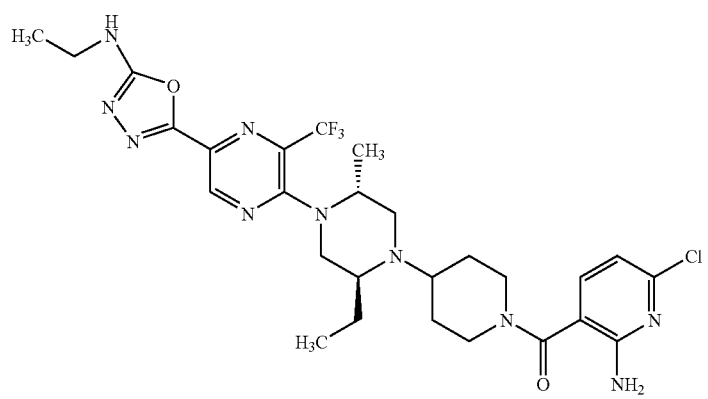
98
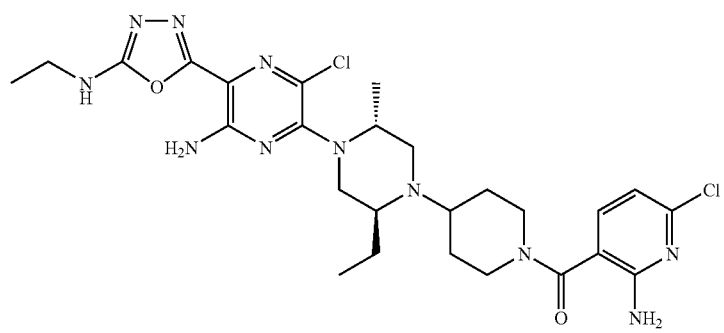
93

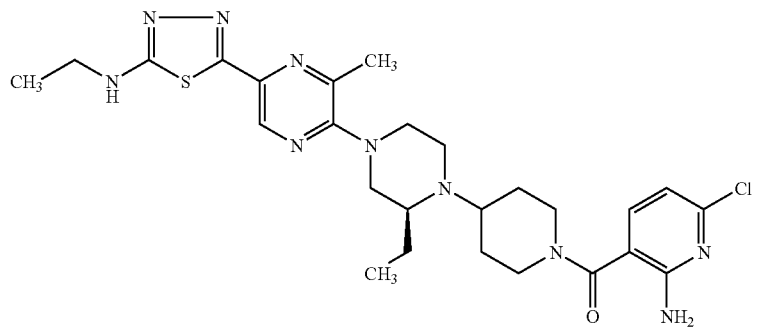
13
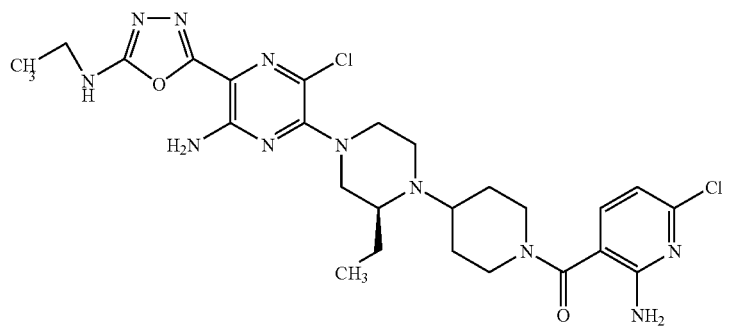
14
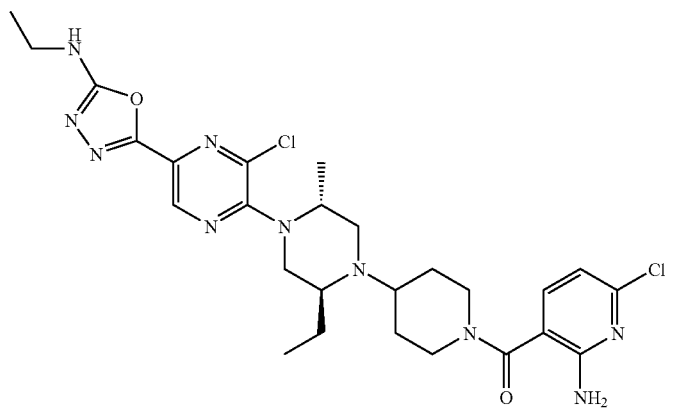
100
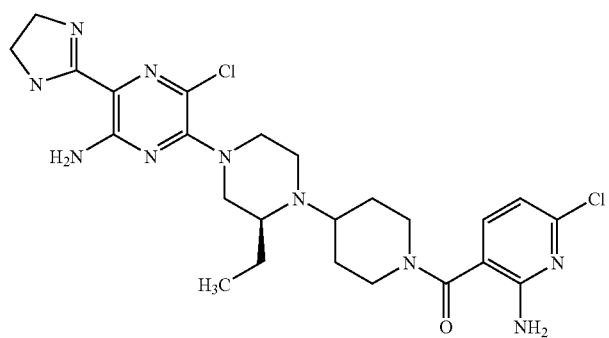
24

-continued
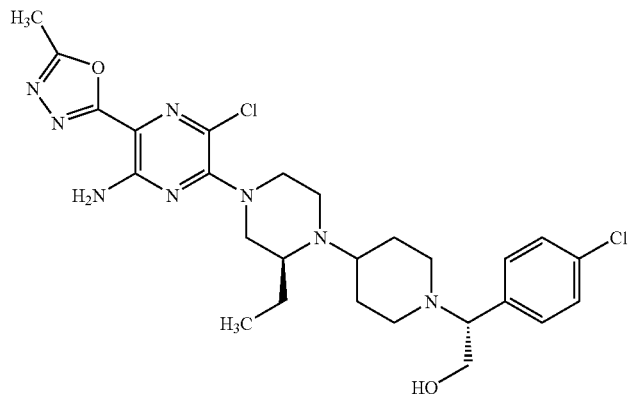
5
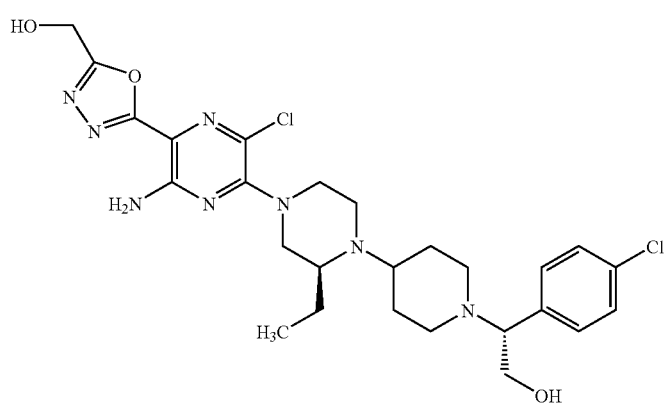
6
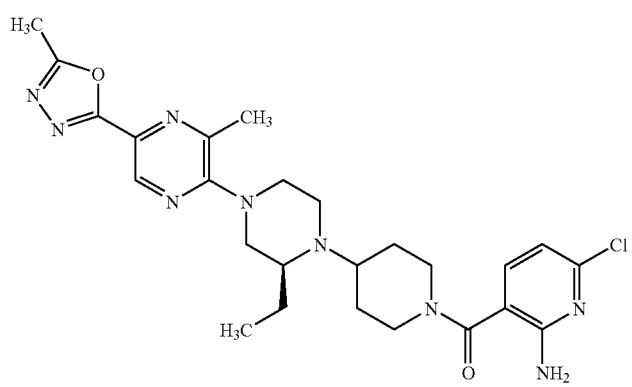
21
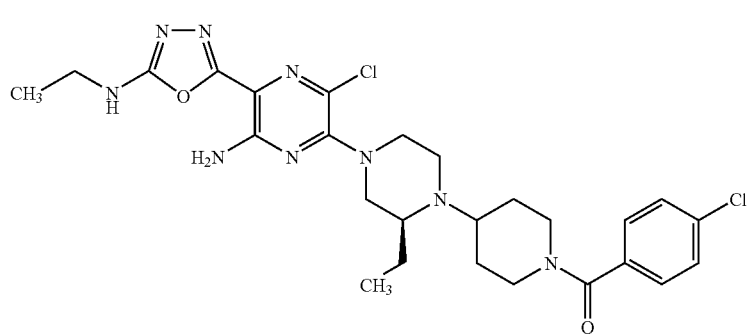
20

-continued
96
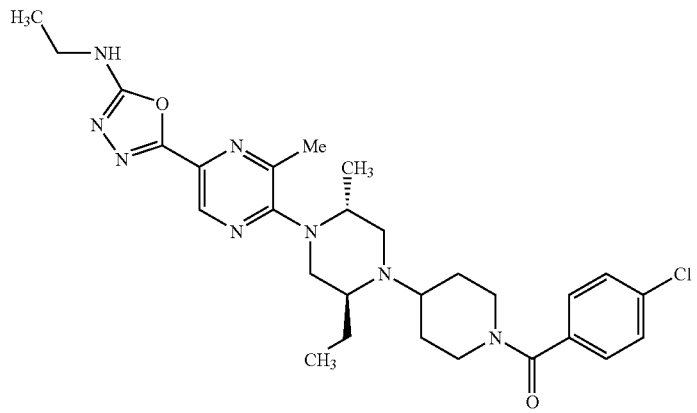
102
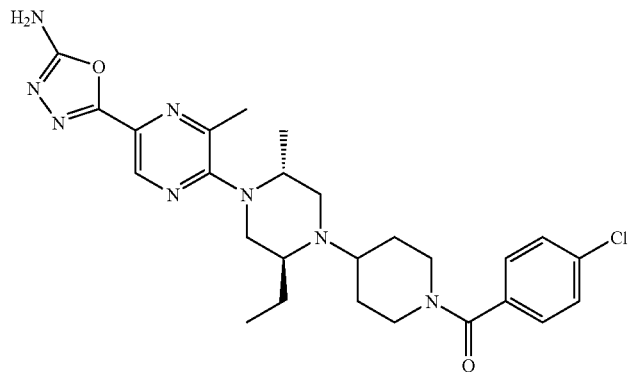
101
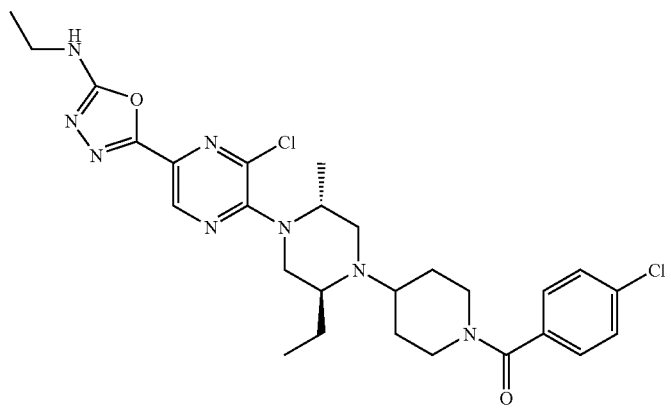
104
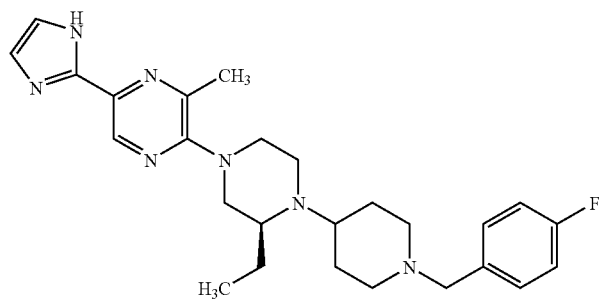

-continued

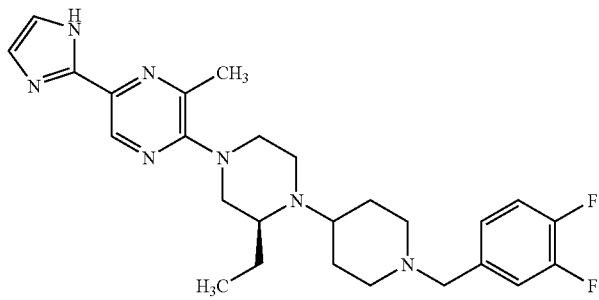
108

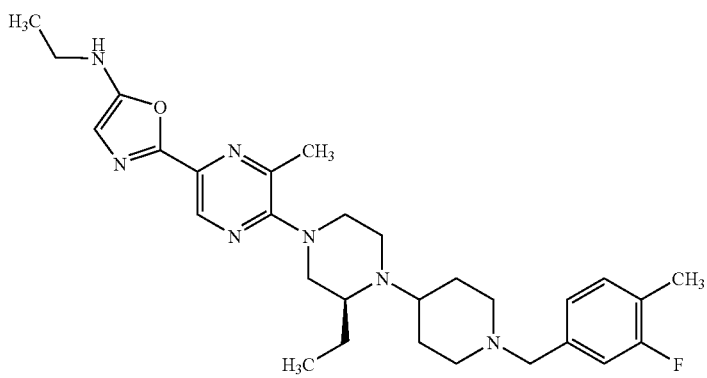
127

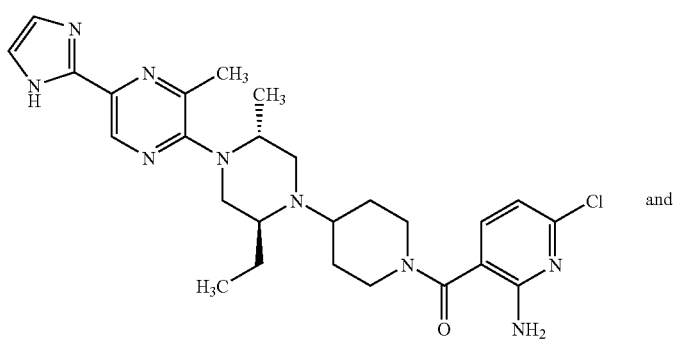
130 and

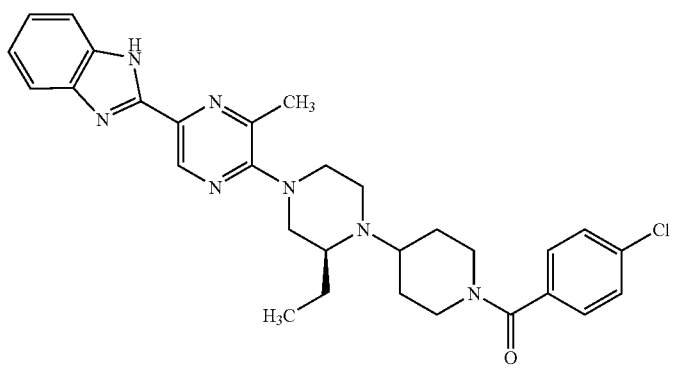
146 or a pharmaceutically acceptable salt, solvate or ester thereof. The human $IC_{50}$ values (in nM) for some of the compounds above have been provided (underneath the structure in paretheses).

In still another embodiment of the present invention, a compound is selected from the list of compounds shown in Table 1 below (or pharmaceutically acceptable salts, solvates or esters thereof). In this Table 1, the compounds are shown along with their $IC_{50}$ ratings. The $IC_{50}$ values are rated, "A" for $IC_{50}$ values less than about 25 nanomolar (nM), "B" for $IC_{50}$ values in the range of from about 25 to about 100 nM and "C" for $IC_{50}$ values greater than about 100 nM. For instance, Compound Number 1 has an $IC_{50}$ value of 0.2 nM.

TABLE 1

| Compound Number | STRUCTURE | IC$_{50}$ |
|---|---|---|
| 1 | 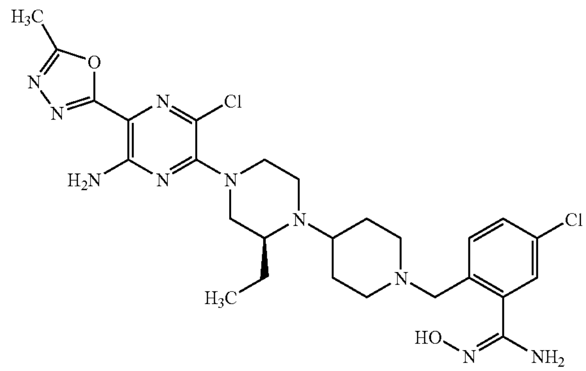 | A |
| 2 | 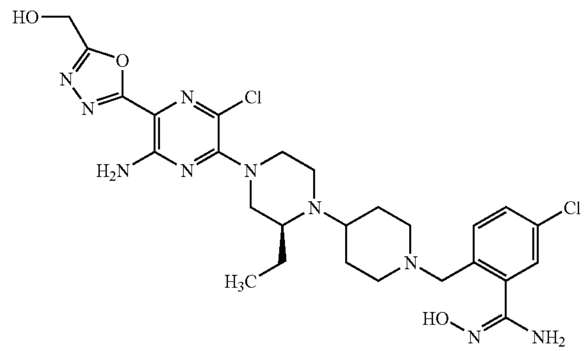 | A |
| 3 | 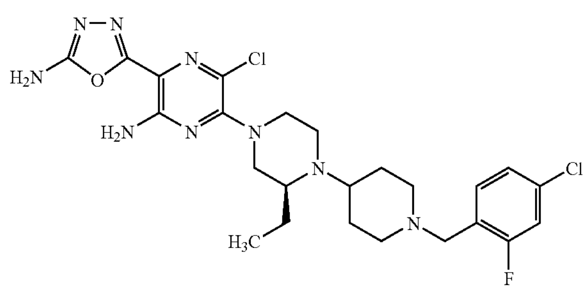 | A |
| 4 | 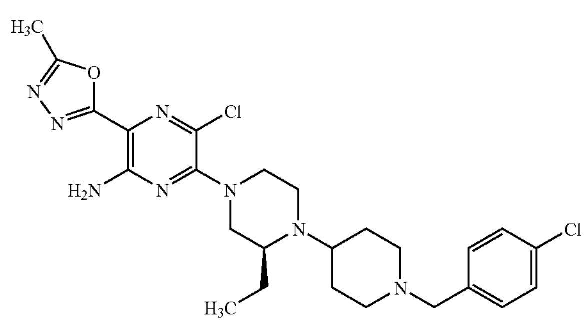 | A |

TABLE 1-continued

| Compound Number | STRUCTURE | IC$_{50}$ |
|---|---|---|
| 5 | 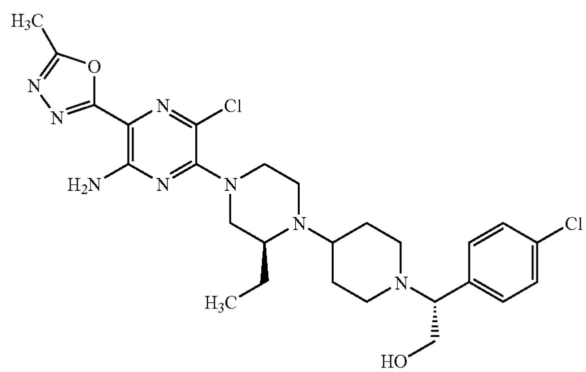 | A |
| 6 | 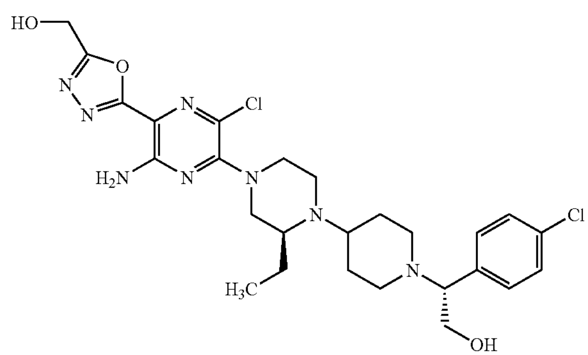 | A |
| 7 | 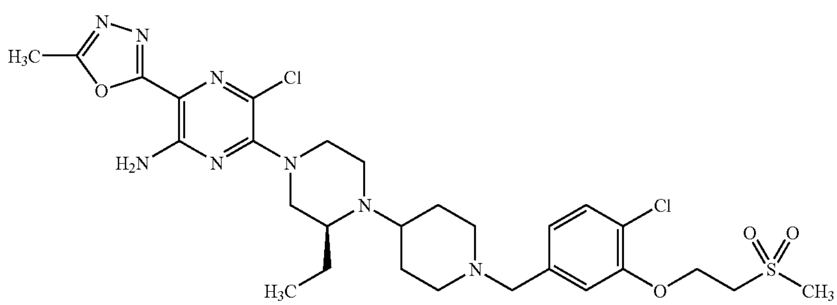 | A |
| 8 | 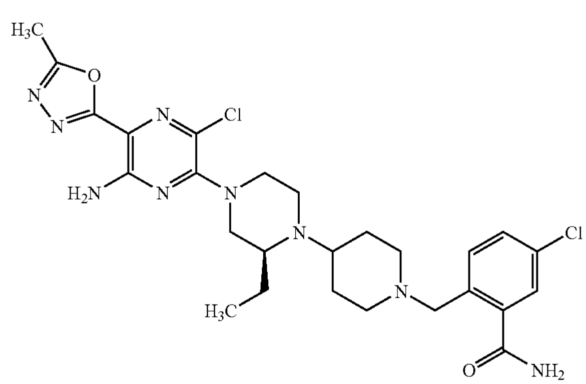 | A |

TABLE 1-continued
| Compound Number | STRUCTURE | IC$_{50}$ |
|---|---|---|
| 9 | 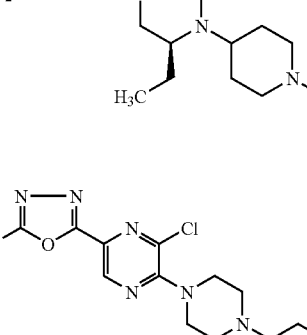 | A |
| 10 | 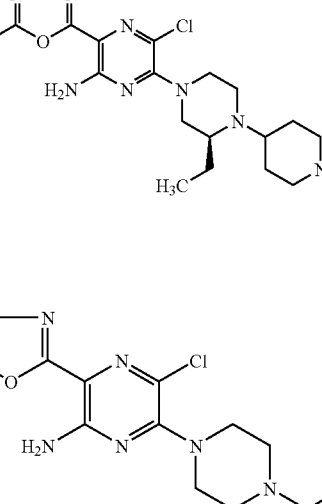 | A |
| 11 | 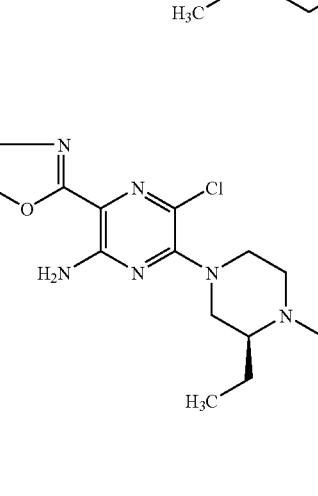 | A |
| 12 | 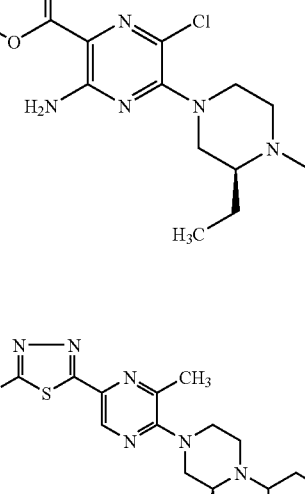 | A |
| 13 | 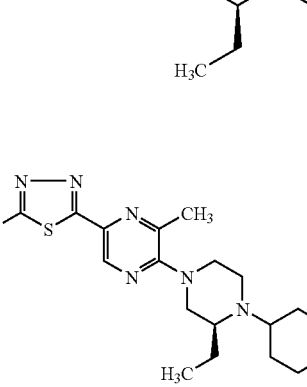 | A |

TABLE 1-continued
| Compound Number | STRUCTURE | IC$_{50}$ |
|---|---|---|
| 14 | 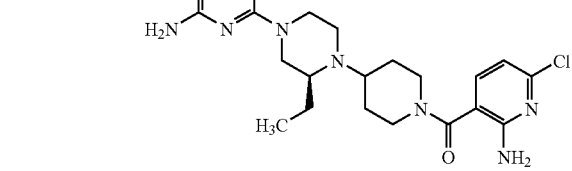 | A |
| 15 | 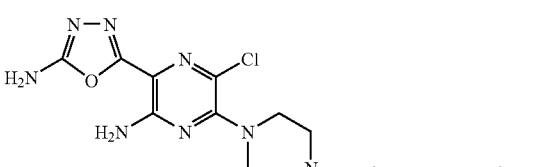 | A |
| 16 | 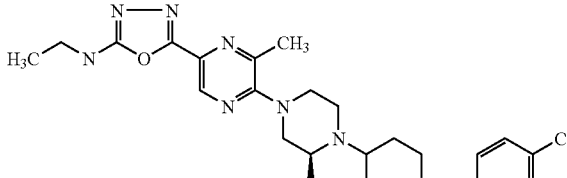 | A |
| 17 | 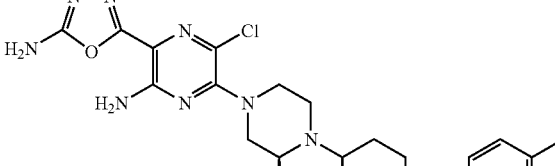 | A |
| 18 | 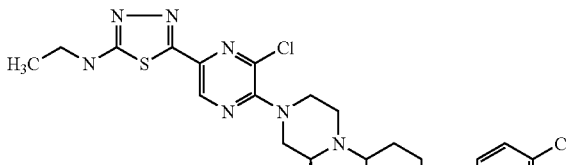 | A |

TABLE 1-continued
| Compound Number | STRUCTURE | IC$_{50}$ |
|---|---|---|
| 19 | 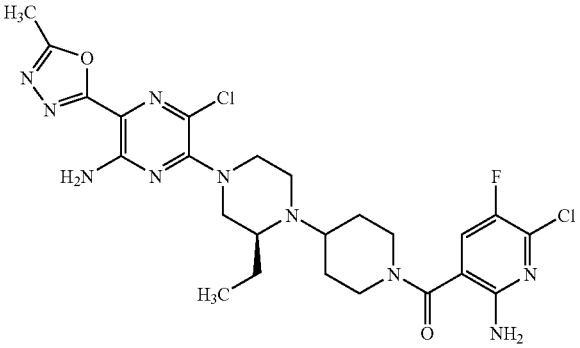 | A |
| 20 | 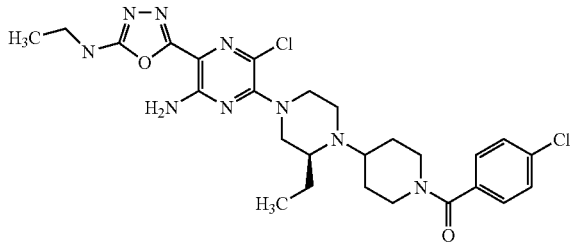 | A |
| 21 | 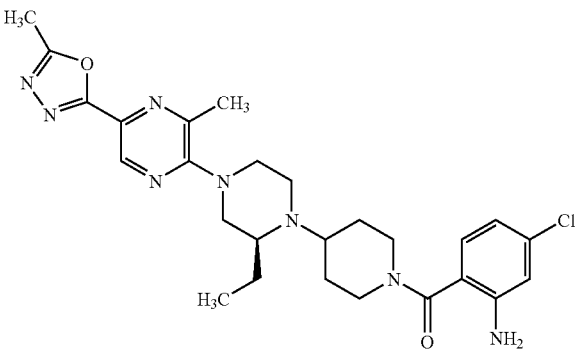 | A |
| 22 | 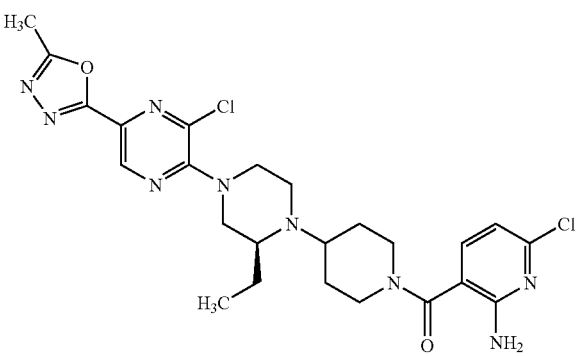 | A |

TABLE 1-continued
| Compound Number | STRUCTURE | IC$_{50}$ |
|---|---|---|
| 23 | 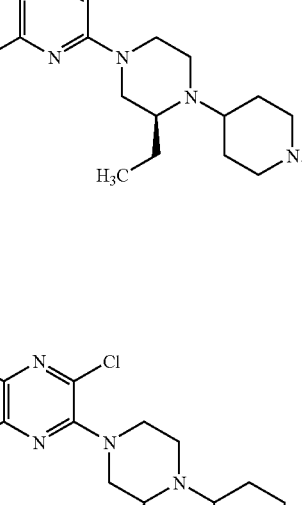 | A |
| 24 | 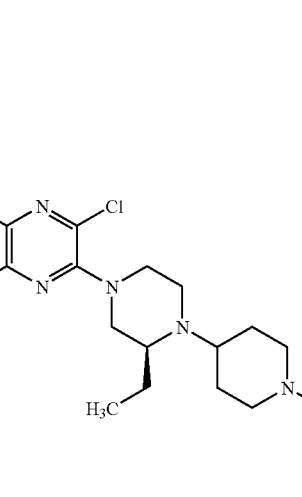 | A |
| 25 | 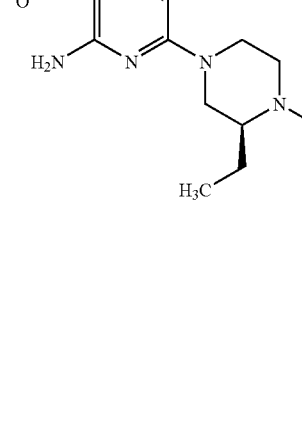 | A |
| 26 | 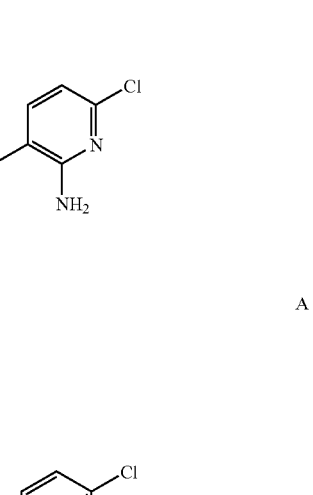 | A |

TABLE 1-continued
| Compound Number | STRUCTURE | IC$_{50}$ |
|---|---|---|
| 27 | 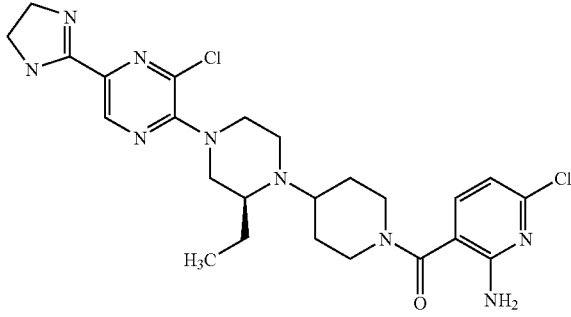 | A |
| 28 | 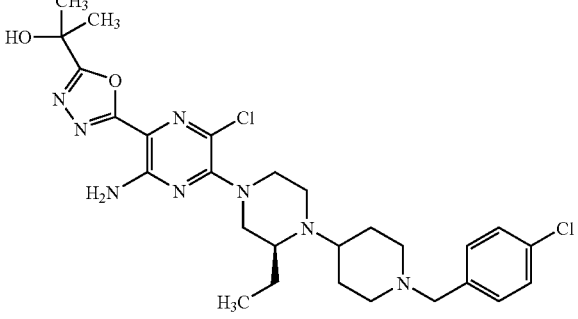 | A |
| 29 | 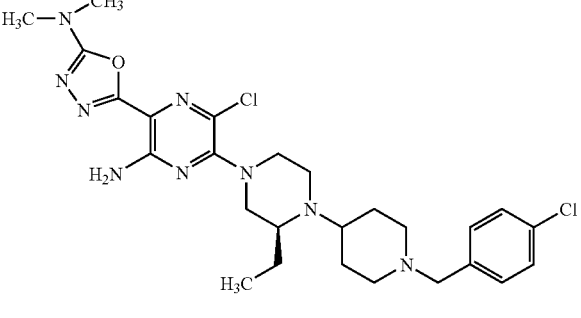 | A |
| 30 | 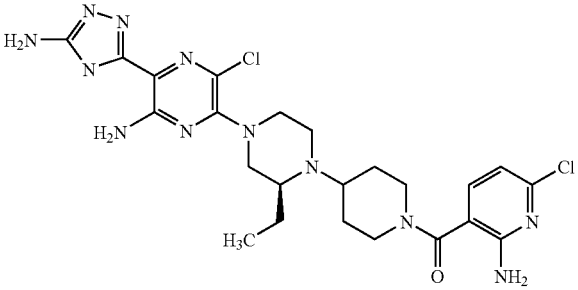 | A |

TABLE 1-continued
| Compound Number | STRUCTURE | IC$_{50}$ |
|---|---|---|
| 31 | 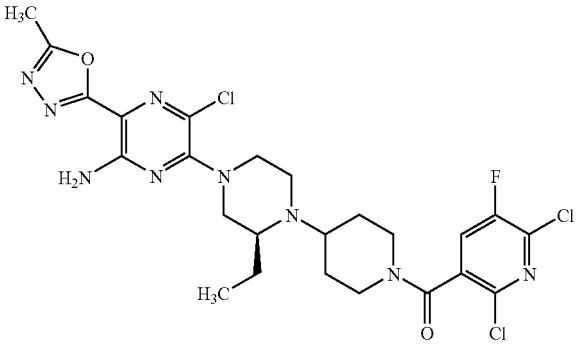 | A |
| 32 | 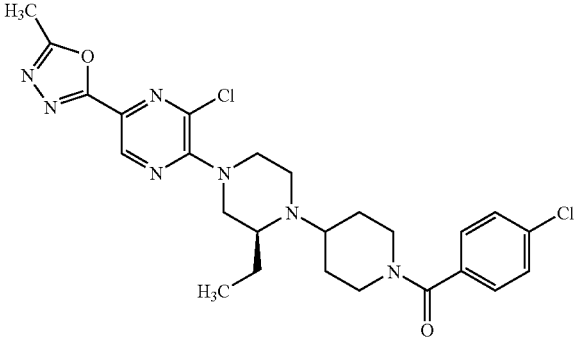 | A |
| 33 | 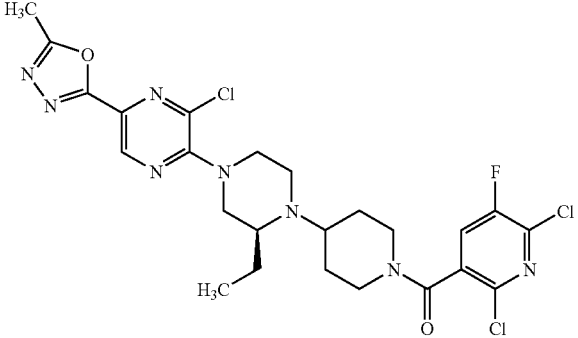 | A |
| 34 | 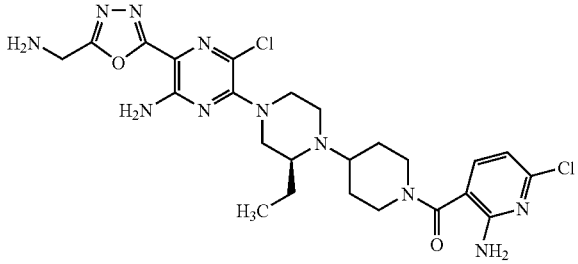 | A |

TABLE 1-continued
| Compound Number | STRUCTURE | IC$_{50}$ |
| --- | --- | --- |
| 35 | 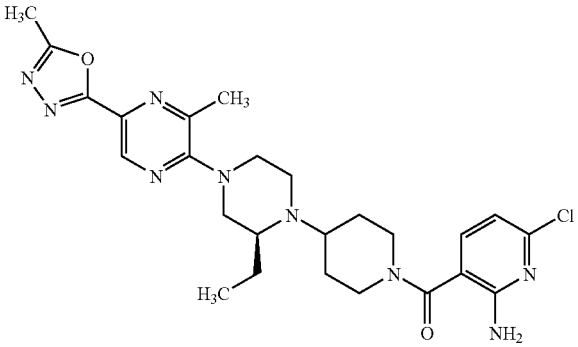 | A |
| 36 | 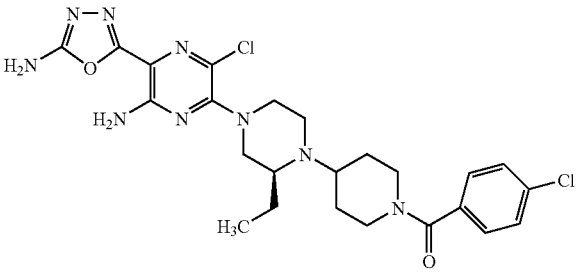 | A |
| 37 | 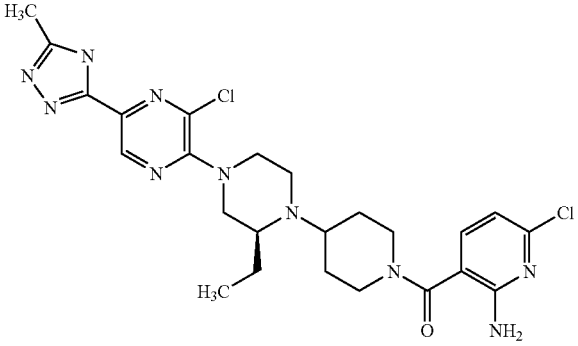 | A |
| 38 | 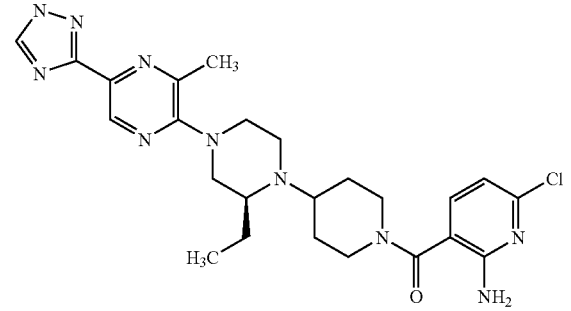 | A |

TABLE 1-continued
| Compound Number | STRUCTURE | IC$_{50}$ |
|---|---|---|
| 39 | 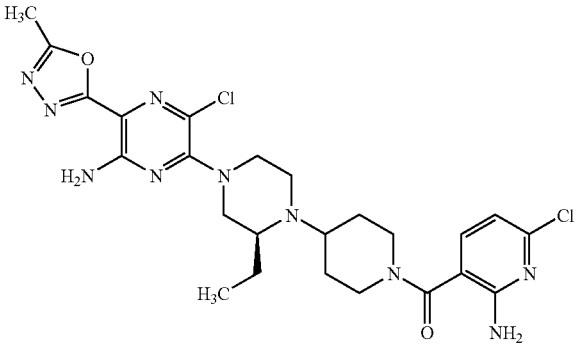 | A |
| 40 | 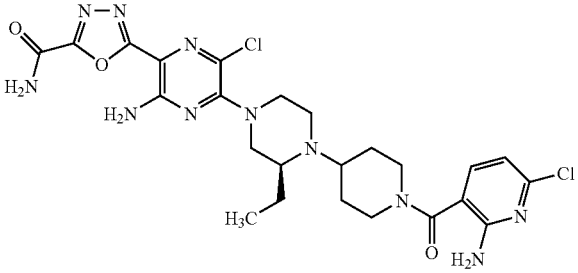 | A |
| 41 | 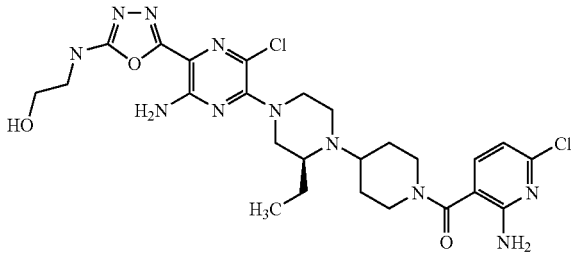 | A |
| 42 | 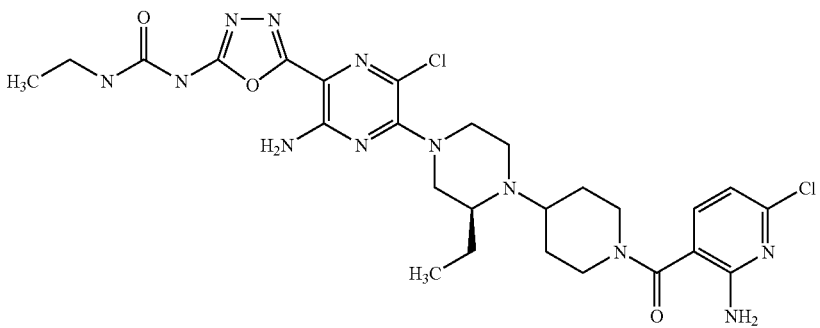 | A |

TABLE 1-continued

| Compound Number | STRUCTURE | IC$_{50}$ |
|---|---|---|
| 43 | 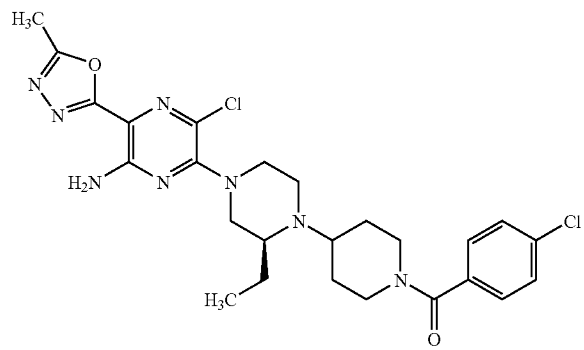 | A |
| 44 | 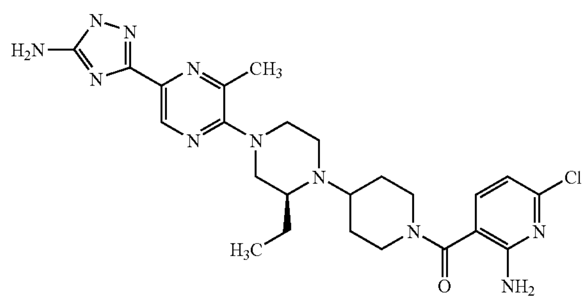 | A |
| 45 | 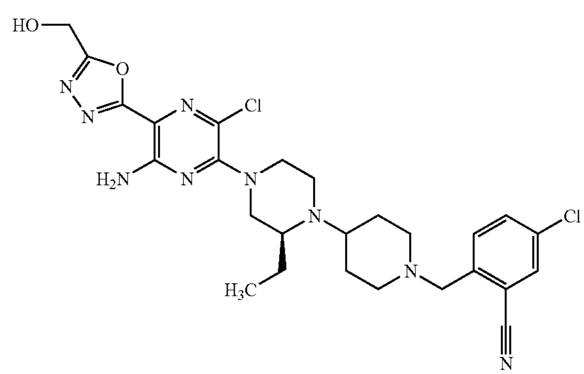 | A |
| 46 | 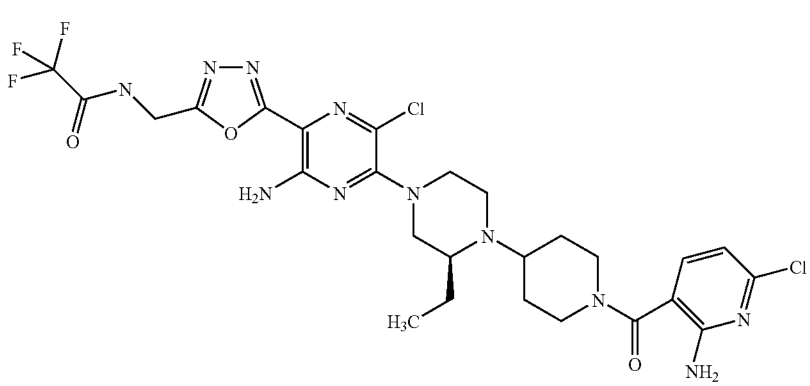 | A |

TABLE 1-continued
| Compound Number | STRUCTURE | IC$_{50}$ |
|---|---|---|
| 47 | 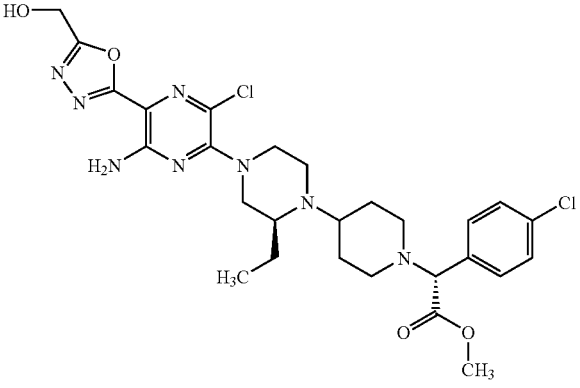 | A |
| 48 | 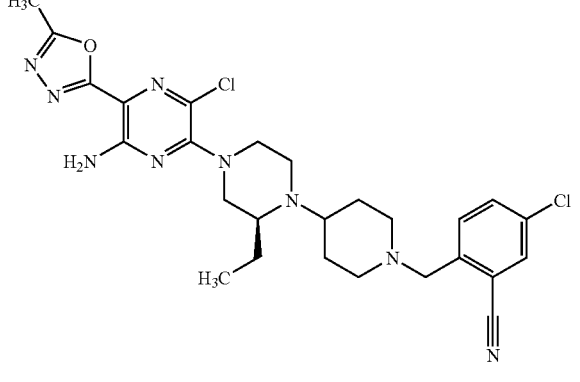 | A |
| 49 | 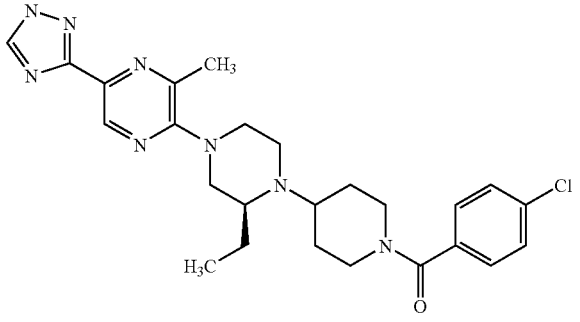 | A |
| 50 | 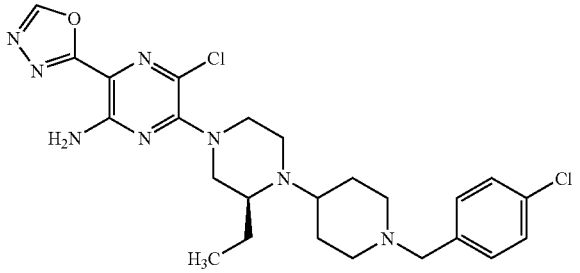 | A |

TABLE 1-continued
| Compound Number | STRUCTURE | IC50 |
|---|---|---|
| 51 | 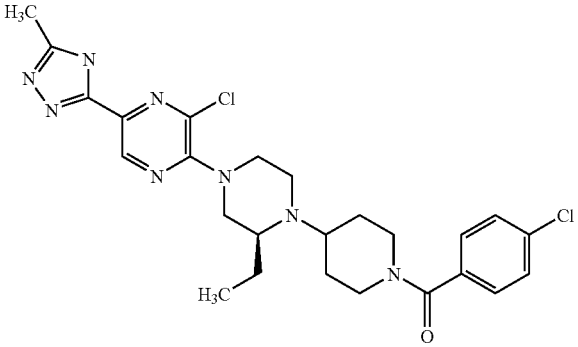 | A |
| 52 | 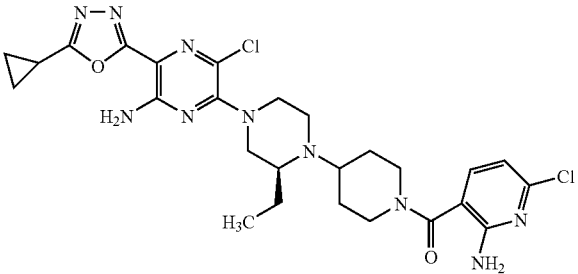 | A |
| 53 | 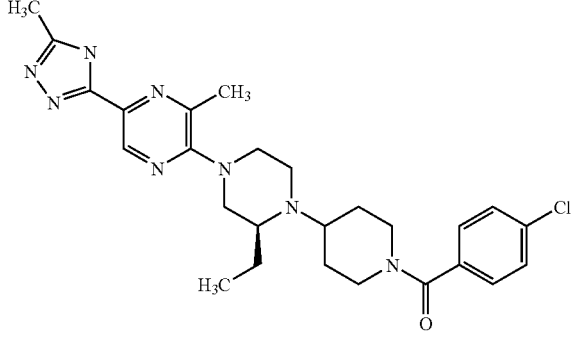 | A |
| 54 | 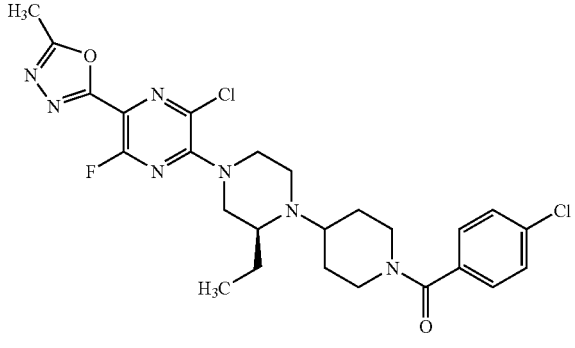 | A |

TABLE 1-continued
| Compound Number | STRUCTURE | IC$_{50}$ |
|---|---|---|
| 55 | 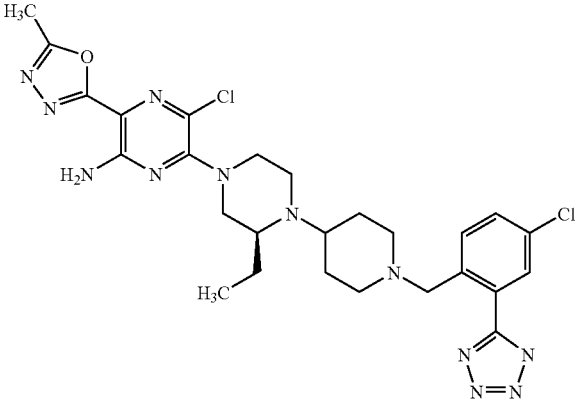 | A |
| 56 | 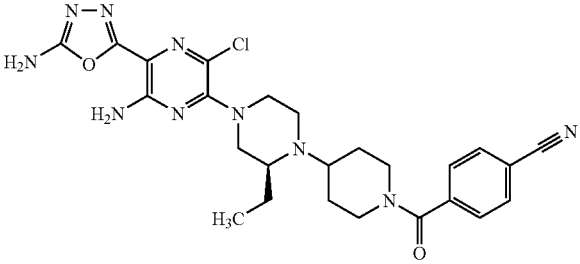 | A |
| 57 | 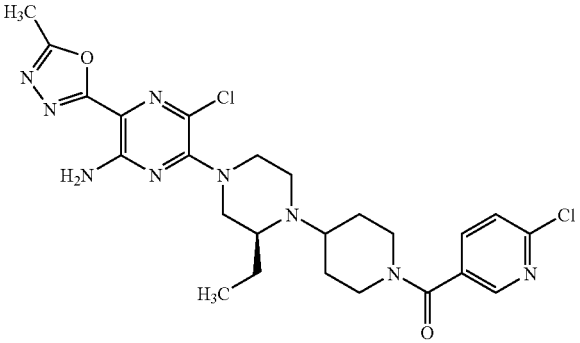 | A |
| 58 | 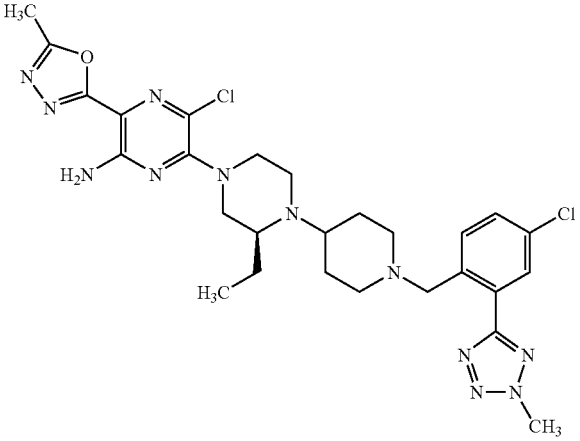 | A |

TABLE 1-continued
| Compound Number | STRUCTURE | IC$_{50}$ |
|---|---|---|
| 59 | 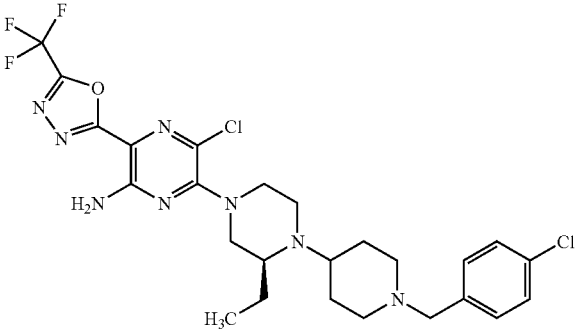 | A |
| 60 | 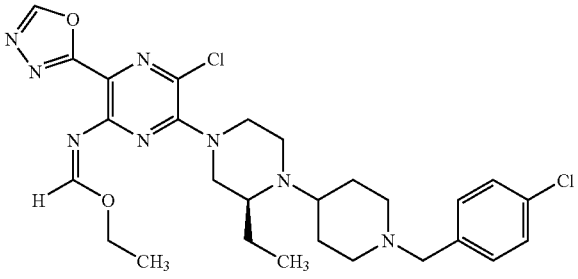 | A |
| 61 | 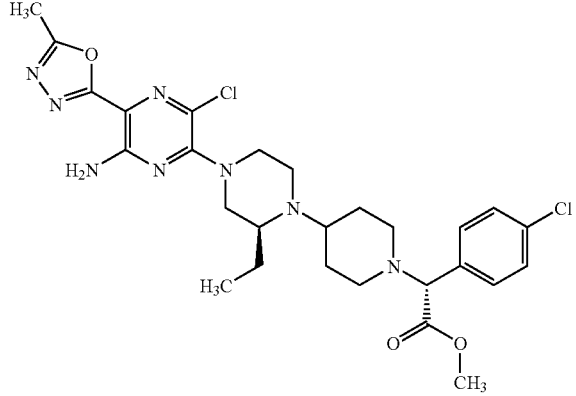 | A |
| 62 | 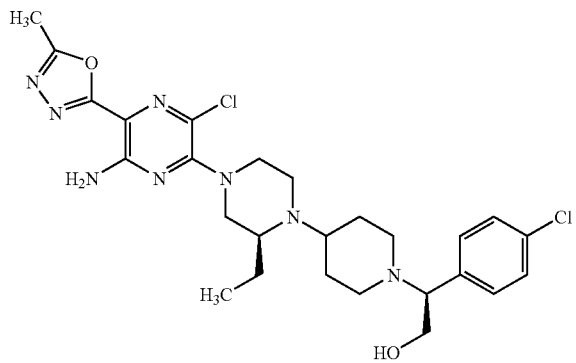 | A | ns
TABLE 1-continued

| Compound Number | STRUCTURE | IC$_{50}$ |
|---|---|---|
| 63 | 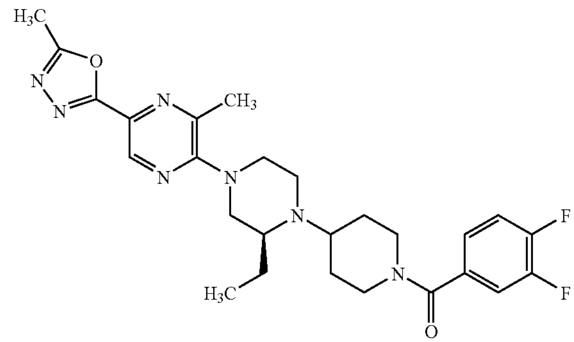 | A |
| 64 | 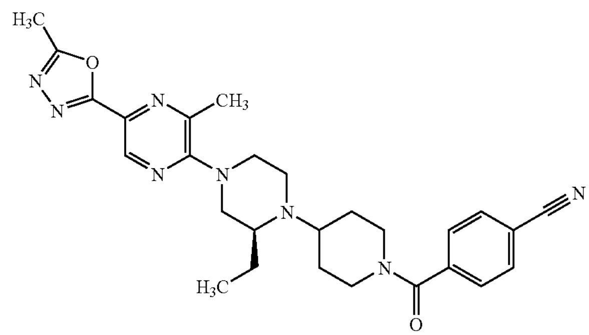 | A |
| 65 | 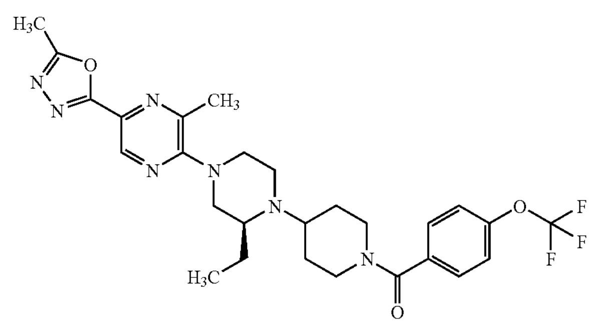 | A |
| 66 | 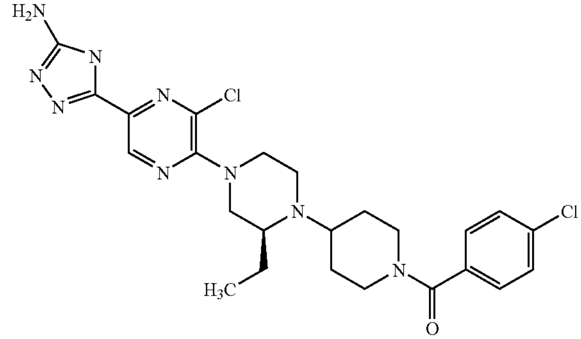 | A |

TABLE 1-continued

| Compound Number | STRUCTURE | IC$_{50}$ |
|---|---|---|
| 67 | 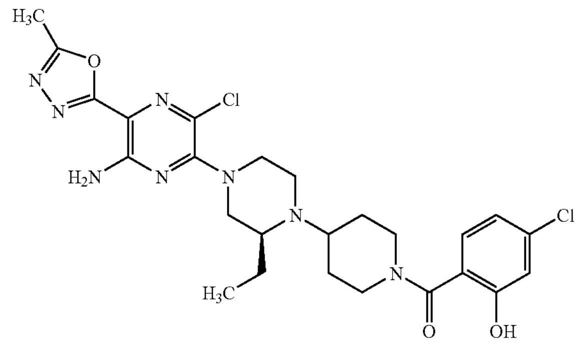 | A |
| 68 | 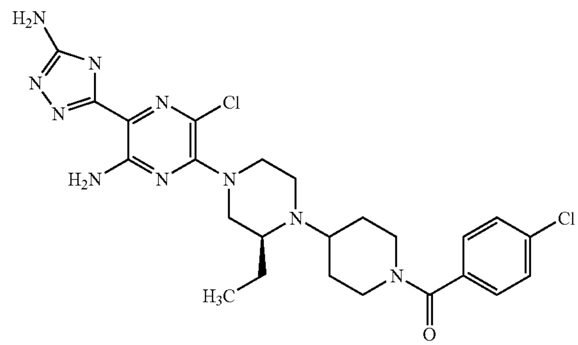 | A |
| 69 | 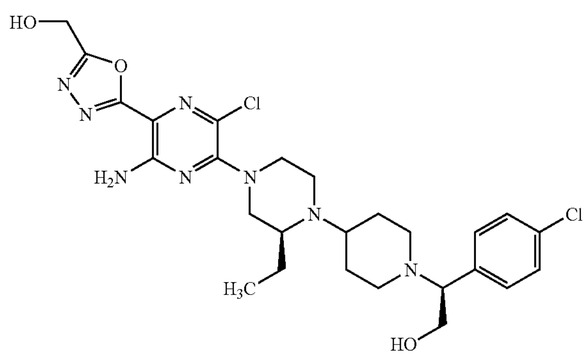 | A |
| 70 | 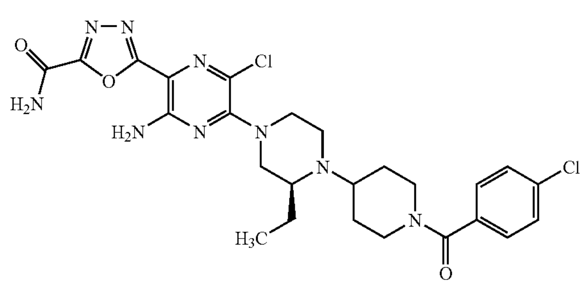 | A |

TABLE 1-continued

| Compound Number | STRUCTURE | IC$_{50}$ |
|---|---|---|
| 71 | 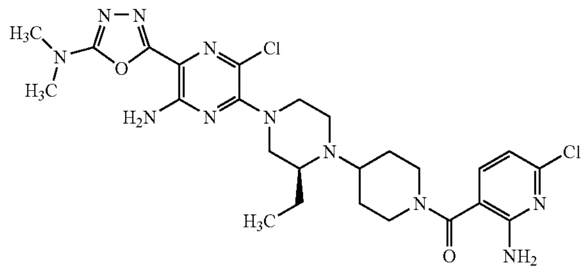 | A |
| 72 | 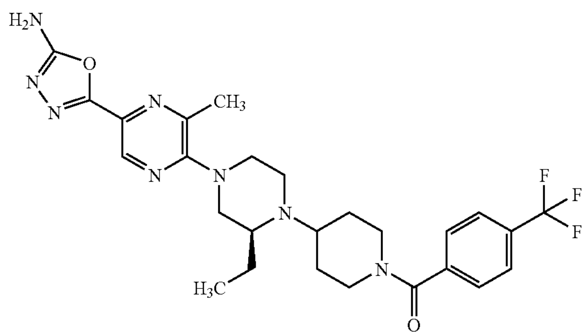 | A |
| 73 | 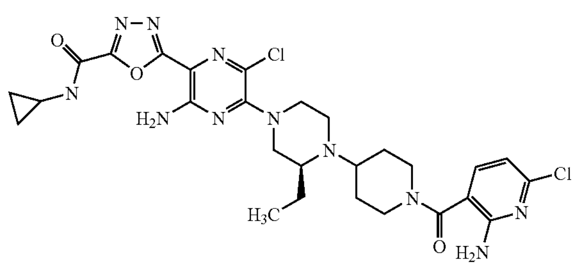 | B |
| 74 | 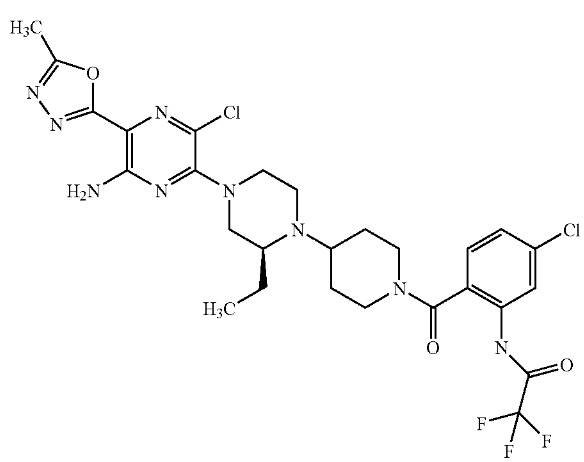 | B |

TABLE 1-continued

| Compound Number | STRUCTURE | IC$_{50}$ |
|---|---|---|
| 75 | 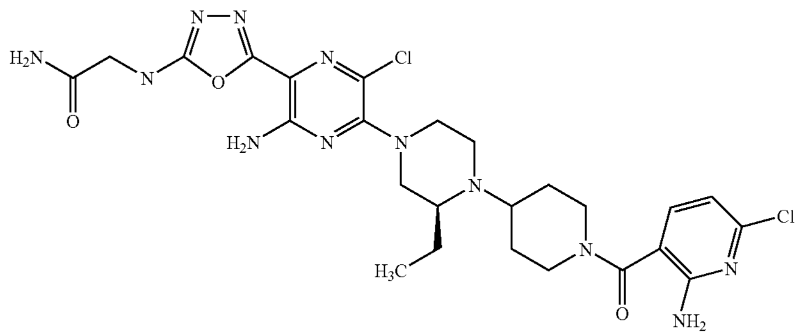 | B |
| 76 | 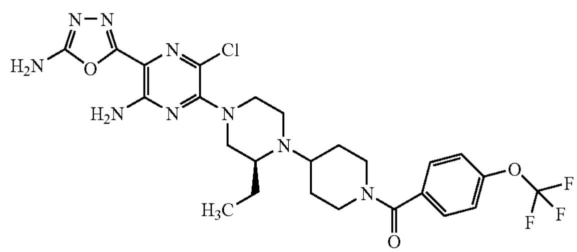 | B |
| 77 | 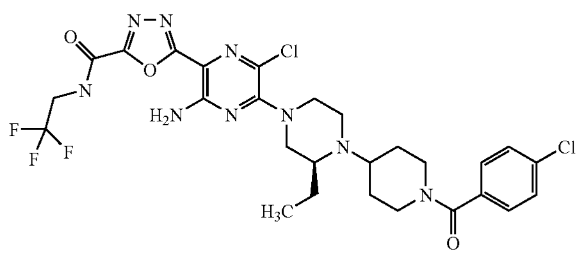 | B |
| 78 | 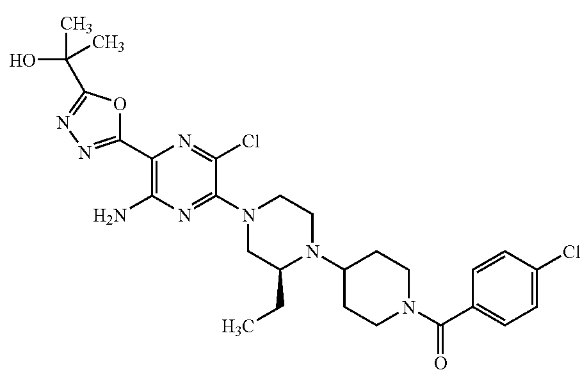 | B |
| 79 | 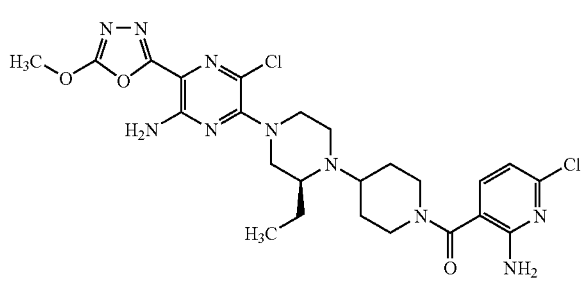 | C |

TABLE 1-continued
| Compound Number | STRUCTURE | IC$_{50}$ |
|---|---|---|
| 80 | 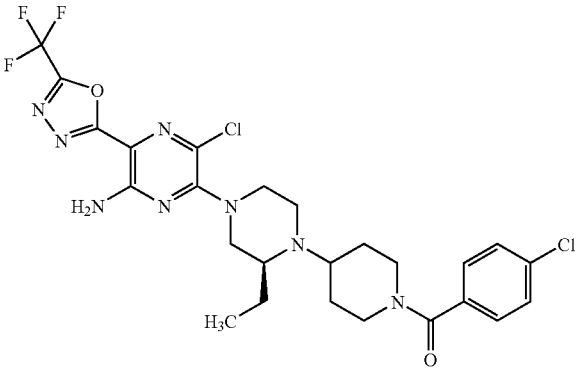 | C |
| 81 | 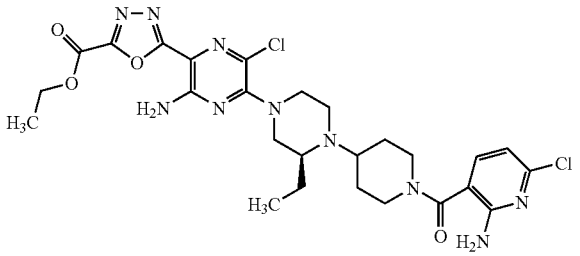 | C |
| 82 | 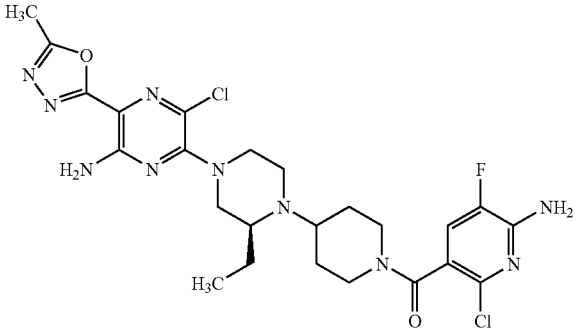 | C |
| 83 | 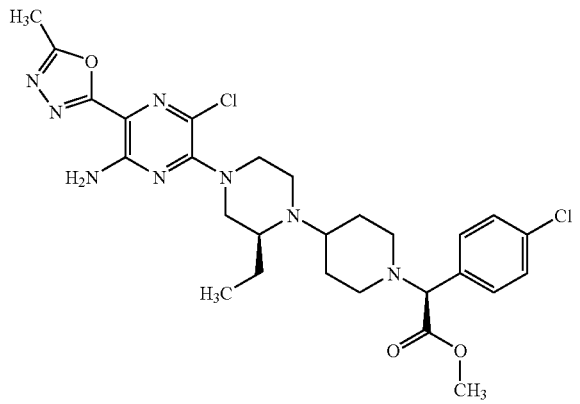 | C |

TABLE 1-continued

| Compound Number | STRUCTURE | IC$_{50}$ |
|---|---|---|
| 84 | 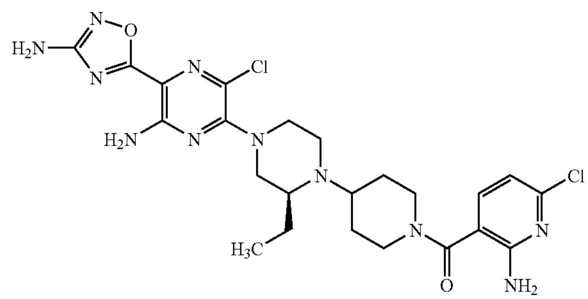 | C |
| 85 | 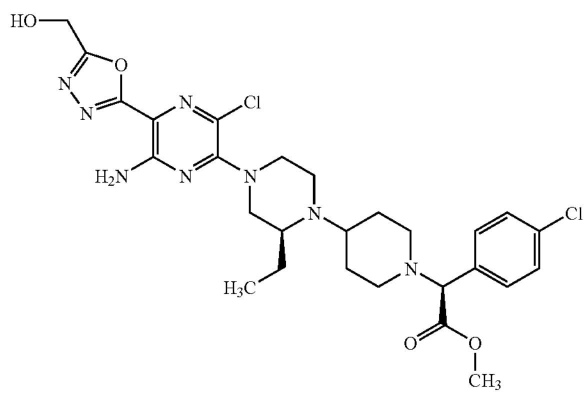 | C |
| 86 | 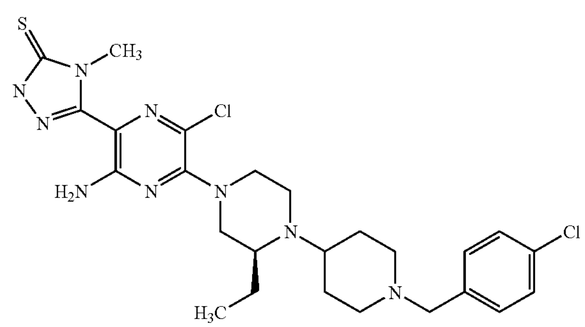 | C |
| 87 | 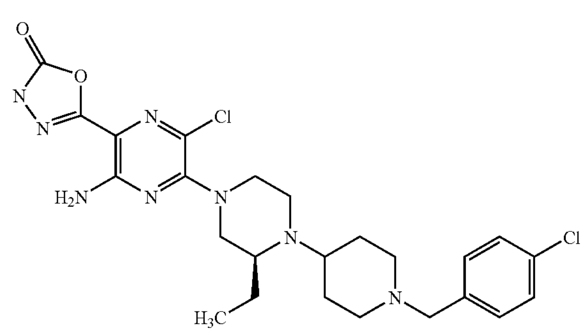 | C |

TABLE 1-continued

| Compound Number | STRUCTURE | IC$_{50}$ |
|---|---|---|
| 88 | 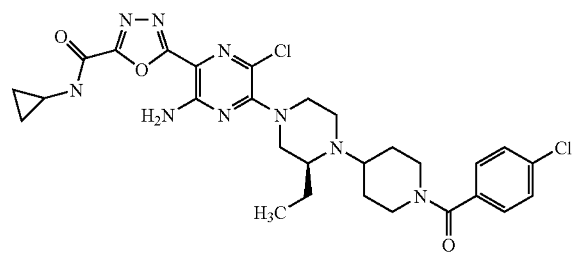 | C |
| 89 | 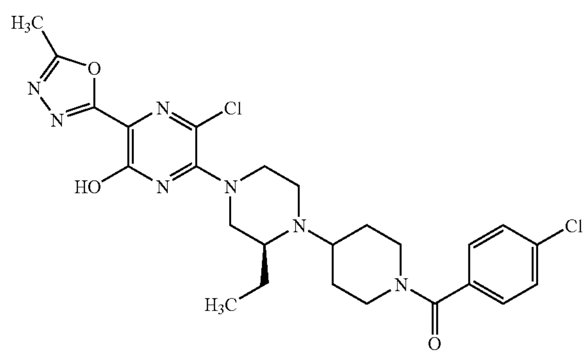 | C |
| 90 | 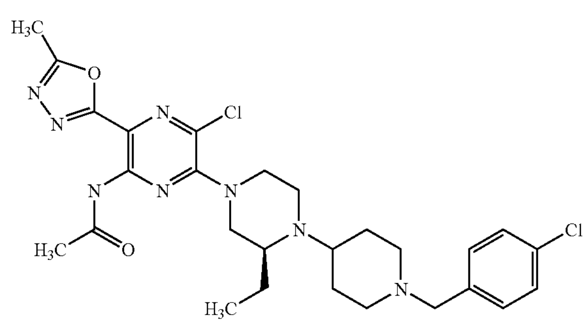 | C |
| 91 | 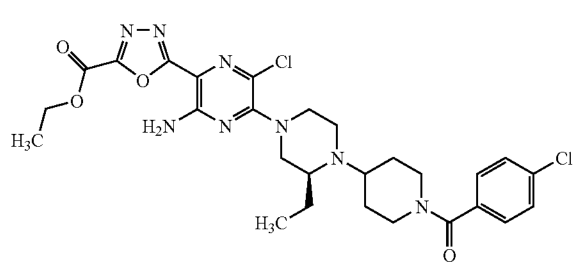 | C |

TABLE 1-continued
| Compound Number | STRUCTURE | IC$_{50}$ |
|---|---|---|
| 92 | 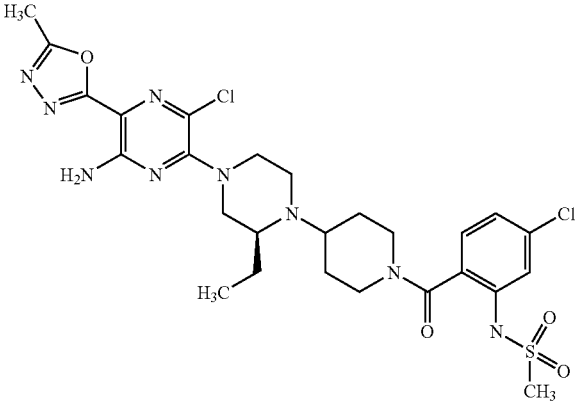 | C |
| 93 | 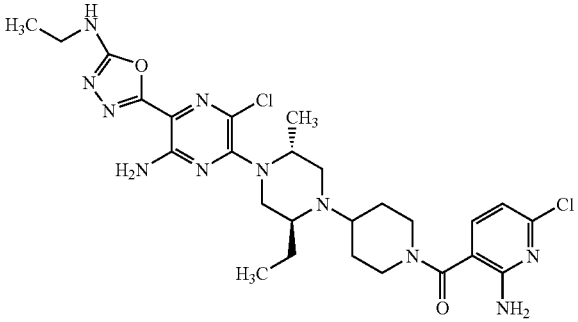 | A |
| 95 | 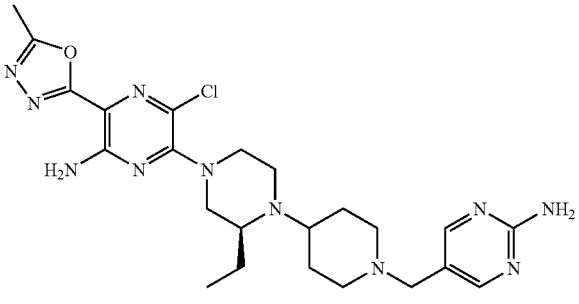 | C |
| 96 | 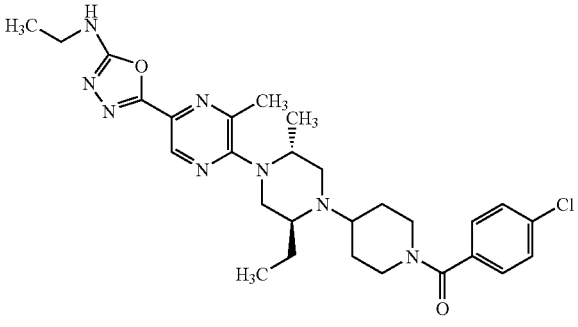 | A |

TABLE 1-continued
| Compound Number | STRUCTURE | IC$_{50}$ |
|---|---|---|
| 97 | 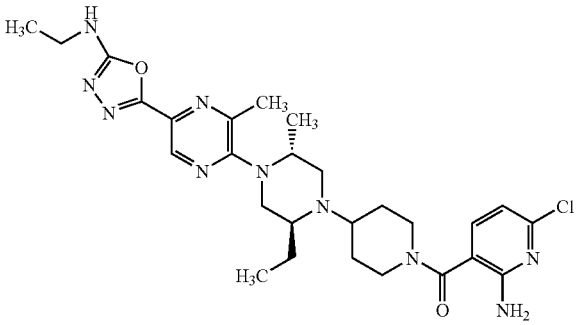 | A |
| 98 | 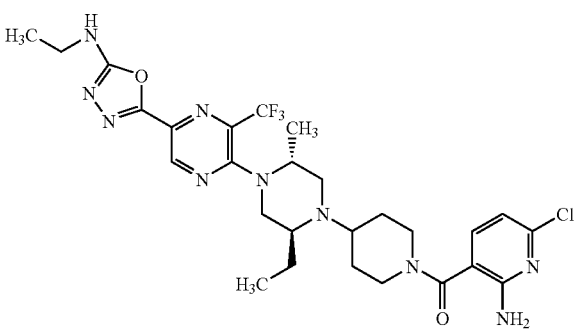 | A |
| 100 | 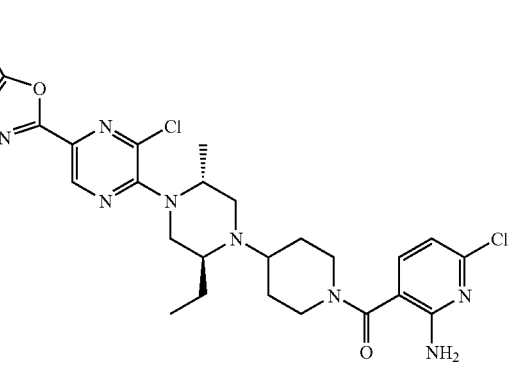 | A |
| 101 | 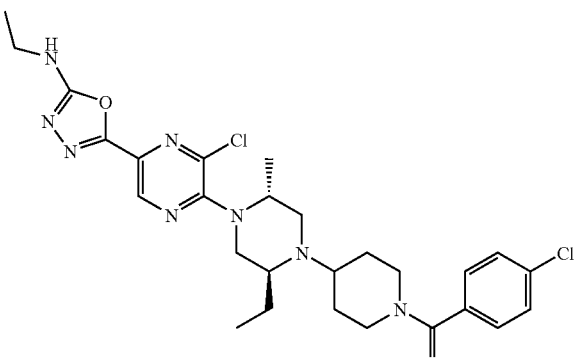 | A |

TABLE 1-continued

| Compound Number | STRUCTURE | IC$_{50}$ |
| --- | --- | --- |
| 102 | 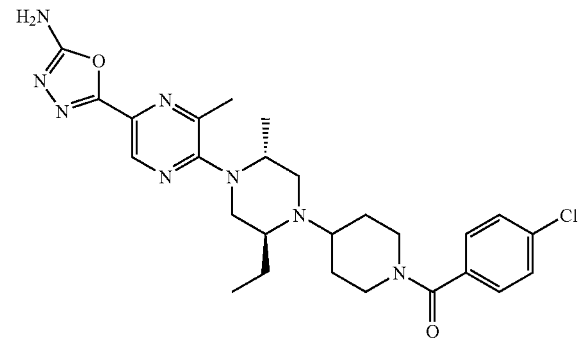 | A |
| 103 | 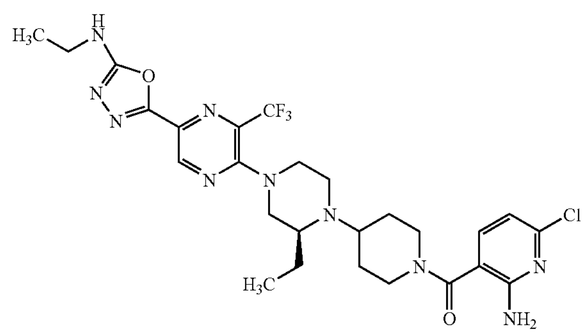 | A |
| 104 | 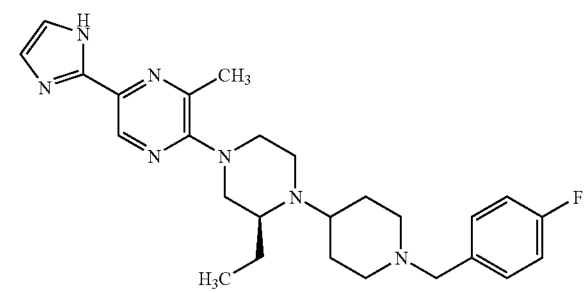 | A |
| 105 | 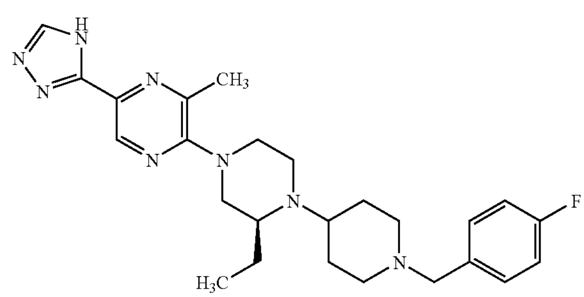 | A |
| 106 | 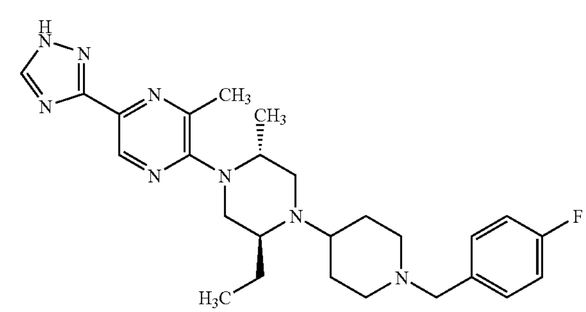 | A |

TABLE 1-continued

| Compound Number | STRUCTURE | IC$_{50}$ |
| --- | --- | --- |
| 107 | 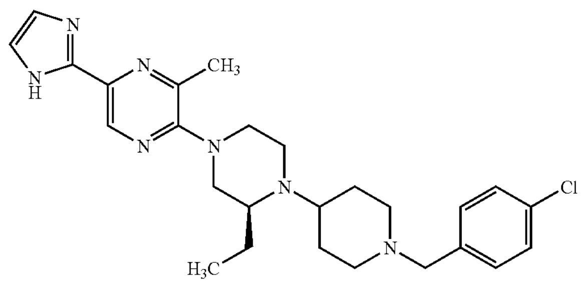 | A |
| 108 | 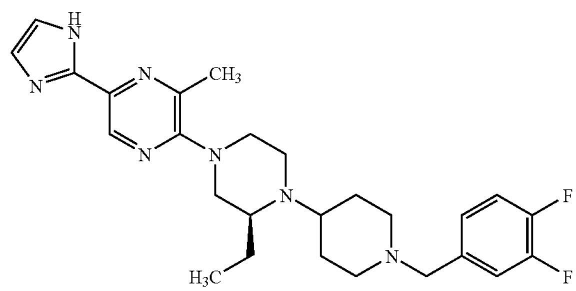 | A |
| 109 | 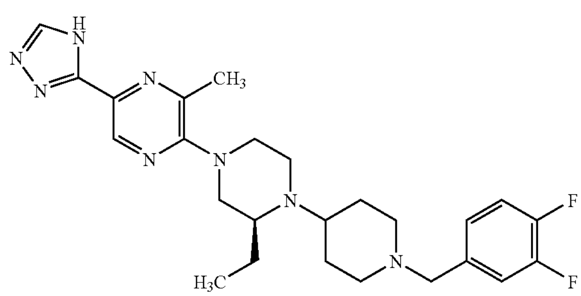 | A |
| 110 | 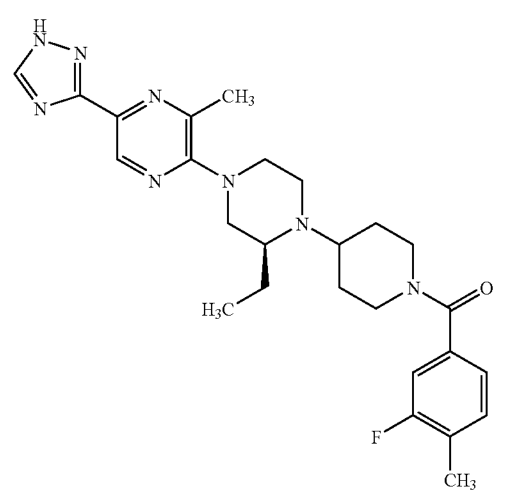 | A |

TABLE 1-continued

| Compound Number | STRUCTURE | IC$_{50}$ |
|---|---|---|
| 111 | 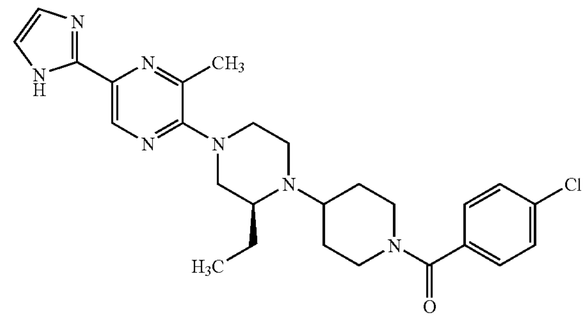 | A |
| 112 | 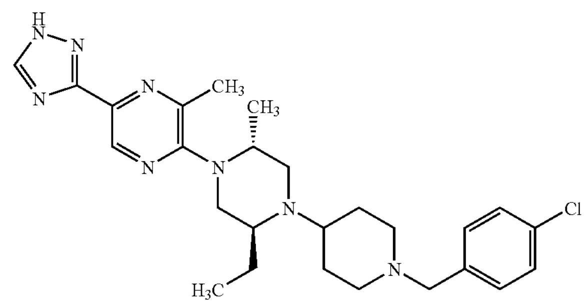 | A |
| 113 | 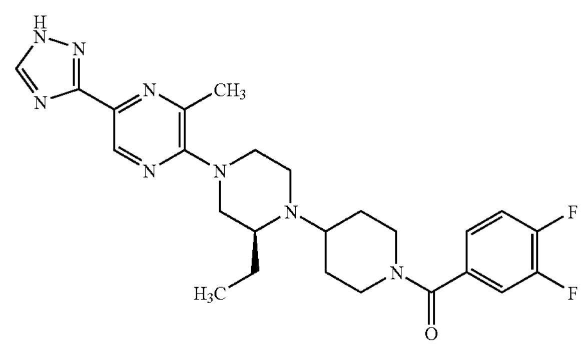 | A |
| 114 | 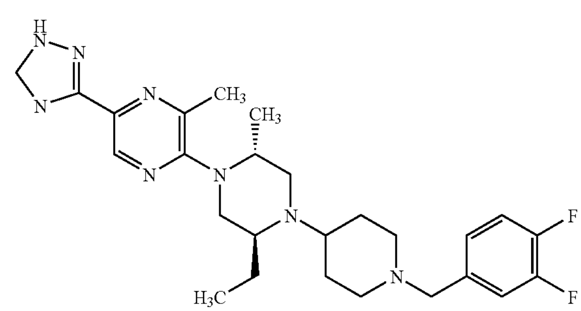 | A |

TABLE 1-continued
| Compound Number | STRUCTURE | IC$_{50}$ |
|---|---|---|
| 115 | 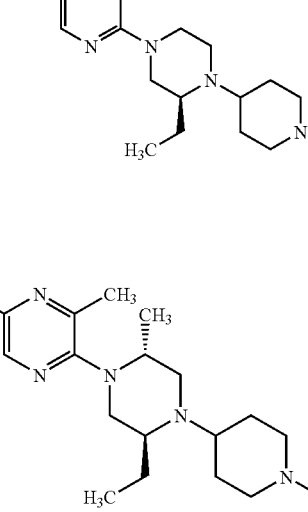 | A |
| 116 | 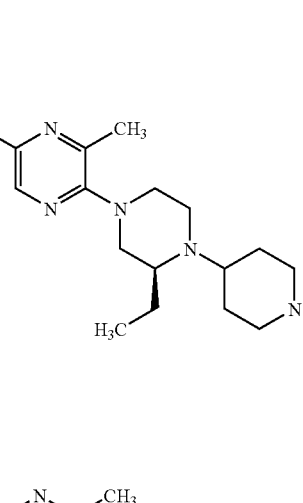 | A |
| 117 | 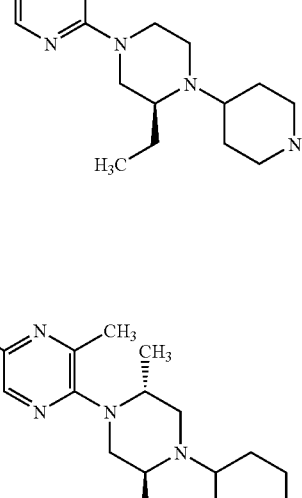 | A |
| 118 | 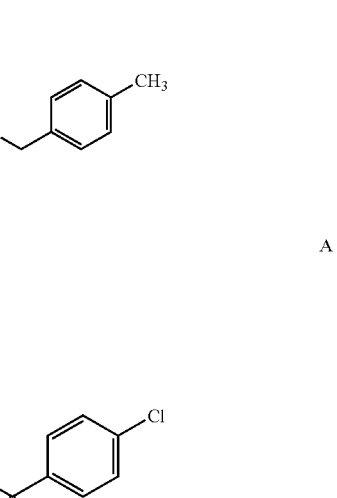 | B |

TABLE 1-continued

| Compound Number | STRUCTURE | IC$_{50}$ |
|---|---|---|
| 119 | 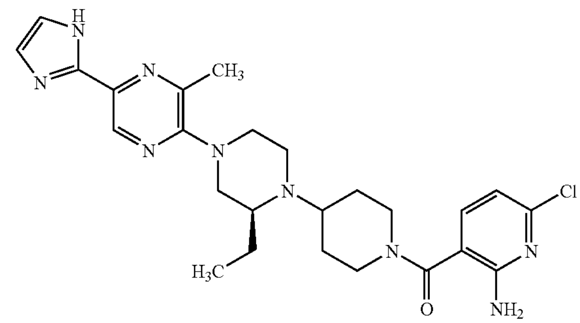 | A |
| 120 | 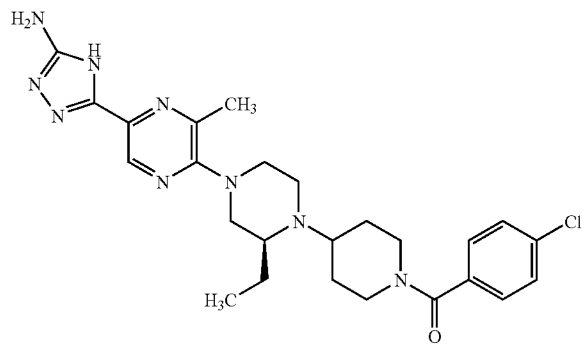 | A |
| 121 | 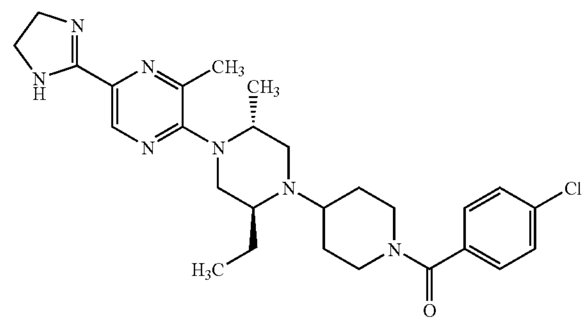 | A |
| 122 | 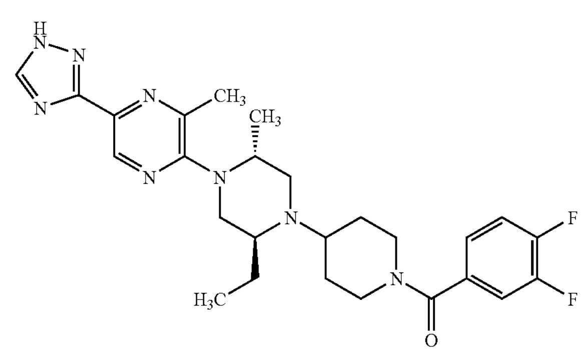 | B |

TABLE 1-continued

| Compound Number | STRUCTURE | IC$_{50}$ |
|---|---|---|
| 123 | 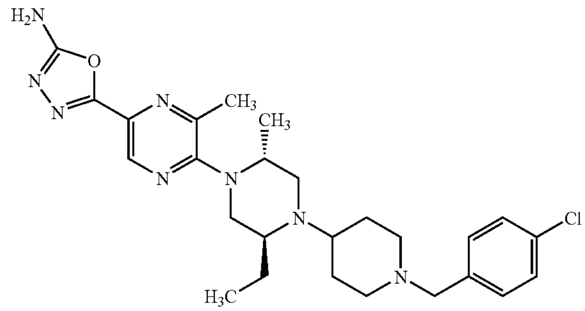 | A |
| 124 | 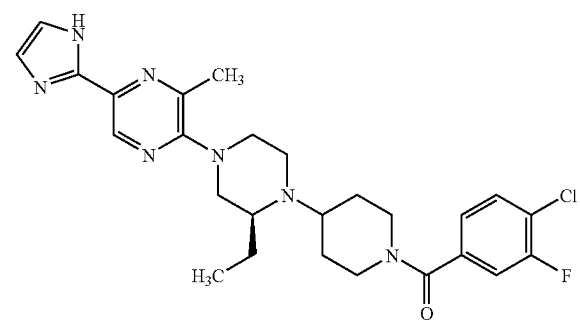 | A |
| 125 | 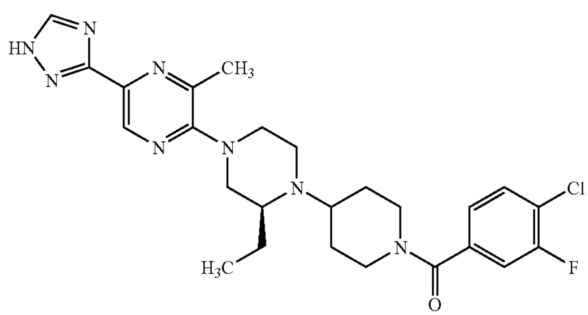 | A |
| 126 | 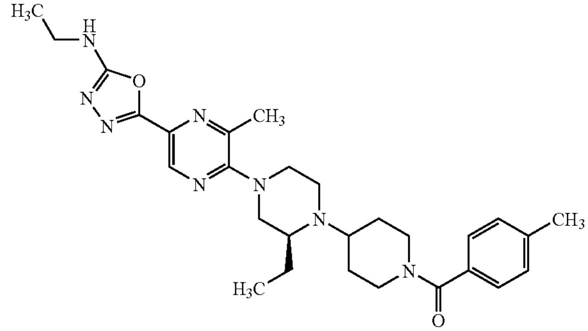 | A |

TABLE 1-continued

| Compound Number | STRUCTURE | IC$_{50}$ |
|---|---|---|
| 127 | 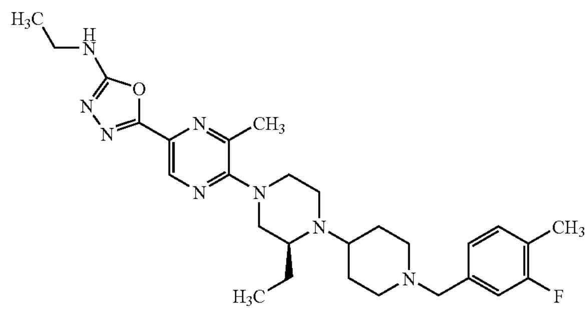 | A |
| 128 | 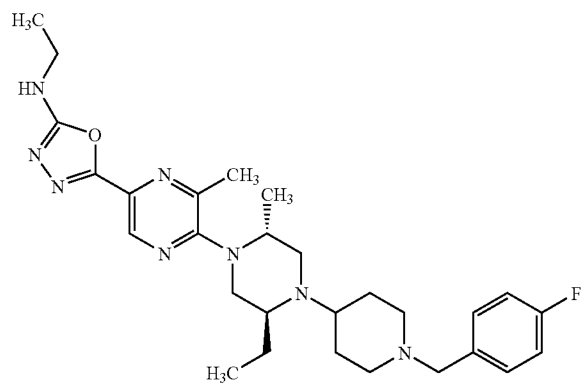 | A |
| 129 | 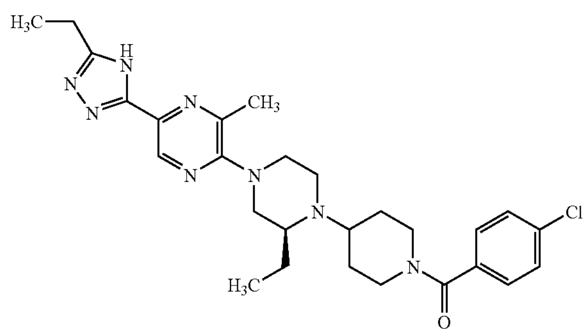 | A |
| 130 | 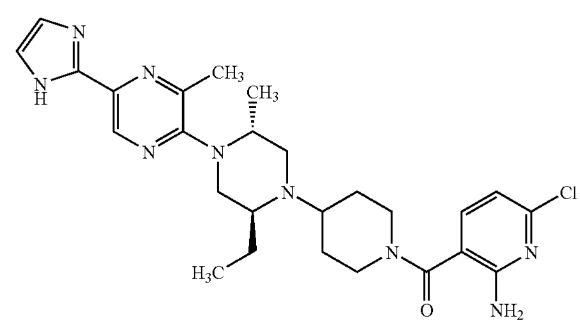 | A |

TABLE 1-continued

| Compound Number | STRUCTURE | IC$_{50}$ |
|---|---|---|
| 131 | 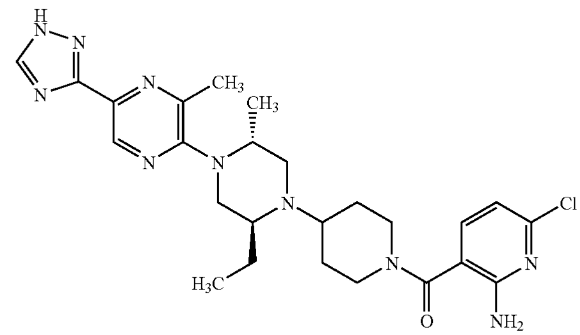 | A |
| 132 | 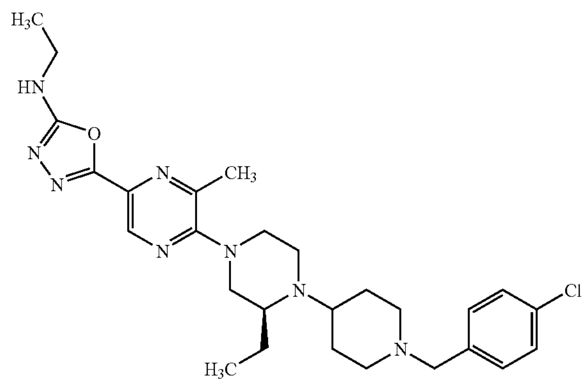 | A |
| 133 | 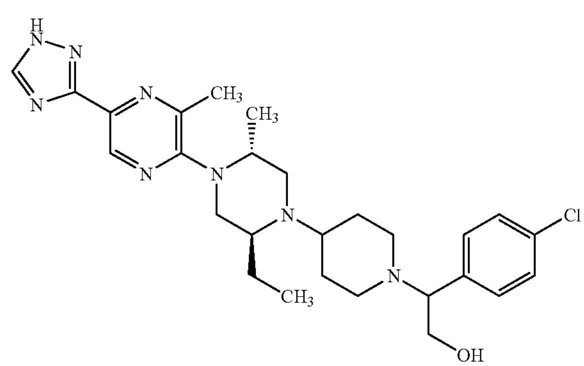 | A |
| 134 | 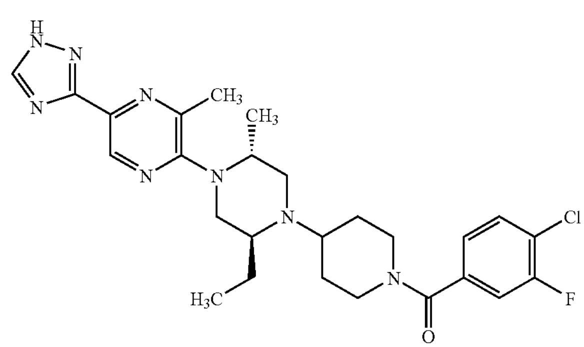 | A |

TABLE 1-continued

| Compound Number | STRUCTURE | IC$_{50}$ |
|---|---|---|
| 135 | 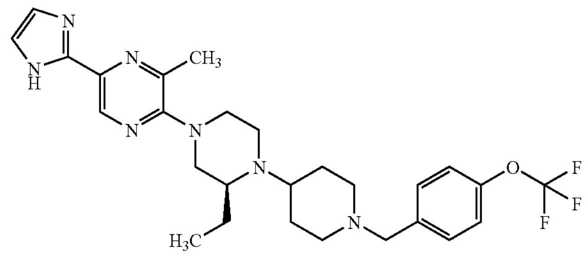 | A |
| 136 | 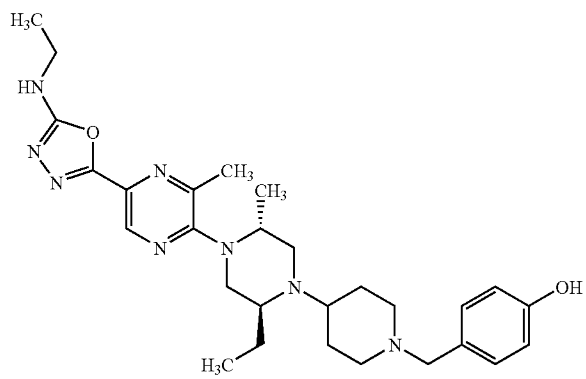 | A |
| 137 | 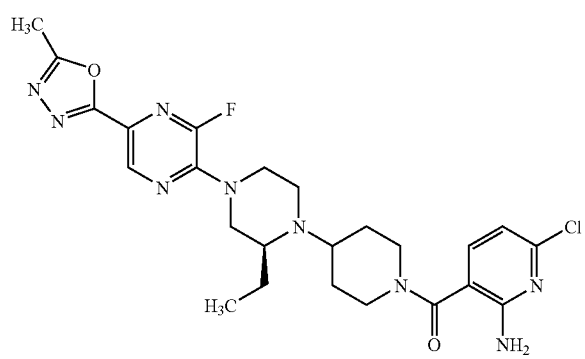 | B |
| 138 | 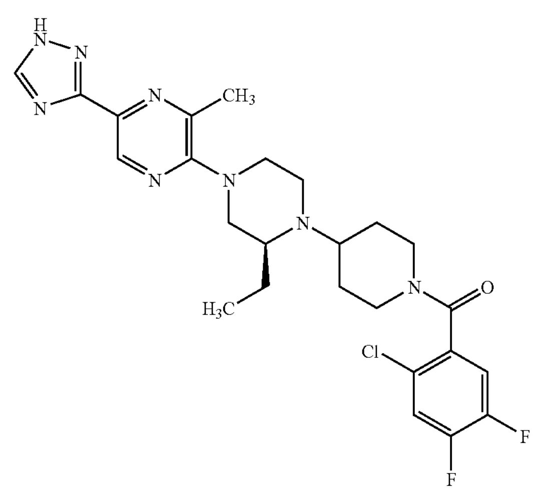 | B |

TABLE 1-continued
| Compound Number | STRUCTURE | IC₅₀ |
|---|---|---|
| 139 | 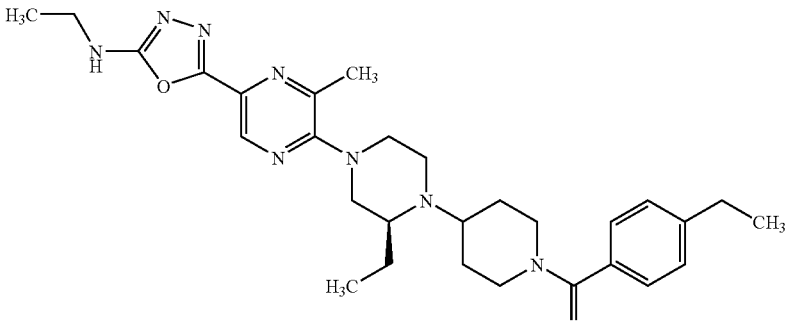 | B |
| 140 | 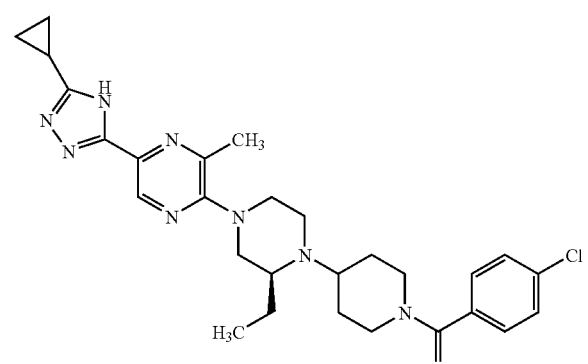 | A |
| 141 | 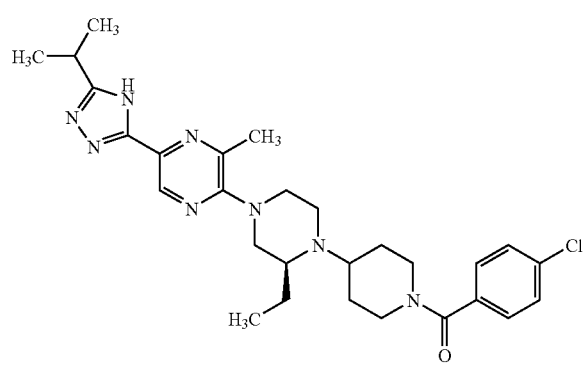 | B |
| 142 | 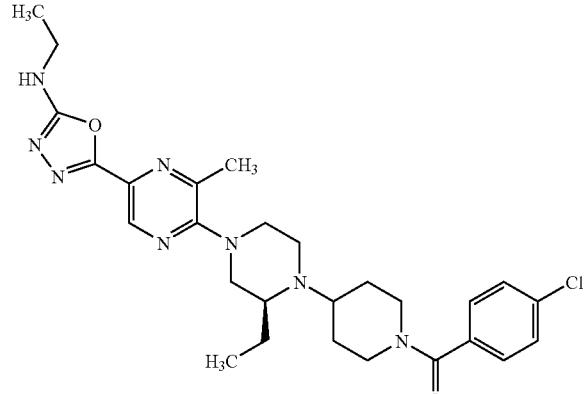 | A |

TABLE 1-continued

| Compound Number | STRUCTURE | IC$_{50}$ |
| --- | --- | --- |
| 143 | 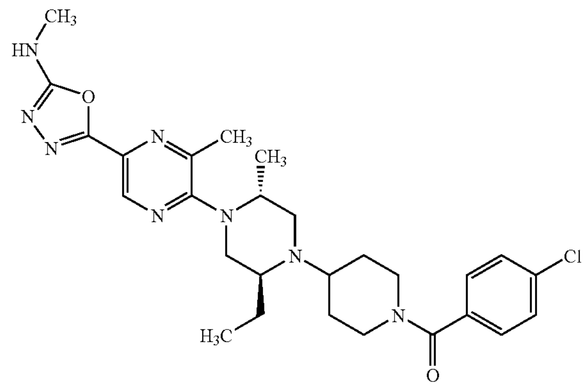 | A |
| 144 | 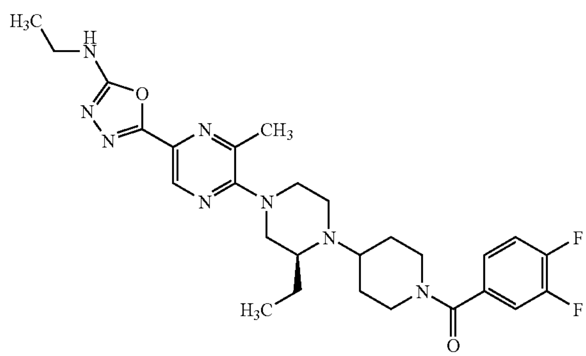 | A |
| 145 | 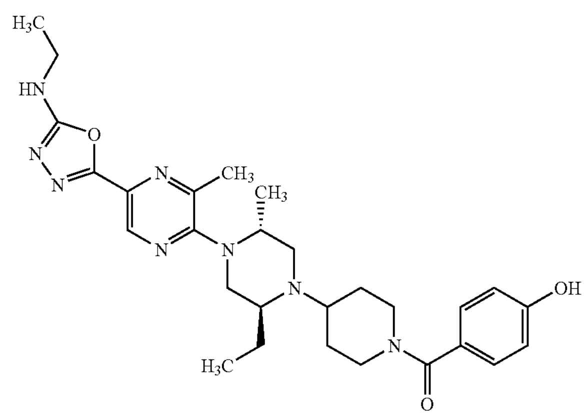 | B |
| 146 | 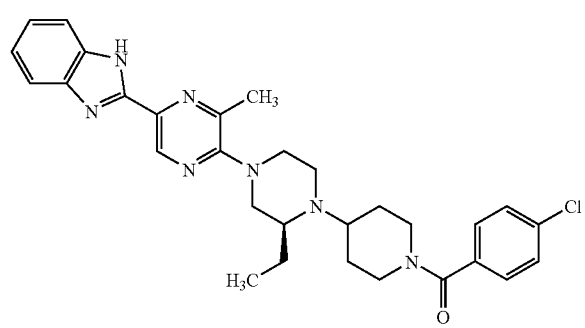 | A |

TABLE 1-continued

| Compound Number | STRUCTURE | IC$_{50}$ |
|---|---|---|
| 147 | 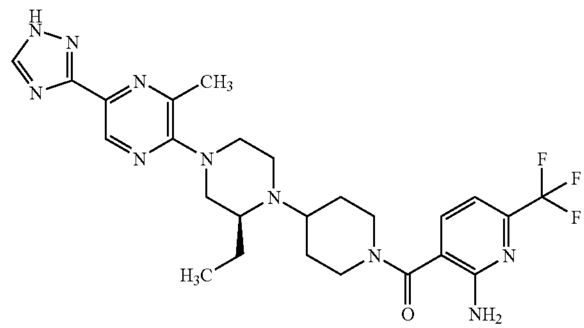 | B |
| 148 | 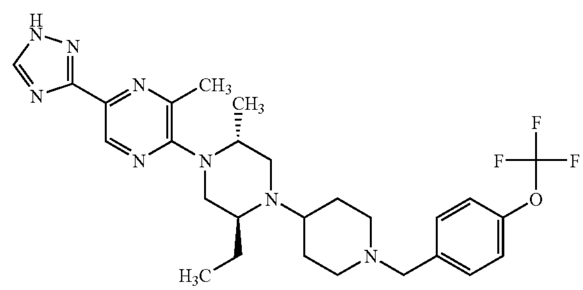 | A |
| 149 | 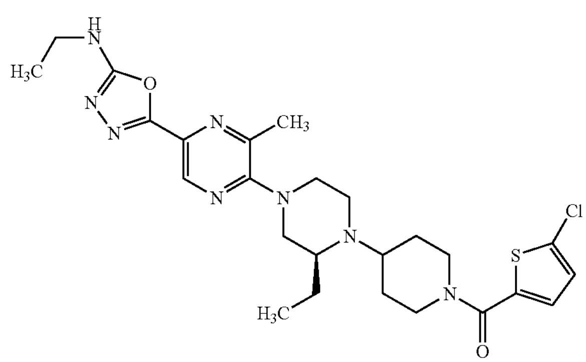 | A |
| 150 | 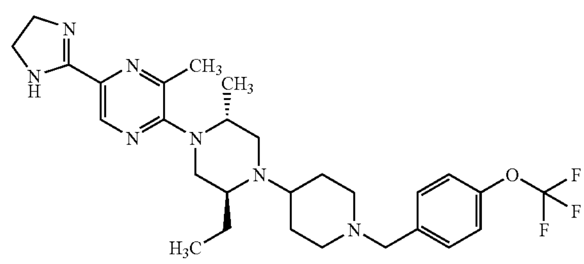 | A |

TABLE 1-continued
| Compound Number | STRUCTURE | IC$_{50}$ |
|---|---|---|
| 151 | 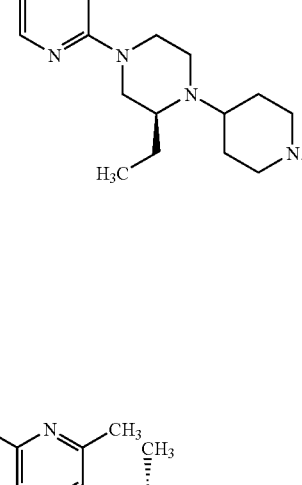 | A |
| 152 | 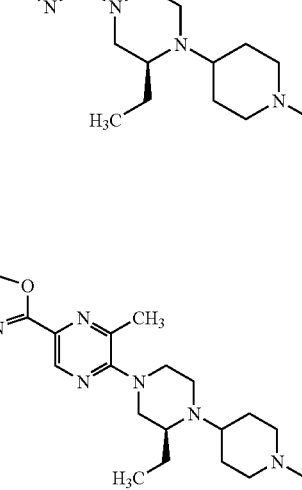 | B |
| 153 | 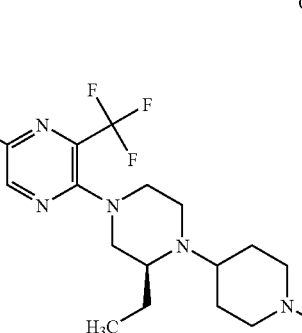 | B |
| 154 | 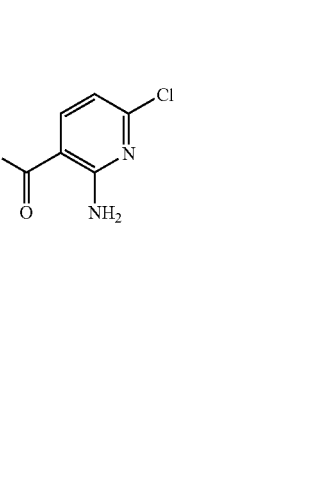 | A |

TABLE 1-continued

| Compound Number | STRUCTURE | IC$_{50}$ |
|---|---|---|
| 155 | 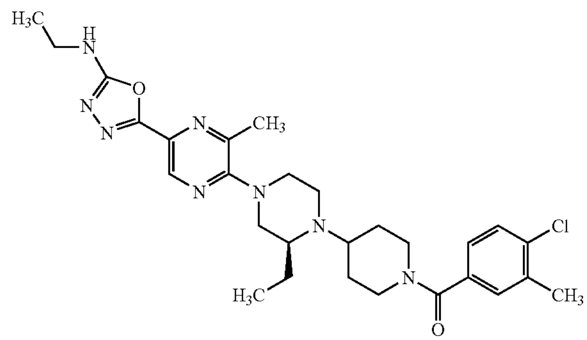 | A |
| 156 | 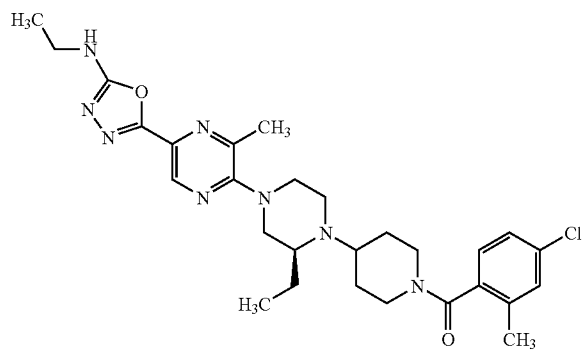 | A |
| 157 | 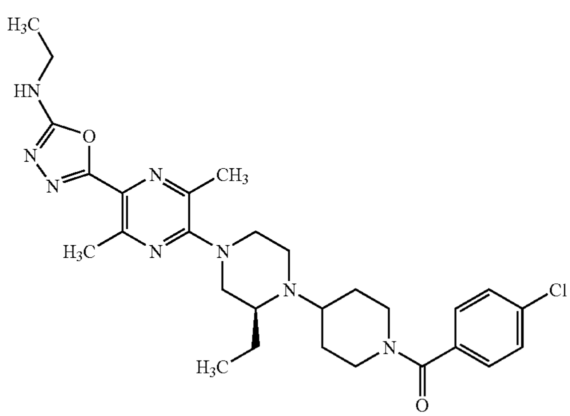 | A |
| 158 | 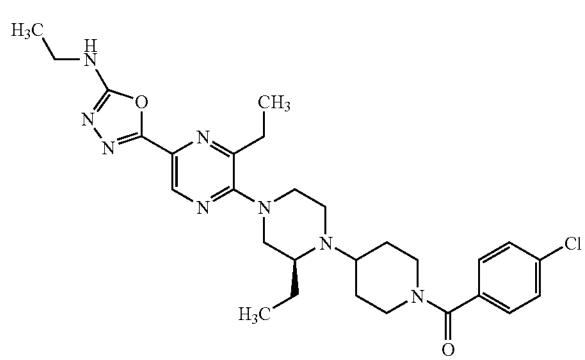 | A |

TABLE 1-continued
| Compound Number | STRUCTURE | IC$_{50}$ |
|---|---|---|
| 159 | 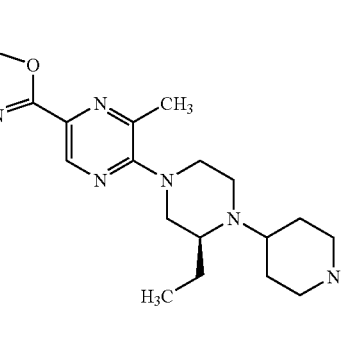 | A |
| 160 | 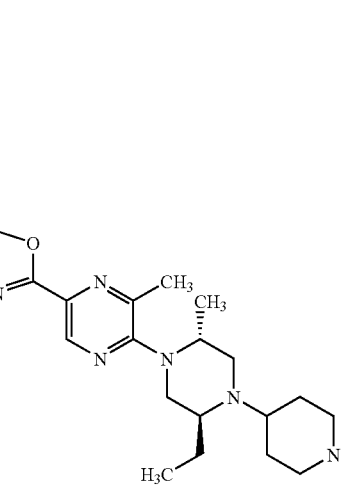 | A |
| 161 | 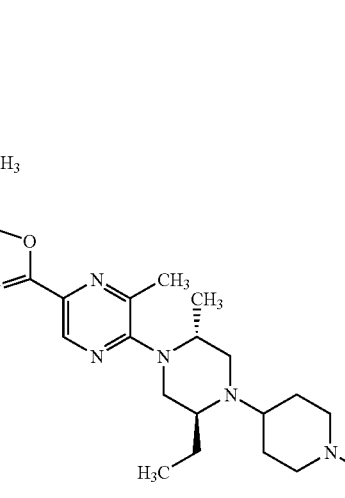 | A |

TABLE 1-continued

| Compound Number | STRUCTURE | IC$_{50}$ |
|---|---|---|
| 162 | 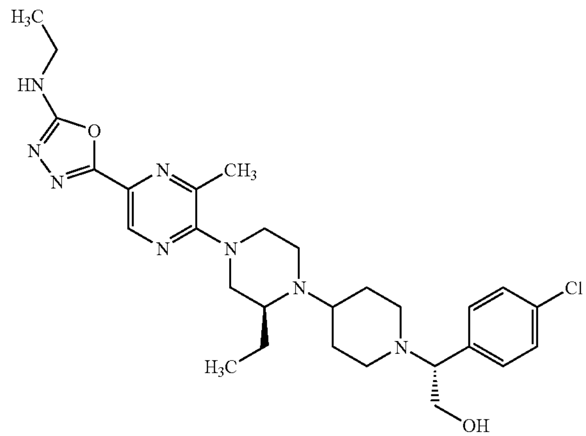 | A |
| 163 | 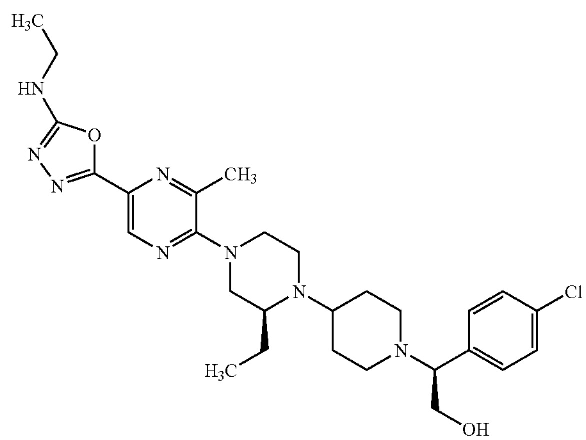 | A |
| 164 | 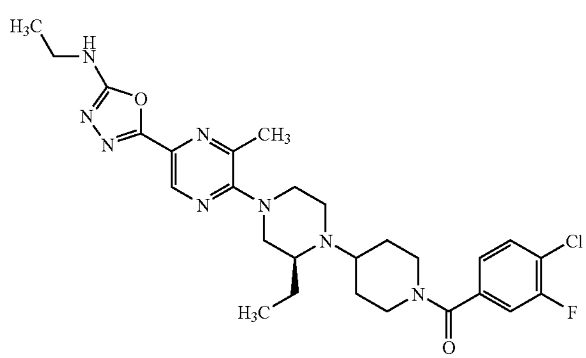 | A |
| 165 | 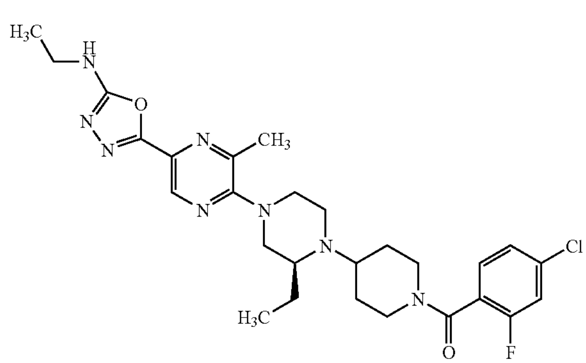 | A |

TABLE 1-continued

| Compound Number | STRUCTURE | IC$_{50}$ |
|---|---|---|
| 166 | 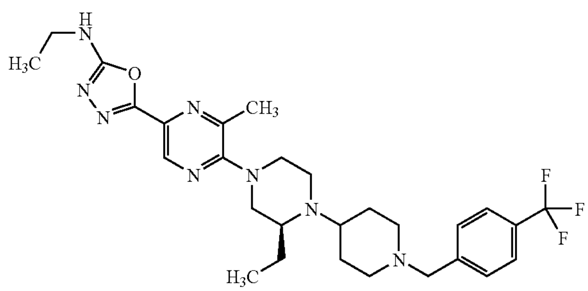 | A |
| 167 | 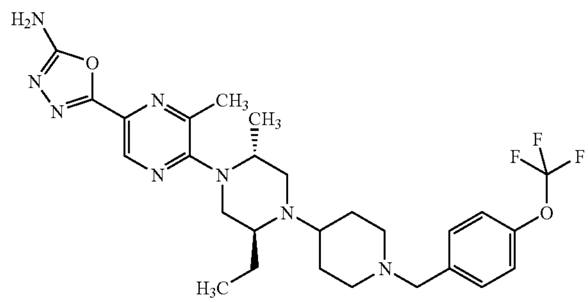 | A |
| 168 | 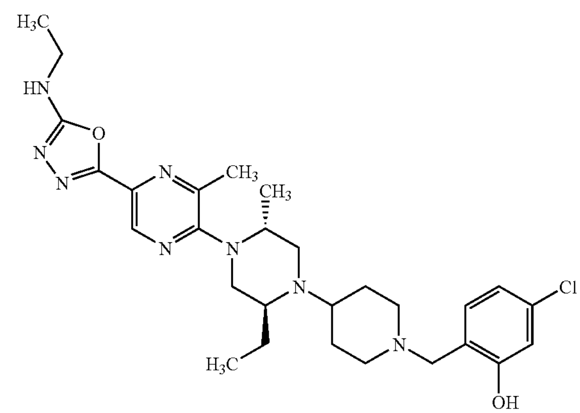 | A |
| 169 | 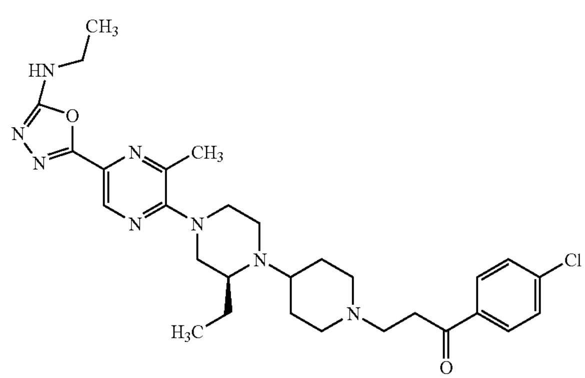 | A |

TABLE 1-continued

| Compound Number | STRUCTURE | IC$_{50}$ |
|---|---|---|
| 170 | 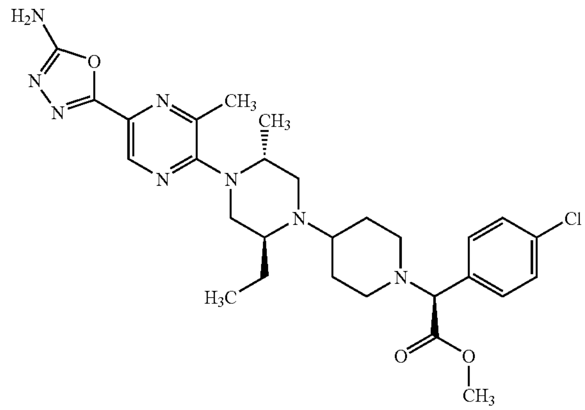 | B |
| 171 | 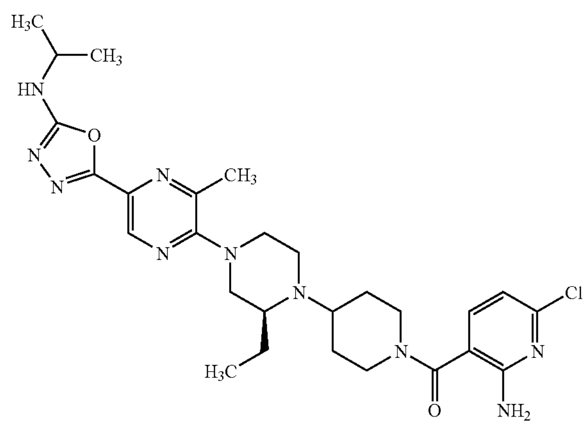 | A |
| 172 | 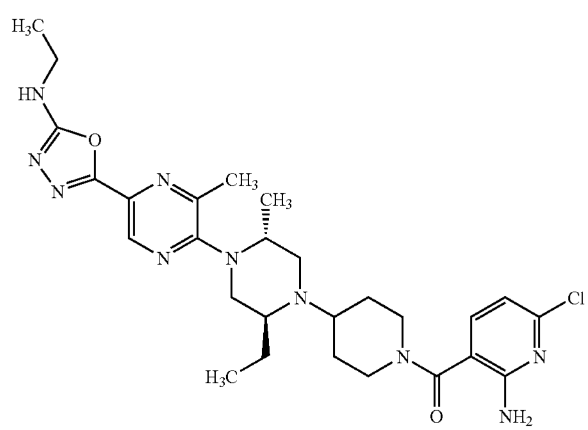 | A |

TABLE 1-continued

| Compound Number | STRUCTURE | IC$_{50}$ |
| --- | --- | --- |
| 173 | 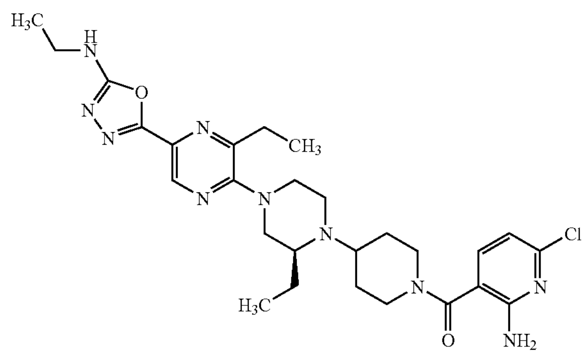 | A |
| 174 | 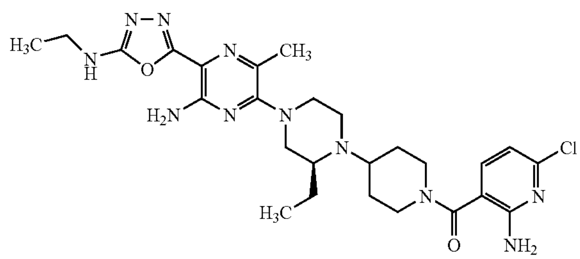 | A |
| 175 | 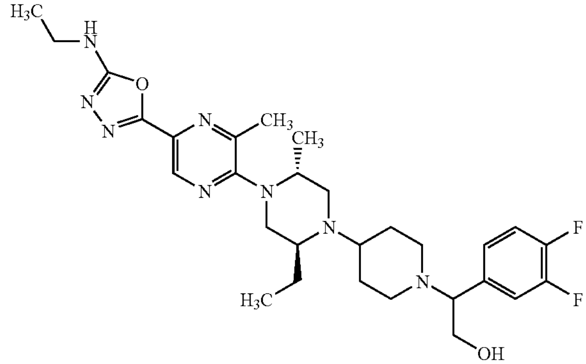 | A |
| 176 | 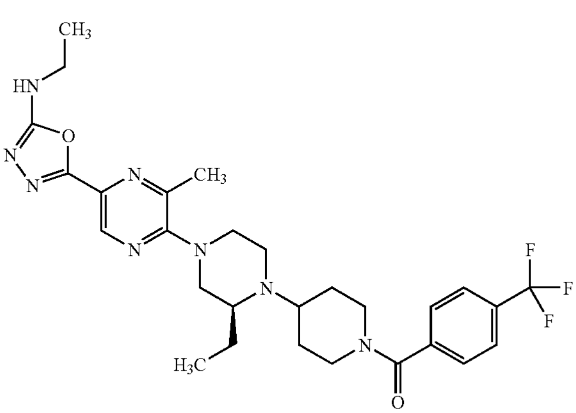 | A |

TABLE 1-continued

| Compound Number | STRUCTURE | IC$_{50}$ |
|---|---|---|
| 177 | 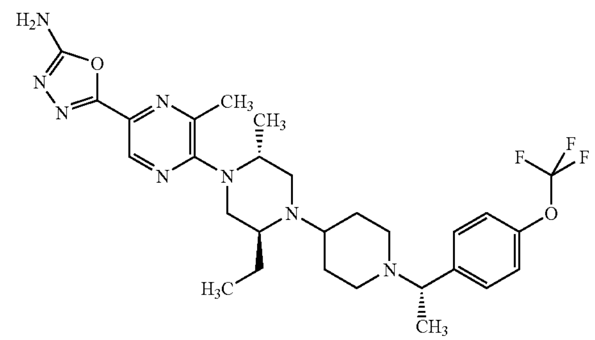 | A |
| 178 | 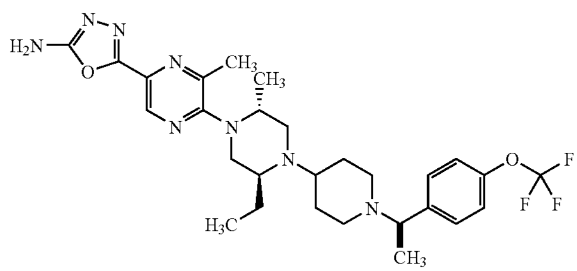 | A |
| 179 | 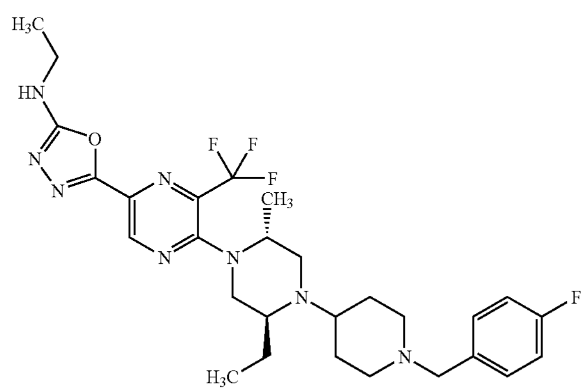 | A |
| 180 | 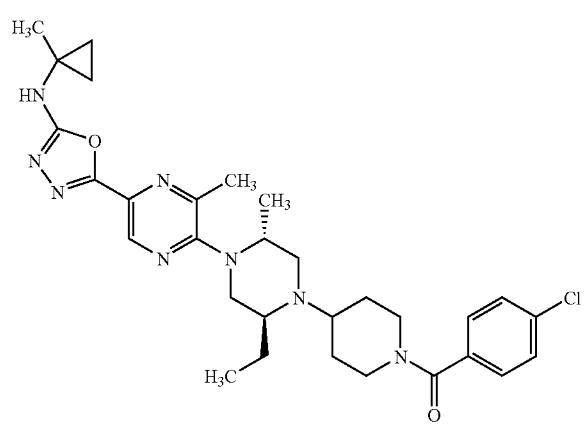 | A |

TABLE 1-continued

| Compound Number | STRUCTURE | IC$_{50}$ |
|---|---|---|
| 181 | 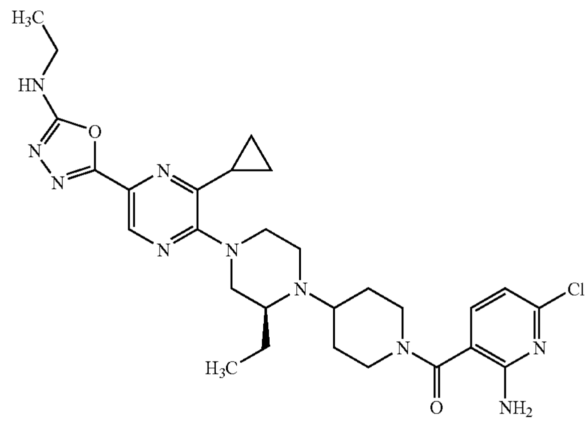 | B |
| 182 | 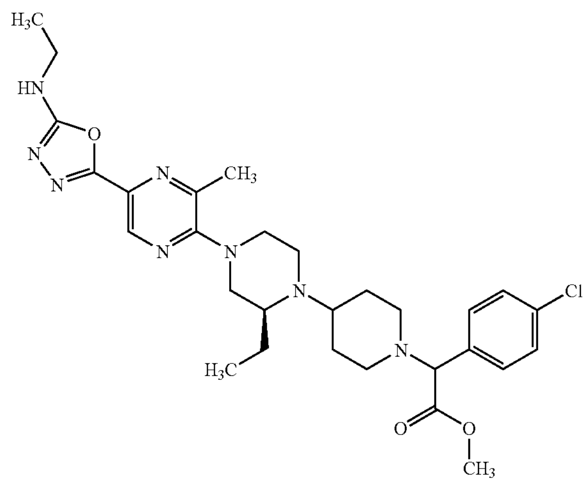 | A |
| 183 | 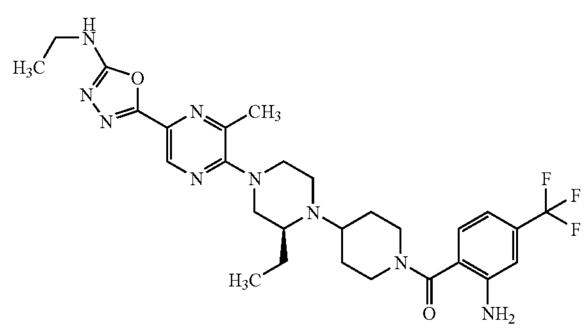 | A |
| 184 | 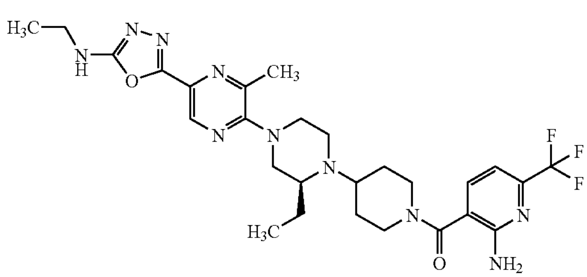 | A |

TABLE 1-continued
| Compound Number | STRUCTURE | IC$_{50}$ |
|---|---|---|
| 185 | 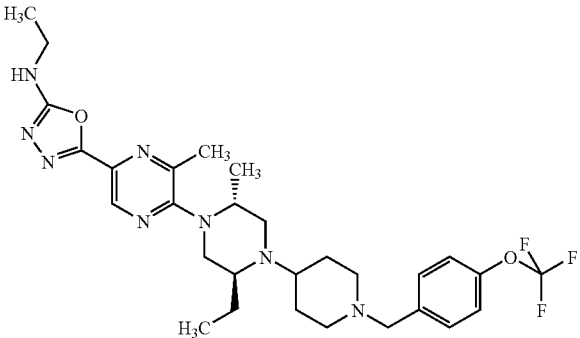 | A |
| 186 | 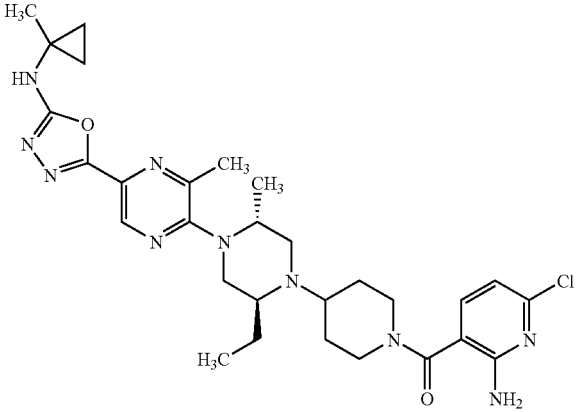 | A |
| 187 | 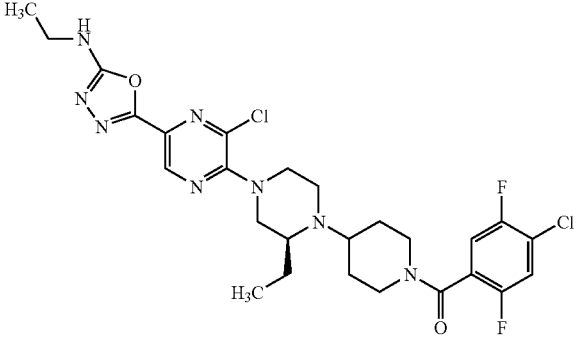 | A |
| 188 | 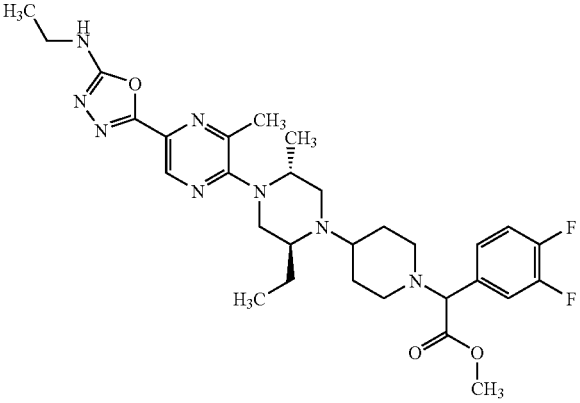 | A |

TABLE 1-continued

| Compound Number | STRUCTURE | IC$_{50}$ |
|---|---|---|
| 189 | 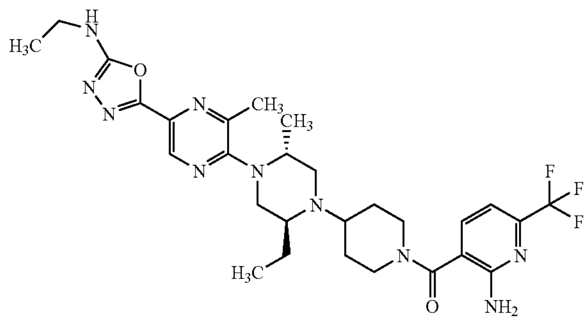 | A |
| 190 | 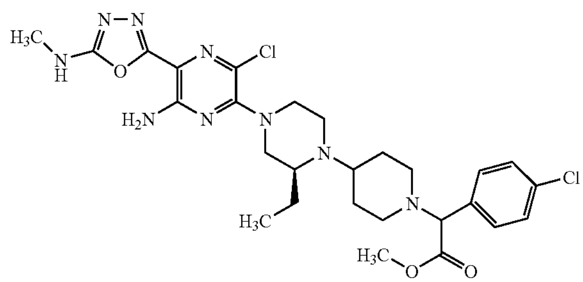 | A |
| 191 | 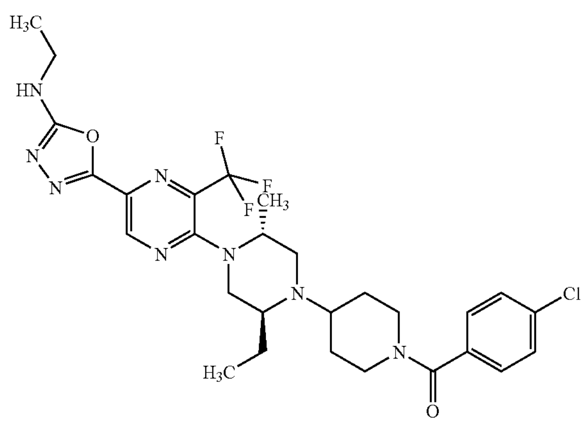 | A |
| 192 | 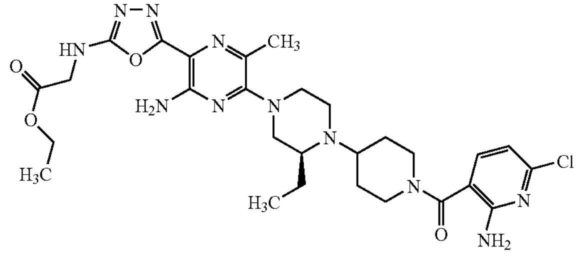 | A |

TABLE 1-continued

| Compound Number | STRUCTURE | IC$_{50}$ |
| --- | --- | --- |
| 193 | 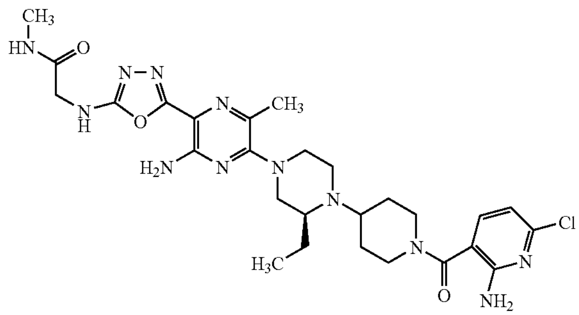 | A |
| 194 | 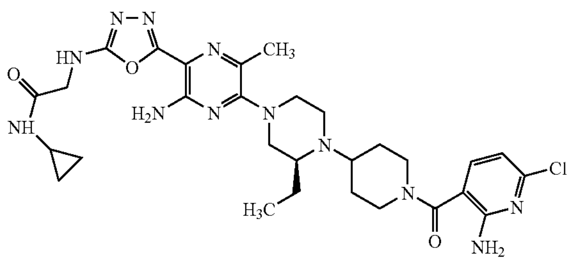 | A |
| 195 | 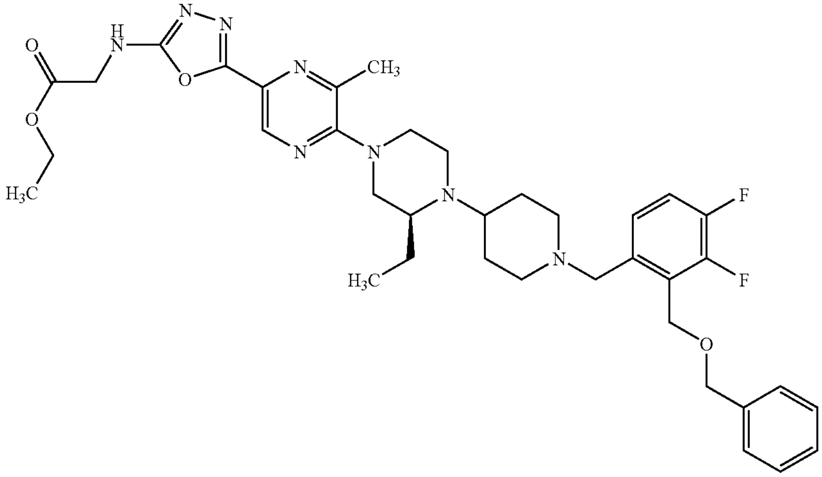 | B |
| 196 | 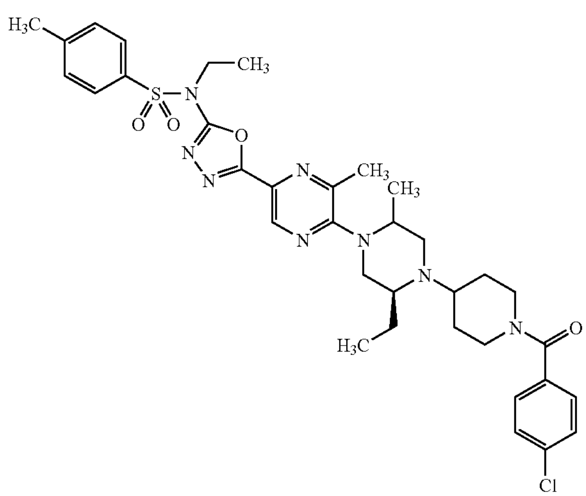 | B |

In yet another aspect, the compound according to Formula 1 is in purified form.

In another embodiment, this invention provides a pharmaceutical composition comprising at least one compound of Formula 1, or a pharmaceutically acceptable salt, solvate or ester thereof in combination with at least one pharmaceutically acceptable carrier.

In still another embodiment, the invention provides a pharmaceutical composition of Formula 1, further comprising at least one additional agent, drug, medicament, antibody and/or inhibitor for treating a CXCR3 chemokine receptor mediated disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In yet another embodiment, the present invention discloses methods for preparing pharmaceutical compositions comprising the inventive heterocyclic substituted piperazine compounds of Formula 1 as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'1-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention. Certain compounds of the present invention may exist in multiple crystalline forms or amorphous forms. All physical forms of the current invention are contemplated.

Compounds of this invention which contain unnatural proportions of atomic isotopes (i.e. "radiolabeled compounds") whether their use is therapeutic, diagnostic or as a research reagent are contemplated under this invention.

Another embodiment of the invention discloses the use of the pharmaceutical compositions disclosed above for treatment of diseases of a CXCR3 chemokine receptor mediated disease in a patient in need of such treatment comprising administering to the patient a therapeutically effective amount of at least one compound according to Formula 1, or a pharmaceutically acceptable salt, solvate or ester thereof.

In another embodiment, the method is directed to administering to the patient (a) an effective amount of at least one compound according to Formula 1, or a pharmaceutically acceptable salt, solvate or ester thereof concurrently or sequentially with (b) at least one additional agent, drug, medicament, antibody and/or inhibitor for treating a CXCR3 chemokine receptor mediated disease, in combination with a pharmaceutically acceptable carrier.

In another embodiment, at least one compound of Formula 1 binds to a CXCR3 receptor.

The method can further comprise administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics. The disease can be an inflammatory disease (e.g., psoriasis, inflammatory bowel disease)

Another embodiment of this invention is directed to a method of inhibiting or blocking T-cell mediated chemotaxis in a patient in need of such treatment the method comprising administering to the patient a therapeutically effective amount of at least one compound according to Formula 1 or a pharmaceutically acceptable salt, solvate or ester thereof.

Another embodiment of this invention is directed to a method of treating inflammatory bowel disease (such Crohn's disease, ulcerative colitis) in a patient in need of such treatment comprising administering to the patient a therapeutically effective amount of at least one compound according to Formula 1, or a pharmaceutically acceptable salt, solvate or ester thereof.

Another embodiment of this invention is directed to a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Another embodiment of this invention is directed to a method of treating or preventing graft rejection in a patient in need of such treatment comprising administering to the patient a therapeutically effective amount of at least one compound according to Formula 1, or a pharmaceutically acceptable salt, solvate or ester thereof.

Another embodiment of this invention is directed to a method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Another embodiment of this invention is directed to a method of treating multiple sclerosis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA-4 inhibitors, FTY720, anti-IL-12 inhibitors, and CB2-selective inhibitors.

Another embodiment of this invention is directed to a method of treating multiple sclerosis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Another embodiment of this invention is directed to a method of treating rheumatoid arthritis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Another embodiment of this invention is directed to a method of treating psoriasis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Another embodiment of this invention is directed to a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Another embodiment of this invention is directed to a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

Another embodiment of the invention discloses a method of making the substituted pyrazine compounds, disclosed above.

Unless otherwise stated, the following abbreviations have the stated meanings in the Examples below:

DBU=1,8-diazabicyclo[5.4.0]undec-7-ene
DBN=1,5-diazabicyclo[4.3.0]non-5-ene
EDCI=1-(3-dimethylaminopropyl)-3-ethylcarbodiimide HATU=O-(7-Azabenzotriazol-1-yl)-N,N,N',N'-tetramethyluronium hexafluorophosphate
HOBT=1-hydroxybenzotriazole
DCC=dicyclohexylcarbodiimide
Dibal-H=diisobutylaluminum hydride
LAH=lithium aluminum hydride
$NaBH(OAc)_3$=sodium triacetoxyborohydride
$NaBH_4$=sodium borohydride
$NaBH_3CN$=sodium cyanoborohydride
NBS=N-Bromosuccinamide
NCS=N-Chlorosuccinamide
LDA=lithium diisopropylamide
p-TsOH=p-toluenesulfonic acid
m-CPBA=m-Chloroperbenzoic acid
TMAD=N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=$-logEC_{50}$, as defined by J. Hey, *Eur. J. Pharmacol.*, (1995), Vol. 294, 329-335.
Ci/mmol=Curie/mmol (a measure of specific activity)
Tr=Triphenylmethyl
Tris=Tris (hydroxymethyl)aminomethane General Synthesis Compounds of the present invention can be prepared by a number of ways evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Two such methods for the preparation of compounds of Formula 1 where variables [$R^3$, $R^6$, $R^9$, $R^{10}$, $R^{11}$, $R^{12}$, $R^{20}$, Y, m, n, and p] are as defined above, are shown in Scheme 1. $Pr^1$ and $Pr^2$ are protecting groups exemplified below.

The thus prepared compounds may be analyzed for their composition and purity as well as characterized by standard analytical techniques such as, for example, elemental analysis, NMR, mass spectroscopy, and IR spectra.

Scheme 1.

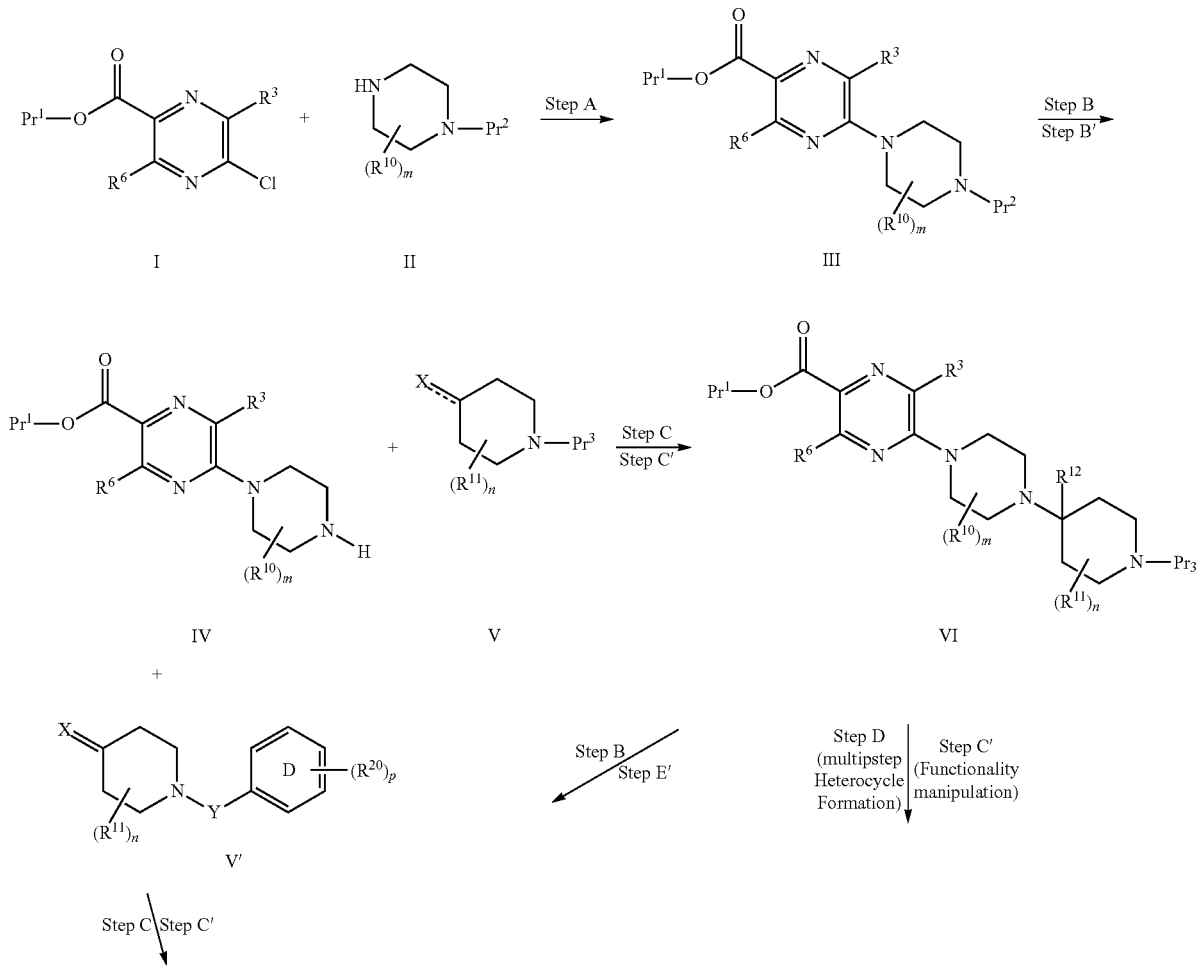

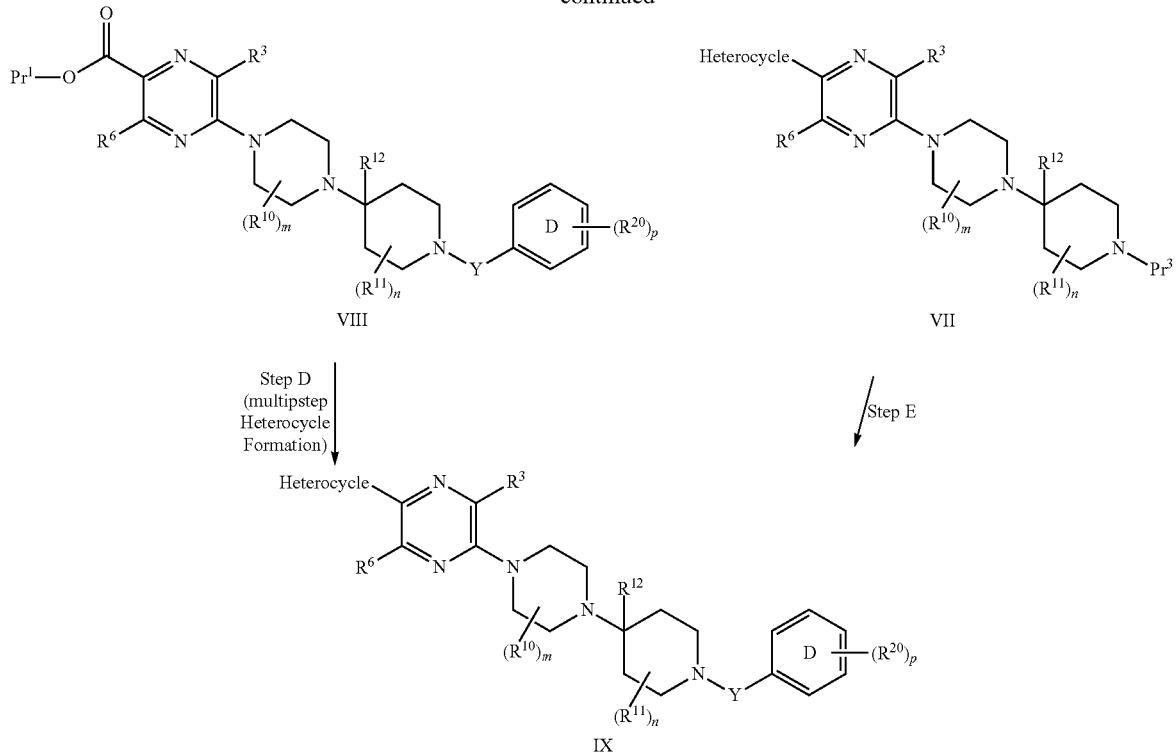

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

The preparation of arylpiperazine compounds related to intermediate III has been reported in WO-03037862 (Nippon Shinyaku).

One skilled in the art will recognize that the synthesis of compounds of Formula 1 may require the need for the protection of certain functional groups (i.e. derivatization for the purpose of chemical compatibility with a particular reaction condition). Suitable protecting groups for a carboxylic acid, $Pr^1$, are methyl, ethyl, isopropyl, or benzyl ester and the like. A suitable protecting group for an amine ($Pr^2$ and $Pr^3$) is methyl, benzyl, ethoxyethyl, t-butoxycarbonyl, phthaloyl and the like. All protecting groups can be appended to and removed by literature methods known to those skilled in the art.

One skilled in the art will recognize that the synthesis of compounds of Formula 1 may require the construction of an amide bond. Methods include but are not limited to the use of a reactive carboxy derivative (e.g. acid halide, or ester at elevated temperatures) or the use of an acid with a coupling reagent (e.g. DECI, DCC, HATU) with an amine at 0° C. to 100° C. Suitable solvents for the reaction are halogenated hydrocarbons, ethereal solvents, dimethylformamide and the like. The reaction may be conducted under pressure or in a sealed vessel.

One skilled in the art will recognize that the synthesis of compounds of Formula 1 may require the construction of an amine bond. One such method is but not limited to the reaction of a primary or secondary amine with a reactive carbonyl (e.g. aldehyde or ketone) under reductive amination conditions. Suitable reducing reagents of the intermediate imine are sodium borohydride, sodium triacetoxyborohydride and the like at 0° C. to 100° C. Suitable solvents for the reaction are halogenated hydrocarbons, ethereal solvents, dimethylformamide and the like. Another such method is for example the reaction of a primary or secondary amine with a reactive alkylating agent such as an alkyl halide, benzyl halide, mesylate, tosylate and the like. Suitable solvents for the reaction are halogenated hydrocarbons, ethereal solvents, dimethylformamide and the like. The reaction may be conducted under pressure or in a sealed vessel at 0° C. to 100° C.

One skilled in the art will recognize that the synthesis of compounds of Formula 1 may require the reduction of a reducible functional group. Suitable reducing reagents include sodium borohydride, lithium aluminum hydride, diborane and the like at −20° C. to 100° C. Suitable solvents for the reaction are halogenated hydrocarbons, ethereal solvents, dimethylformamide and the like.

One skilled in the art will recognize that the synthesis of compounds of Formula 1 may require the oxidation of a functional group. Suitable oxidizing reagents include oxygen, hydrogen peroxide, m-chloroperoxybenzoic acid and the like at −20° C. to 100° C. Suitable solvents for the reaction are halogenated hydrocarbons, ethereal solvents, water and the like.

One skilled in the art will note that compounds of Formula 1 require the construction of a heterocyclic ring. Numerous reviews of methodology for the construction of specific heterocyclic systems are in the open literature. In addition to the open literature, monographs and compendiums such as Comprehensive Heterocyclic Synthesis (Pergamon Press) are available. Shown below is in one such general scheme for the title compounds through a common intermediate.

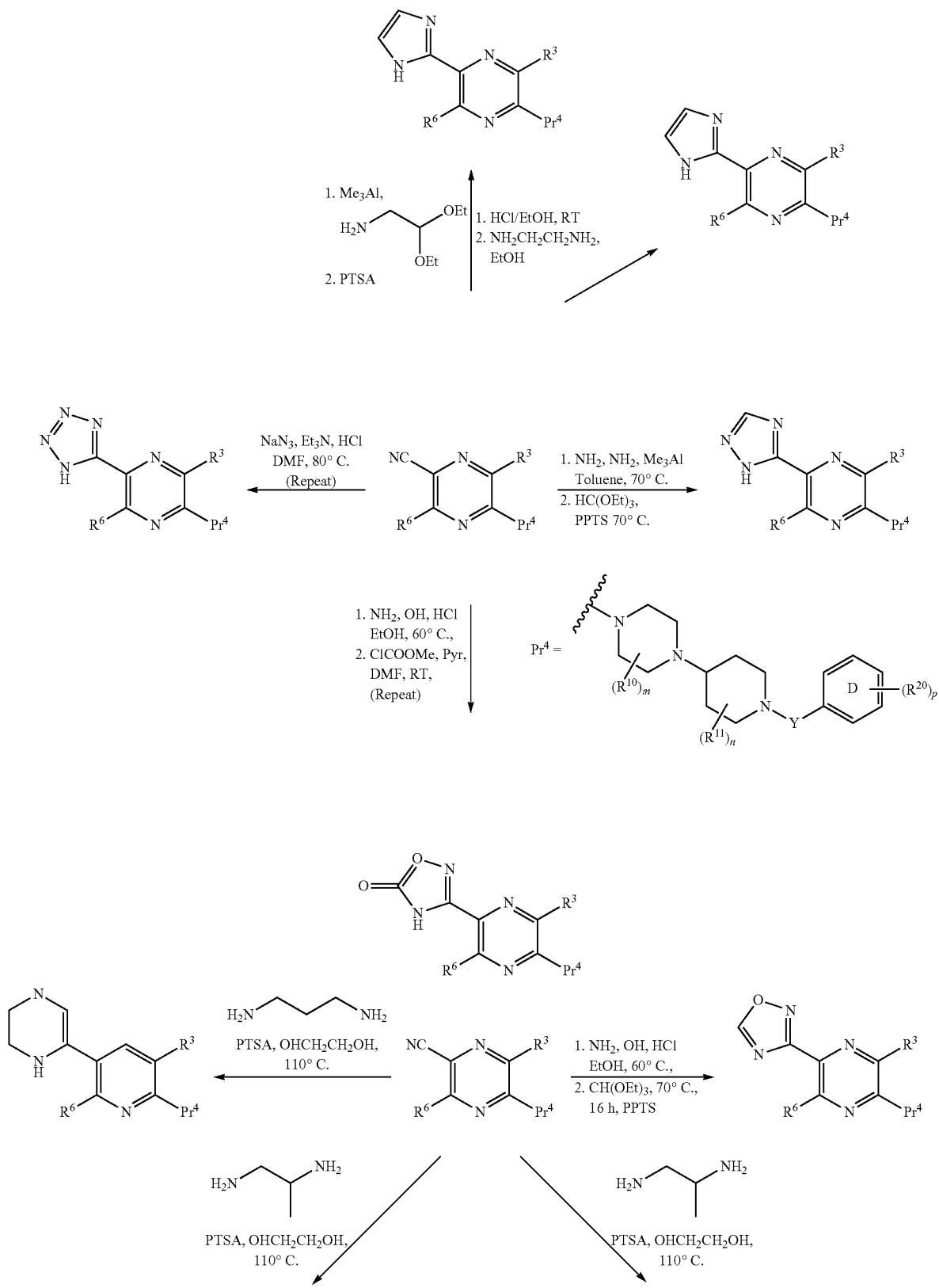

-continued

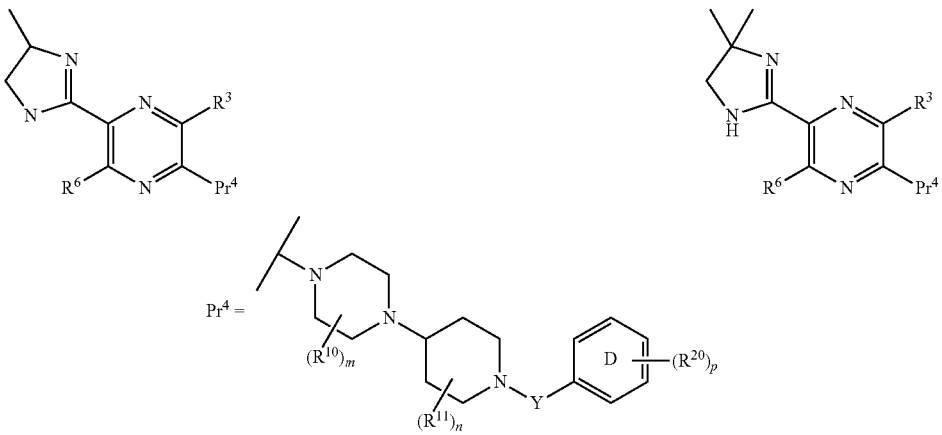

The starting materials and the intermediates of a reaction may be isolated and purified if desired using conventional techniques, including but not limited to filtration, distillation, crystallization, chromatography and the like. Such materials can be characterized using conventional means, including physical constants and spectral data.

General Description of Methods

Step A. Amination of a 2-halo Pyrazine

A suitably protected 2-halo Pyrazine of structure I is reacted with a piperazine of structure II to form a compound of general structure III. Preferably the reaction is carried out in a solvent such as dioxane or DMF in the presence of a base such as potassium carbonate or cesium carbonate. Additional catalysts such as palladium acetate may be added. Alternatively, other leaving groups may replace the chlorine (O-mesyl, Br etc.) or a group capable of activation under the reaction conditions (H, OH, etc.) may be used. The reaction may require heating to a temperature of 35 to 150° C.

Step B.

Optionally, if the product of step A is an unprotected piperazine of structure III, protection may be required.

Optionally, if the product of step A or Step C is a protected piperazine of structure III or VI, deprotection is required. When $Pr^2$ or $Pr^3$ is benzyl or substituted benzyl deprotection can be effected by reaction under a pressure of hydrogen gas in the presence of a catalyst such as palladium. When $Pr^2$ or $Pr^3$ is ethoxyethyl deprotection can be effected by reaction with trimethylsilyl iodide. When $Pr^2$ or $Pr^3$ is t-butoxycarbonyl deprotection can be effected with a strong acid such as trifluoroacetic acid.

Step B'

Optionally, functional group introduction such as ring halogenation with chlorine, bromine, NCS, or NBS can be accomplished. Optionally, functional group manipulation (such as reduction, hydrolysis, alkylation) can be accomplished or if $R^3$=halogen, reaction with an organometallic coupling reagent can accomplished. Optionally, selective protection of a functional group may be required before or after other functional group manipulations.

Step C.

A piperazine of structure IV is reacted with a compound of structure V or V' in the presence of a reducing agent to form a compound of structure VI or VIII where $R^{12}$ is a cyanide residue. Typical conditions are the reaction of an equi-molar quantity of a piperazine of structure IV and a ketone of structure V or V' in the presence of titanium isopropoxide in a halogenated solvent such as methylene chloride for 1-48 hours. Subsequent addition of a cyanide source such as dimethylaluminum cyanide affords a compound of structure VI or VIII where $R^{12}$ is a cyanide residue.

Step C'

Optionally, functional group introduction such as ring halogenation with chlorine, bromine, NCS, or NBS can be accomplished. Optionally, functional group manipulation (such as reduction, hydrolysis, alkylation) can be accomplished or if $R^3$=halogen, reaction with an organometallic coupling reagent can accomplished.

Step D

Formation of the heterocyclic ring can be accomplished in a single step or require a multi-step reaction sequence. References to such procedures are described above.

Steps E and E'

A secondary piperidine of (deprotected form of structure VI or VII) is either alkylated or acylated to provide compounds of structure VIII or IX. General methods for such alkyations and acylations are described above and are well known to those skilled in the art.

Compounds of Formula 1 can be prepared by the general methods outlined in Scheme 1. Syntheses of the specifically exemplified compounds were prepared as described in detailed below. The following EXAMPLES are being provided to further illustrate the present invention. They are for illustrative purposes only; the scope of the invention is not to be considered limited in any way thereby.

EXAMPLES

The following Preparative Examples are intended to illustrate, but not to limit, the scope of the invention.

Preparative Examples

Preparative Example 1

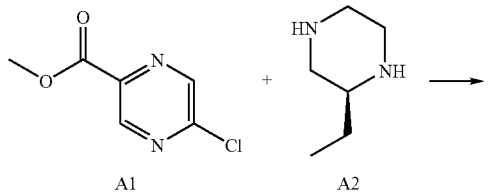

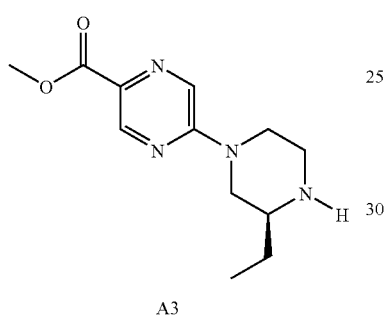

A round bottomed flask was charged with methyl 2-chloropyrazine-5-carboxylate (Lonza, 25.9 g, 145 mmol), 2-S-ethyl piperazine (prepared as per Williams et al J. Med. Chem 1996, 39, 1345, 85% active, 28.0 g, 208 mmol), cesium carbonate (Aldrich, 110 g, 338 mmol) and 1,4 dioxane (400 ml). The resulting suspension was stirred at room temperature for 18 hours and then filtered. The solid was washed with ethyl acetate (3×400 ml). The combined organic solutions were concentrated on a rotary evaporator to remove the solvent. The residue was purified by flash chromatography on silica gel using 5% to 10% methanol in dichloromethane as an eluent to provide A3 as a white solid (28.0 g, 77%).

Preparative Example 2

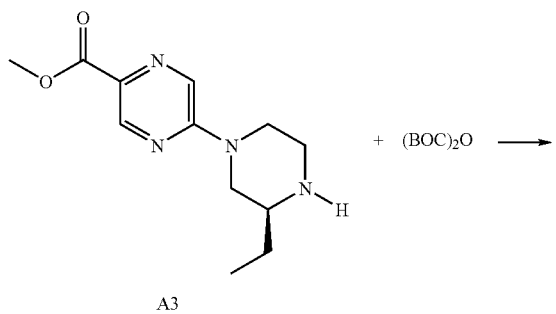

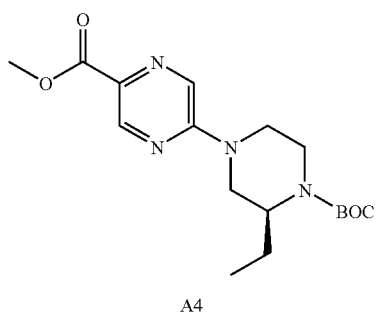

The starting materials A3 (28.0 g, 112 mmol), di-tert-butyl dicarbonate (24.5 g, 112 mmol), and dichloromethane (200 ml) were added to a 1000 ml flask. The resulting solution was stirred at room temperature for 20 hours, treated with 1.0 M aqueous NaOH solution (300 ml), and extracted with dichloromethane (3×200 ml). The combined dichloromethane solutions were dried over sodium sulfate, concentrated on a rotary evaporator to remove the solvent. The residue was dried on house vacuum to afford A4 as a gel (42 g) which was used for the next reaction without further purification.

Preparative Example 3

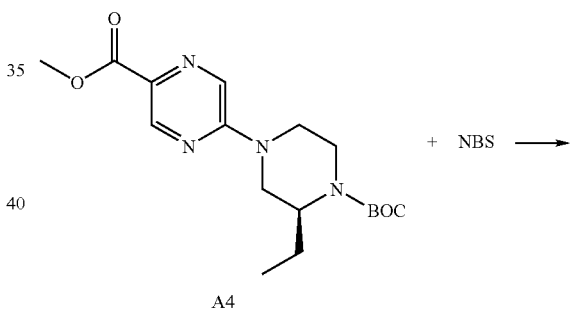

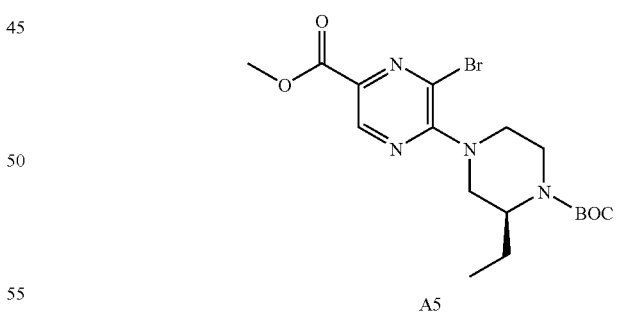

The compound A4 (crude, 42 g) and DMF (300 ml) were charged in a 1000 ml flask. To the stirring solution, NBS (32.0 g, 180 mmol) was added slowly at room temperature. The resulting solution was maintained at the same temperature with stirring for 17 hours, treated with saturated sodium sulfite (200 ml), diluted with ethyl acetate, and separated. The organic layer was washed with water (2×300 ml), dried over sodium sulfate, and concentrated under reduced pressure. Purification of the residue by flash chromatography on silica gel using 3% methanol in dichloromethane afforded A5 as an orange gel (47 g, 98% for 2 steps).

Preparative Example 4

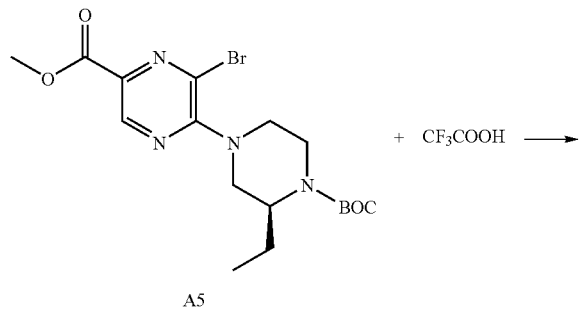

A5

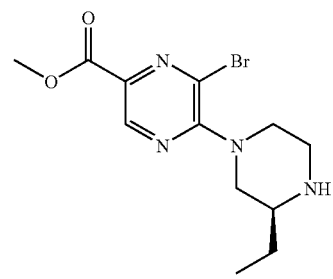

A6

A round bottomed flask was charged with A5 (49.8 g, 116 mmol), trifluoroacetic acid (Acros, 100 ml), and dichloromethane (Aldrich, 100 ml). The resulting solution was stirred at room temperature for 4.5 hours and concentrated to remove the acid. The residue was treated with solid potassium carbonate (35 g), water (100 ml) and 1.0 M NaOH solution at 0° C. The mixture was extracted with dichloromethane (4×300 ml) and the combined organic layers were dried over sodium sulfate and concentrated under reduced pressure. The residue was dried on house vacuum to provide A6 as a brown oil (36.20 g) which was used for the next reaction without purification.

Preparative Example 5

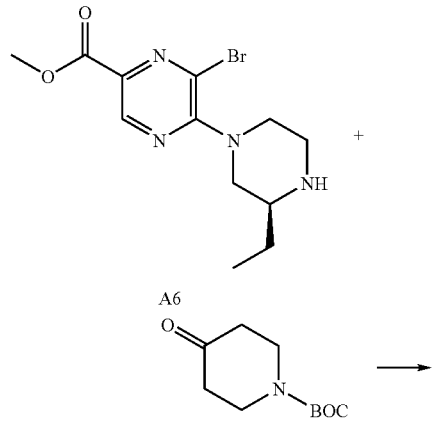

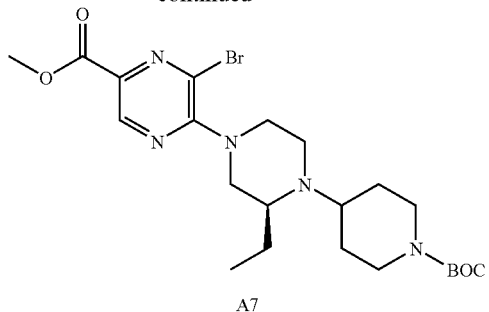

A7

A round-bottomed flask was charged with A6 (36.0 g, 110 mmol), N-Boc piperidine-4-one (70.0 g, 351 mmol), and 1,2-dichloroethane (600 ml). The reducing reagent NaB(OAc)$_3$H (70.0 g, 330 mmol) was added slowly with stirring. The resulting suspension was stirred at room temperature for 3 days before it was treated with 1.0 M sodium hydroxide (800 ml) solution. The mixture was separated and the aqueous solution was extracted with dichloromethane (2×500 ml). The combined organic solutions were dried on sodium sulfate and concentrated on a rotary evaporator. The residue was purified by flash chromatography on silica gel using 20% ethyl acetate in hexanes and 2% methanol in dichloromethane as an eluent to provide A7 as a red gel (38.0 g, 68%).

Preparative Example 6

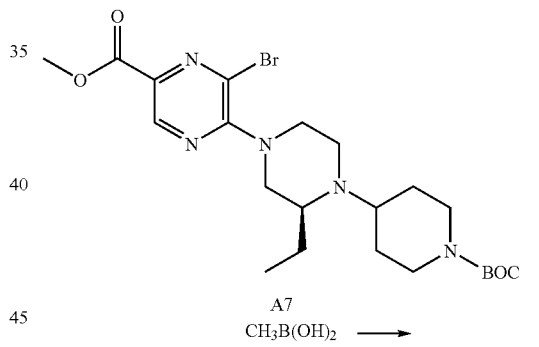

A7
CH$_3$B(OH)$_2$ ⟶

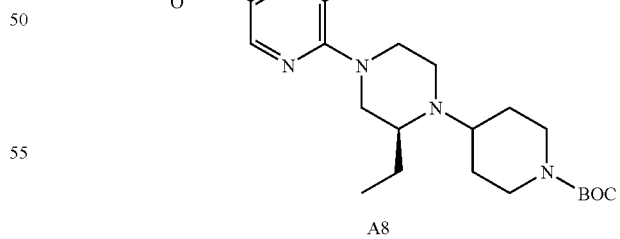

A8

A round-bottomed flask was charged with A7 (10.87 g, 21.21 mmol), methylboronic acid (Aldrich, 3.82 g, 63.82 mmol), potassium carbonate (Aldrich, 15.0 g, 109 mmol), and DMF (100 ml). The resulting suspension was degassed for 30 min via bubbling nitrogen prior to the addition of dichlorobis(triphenylphosphine)palladium (II) (Aldrich, 1.5 g, 2.1 mmol). The reaction mixture was maintained at 85° C.

for 20 hours with stirring, cooled to room temperature, and filtered. The filtrate was diluted with ethyl acetate (800 ml), washed with water (4×300 ml), dried on sodium sulfate, and concentrated on rotary evaporator. The residue was purified by flash chromatography on silica gel using 2% methanol in dichloromethane as an eluent to afford A8 as a red gel (5.95 g, 62%).

Preparative Example 7

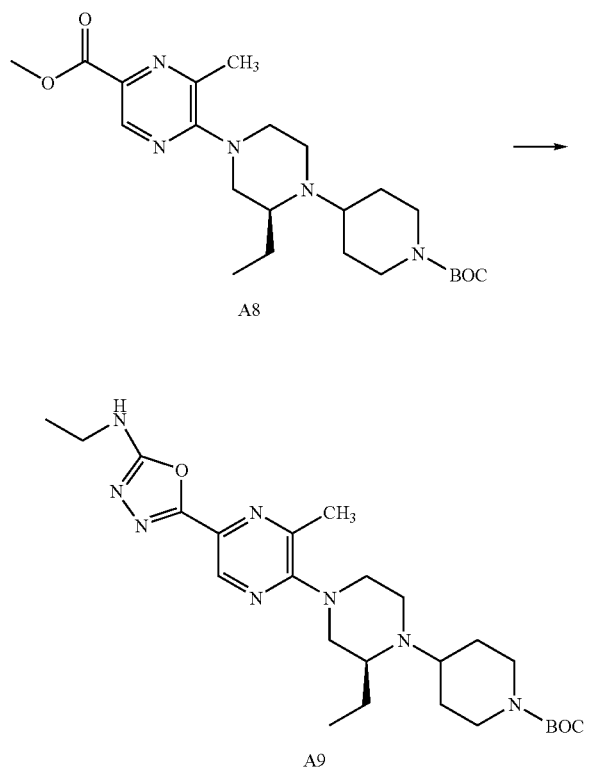

A pressure vessel was charged with A8 (4.23 g, 8.86 mmol), hydrazine (2.83 g, 88.6 mmol), and ethanol (45 ml). The resulting solution was heated to 70° C. for 2 hours, cooled to room temperature, and concentrated on rotary evaporator to dryness. The residue was dissolved in ethyl acetate, washed with water and brine, dried on sodium sulfate, and concentrated under reduced pressure to give a yellow oil. The crude product was dissolved in dichloromethane (20 ml) and treated with ethyl isocyanate (0.92 g, 12.9 mmol). The resulting reaction solution was stirred at room temperature for 3.5 hours prior to the additions of 4-dimethylaminopyridine (0.25 g, 2.05 mmol), triethylamine (6.0 ml, 43 mmol), and p-toluenesulfonyl chloride (1.97 g, 10.4 mmol) at room temperature. The reaction was maintained at room temperature with stirring for 20 hours, diluted with dichloromethane (600 ml). The solution was washed with water (300 ml) and brine (200 ml), dried on sodium sulfate, and concentrated on a rotary evaporator. The residue was purified by flask chromatography on silica gel using 3% to 5% methanol in dichloromethane to provide A9 as a yellow oil (2.62 g, 60%). M+H=501.

Preparative Example 8

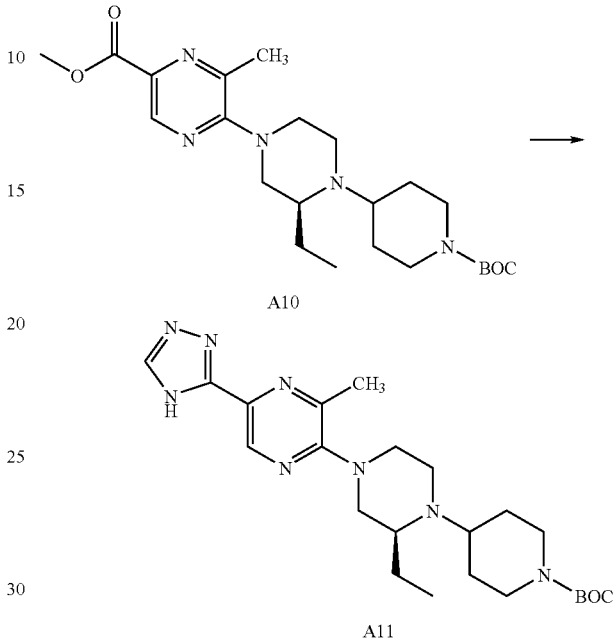

A pressure vessel was charged with ester intermediate A10 (0.083 g, 0.185 mmol) and a solution of ammonia in 1,4-dioxane (10 ml of 0.5 M, 5 mmol). The solution was heated to 100° C. for 12 hours and cooled to room temperature. After evaporation of the solvent, the residue was charged in another pressure vessel and treated with N,N-dimethylformamide dimethyl acetal (2 mL). The reaction vessel was sealed and heated at 110° C. for 2.5 hours. The solvent was evaporated and the brown solid was dissolved in acetic acid (2 mL) in a pressure vessel. To the vessel was added hydrazine monohydrate (0.3 mL, 6.2 mmol), and the sealed reaction vessel was heated at 90° C. for 2 hours. The solvent was removed in vacuo, and the product was purified by reverse phase preparative HPLC to yield intermediate A11 as a TFA salt (0.093 g, 88%). MS, M+H=457.

Preparative Example 9

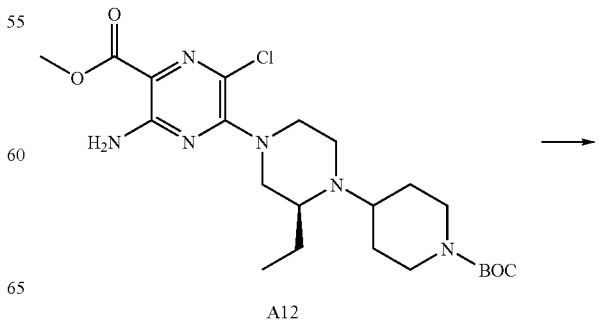

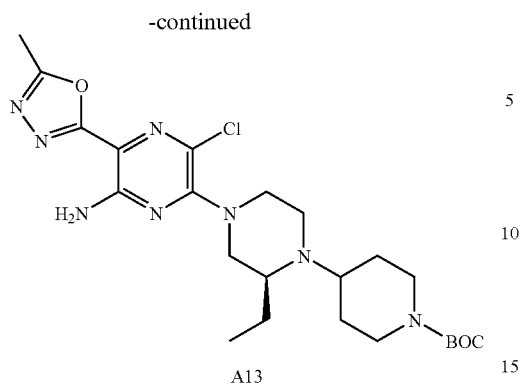

A13

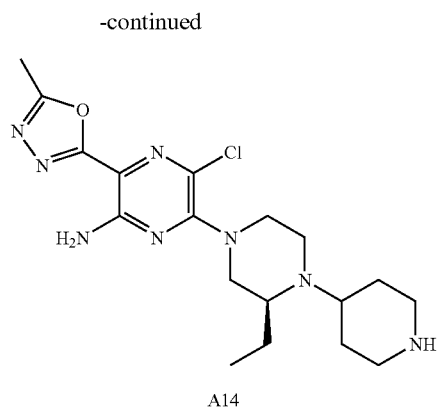

A14

A pressure vessel was charged with A12 (2.0 g, 4.14 mmol), hydrazine (1.6 g, 52.3 mmol), and ethanol (40 ml). The resulting solution was heated to 100° C. for 20 hours, cooled to room temperature, and concentrated to remove the solvent. The residue was purified by flash chromatography on silica gel using 2-7% methanol in dichloromethane as the eluent to afford a yellow oil (1.91 g, 95%). This product was dissolved in dichloromethane (20 ml), treated with acetic anhydride (0.525 g, 5.14 mmol) and triethylamine (0.80 g, 7.9 mmol) at 0° C. The reaction solution was stirred at 0° C. for 4 hours and warmed to room temperature, diluted with dichloromethane, and poured into saturated sodium bicarbonate solution. The organic layer was separated and the aqueous solution was extracted with dichloromethane (3×100 ml). The combined extracts were washed with brine, dried over sodium sulfate, and concentrated on rotary evaporator. The residue was purified by flash chromatography on silica gel using 2% to 10% methanol in dichloromethane to deliver a yellow oil (1.89 g, 91%). This compound was dissolved in dichloromethane (5 ml), treated with p-toluenesulfonyl chloride (0.756 g, 3.96 mmol) and triethylamine (2.18 g, 21.6 mmol) at room temperature. The resulting solution was maintained at that temperature for 20 hours, diluted with dichloromethane (200 ml) and poured into water (200 ml). The aqueous layer was separated and extracted. The combined organic solutions were washed with brine, dried on sodium sulfate, and concentrated under reduced pressure. The residue was purified by flash chromatography on silica gel using 1% to 5% methanol in dichloromethane to provide A13 as a yellow oil (1.45 g, 79%). M+H=507.

A round-bottomed flask was charged with A13 (1.45 g, 2.86 mmol), trifluoroacetic acid (23 g, 202 mmol), and dichloromethane (15 ml). The resulting solution was stirred at room temperature for 5 hours and concentrated under reduced pressure. The dried residue in a flask was treated with sodium carbonate (8 g), 1.0 M NaOH (10 ml), and water (10 ml). After 10 minutes stirring, the mixture was extracted with dichloromethane (3×100 ml). The combined organic solutions were dried over sodium sulfate and concentrated. The residue was dried on house vacuum to afford A14 as a yellow gel (0.85 g, 73%) without further purification.

Preparative Example 11

Preparation of Table 1 Compound No. 23

Preparative Example 10

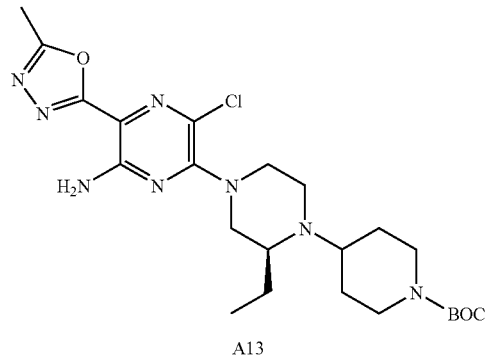

A13

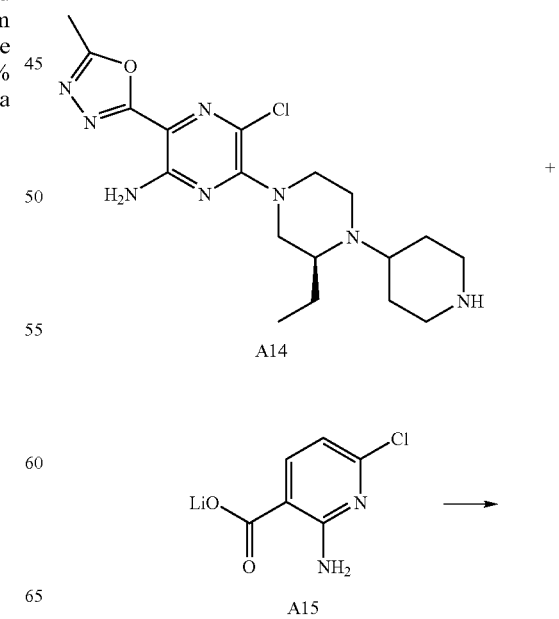

A14

A15

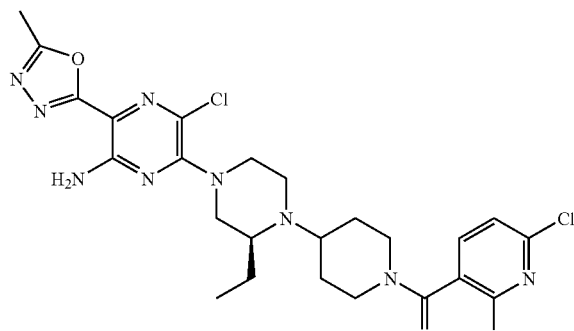

A16

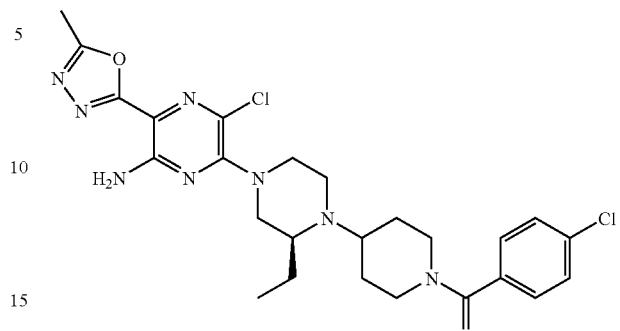

A17

A round bottomed flask was charged with intermediate A14 (0.79 g, 1.94 mmol), lithium 2-amino-6-chloronicotinate (0.52 g, 2.91 mmol, preparation below), 1-[3-(dimethylamino)propyl]-3-ethylcarbodiimide hydrochloride (1.11 g, 5.83 mmol), 1-hydroxybenzotriazole (0.79 g, 5.83 mmol), N,N-diisopropylethylamine (2.51 g, 19.4 mmol) and DMF (7 ml). The resulting solution was stirred at 70° C. After one day the solution was cooled to room temperature, diluted with ethyl acetate (300 ml), washed with water (4×50 ml), dried over sodium sulfate, and concentrated in vacuo. The residue was purified by flash chromatography on silica gel (3% to 8% methanol in methylene chloride as the eluent) to provide the title compound A16 (0.712 g, 65%). M+H=561.

Preparative Example 12

Preparation of Table 1 Compound No. 43

A round bottomed flask was charged with A14 (429 mg, 1.05 mmol), 4-chlorobenzoyl chloride (0.161 ml, 1.26 mmol), triethylamine (0.293 ml, 2.1 mmol), and dichloromethane (20 ml). The resulting solution was stirred at room temperature for 1.5 hours, diluted with dichloromethane, washed with saturated sodium carbonate, and dried over sodium sulfate. The solvent was removed under vacuo and the residue was purified by flash chromatography on silica gel using 5% methanol in dichloromethane to provide the desired compound A17 (565 mg, 99%). M+H=545.

Preparative Example 13

Preparation of Table 1 Compound No. 5 & Compound Example Number 62

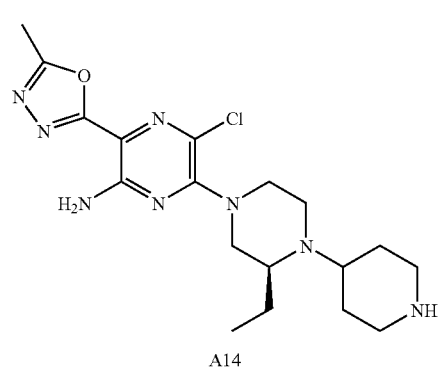

A14

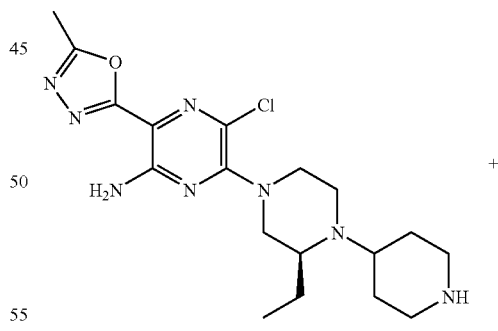

A14

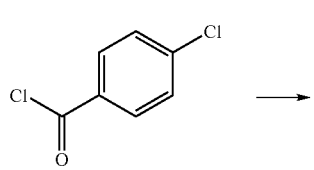

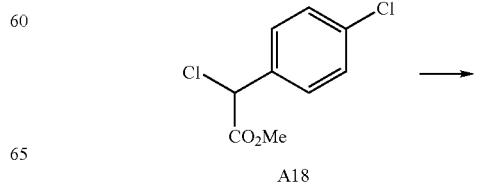

A18

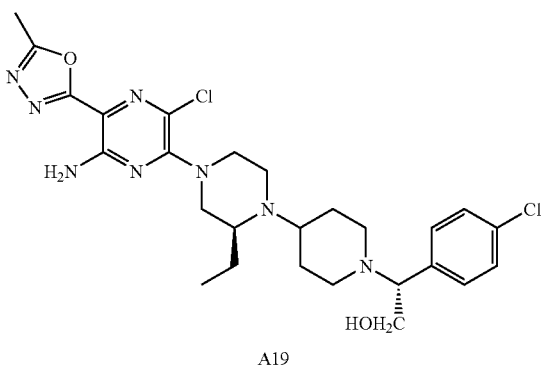

A19

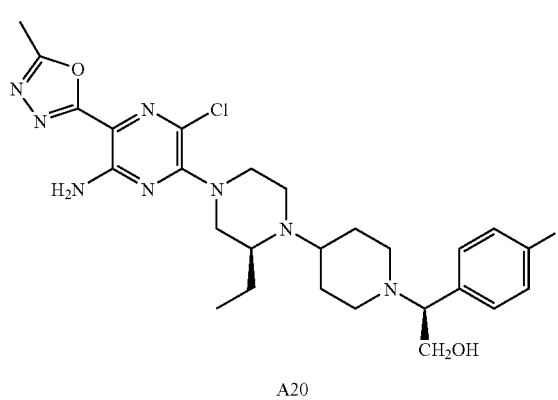

A20

A round-bottomed flask was charged with A14 (142 mg, 1.35 mmol), A18 (92 mg, 1.42 mmol), triethylamine (0.098 ml, 2.70 mmol), sodium iodide (5.3 mg, 0.035 mmol), and DMF (1.5 ml). The resulting solution was stirred at room temperature for 5 hours, diluted with ethyl acetate, and poured into saturated sodium bicarbonate solution. The mixture was extracted with ethyl acetate. The combined organic layers were washed with brine and dried over sodium sulfate. After concentration, the residue was purified on silica gel preparative TLC to afford two isomers (99 mg and 101 mg respectively, 97%). The more polar isomer (44 mg) was dissolved in THF (2 ml) and treated with DIBAL in cyclohexane (0.74 ml of 1.0M, 0.74 mmol) at −15° C. The resulting reaction mixture was maintained at that temperature for 30 min, treated with methanol and saturated sodium bicarbonate. The mixture was extracted with ethyl acetate. The combined organic layers were dried over sodium sulfate and concentrated. The purification of the residue on silica gel preparative TLC provided A19 as a yellow solid (31 mg, 76%). M+H=561. The same procedure from the less polar isomer delivered the desired product A20 in a 69% yield. The configurations of the benzylic chiral center in A19 and A20 were tentatively assigned.

Preparative Example 14

Preparation of Table 1 Compound No. 59

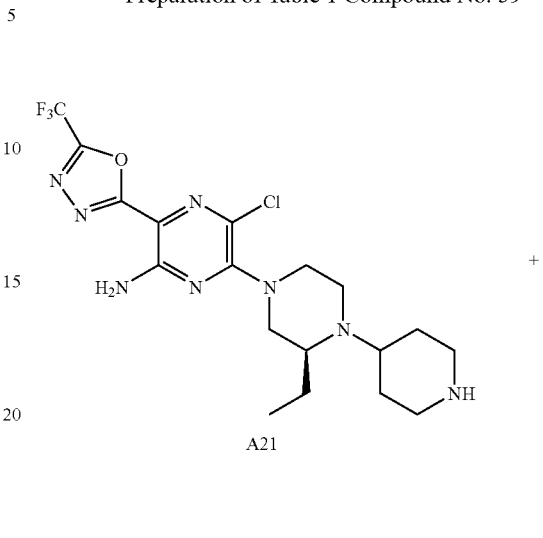

A21

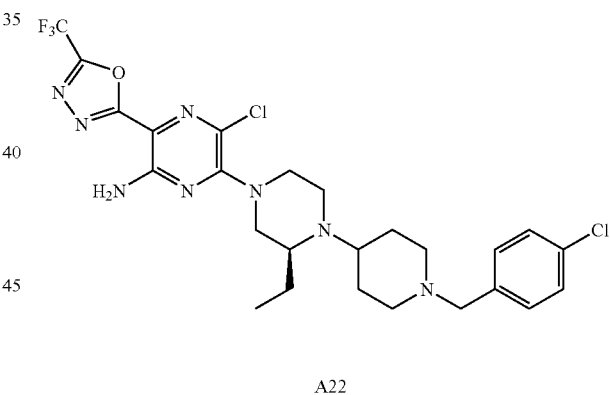

A22

A round-bottomed flask was charged with A21 (36 mg, impure, ~0.048 mmol), 4-chlorobenzyl chloride (0.012 ml, 0.072 mmol), sodium iodide (11 mg, 0.072 mmol), triethylamine (0.02 ml, 0.14 mmol), and DMF (0.5 ml). The resulting reaction mixture was stirred at room temperature for 5.5 hours, diluted with dichloromethane, and treated with saturated sodium sulfate solution. The mixture was extracted with dichloromethane. The combined extracts were washed with brine, dried over sodium sulfate, and concentrated on a rotary evaporator. The purification of the residue by silica preparative TLC afforded A22 as a solid (16.5 mg, 59%). M+H=585.

Preparative Example 15

Preparation of Table 1 Compound No. 28

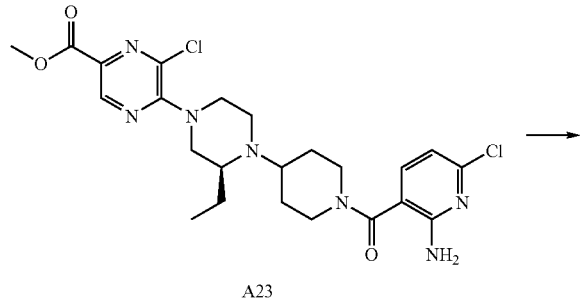

A23

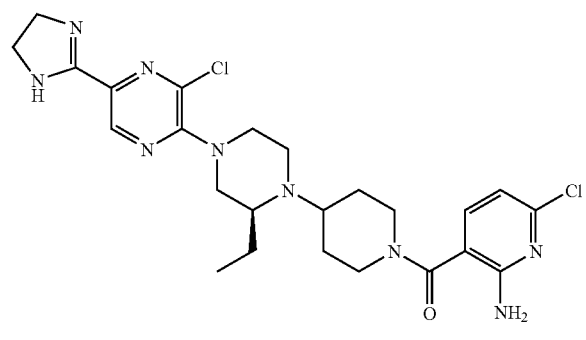

A24

A pressure vessel was charged with intermediate A23 (19 mg, 0.035 mmol) and a solution of ammonia in 1,4-dioxane (5 ml of 0.5 M, 2.5 mmol). The solution was heated to 100° C. for 12 hours and cooled to room temperature. After evaporation of the solvent, the residue was charged in a round-bottomed flask and treated with dichloromethane (0.5 ml) and pyridine (0.015 ml, 0.18 mmol). The resulting solution was added with trifluoroacetic anhydride (0.016 ml, 0.11 mmol) at 0° C., stirred for 6 hours at 0° C. to room temperature, diluted with ethyl acetate, and poured into saturated sodium bicarbonate. The mixture was extracted with ethyl acetate. The combined organic layers were washed with brine and dried over sodium sulfate. After concentration, the residue was purified by silica preparative TLC to afford a cyano compound (17 mg, 85%). A round-bottomed flask was charged with toluene (0.5 ml), ethylene diamine (0.02 ml, 0.29 mmol), and a solution of trimethylaluminum in toluene (0.1 ml Of 2 M, 0.20 mmol). To this mixture was added a solution of the above cyano compound (17 mg, 0.029 mmol) in toluene (1 ml). The resulting solution was heated to 70° C. for 10 hours, cooled to room temperature, diluted with ethyl acetate, and treated with saturated sodium carbonate. The mixture was extracted with ethyl acetate. The combined organic layers were washed with brine and dried on sodium sulfate. After concentration, the residue was purified by silica gel preparative TLC (10% methanol in dichloromethane) to afford A24 as a solid (5.7 mg, 35%). M+H=532.

Preparative Example 16

Preparation of Table 1 Compound No. 4

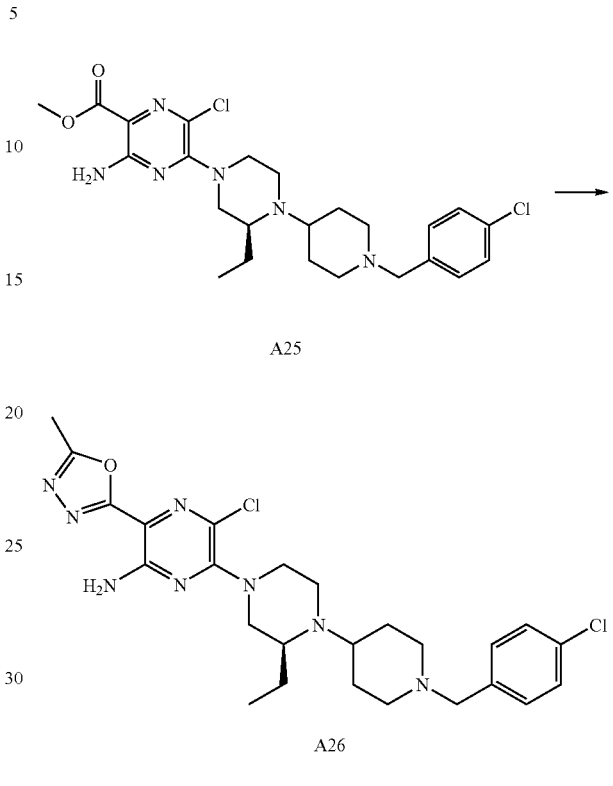

A pressure vessel was charged with A25 (142 mg, 0.28 mmol), hydrazine (0.04 ml, 1.12 mmol), and ethanol (3 ml). The resulting solution was heated to 100° C. for 20 hours, cooled to room temperature, and concentrated to remove the solvent. The residue was purified by flash chromatography on silica gel using 5% to 10% methanol in dichloromethane as the eluent to afford an intermediate (115 mg, 81%). This product (42 mg, 0.082 mmol) was dissolved in dichloromethane (1 ml), treated with acetic anhydride (0.010 ml, 0.11 mmol) and triethylamine (0.027 ml, 0.164 mmol) at 0° C. The reaction solution was stirred at 0° C. and warmed to room temperature for 1.5 hours, diluted with dichloromethane, and poured into saturated sodium bicarbonate solution. The organic layer was separated and the aqueous solution was extracted with dichloromethane. The combined extracts were washed with brine, dried over sodium sulfate, and concentrated on a rotary evaporator. The residue was purified by flash chromatography on silica gel using 10% methanol in dichloromethane to deliver an amide (43.2 mg, 96%). This compound (8.7 mg, 0.016 mmol) was dissolved in dichloromethane (0.2 ml), treated with trifluoroacetic anhydride (0.008 ml, 0.045 mmol) and pyridine (0.004 ml, 0.048 mmol) at −10° C. The resulting solution was warmed to room temperature and maintained at that temperature for 20 hours, diluted with dichloromethane (10 ml), and poured into 10% NaOH aqueous solution. The aqueous layer was separated and extracted. The combined organic solutions were washed with brine, dried on sodium sulfate, and concentrate under reduced pressure. The residue was purified by silica gel preparative TLC to provide A26 (5.3 mg, 63%). M+H=531.

Preparative Example 17

Preparation of Table 1 Compound No. 16

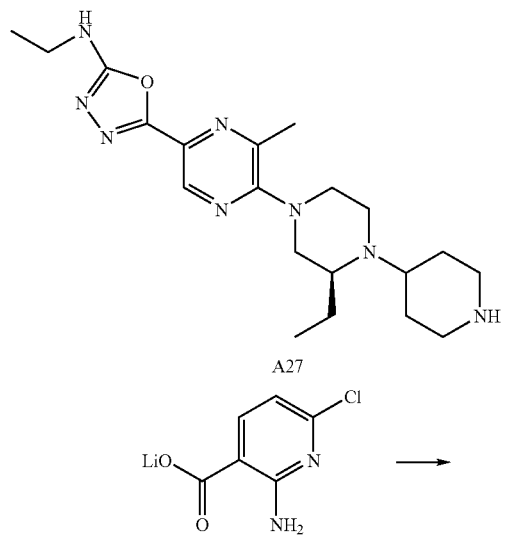
A27

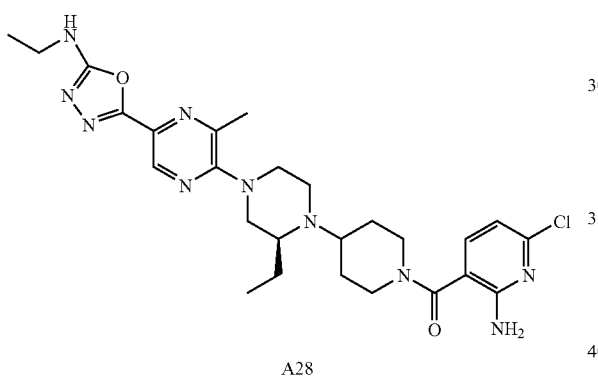
A28

Compound A28 was prepared by the same method shown for Preparative Example 11. M+H=555.

Preparative Example 18

Preparation of Table 1 Compound No. 93

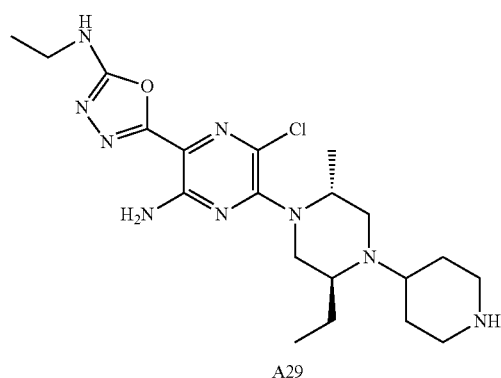
A29

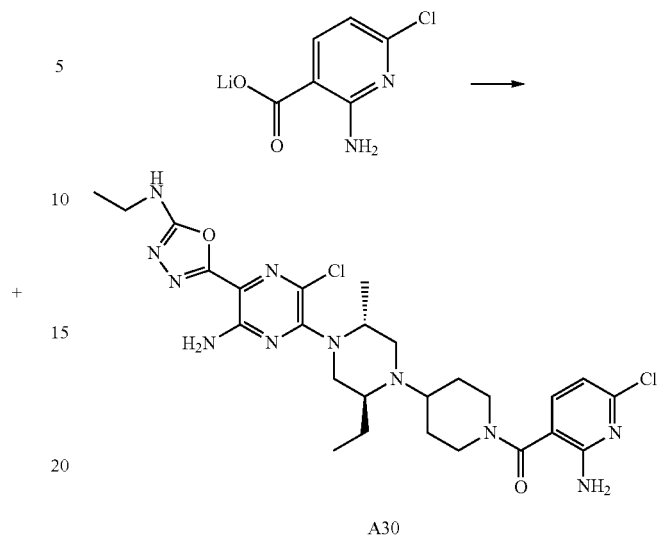
A30

Compound A30 was prepared by the same method shown for Preparative Example 11. M+H=604.

Preparative Example 19

Preparation of Table 1 Compound No. 94

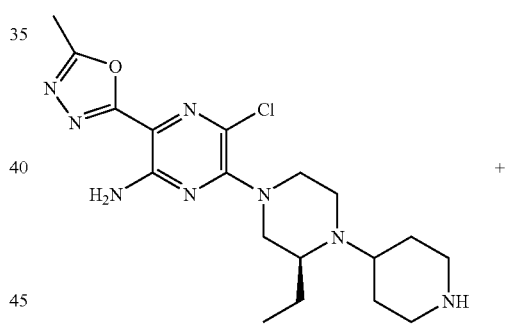
A31

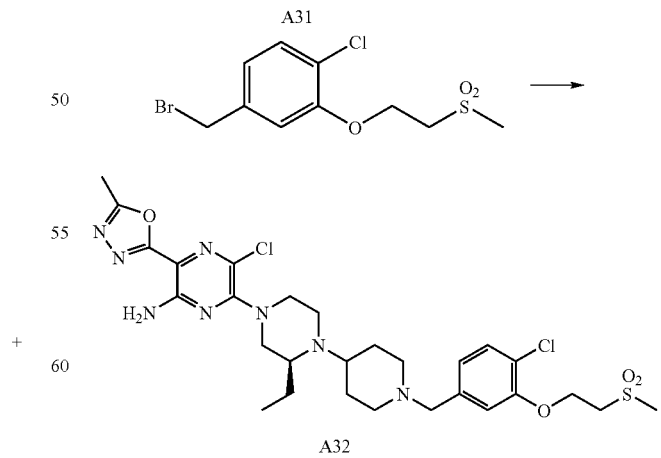
A32

Compound A32 was prepared by the same method shown for Preparative Example 14. M+H=653.

Preparative Example 20

Preparation of Table 1 Compound No. 1

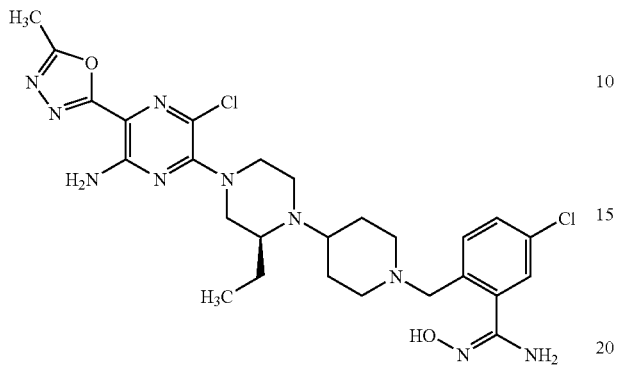

Compound No. 1 of Table 1, was prepared by alkylation of Compound A14 with 2-cyano benzyl bromide as in Preparative Example 14. Further treatment of the intermediate ester with hydroxylamine hydrochloride (13 mg, 300 mole %) in sodium carbonate and reflux for 16 h afforded Compound No 1. (11 mg).

Preparative Example 21

Step A

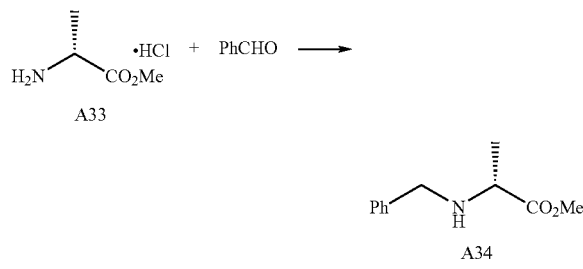

Benzaldehyde (19 mL, 19 g, 0.18 mol) was added to a solution of D-alanine methyl ester hydrochloride (25 g, 0.18 mol) in dry CH$_2$Cl$_2$ (300 mL). The solution was stirred at 22° C. for 19 h. The reaction mixture was cooled with an ice-water bath and solid sodium triacetoxyborohydride (46 g, 0.22 mol) was added in portions over ~15 min. The cooling bath was removed and the milky white solution was stirred at 22° C. for 7 h. The solvent was removed by rotary evaporation under reduced pressure and the resulting slush was partitioned between EtOAc (~100 mL) and 1 N HCl (~400 mL). The aqueous layer was extracted with EtOAc (~50 mL). The aqueous layer was adjusted to pH ~10 with 1 N NaOH (450 mL) and the milky aqueous layer was extracted immediately with EtOAc (3×250 mL). The combined organic layers were washed with brine (~250 mL), dried over anhydrous MgSO$_4$, filtered and concentrated under reduced pressure to afford N-benzyl-D-alanine methyl ester (28 g, 80%) as a colorless semi-solid.

Step B.

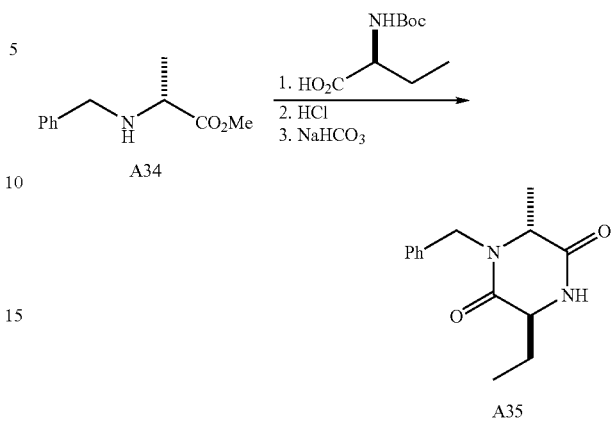

To a solution of N-benzyl-D-alanine methyl ester (28 g, 0.15 mol) and EDCl.HCl (30.6 g, 0.160 mmol) in CH$_2$Cl$_2$ (250 mL) was added a solution of N-Boc-2(S)-aminobutyric acid (29.5 g, 0.145 mol; Anaspec, Inc.) in CH$_2$Cl$_2$ (100 mL). The reaction mixture was stirred at 22° C. for 16 h. Additional N-Boc-2(S)-aminobutyric acid (5.9 g, 29 mmol) and EDCl.HCl (11.1 g, 58 mmol) and DMF (20 mL) were added. After 1 day, the solvents were removed under reduced pressure, and the residue was dissolved in EtOAc. The organic solution was washed with 0.5 N aqueous HCl, saturated aq. sodium carbonate, brine, and was then dried over anhydrous sodium sulfate. Subsequent filtration and concentration gave a colorless oil The oil was dissolved in CH$_2$Cl$_2$ (200 mL) and HCl gas was bubbled into the stirred solution for 1.5 h. After removal of solvent under reduced pressure, the resulting white solid was suspended in EtOAc (500 mL) and aqueous NaHCO$_3$ solution (150 mL). The mixture was stirred at rt for 18 h. The organic layer was separated, washed with brine, dried over anhydrous MgSO$_4$, filtered, and concentrated to give Compound A35 (21.9 g, 61% over 2 steps).

Step C.

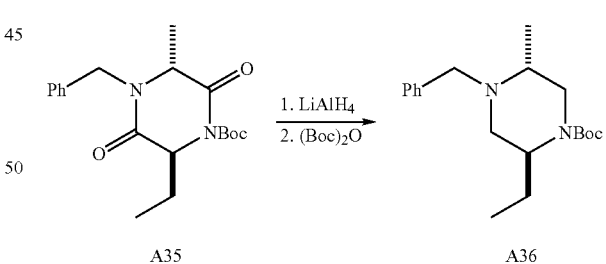

The diketopiperazine A35 (21.9 g, 89 mmol) was dissolved in dry THF (500 mL). Powdered LiAlH$_4$ (10.1 g, 267 mmol) was added cautiously and in portions over ~30 min. The reaction mixture was stirred at 22° C. for 1 h, at 65° C. for 1 d, and then at 22° C. for a further 24 h. The reaction was quenched by cautious dropwise addition of water (10 mL) over 1 h. 1 N aqueous NaOH solution (20 mL) and water (30 mL) were added sequentially and the milky white reaction mixture was stirred at rt for 1 h. The white gelatinous precipitate that formed was removed by filtration through Celite®. The filter cake was washed copiously with EtOAc (~500 mL). The combined filtrates were evaporated. The residue was dissolved in Et₂O (~500 mL) and then taken to dryness to afford 2(S)-ethyl-4-benzyl-5(R)-methylpiperazine (18.4 g, 93%) as a pale golden yellow oil.

The piperazine above (18.3 g, 84 mmol) was dissolved in CH₂Cl₂ (40 mL) and solid di-t-butyl dicarbonate (18.3 g, 84 mmol) was added. After stirring for 30 min at rt, the solvent was removed and the resulting yellow liquid was purified by flash column chromatography, eluting with 3:1 hexanes-Et₂O, to afford 1-Boc-2(S)-ethyl-4-benzyl-5(R)-methylpiperazine (A36) as a clear, colorless liquid (24.9 g, 93%).

Step D.

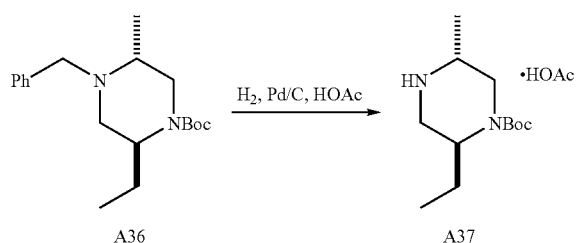

A mixture of 1-Boc-2(S)-ethyl-4-benzyl-5(R)-methylpiperazine (A36; 13.6 g, 43 mmol), glacial acetic acid (2.5 mL) and 10% Pd/C (4.5 g) in methanol (150 mL) was shaken under H₂ atmosphere (50 psi) for 24 h. The mixture was filtered through Celite® and the filter cake was washed copiously with EtOAc (~500 mL). The combined filtrates were dried over anhydrous MgSO₄, filtlered, and concentrated under reduced pressure to afford a clear colorless oil. Further co-evaporation with CH₂Cl₂ (200 mL) and Et₂O (2×200 mL) gave the desired 1-Boc-2(S)-ethyl-5(R)-methylpiperazine acetic acid salt (A37, 9.7 g) as a viscous oil.

Preparative Example 22

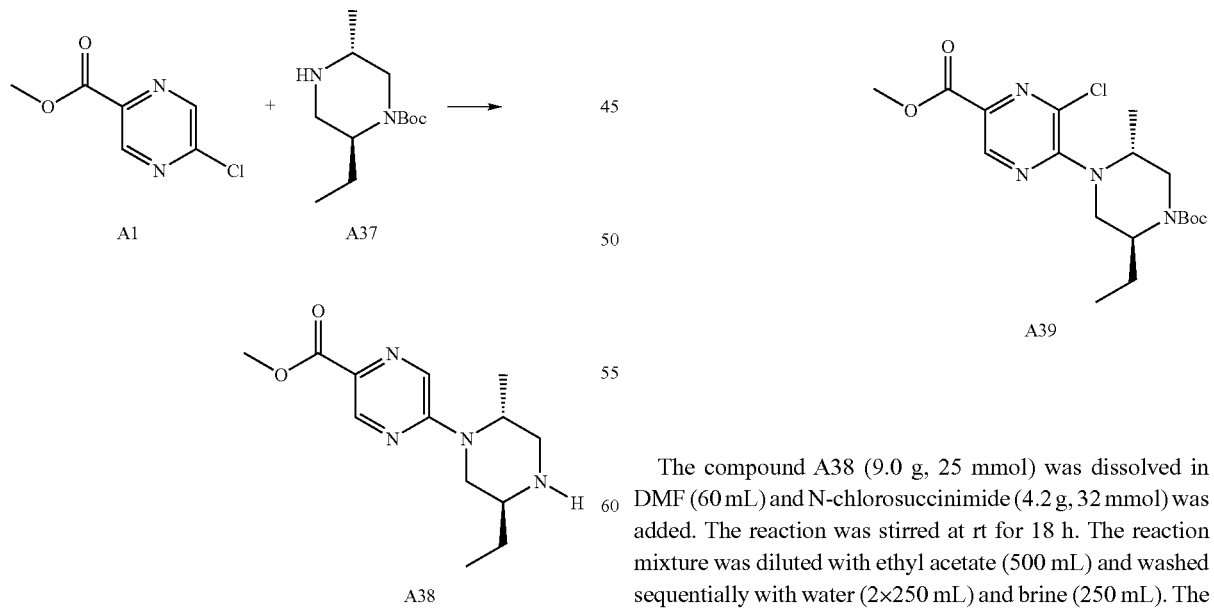

1-Boc-2(S)-ethyl-5(R)-methylpiperazine acetic acid salt (10 g) was dissolved in dichloromethane (100 mL) and treated with triethylamine (4 mL, 3 g). Solvent was evaporated and the residue was passed through a silica gel column, eluting with 3% methanol (containing ammonia) in dichloromethane, to give 1-Boc-2(S)-ethyl-5(R)-methylpiperazine free base (7.2 g).

A round bottomed flask was charged with methyl 2-chloropyrazine-5-carboxylate (Lonza, 4.83 g, 28 mmol), 1-Boc-2(S)-ethyl-5(R)-methylpiperazine free base (6.4 g, 28 mmol), cesium carbonate (Aldrich, 14 g, 42 mmol) and 1,4 dioxane (100 ml). The resulting suspension was stirred at 100° C. for 2 d and then filtered. The solid was washed with ethyl acetate (3×400 ml). The combined organic solutions were concentrated on a rotary evaporator to remove the solvent. The residue was purified by flash chromatography on silica gel using 1% methanol (containing 10% ammonium hydroxide) in dichloromethane as an eluent to provide A38 (9.0 g, 90%), as a beige solid Preparative Example 23

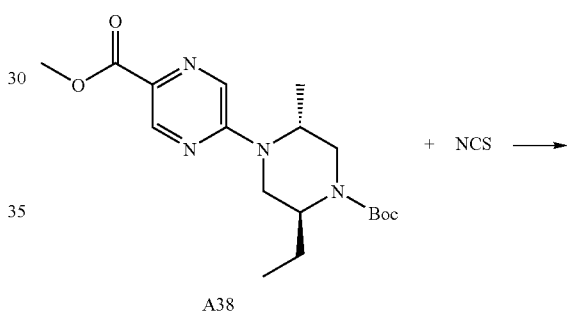

The compound A38 (9.0 g, 25 mmol) was dissolved in DMF (60 mL) and N-chlorosuccinimide (4.2 g, 32 mmol) was added. The reaction was stirred at rt for 18 h. The reaction mixture was diluted with ethyl acetate (500 mL) and washed sequentially with water (2×250 mL) and brine (250 mL). The organic phase was dried over anhydrous magnesium sulftate, filtered, and concentrated under reduced pressure to afford A39 (7.95 g, 81%) as a pale yellow solid.

Preparative Example 24

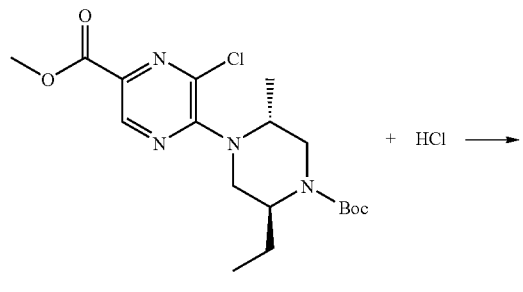

A39

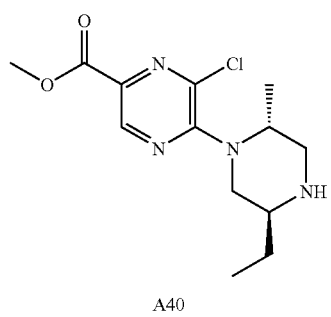

A40

The compound A39 (7.95 g, 20 mmol) was dissolved in methanol (15 mL) and was treated with HCl (25 mL, 4 M in dioxane, 100 mmol). After stirring for 3 h at rt, solvent was removed to afford a yellow crude product. The crude product was taken up in methanol (100 mL), treated with triethylamine (10 mL), the solution concentrated under reduced pressure, and the residue purified by flash column chromatography, eluting with 4.5% methanol (containing ammonia) in dichloromethane. The desired product A40 (4.8 g, 81%).

Preparative Example 25

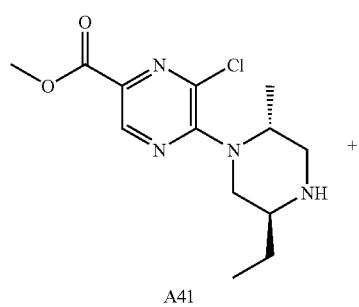

A41

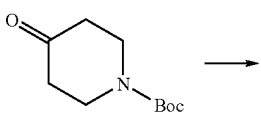

-continued

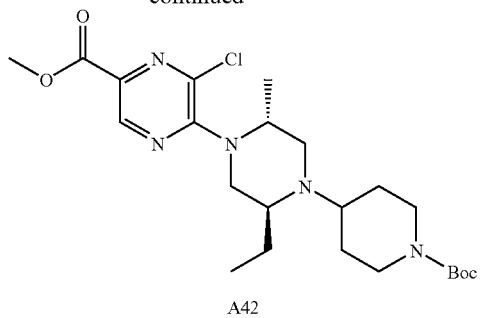

A42

A round-bottomed flask was charged with A41 (4.8 g, 16 mmol), N-Boc-4-piperidone (9.61 g, 48 mmol), and dichloromethane (60 mL) and the resulting solution was stirred at rt for 30 min. The reducing reagent $NaBH(OAc)_3$ (10.2 g, 48 mmol) was added slowly with stirring. The resulting suspension was stirred at rt for 1 h, then diluted with dichloromethane (40 mL), and stirred at rt for 18 h. 1.0 M Aqueous sodium bicarbonate (300 mL) solution was added and the mixture was stirred at rt for 2 h. The mixture was separated and the aqueous solution was extracted with dichloromethane (2×500 mL). The combined organic solutions were dried on sodium sulfate and concentrated on a rotary evaporator. The residue was purified by flash chromatography on silica gel using 1.5% methanol (containing 10% ammonium hydroxide) in dichloromethane as an eluent to provide A42 as a pale yellow solid (6.50 g, 85%).

Preparative Example 26

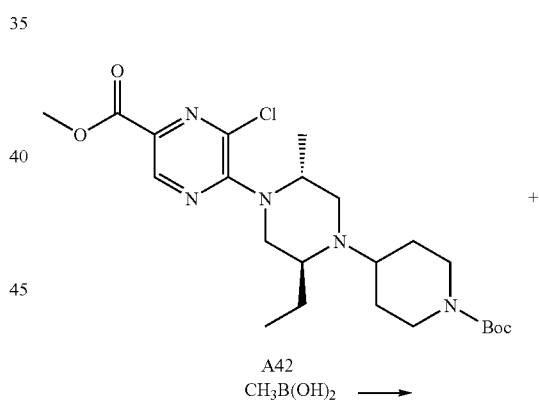

A42
$CH_3B(OH)_2$

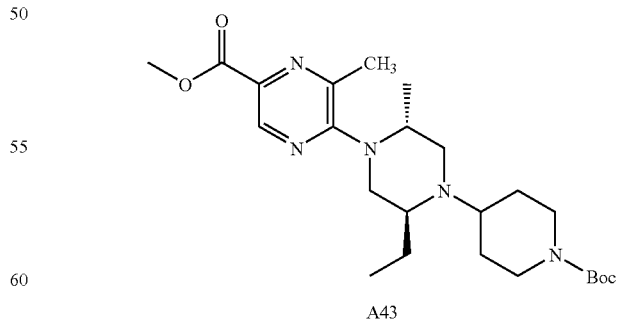

A43

A round-bottomed flask was charged with A42 (4.83 g, 10 mmol), methylboronic acid (Aldrich, 1.8 g, 30 mmol), potassium carbonate (Aldrich, 6.9 g, 50 mmol), and DMF (30 mL). The resulting suspension was degassed for 30 min via bub-

Preparative Example 27 bling nitrogen prior to the addition of dichlorobis(triphenylphosphine)palladium(II) (Aldrich, 351 mg, 0.5 mmol). The reaction mixture was maintained at 100° C. for 3 hours with stirring, cooled to room temperature, and filtered. The filtrate was diluted with ethyl acetate (200 mL), washed with water (3×150 mL) and brine (150 mL). The organic phase was dried on sodium sulfate and concentrated under reduced pressure to afford crude product A43 as a light brown solid (4.16 g), which was used subsequently without further purification.

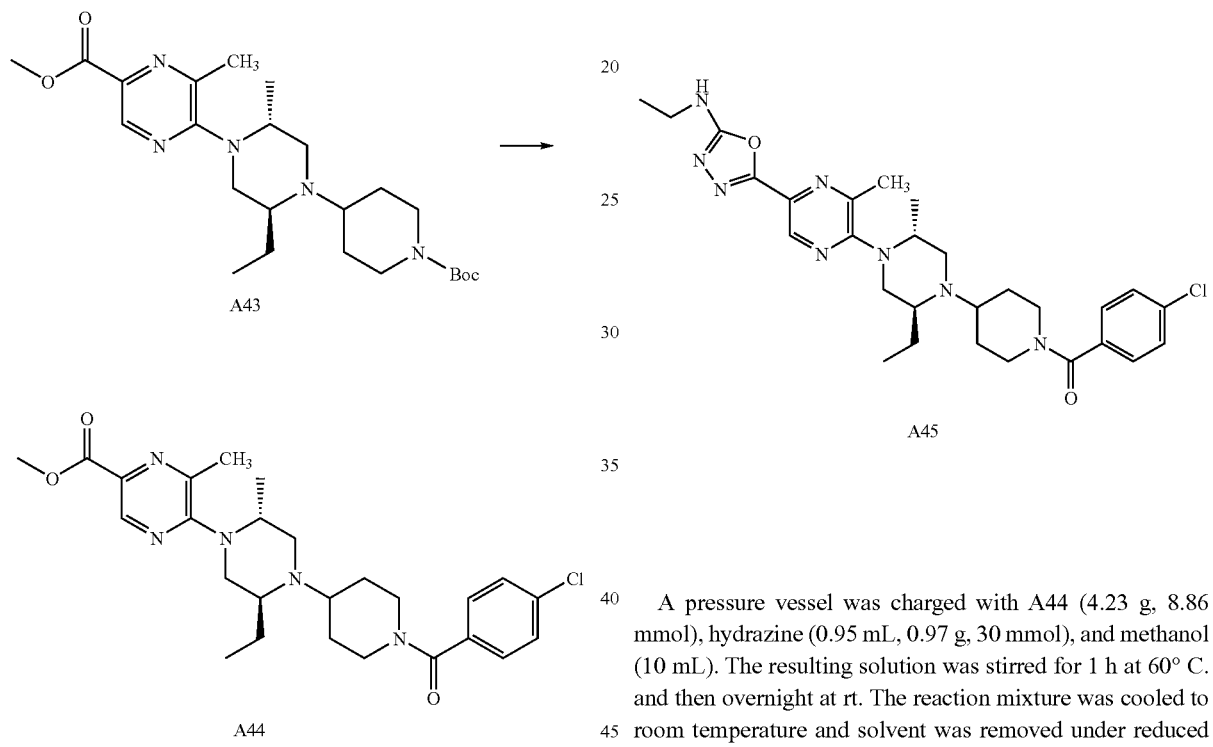

The crude product A43 (4.2 g) was stirred with hydrogen chloride solution (10 mL, 4 M in 1,4-dioxane) in methanol (10 mL) at rt for 18 h. Evaporation of solvent gave a light brown solid (4.6 g), a portion of which (2.5 g) was suspended in DMF (10 mL). Triethylamine (3.5 mL, 2.5 g, 25 mmol), 4-chlorobenzoic acid (1.5 g, 7.3 mmol), and HATU (2.81 g, 7.4 mmol) were added sequentially, and the mixture was stirred overnight at rt. The reaction mixture was diluted with water (50 mL) and extracted with EtOAc (2×200 mL). The organic extracts were washed with brine (100 mL), dried over anhydrous MgSO$_4$, filtered, and concentrated under reduced pressure. The residue was purified by flash chromatography on silica gel using 2% methanol (containing 10% ammonium hydroxide) in dichloromethane as an eluent to provide A44 as a pale yellow solid (1.50 g, 61%).

Preparative Example 28

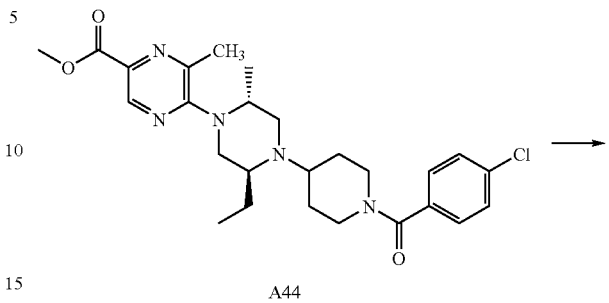

A pressure vessel was charged with A44 (4.23 g, 8.86 mmol), hydrazine (0.95 mL, 0.97 g, 30 mmol), and methanol (10 mL). The resulting solution was stirred for 1 h at 60° C. and then overnight at rt. The reaction mixture was cooled to room temperature and solvent was removed under reduced pressure. The residue was dissolved in ethyl acetate, washed with water and brine, dried on sodium sulfate, and concentrated under reduced pressure to give a yellow oil. The crude product was dissolved in dichloromethane (10 mL) and treated with ethyl isocyanate (0.23 mL, 207 mg, 3.0 mmol). The resulting reaction solution was stirred at room temperature for 1 h prior to the additions of 4-dimethylaminopyridine (146 mg, 1.2 mmol), triethylamine (0.40 mL, 290 mg, 2.9 mmol), and p-toluenesulfonyl chloride (550 mg, 2.9 mmol) at room temperature. The reaction was maintained at room temperature with stirring for 20 h. The solvent was removed under reduced pressure and replaced with ethyl acetate (100 mL), washed with saturated sodium bicarbonate solution (25 mL), water (25 mL), and brine (25 mL). The organic phase was dried on magnesium sulfate, filtered, and concentrated on a rotary evaporator. The residue was purified by flash chromatography on silica gel using 3% methanol (containing 10% ammonium hydroxide) in dichloromethane to provide A45 as a beige solid (0.90 g, 54%). M+H=553.

Lithium 2-amino-5-chloronicotinate

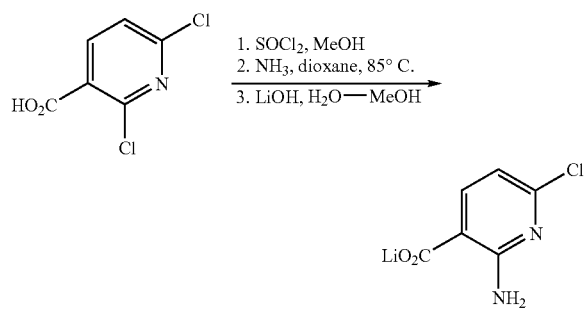

A solution of 2,5-dichloronicotinic acid (20.2 g, 0.105 mol) in methanol (500 mL) was cooled to 0° C. and neat thionyl chloride (38 mL, 63 g, 0.525 mol) was added over ~30 min. The reaction mixture was stirred at 0° C. for 1 hour. The cooling bath was removed, the reaction temperature was allowed to warm to rt, and the reaction was allowed to stir for an additional 2 days at room temperature and the solvent was removed under reduced pressure to give an off-white residue. The residue was dissolved in $Et_2O$ (~500 mL) and the resulting solution was washed successively with saturated aqueous $NaHCO_3$ solution (~300 mL), water (~300 mL), and brine (~300 mL). The organic layer was separated, dried over anhydrous $MgSO_4$, and filtered. Removal of the solvent under reduced pressure yielded methyl 2,5-dichloronicotinate (21.0 g, 97%) as a white solid.

Performed in duplicate on identical scales in two pressure vessels, methyl 2,5-dichloronicotinate (4.5 g, 22 mmol) was dissolved in ammonia solution (250 mL, 0.5 M in 1,4-dioxane; 0.125 mol). The pressure vessels were sealed and heated at (85±5)° C. for 9 days. The two reaction mixtures were allowed to cool to room temperature, then combined and concentrated under reduced pressure to yield a white solid. Dissolution of the solid in 1:1 acetone-MeOH (~500 mL), followed by adsorption onto silica gel (25 g) and then purification by flash column chromatography (25:10:1 hexane-$CH_2Cl_2$-$Et_2O$), gave 6.08 g (75%) of methyl 2-amino-5-chloronicotinate.

A solution of $LiOH.H_2O$ (1.38 g, 33 mmol) in water (33 mL) was added in one portion to a suspension of methyl 2-amino-5-chloronicotinate (6.08 g, 27 mmol) in MeOH (110 mL). The reaction mixture was stirred at 70° C. for 24 hours, and gradually became homogeneous. The solvents were removed under reduced pressure, and after the resulting white solid was dried under vacuum (<1 mmHg) to constant weight, 5.51 g (95%) of lithium 2-amino-5-chloronicotinate was obtained.

Biological Examples

The inventive compounds can readily be evaluated to determine activity at The CXCR3 receptors by known methods, such as, for example, Development of Human CXCR3 (N-delta 4) Binding Assay.

Cloning and Expression of Human CXCR3 (N-delta 4):
The DNA encoding human CXCR3 was cloned by PCR using human genomic DNA (Promega, Madison, Wis.) as a template. The PCR primers were designed based on the published sequence of human orphan receptor GPR9 (1) with incorporated restriction sites, a Kozak consensus sequence, CD8 leader and Flag tag. The PCR product was subcloned into the mammalian expression vector pME18Sneo, a derivative of the SR-alpha expression vector (designated as pME18Sneo-hCXCR3 (N-delta 4).

IL-3-dependent mouse pro-B cells Ba/F3 were transfected by electroporation in 0.4 ml Dulbecco's PBS containing $4 \times 10^6$ cells with 20 µg of pME18Sneo-hCXCR3 (N-delta 4) plasmid DNA. Cells were pulsed at 400 Volts, 100 OHMs, 960 µFd. The transfected cells were under selection with 1 mg/ml G418 (Life Technologies, Gaithersburg, Md.). G418-resistant Ba/F3 clones were screened for CXCR3 expression by specific binding of [$^{125}$I] IP-10 (NEN Life Science Products, Boston, Mass.).

Preparation of Ba/F3-hCXCR3 (N-delta 4) Membranes:

Ba/F3 cells expressing human CXCR3 (N-delta 4) were pelleted and resuspended in the lysis buffer containing 10 mM HEPES, pH 7.5 and Complete® protease inhibitors (1 tablet per 100 ml) (Boehringer Mannheim, Indianapolis, Ind.) at a cell density of $20 \times 10^6$ cells per ml. After 5 minutes incubation on ice, cells were transferred to 4639 cell disruption bomb (Parr Instrument, Moline, Ill.) and applied with 1,500 psi of nitrogen for 30 minutes on ice. Large cellular debris was removed by centrifugation at 1,000×g. Cell membrane in the supernatant was sedimented at 100,000×g. The membrane was resuspended in the lysis buffer supplemented with 10% sucrose and stored at −80° C. Total protein concentration of the membrane was determined by BCA method from Pierce (Rockford, Ill.).

Human CXCR3 (N-delta 4) Scintillation Proximity Assay (SPA):

For each assay point, 2 µg of membrane was preincubated for 1 hr with 300 µg wheat germ agglutinin (WGA) coated SPA beads (Amersham, Arlington Heights, Ill.) in the binding buffer (50 mM HEPES, 1 mM $CaCl_2$, 5 mM $MgCl_2$, 125 mM NaCl, 0.002% $NaN_3$, 1.0% BSA) at room temperature. The beads were spun down, washed once, resuspended in the binding buffer and transferred to a 96-well Isoplate (Wallac, Gaithersburg, Md.). 25 pM of [$^{125}$I] IP-10 with tested compounds in a series of titration were added to start the reaction. After 3 hr reaction at room temperature, the amount of [$^{125}$I] IP-10 bound to the SPA beads was determined with a Wallac 1450 Microbeta counter.

The Ki values for the various example compounds of the present invention are given in the afore-mentioned Table 1. From these values, it would be apparent to the skilled artisan that the compounds of the invention have excellent utility CXCR3 antagonists.

While the present invention has been describe in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:

1. A compound having the general structure shown in Formula 1:

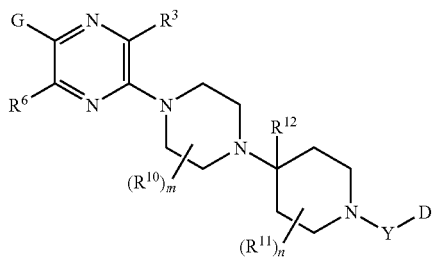

Formula 1 or a pharmaceutically acceptable salt thereof, wherein:
G is selected from the group consisting of:

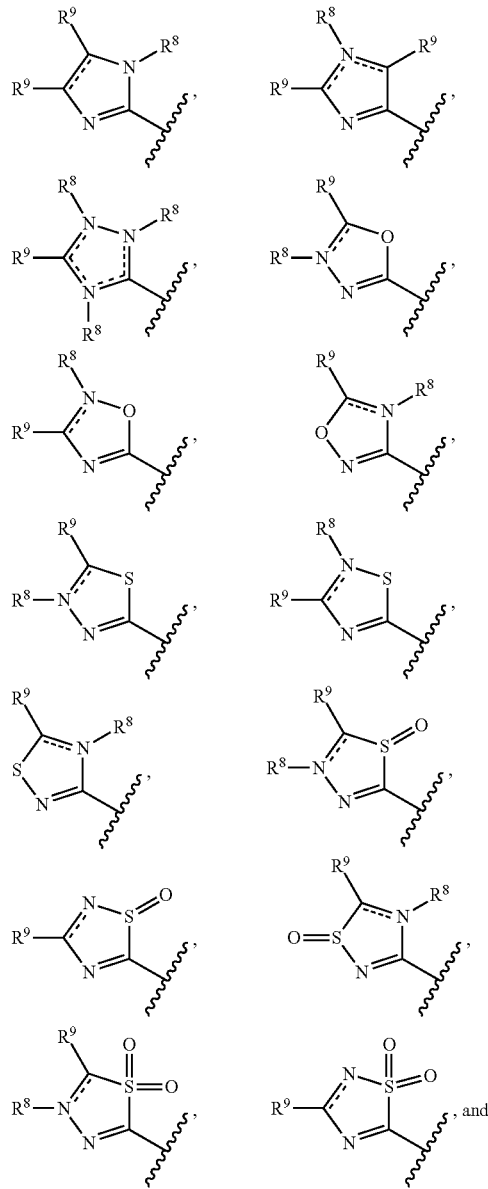

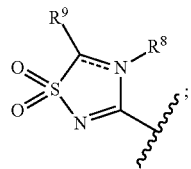

wherein ═══ is a single bond or double bond;
$R^3$ is selected from the group consisting of alkyl, haloalkyl, cycloalkyl, and halogen;
$R^6$ is selected from the group consisting of H, alkyl, halogen, —N($R^{30}$)$_2$, and —N$R^{30}$C(═O)alkyl;
the $R^8$ moieties can be the same or different, each being independently selected from the group consisting of H, alkyl, alkenyl, alkylaryl, arylalkyl, cycloalkyl, aryl, heteroaryl, heterocyclyl, —C(═O)-aryl-halogen, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(═O)NHR$^{31}$, (CH$_2$)$_q$C(═O)OR$^{31}$, —(CH$_2$)$_q$SO$_2$R$^{31}$, —(CH$_2$)$_q$N(H)SO$_2$R$^{31}$, or —(CH$_2$)$_q$SO$_2$NHR$^{31}$;
the $R^9$ moieties can be the same or different, each being independently selected from the group consisting of H, alkyl, —CF$_3$, alkenyl, alkylaryl, arylalkyl, alkoxy, amidinyl, aryl, cycloalkyl, cyano, heteroaryl, heterocyclyl, hydroxyl, —C(═O)OR$^{30}$, —C(═O)N(R$^{30}$)$_2$, —C(═O)N(H)CH$_2$CF$_3$, —C(═S)N(R$^{30}$)$_2$, —C(═O)alkyl, —C(CH$_3$)$_2$OH, —(CH$_2$)$_q$OH, —(CH$_2$)$_q$OR$^{31}$, —(CH$_2$)$_q$NH$_2$, —CH$_2$N(H)C(═O)CF$_3$, —(CH$_2$)$_q$NHR$^{31}$, —(CH$_2$)$_q$C(═O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, —N(R$^{30}$)$_2$, —N(H)-cyclopropyl-CH$_3$, —N(R$^{30}$)S(O$_2$)R$^{31}$, —N(R$^{30}$)C(═O)N(R$^{30}$)$_2$, —OR$^{30}$, —SO$_2$(R$^{31}$), —SO$_2$N(R$^{30}$)$_2$, ═O and ═S;
$R^{10}$ is alkyl;
the $R^{11}$ moieties can be the same or different, each being independently selected from the group consisting of H, alkyl, cycloalkyl, aryl, heteroaryl, heterocyclyl, heterocyclenyl, alkylaryl, arylalkyl, carboxamide, CO$_2$H, —(CH$_2$)$_q$OH, —(CH$_2$)$_q$OR$^{31}$, —OR$^{30}$, halogen, ═O , and —C(═O)R$^{31}$;
$R^{12}$ moieties can be the same or different, each being independently selected from the group consisting of H, alkyl, —CN, —C(═O)N(R$^{30}$)$_2$, —(CH$_2$)$_q$OH, —(CH$_2$)$_q$OR$^{31}$ and —S(O$_2$)R$^{31}$;
ring D is selected from the group consisting of phenyl, pyridyl, thienyl and pyrimidinyl, wherein ring D is unsubstituted or optionally substituted with 1-5 independently selected $R^{20}$ moieties;
the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(═O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, -alkynylC(R$^{31}$)$_2$OR$^{31}$, —C(═O)R$^{30}$, —C(═O)N(R$^{30}$)$_2$, —C(═NR$^{30}$)NHR$^{30}$, —C(═NOH)N(R$^{30}$)$_2$, —C(═NOR$^{31}$)N(R$^{30}$)$_2$, —C(═O)OR$^{30}$, —N(R$^{30}$)$_2$, —N(R$^{30}$)C(═O)R$^{31}$, —NHC(═O)N(R$^{30}$)$_2$, —N(R$^{30}$)

—C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), —OSi(R$^{30}$)$_3$,

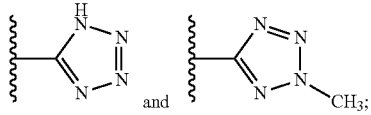
and or alternatively two R$^{20}$ moieties are linked together to form a five or six membered aryl or cycloalkyl, ring wherein said five or six membered aryl or cycloalkyl ring is fused to ring D and the fused ring is optionally substituted with 0-4 R$^{21}$ moieties;

the R$^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N (R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —C(=O)—, and —(CHR$^{13}$)$_r$C(=O)—;

the R$^{13}$ moieties can be the same or different, each being independently selected from the group consisting of H, alkyl, alkylaryl, cycloalkyl, alkoxy, aryl, heteroaryl, heterocyclenyl, heterocyclyl, —CN, —CO$_2$H, —C(=O)OR$^{31}$, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CH R$^{30}$)$_q$NHR$^{31}$, —(CH$_2$)$_q$C(=O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the R$^{30}$ moieties can be the same or different, each being independently selected from the group consisting of H, alkyl, alkylaryl, aryl, aralkyl, cycloalkyl, -cycloalkylalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)O-alkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$N(H)SO$_2$alkyl, —(CH$_2$)$_q$N(H)SO$_2$alkylaryl, —(CH$_2$)$_q$N(H)SO$_2$aryl, —(CH$_2$)$_q$N(H)SO$_2$cycloalkyl, —(CH$_2$)$_q$ SO$_2$NHalkyl, —(CH$_2$)$_q$SO$_2$NHalkylaryl, —(CH$_2$)$_q$ SO$_2$NHaryl, —(CH$_2$)$_q$SO$_2$NHaralkyl, —(CH$_2$)$_q$ SO$_2$NHcycloalkyl, heterocyclenyl, heterocyclyl, and heteroaryl;

the R$^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$N(H)SO$_2$alkyl, —(CH$_2$)$_q$N(H)SO$_2$alkylaryl, —(CH$_2$)$_q$N(H)SO$_2$aryl , —(CH$_2$)$_q$NSO$_2$aralkyl, —(CH$_2$)$_q$N(H)SO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

m is 0 to 4;

n is 0 to 4;

each q can be the same or different, each being independently selected from 1 to 5; and r is 1 to 4;

wherein said aryl of R$^8$, R$^9$, R$^{11}$, R$^{13}$, R$^{20}$, R$^{21}$, R$^{30}$, and R$^{31}$ is independently an aromatic monocyclic or multicyclic ring system comprising 6 to 14 carbon atoms;

wherein said heteroaryl of R$^8$, R$^9$, R$^{11}$, R$^{13}$, R$^{21}$, R$^{30}$, and R$^{31}$ is an aromatic monocyclic or multicyclic ring system comprising from 5 to 14 ring atoms wherein one or more of the ring atoms of the heteroaryl is nitrogen, oxygen, or sulfur;

wherein said heterocyclyl of R$^8$, R$^9$, R$^{11}$, R$^{13}$, R$^{21}$, R$^{30}$, and R$^{31}$ is a non-aromatic saturated monocyclic or multicyclic ring system comprising 3 to 10 ring atoms, wherein one or more of the ring atoms of the heterocyclyl is nitrogen, oxygen, or sulfur;

wherein said heterocyclenyl of R$^{11}$, R$^{13}$, R$^{21}$, R$^{30}$, and R$^{31}$ is a non-aromatic monocyclic or multicyclic ring system comprising 3 to 10 ring atoms, wherein one or more of the ring atoms of the heterocyclenyl is nitrogen, oxygen, or sulfur, and wherein the heterocyclenyl contains at least one carbon-carbon double bond or carbon-nitrogen double bond;

with the proviso that there are no two adjacent double bonds in any ring, and that when a nitrogen is substituted by two alkyl groups, said two alkyl groups may be optionally joined to each other to form a ring.

2. The compound according to claim 1, wherein G represents a dihydroimidazole, imidazole, dihydrooxadiazole, oxadiazole, or triazole ring.

3. The compound according to claim 1, wherein R$^3$ is selected from the group consisting of —CH$_3$, —CH$_2$CH$_3$, cyclopropyl, —Cl, and CF$_3$.

4. The compound according to claim 1, wherein R$^6$ is selected from the group consisting of H, —NH$_2$, —NHC(=O)CH$_3$, —CH$_3$, and —F.

5. The compound according to claim 1, wherein R$^8$ is selected from the group consisting of H, alkyl, alkenyl, arylalkyl, cycloalkyl, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, and —C(=O)-aryl-halogen.

6. The compound according to claim 1, wherein the R$^9$ moieties can be the same or different, each being independently selected from the group consisting of H, alkyl, cycloalkyl, —C(=O)N(H)R$^{30}$, —C(=O)OR$^{30}$, —C(=O)alkyl, —(CH$_2$)$_q$OH, —(CH$_2$)$_q$OR$^{31}$, —(CH$_2$)$_q$NH$_2$, —(CH$_2$)$_q$NHR$^{31}$, —N(H)R$^{30}$, —N(H)S(O$_2$)R$^{31}$, —N(H)C(=O)NH(R$^{30}$), —OR$^{30}$, —SO$_2$(R$^{31}$), and —SO$_2$N(H)R$^{30}$.

7. The compound according to claim 1, wherein the R$^9$ moieties can be the same or different, each being independently selected from the group consisting of H, —OH, cyclopropyl, —CF$_3$, —CH$_3$, —CH$_2$OH, —CH$_2$CH$_2$OH, —C(CH$_3$)$_2$OH, —CH$_2$CH$_2$OCH$_3$, —C(=O)OCH$_3$, —C(=O)OCH$_2$CH$_3$, —CH$_2$NH$_2$, —CH$_2$CH$_2$NH$_2$, —CH$_2$CH$_2$NHSO$_2$CH$_3$, —CH$_2$CH$_2$SO$_2$CH$_3$, —C(=O)NH$_2$, —C(=O)N(H)CH$_2$CH$_2$OH, —CH$_2$N(H)C(=O)CF$_3$, —C(=O)N(H)-cyclopropyl, —C(=O)N(H)CH$_2$CF$_3$, —NH$_2$, —NHCH$_3$, —N(CH$_3$)$_2$, —N(H)CH$_2$CH$_3$, —N(H)-cyclopropyl-CH$_3$, —N(H)CH(CH$_3$)$_2$, —N(H)CH$_2$CH$_2$CH$_3$, —N(H)CH$_2$C(=O)OCH$_3$, —N(H)CH$_2$C(=O)OCH$_2$CH$_3$, —N(H)CH$_2$C(=O)NH-cyclopropyl, —N(H)CH$_2$CH$_2$OH, —N(H)CH$_2$CH$_2$NH$_2$, —N(H)CH$_2$CH$_2$NHSO$_2$CH$_3$, —N(H)CH$_2$CH$_2$SO$_2$CH$_3$, —N(H)C(=O)N(H)CH$_2$CH$_3$, —N(H)CH$_2$C(=O)NH$_2$, —OCH$_3$, —N(CH$_2$CH$_3$)S(=O)$_2$-phenyl-alkyl, —N(H)S(=O)$_2$-alkyl, =S and =O.

8. The compound according to claim 7, wherein the R$^9$ moieties can be the same or different, each being independently selected from the group consisting of H, —OH, —CF$_3$, —CH$_3$, —CH$_2$CH$_3$, —CH(CH$_3$)$_2$, cyclopropyl, —C(=O)OCH$_3$, —C(=O)OCH$_2$CH$_3$, —CH$_2$CH$_2$OH, —CH$_2$CH$_2$NH$_2$, —NH$_2$, —NHCH$_3$, —N(H)CH$_2$CH$_3$, —N(H)CH(CH$_3$)$_2$, —N(H)CH$_2$CH$_2$CH$_3$, —N(H)-cyclopropyl-CH$_3$, —N(H)CH$_2$C(=O)OCH$_3$, —N(H)CH$_2$C(=O)OCH$_2$CH$_3$, —N(H)CH$_2$C(=O)NHCH$_3$, —N(H)CH$_2$C(=O)NH-cyclopropyl, —N(H)CH$_2$CH$_2$OH, —N(CH$_2$CH$_3$)S(=O)$_2$-phenyl-alkyl, and —N(H)S(=O)$_2$-alkyl.

9. The compound according to claim 1, wherein R$^{10}$ is selected from the group consisting of —CH$_3$, and —CH$_2$CH$_3$, and m is 0-2.

10. The compound according to claim 1, wherein R$^{11}$ is selected from the group consisting of H, alkyl, and carbonyl.

11. The compound according to claim 10, wherein R$^{11}$ is H or —CH$_3$.

12. The compound according to claim 1, wherein R$^{12}$ is selected from the group consisting of H, CN, —C(=O)N(R$^{30}$)$_2$ and alkyl.

13. The compound according to claim 12, wherein R$^{12}$ is selected from the group consisting of H, —CH$_3$, CN and —CH$_2$CH$_3$.

14. The compound according to claim 1, wherein ring D is substituted with 0-4 R$^{20}$ moieties.

15. The compound according to claim 1, wherein the R$^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, hydroxyalkyl, trifluoromethoxy, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —N(R$^{30}$)SO$_2$(R$^{31}$), —N(R$^{30}$)SO$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$.

16. The compound according to claim 1, wherein the R$^{20}$ moieties can be the same or different, each being independently selected from the group consisting of H, alkyl, cycloalkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —N(R$^{30}$)SO$_2$(R$^{31}$), —OR$^{30}$, —OC(=O)N(R$^{30}$)$_2$, and —OSO$_2$(R$^{31}$).

17. The compound according to claim 1, wherein two R$^{20}$ moieties are linked together to form a five or six membered aryl or cycloalkyl ring wherein said five or six membered aryl or cycloalkyl ring is fused to ring D and the fused ring is optionally substituted with 0 to 4 R$^{21}$ moieties.

18. The compound according to claim 1, wherein the R$^{20}$ moieties can be the same or different, each being independently selected from the group consisting of H, —CN, —CH$_3$, —CH$_2$CH$_3$, —CH(CH$_3$)$_2$, cyclopropyl, —CF$_3$, —CH$_2$OH, —CH$_2$—S(=O)$_2$CH$_3$, —C(=O)H, —CO$_2$H, —CO$_2$CH$_3$, —NH$_2$, —N(H)CH$_3$, —N(H)S(=O)$_2$CH$_3$, —OCF$_3$, —OH, F, Cl, Br, —C(=NOH)NH$_2$, —OCH$_2$CH$_2$S(O$_2$)CH$_3$, —C(=O)NH$_2$,

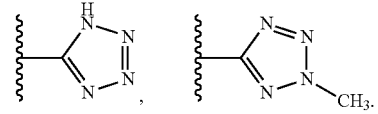

19. The compound according to claim 1, wherein the R$^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy.

20. The compound according to claim 1, wherein Y is selected from the group consisting of —CH$_2$—, —CH(CH$_3$)—, —CH(CH$_2$OH)—, —CH(CH$_2$OCH$_2$-phenyl)-, —C(=O)—, and —CH(C=O)O-alkyl-.

21. The compound according to claim 1, wherein m is 0-2.

22. The compound according to claim 1, wherein n is 0-2.

23. The compound according to claim 1, wherein q is 1 or 2.

24. The compound according to claim 1, wherein r is 1 or 2.

25. The compound according to claim 1, wherein
R$^9$ moieties can be the same or different, each being independently selected from the group consisting of H, alkyl, cycloalkyl, —C(=O)N(H)R$^{30}$, —C(=O)OR$^{30}$, —C(=O)alkyl, —(CH$_2$)$_q$OH, —(CH$_2$)$_q$OR$^{31}$, —(CH$_2$)$_q$NH$_2$, —(CH$_2$)$_q$NHR$^{31}$, —N(H)R$^{30}$, —N(H)S(O$_2$)R$^{31}$, —N(H)C(=O)NH(R$^{30}$), —OR$^{30}$, —SO$_2$(R$^{31}$), and —SO$_2$N(H)R$^{30}$;
R$^{11}$ is selected from the group consisting of: H, alkyl, and =O;
R$^{12}$ is selected from the group consisting of H, CN, —C(=O)N(R$^{30}$)$_2$ and alkyl;
ring D is substituted with 0-4 R$^{20}$ moieties;
the R$^{20}$ moieties can be the same or different, each being independently selected from the group consisting of H, alkyl, cycloalkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$N(H)SO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —N(R$^{30}$)SO$_2$(R$^{31}$), —OR$^{30}$, —OC(=O)N(R$^{30}$)$_2$,

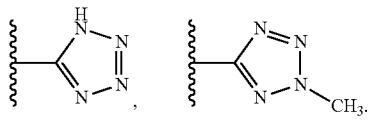

and —OSO$_2$(R$^{31}$);or alternatively, two R$^{20}$moieties are linked together to form a five or six membered aryl or cycloalkyl, ring wherein said five or six membered aryl or cycloalkyl ring is fused to ring D and the fused ring is optionally substituted with 0 to 4 R$^{21}$ moieties;

the R$^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy;

Y is selected from the group consisting of —CH$_2$—, —CH(CH$_3$)—, —CH(CH$_2$OH)—, —CH(CH$_2$OCH$_2$-phenyl)-, —C(=O)—, and —CH[(C=O)O-alkyl]-;

m is 0-2;

n is 0-2; and q is 1 or 2.

26. A compound according to claim 1, wherein Formula 1 is represented by one of structural Formulae 2-10:

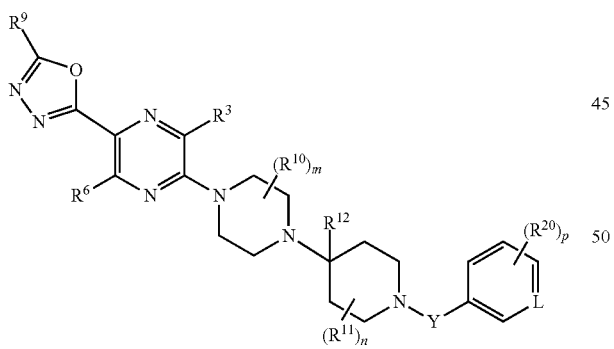

Formula 2

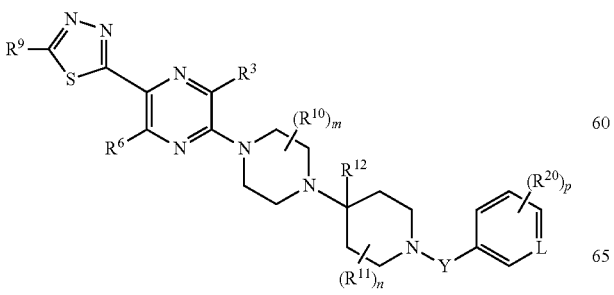

Formula 3

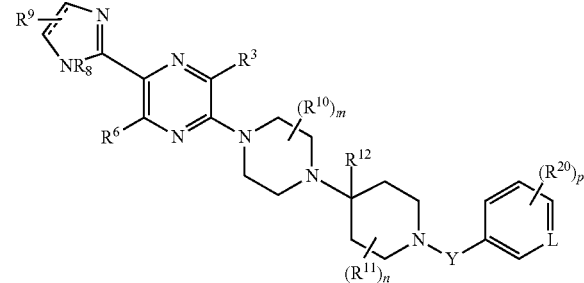

Formula 4

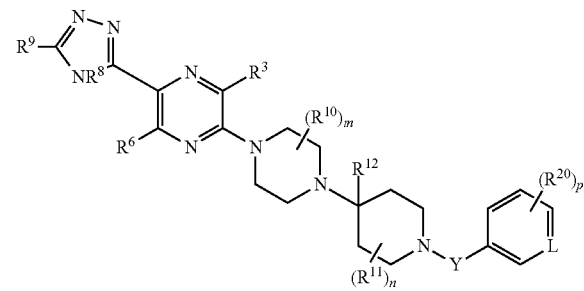

Formula 5

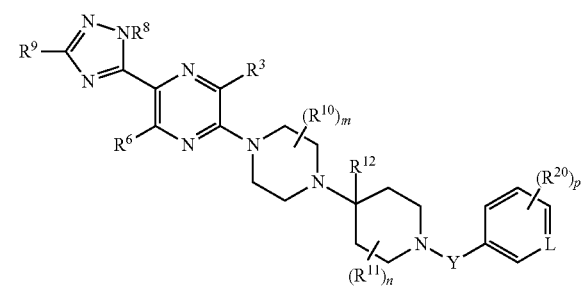

Formula 6

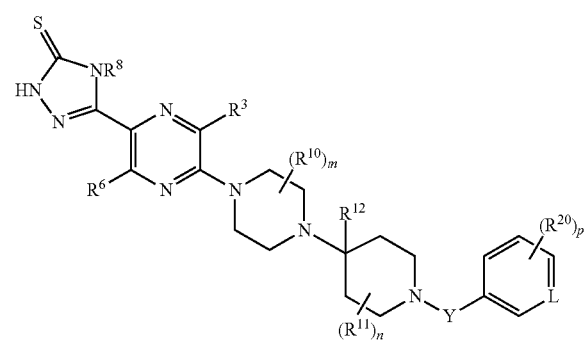

Formula 7

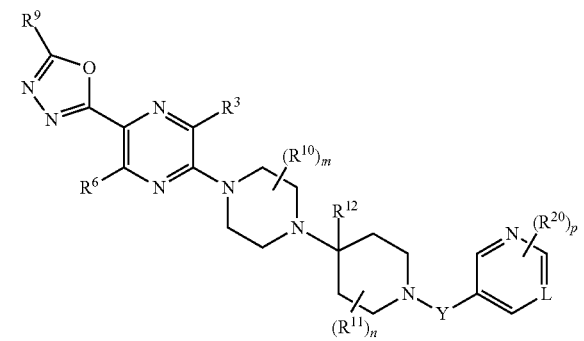

Formula 8

-continued

Formula 9

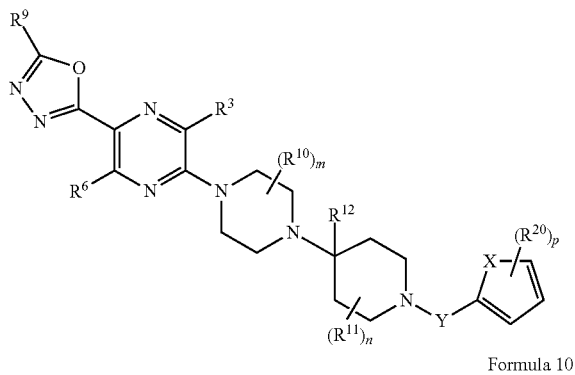

Formula 10

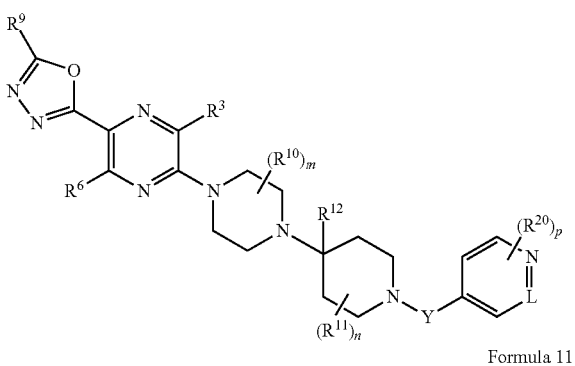

Formula 11

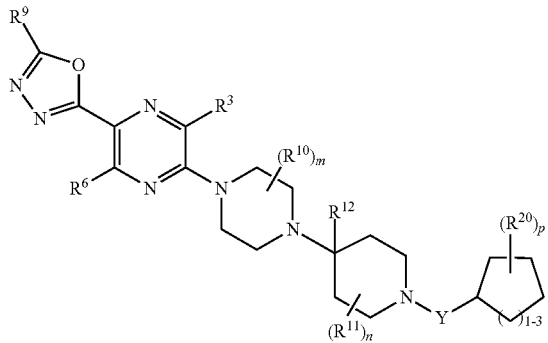

or a pharmaceutically acceptable salt thereof, wherein:
the $R^8$ moieties can be the same or different, each being independently selected from the group consisting of H, alkyl, alkenyl, arylalkyl, cycloalkyl, —$(CH_2)_qOH$, —$(CH_2)_qOR^{31}$, —$(CH_2)_qNH_2$, —$(CH_2)_qNHR^{31}$, —$(CH_2)_qC(=O)NHR^{31}$, —$(CH_2)_qSO_2R^{31}$, —$(CH_2)_qN(H)SO_2R^{31}$, —$(CH_2)_qSO_2NHR^{31}$, and —C(=O)-aryl-halogen;
the $R^9$ moieties can be the same or different, each being independently selected from the group consisting of H, alkyl, cycloalkyl, —$CF_3$, —C(=O)N(H)$R^{30}$, —C(=O)$OR^{30}$, —C(=O)alkyl, —$(CH_2)_qOH$, —C(CH_3)_2OH, —$CH_2N(H)C(=O)CF_3$, —$(CH_2)_qOR^{31}$, —$(CH_2)_qNH_2$, —$(CH_2)_qNHR^{31}$, —N(H)$R^{30}$, —N(H)S(O_2)$R^{31}$, —N(H)C(=O)NH($R^{30}$), —$OR^{30}$, —$SO_2(R^{31})$, and —$SO_2N(H)R^{30}$;
L is C or N;
==== in Formula 4 is a single bond or a double bond;
X in formula 9 is S;
p is 0 to 4; and
m, n, q, $R^{10}$, $R^{11}$, $R^{12}$, $R^{20}$ and Y are as defined in claim 1.

27. The compound according to claim 26, wherein $R^9$ moieties are the same or different, each being independently selected from the group consisting of H, —OH, cyclopropyl, —$CF_3$, —$CH_3$, —$CH_2OH$, —$CH_2CH_2OH$, —C(CH_3)_2OH, —$CH_2CH_2OCH_3$, —C(=O)$OCH_3$, —C(=O)$OCH_2CH_3$, —$CH_2NH_2$, —$CH_2CH_2NH_2$, —C(=O)$NH_2$, —C(=O)N(H)$CH_2CH_2OH$, —$CH_2N(H)C(=O)CF_3$, —C(=O)N(H)-cyclopropyl, —C(=O)N(H)$CH_2CF_3$, —$NH_2$, —$NHCH_3$, —N(H)$CH_2CH_3$, —N(H)-cyclopropyl-$CH_3$, —N(H)CH(CH_3)_2, —N(H)$CH_2CH_2CH_3$, —N(H)$CH_2C(=O)OCH_3$, —N(H)$CH_2C(=O)OCH_2CH_3$, —N(H)$CH_2C(=O)NH$-cyclopropyl, —N(H)$CH_2CH_2OH$, —N(H)$CH_2CH_2NH_2$, —N(H)$CH_2CH_2NHSO_2CH_3$, —N(H)$CH_2CH_2SO_2CH_3$, —N(H)C(=O)N(H)$CH_2CH_3$, —$OCH_3$, and —N(H)S(=O)_2-alkyl.

28. The compound according to claim 26, wherein $R^{11}$ is selected from the group consisting of: of H, alkyl, and =O.

29. The compound according to claim 26, wherein $R^{12}$ is selected from the group consisting of H, —$CH_3$, CN or —$CH_2CH_3$.

30. The compound according to claim 26, wherein $R^{20}$ moieties can be the same or different, each being independently selected from the group consisting of H, alkyl, cycloalkyl, amino, halogen, CN, $CH_3$, $CF_3$, $OCF_3$, —$(CH_2)_qOR^{31}$, —$(CH_2)_qNHR^{31}$, —$(CH_2)_qC(=O)NHR^{31}$, —$(CH_2)_qSO_2R^{31}$, —$(CH_2)_qN(H)SO_2R^{31}$, —$(CH_2)_qSO_2NHR^{31}$, -alkynylC($R^{31}$)_2$OR^{31}$, —C(=O)$R^{30}$, —C(=O)$OR^{30}$, —N($R^{30}$)_2, —N($R^{30}$)C(=O)$R^{31}$, —NHC(=O)N($R^{30}$)_2, —N($R^{30}$)C(=O)$OR^{31}$, —N($R^{30}$)C(=NCN)N($R^{30}$)_2, —N($R^{30}$)C(=O)N($R^{30}$)_2, —N($R^{30}$)SO_2($R^{31}$), —$OR^{30}$, —OC(=O)N($R^{30}$)_2,

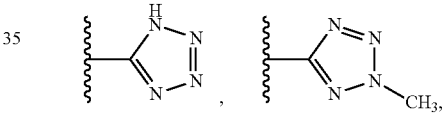

and —OSO_2($R^{31}$); or alternatively, two $R^{20}$ moieties are linked together to form a five or six membered aryl or cycloalkyl ring wherein said five or six membered aryl or cycloalkyl ring is fused to ring D and the fused ring is optionally substituted with 0 to 4 $R^{21}$ moieties;
the $R^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy.

31. The compound according to claim 30, wherein the $R^{20}$ moieties can be the same or different, each being independently selected from the group consisting of H, —CN, —$CH_3$, —$CH_2CH_3$, —CH($CH_3$)_2, cyclopropyl, —$CF_3$, —$CH_2OH$, —$CH_2$—S(=O)_2$CH_3$, —C(=O)H, —$CO_2H$, —$CO_2CH_3$, —$NH_2$, —N(H)$CH_3$, —N(H)S(=O)_2$CH_3$, —$OCF_3$, —OH, F, Cl, Br, —$OCH_2CH_2S(O_2)CH_3$, —C(=O)$NH_2$,

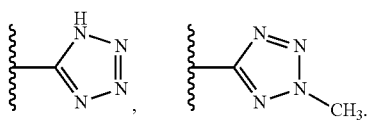

or alternatively, two $R^{20}$ moieties are linked together to form a five or six membered aryl or cycloalkyl ring wherein said five or six membered aryl or cycloalkyl ring is fused to ring D and the fused ring is optionally substituted with 0 to 4 $R^{21}$ moieties;

the $R^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy.

32. The compound according to claim 26, wherein L is carbon.

33. The compound according to claim 26, wherein L is nitrogen.

34. The compound according to claim 26, wherein Y is selected from the group consisting of: —$CH_2$—, —CH($CH_3$)—, —CH($CH_2OH$)—, —CH($CH_2OCH_2$-phenyl)-, —C(=O)—, and —CH[(C=O)O-alkyl]-.

35. The compound according to claim 26, wherein $R^3$ is selected from the group consisting of alkyl, cycloalkyl, halogen, and —$CF_3$;

$R^6$ is selected from the group consisting of H, alkyl, halogen, —N($R^{30}$)$_2$, and —N$R^{30}$C(=O)alkyl,;

the $R^9$ moieties can be the same or different, each being independently selected from the group consisting of H, alkyl, cycloalkyl, —C(=O)N(H)$R^{30}$, —C(=O)O$R^{30}$, —C(=O)alkyl, —($CH_2$)$_q$OH, —($CH_2$)$_q$O$R^{31}$, —($CH_2$)$_q$NH$_2$, —($CH_2$)$_q$NH$R^{31}$, —N(H)$R^{30}$, —N(H)S($O_2$)$R^{31}$, —N(H)C(=O)NH($R^{30}$), —O$R^{30}$, —$SO_2$($R^{31}$), and —$SO_2$N(H)$R^{30}$;

$R^{10}$ is alkyl;

the $R^{20}$ moieties can be the same or different, each being independently selected from the group consisting of H, alkyl, cycloalkyl, amino, halogen, CN, $CH_3$, $CF_3$, $OCF_3$, —($CH_2$)$_q$O$R^{31}$, —($CH_2$)$_q$NH$R^{31}$, —($CH_2$)$_q$C(=O)NH$R^{31}$, —($CH_2$)$_q$$SO_2$$R^{31}$, —($CH_2$)$_q$N(H)$SO_2$$R^{31}$, —($CH_2$)$_q$$SO_2$NH$R^{31}$, -alkynylC($R^{31}$)$_2$O$R^{31}$, —C(=O)$R^{30}$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —N($R^{30}$)$SO_2$($R^{31}$), —O$R^{30}$, —OC(=O)N($R^{30}$)$_2$,

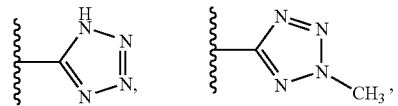

and —$OSO_2$($R^{31}$);or alternatively, two $R^{20}$ moieties are linked together to form a five or six membered aryl or cycloalkyl ring wherein said five or six membered aryl or cycloalkyl ring is fused to ring D and the fused ring is optionally substituted with 0 to 4 $R^{21}$ moieties;

the $R^{21}$ moieties can be the same or different, each being independently selected from the group consisting of H, alkyl, alkenyl, alkylaryl, alkynyl, alkoxy, alkylamino, cyano, cycloalkyl, formyl, halogen, haloalkyl, hydroxyalkyl, nitro, and trifluoromethoxy;

Y is selected from the group consisting of —$CH_2$—, —CH($CH_3$)—, —CH($CH_2OH$)—, —CH($CH_2OCH_2$-phenyl)-, —C(=O)—, and —CH[(C=O)O-alkyl]-;

m is 0-2;

n is 0-2; and q is 1 or 2.

36. The compound of claim 1 selected from the group consisting of:

| Compound Number | STRUCTURE |
|---|---|
| 1 | ![structure 1] |
| 2 | ![structure 2] |

| Compound Number | STRUCTURE |
|---|---|
| 3 | 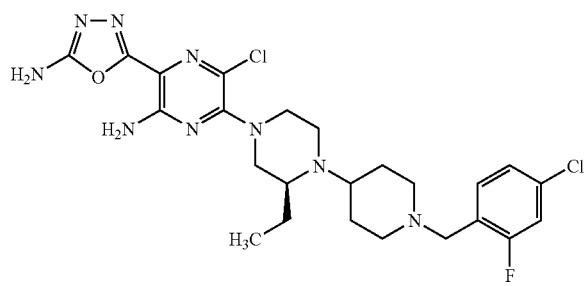 |
| 4 | 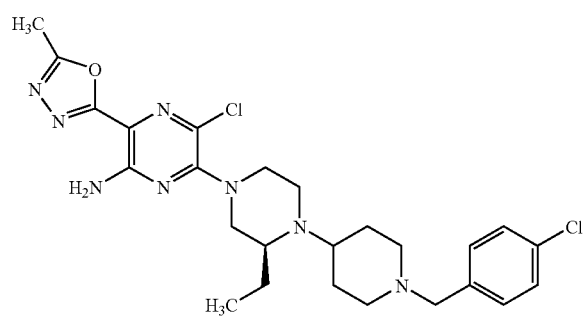 |
| 5 | 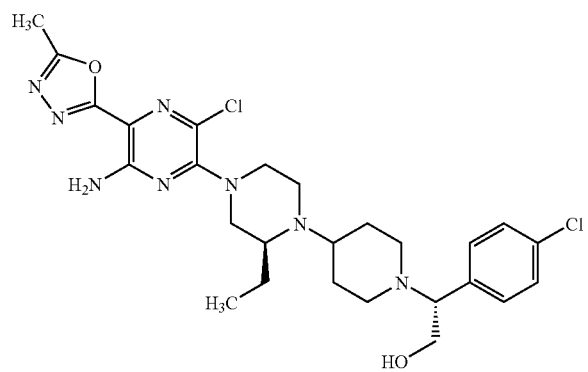 |
| 6 | 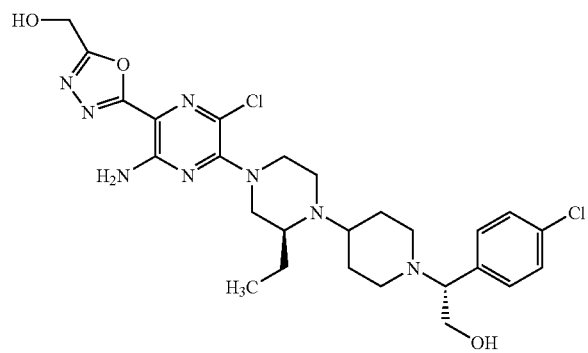 |

| Compound Number | STRUCTURE |
|---|---|
| 7 | 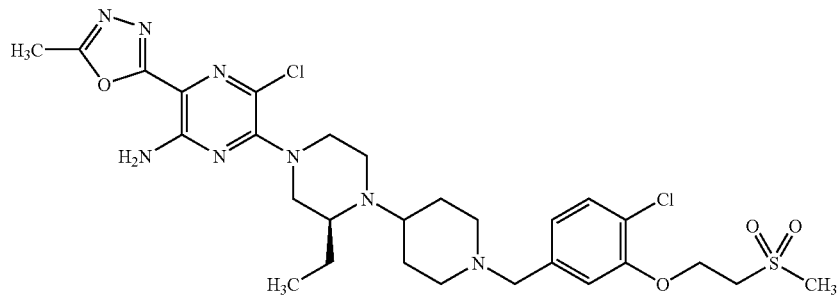 |
| 8 | 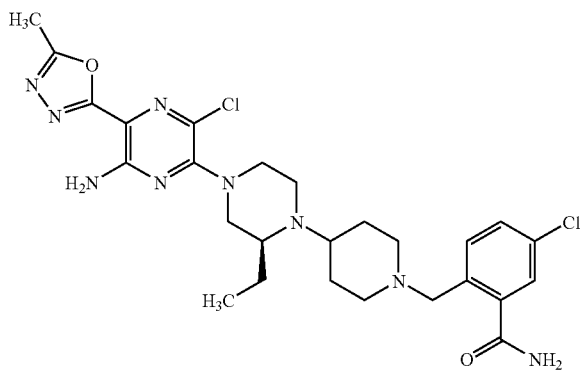 |
| 9 | 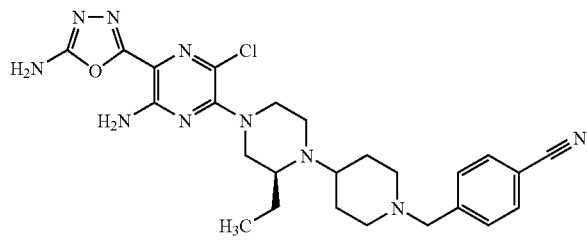 |
| 10 | 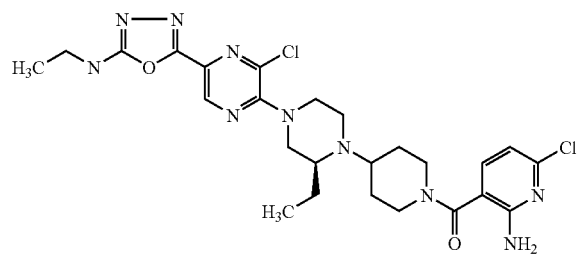 |
| 11 | 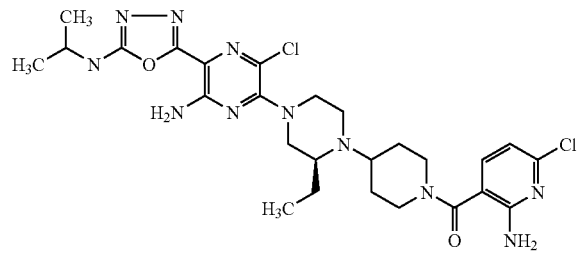 |

-continued
| Compound Number | STRUCTURE |
|---|---|
| 12 | 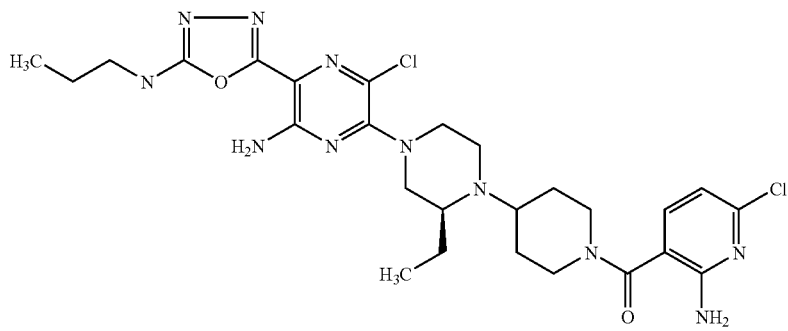 |
| 13 | 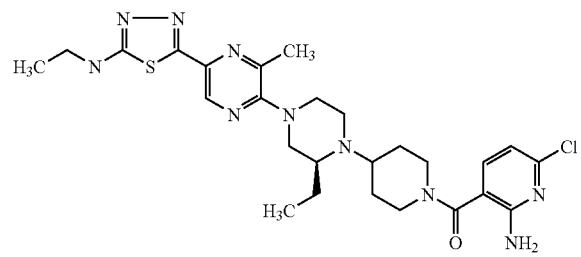 |
| 14 | 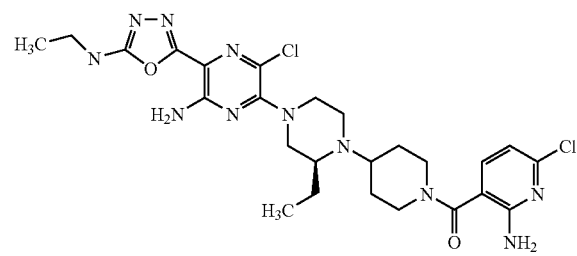 |
| 15 | 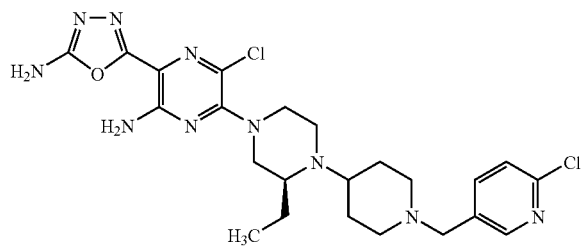 |
| 16 | 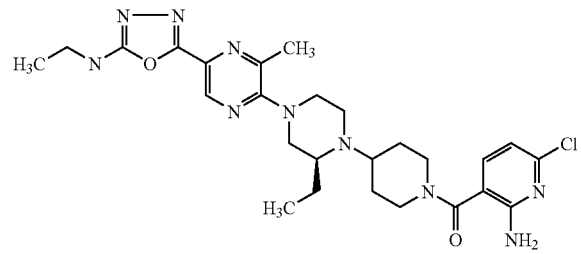 |

-continued
| Compound Number | STRUCTURE |
|---|---|
| 17 | 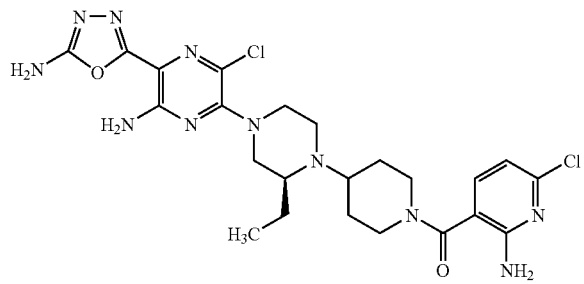 |
| 18 | 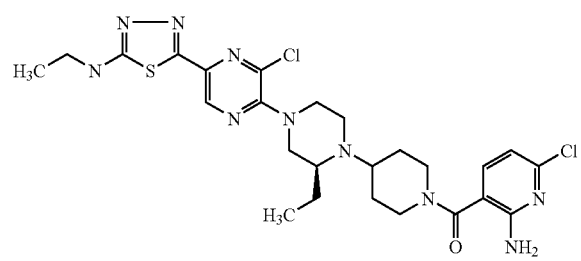 |
| 19 | 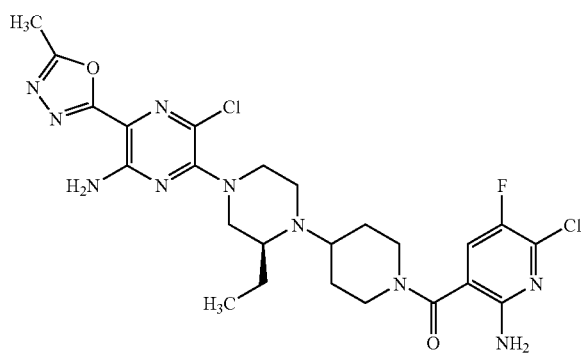 |
| 20 | 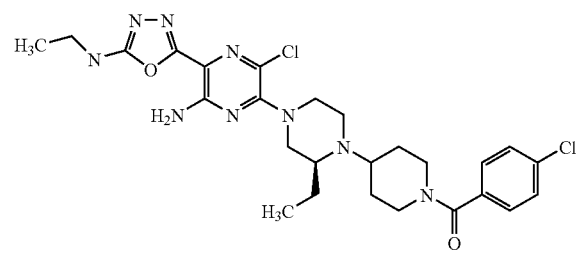 |
| 21 | 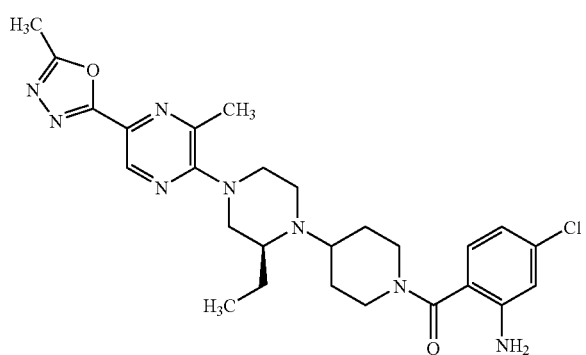 |

-continued
| Compound Number | STRUCTURE |
|---|---|
| 22 | 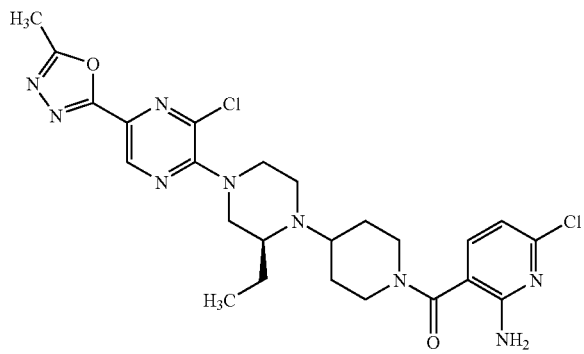 |
| 23 | 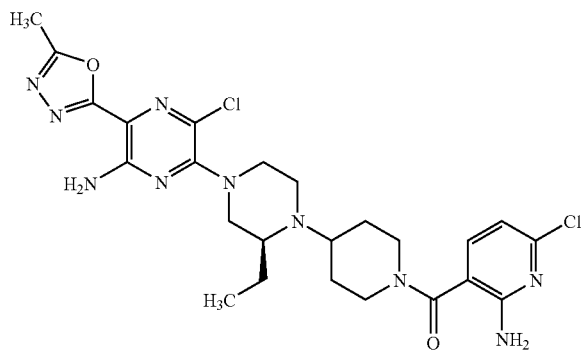 |
| 24 | 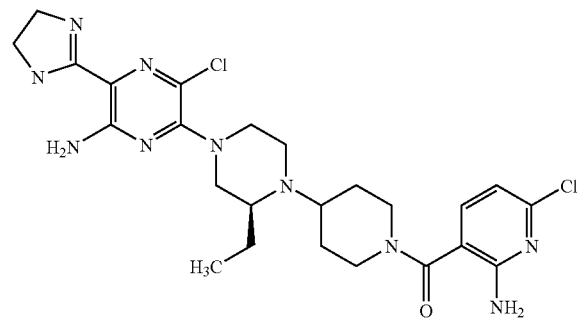 |
| 25 | 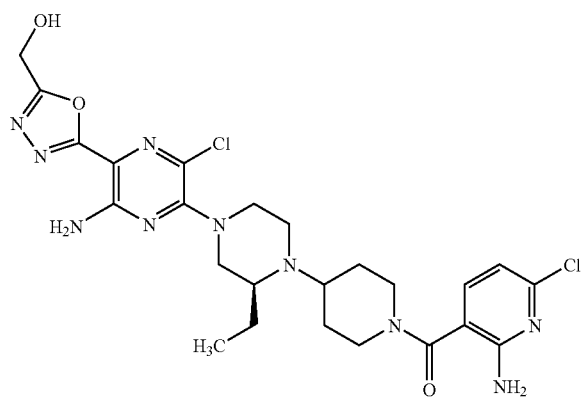 |

| Compound Number | STRUCTURE |
|---|---|
| 26 | 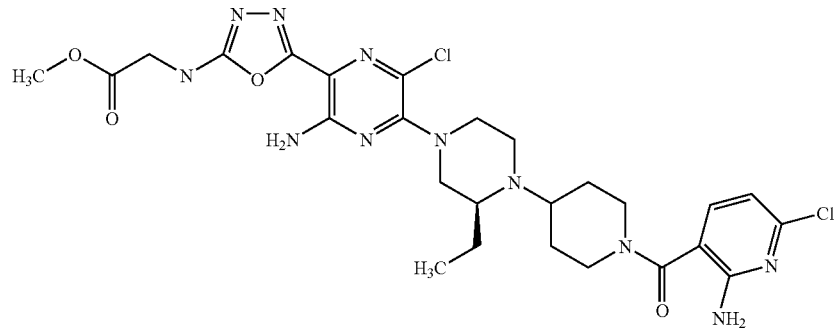 |
| 27 | 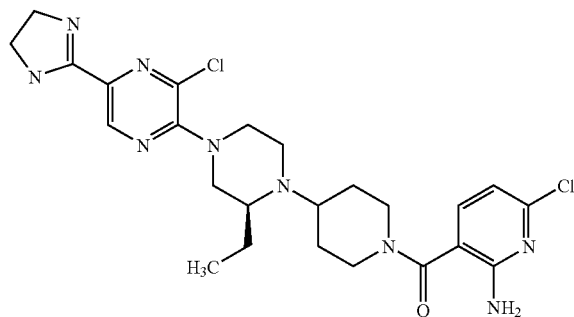 |
| 28 | 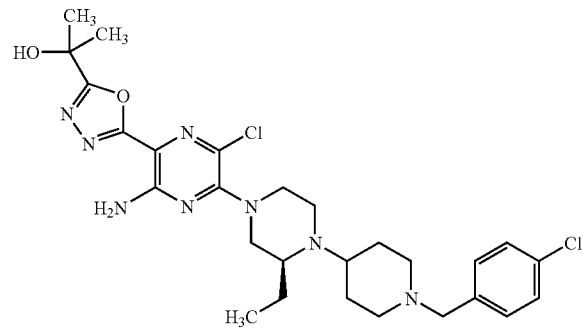 |
| 29 | 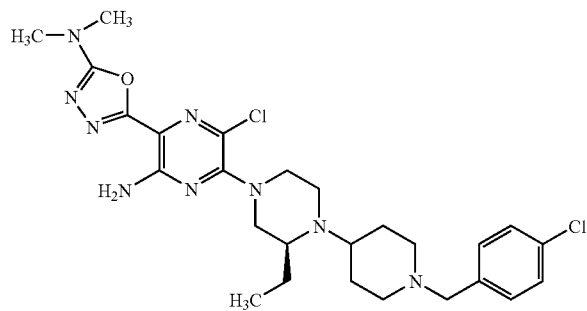 |

| Compound Number | STRUCTURE |
|---|---|
| 30 | 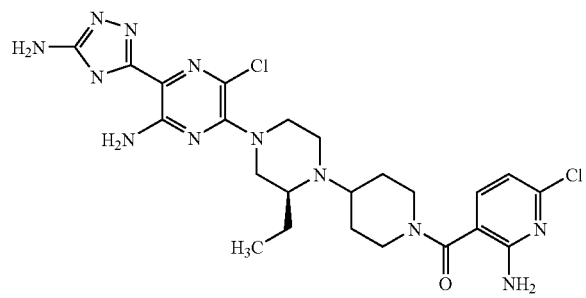 |
| 31 | 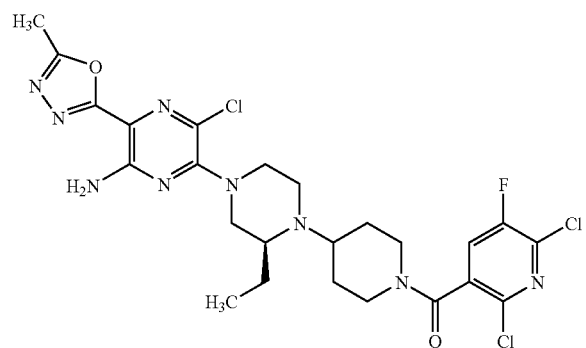 |
| 32 | 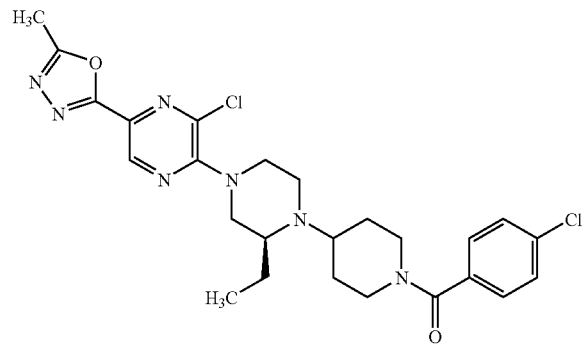 |
| 33 | 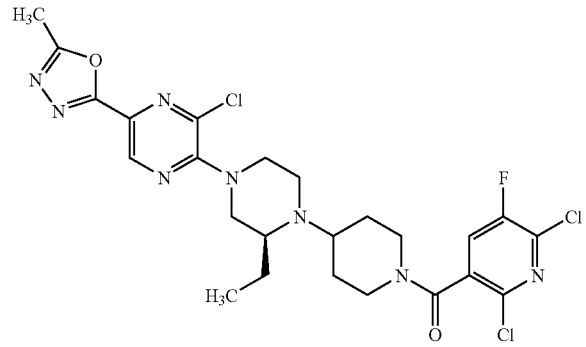 |

-continued
| Compound Number | STRUCTURE |
|---|---|
| 34 | 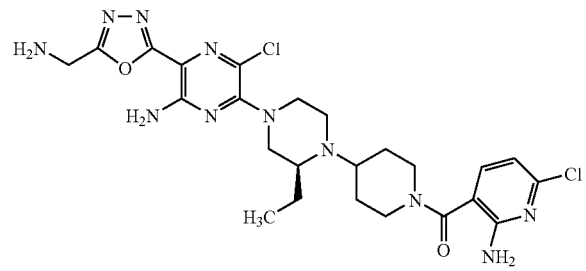 |
| 35 | 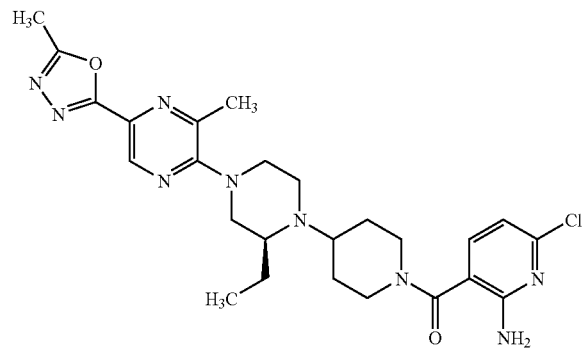 |
| 36 | 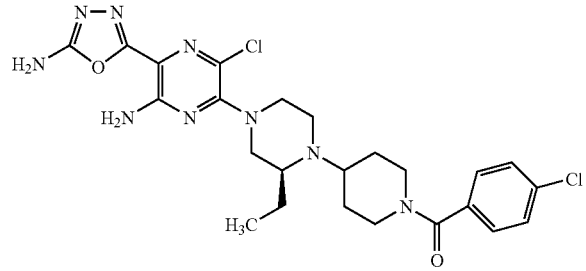 |
| 37 | 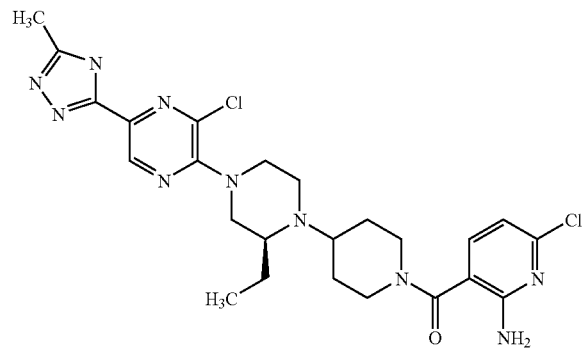 |

-continued
| Compound Number | STRUCTURE |
|---|---|
| 38 | 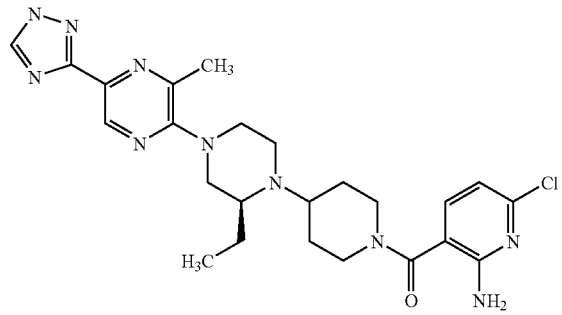 |
| 39 | 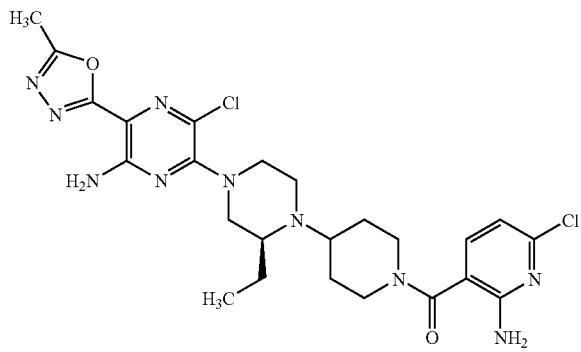 |
| 40 | 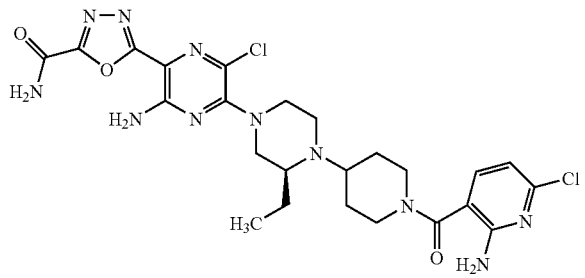 |
| 41 | 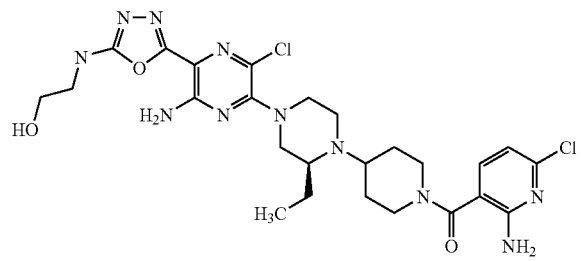 |
| 42 | 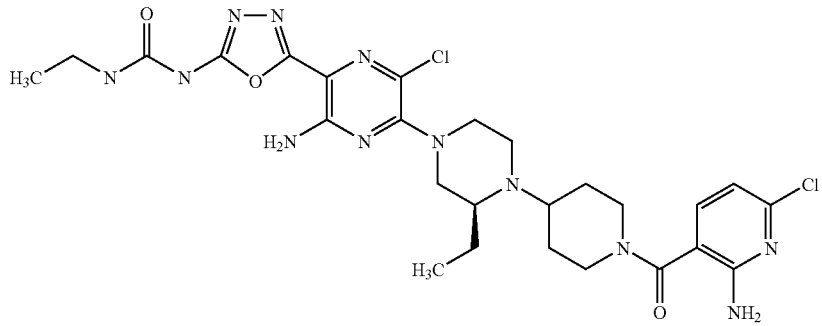 |

-continued
| Compound Number | STRUCTURE |
|---|---|
| 43 | 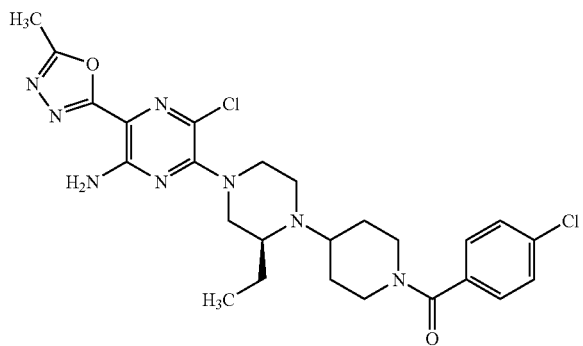 |
| 44 | 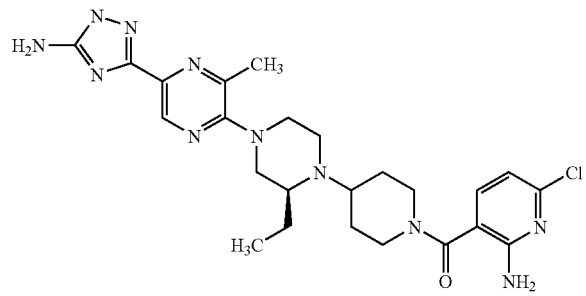 |
| 45 | 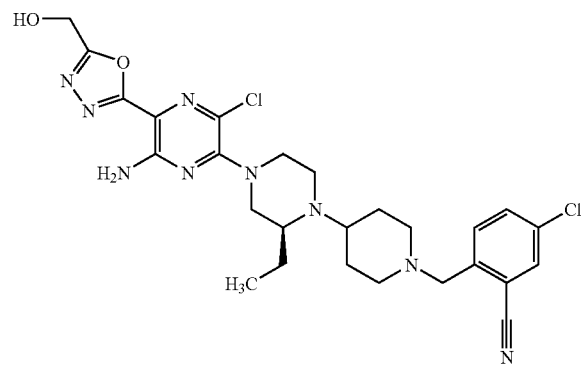 |
| 46 | 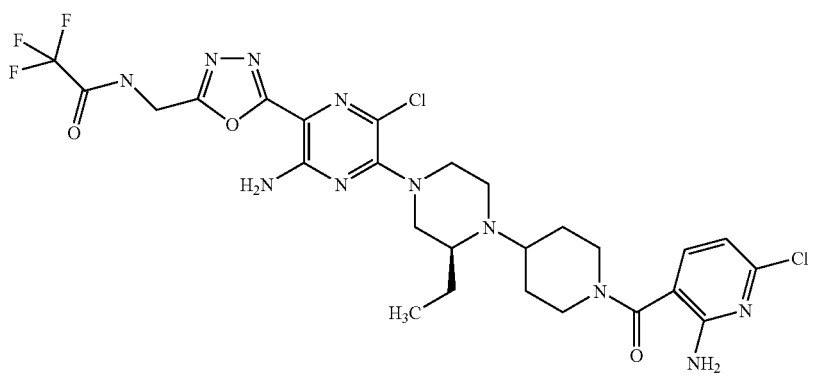 |

-continued
| Compound Number | STRUCTURE |
|---|---|
| 47 | 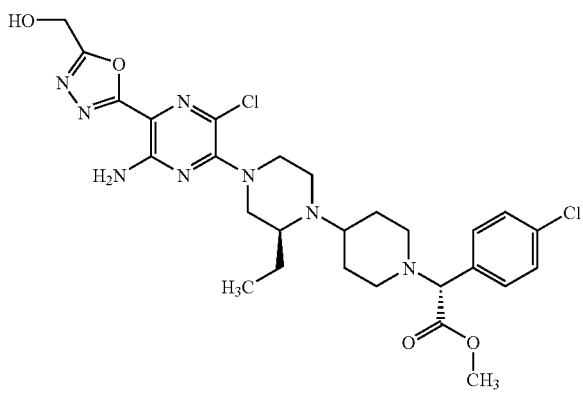 |
| 48 | 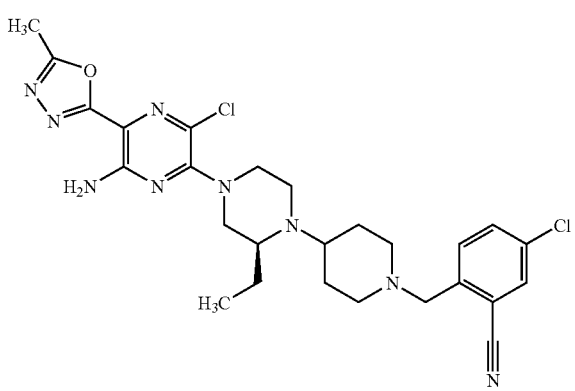 |
| 49 | 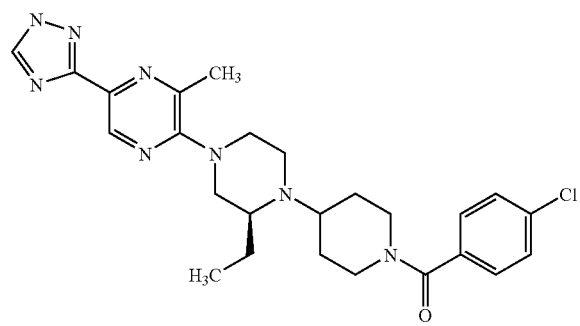 |
| 50 | 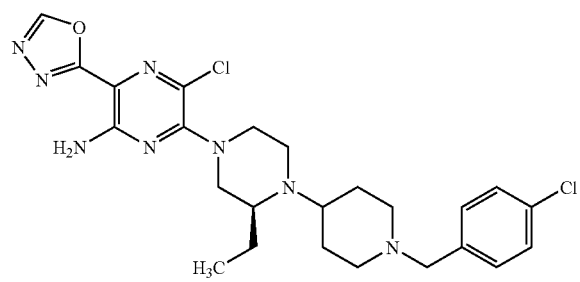 |

-continued
| Compound Number | STRUCTURE |
|---|---|
| 51 | 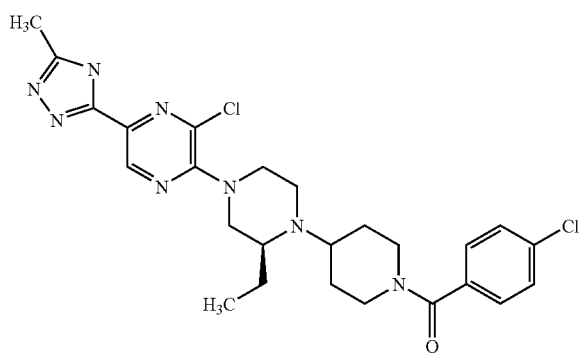 |
| 52 | 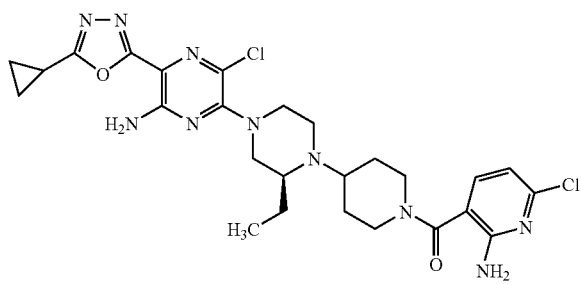 |
| 53 | 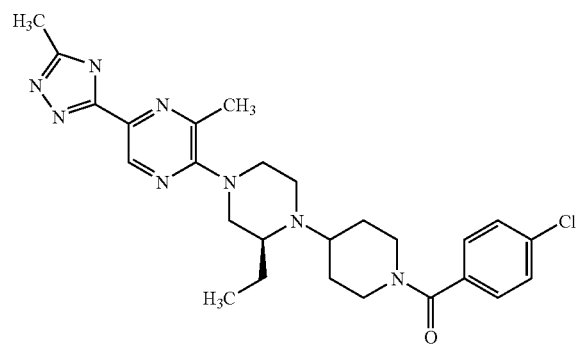 |
| 54 | 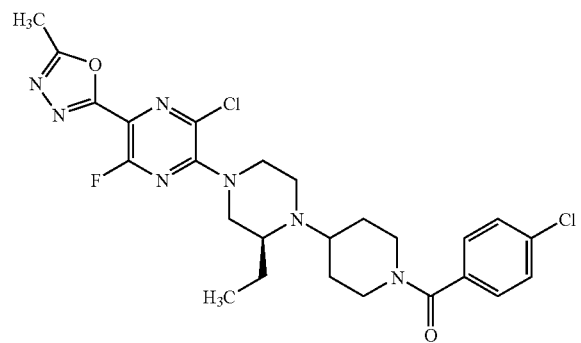 |

-continued
| Compound Number | STRUCTURE |
|---|---|
| 55 | 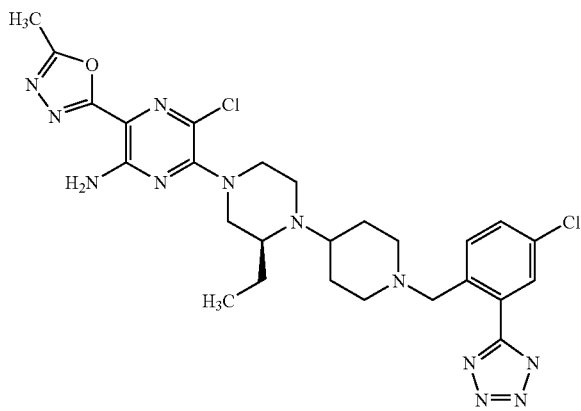 |
| 56 | 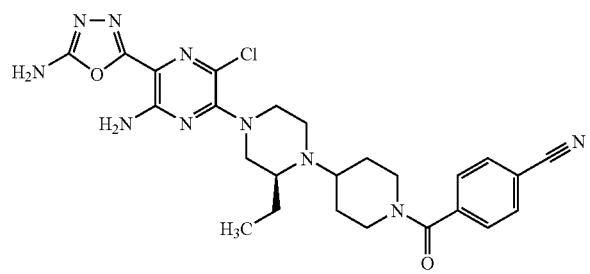 |
| 57 | 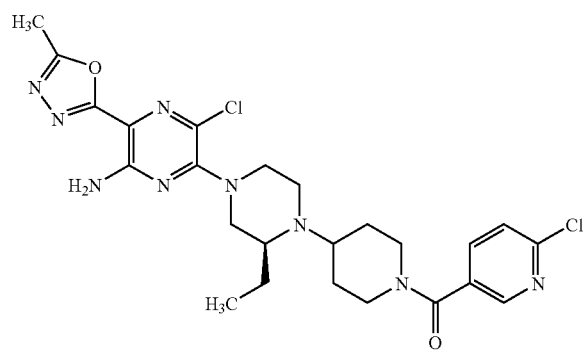 |
| 58 | 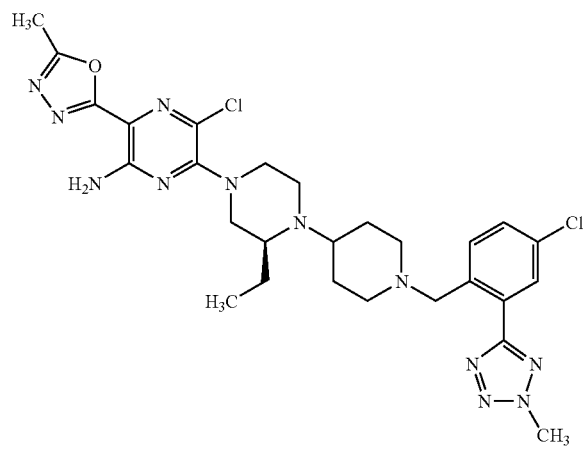 |

-continued
| Compound Number | STRUCTURE |
|---|---|
| 59 | 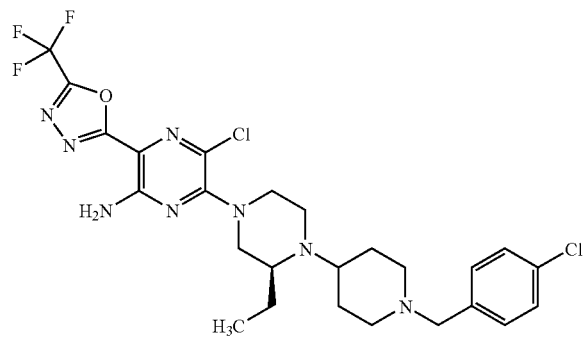 |
| 61 | 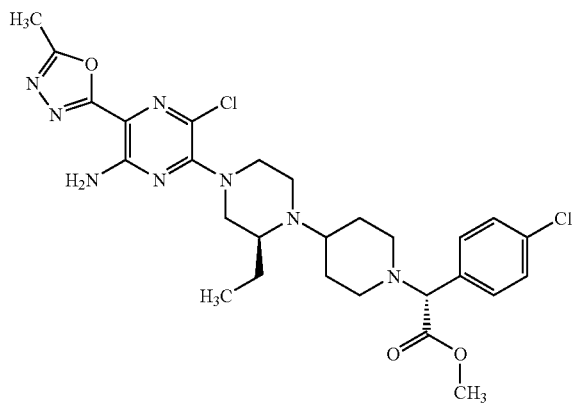 |
| 62 | 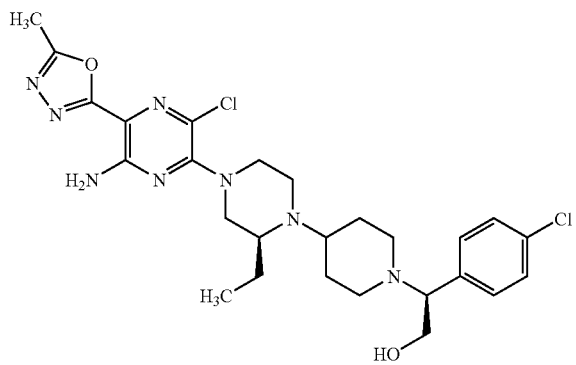 |
| 63 | 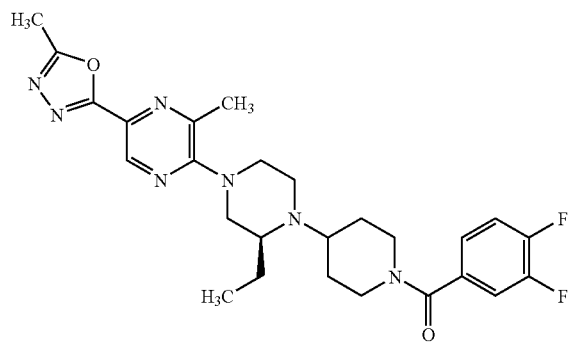 |

-continued
| Compound Number | STRUCTURE |
|---|---|
| 64 | 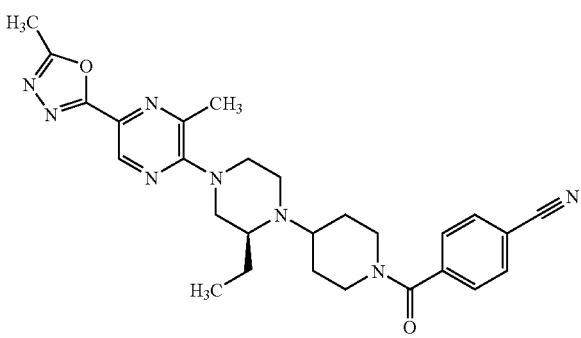 |
| 65 | 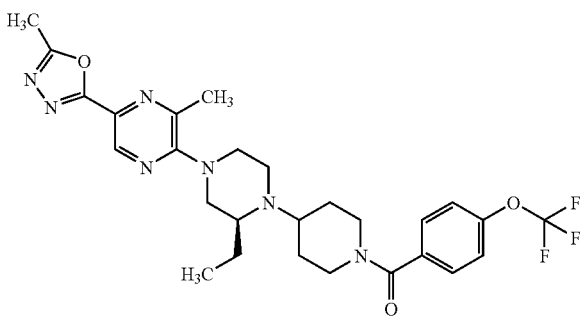 |
| 66 | 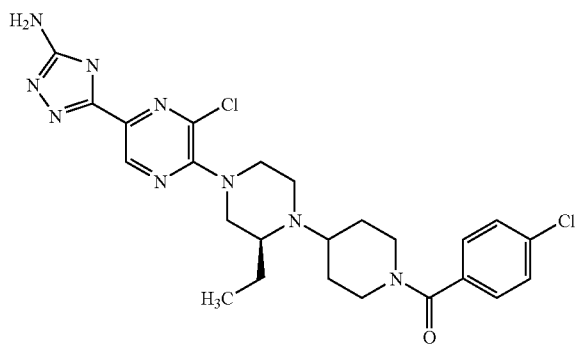 |
| 67 | 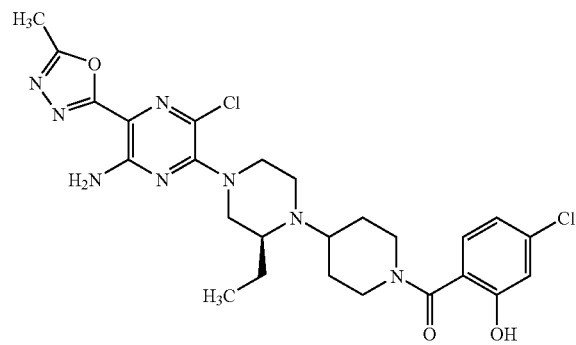 |

-continued
| Compound Number | STRUCTURE |
|---|---|
| 68 | 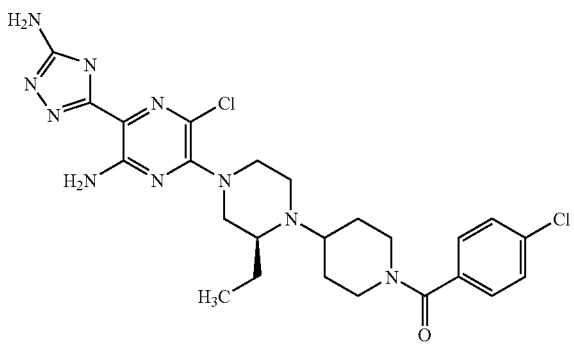 |
| 69 | 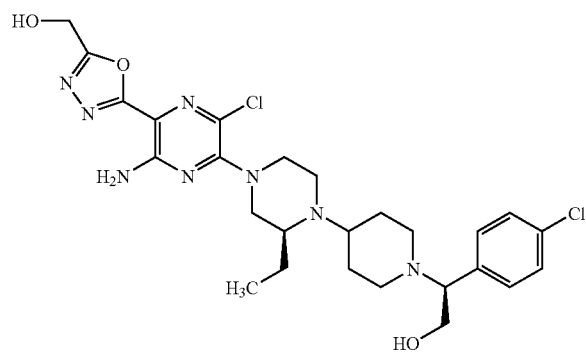 |
| 70 | 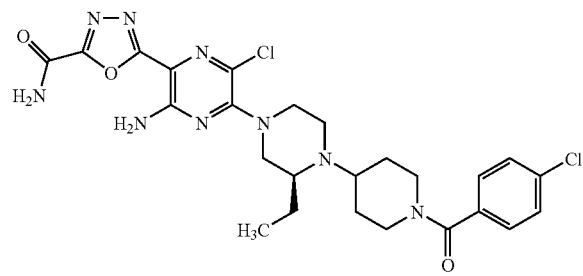 |
| 71 | 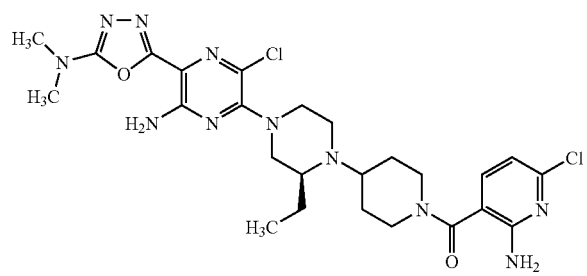 |

-continued
| Compound Number | STRUCTURE |
|---|---|
| 72 | 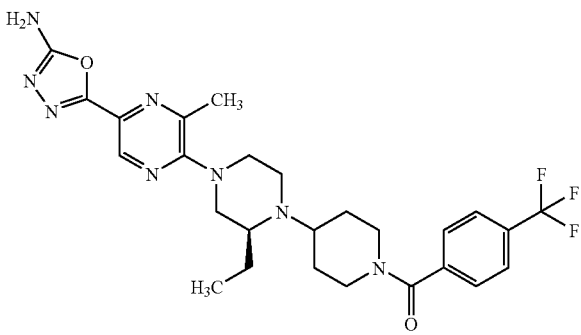 |
| 73 | 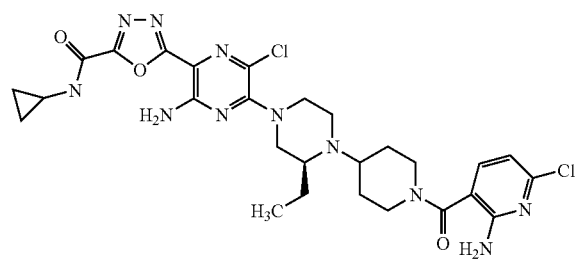 |
| 75 | 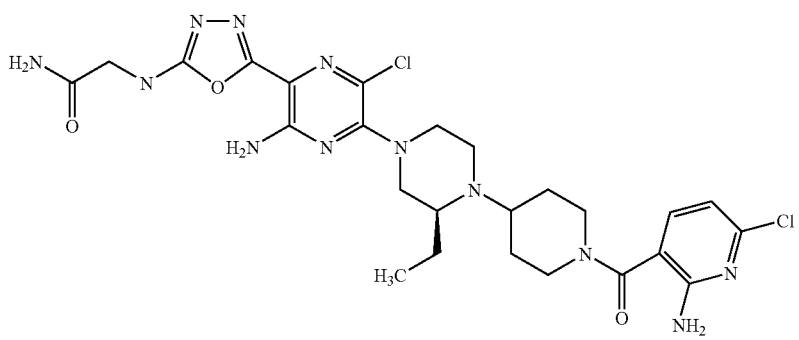 |
| 76 | 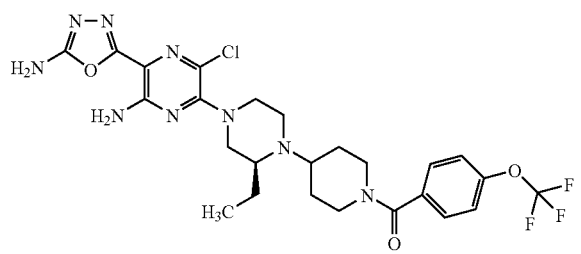 |
| 77 | 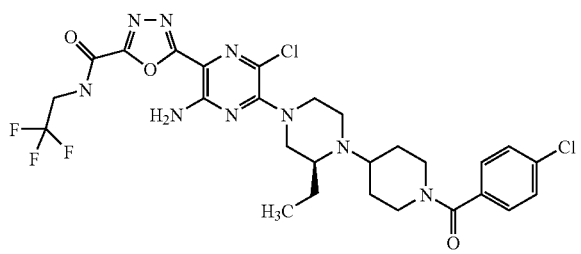 |

-continued
| Compound Number | STRUCTURE |
|---|---|
| 78 | 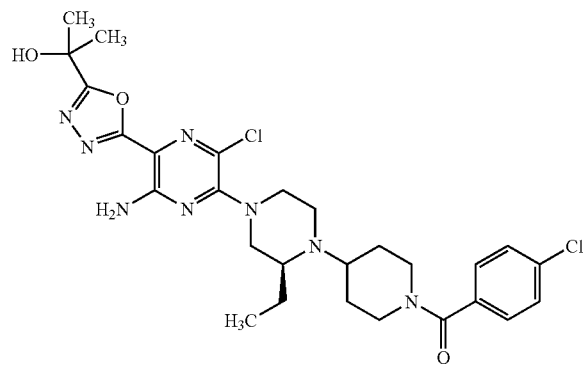 |
| 79 | 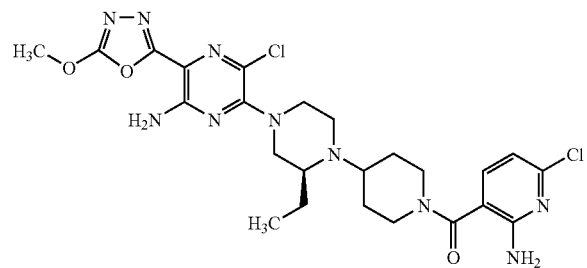 |
| 80 | 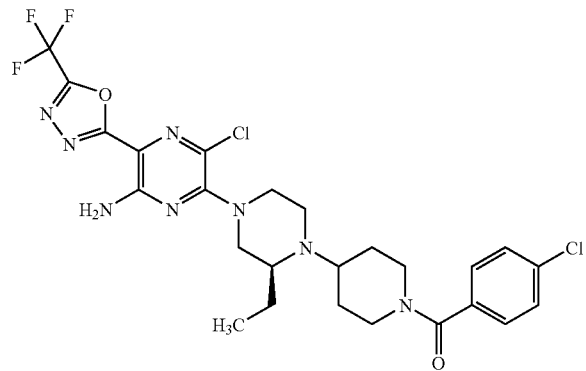 |
| 81 | 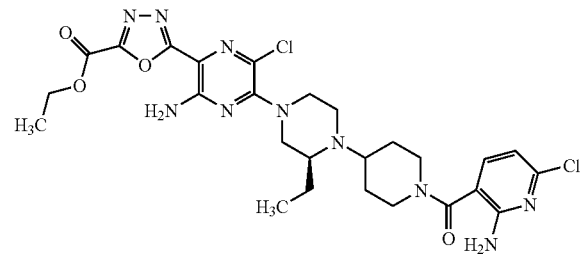 |

-continued
| Compound Number | STRUCTURE |
|---|---|
| 82 | 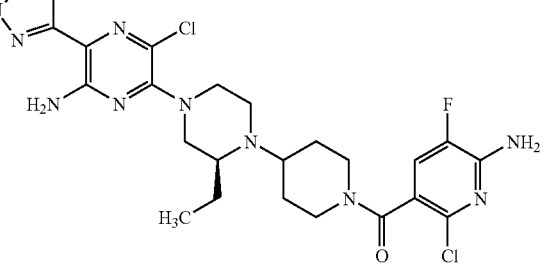 |
| 83 | 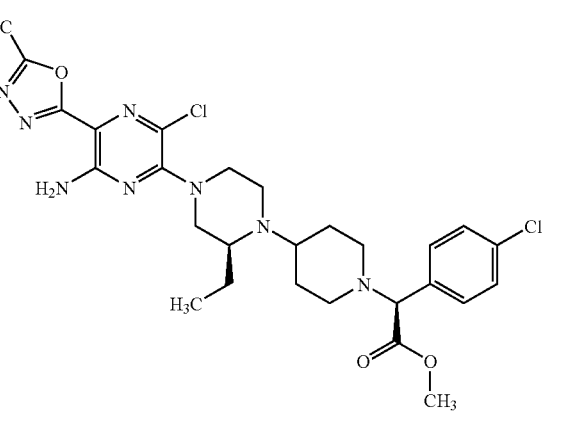 |
| 84 | 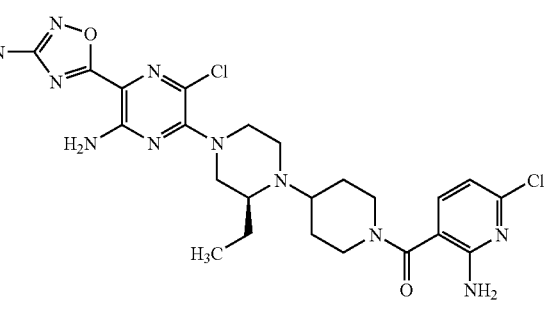 |
| 85 | 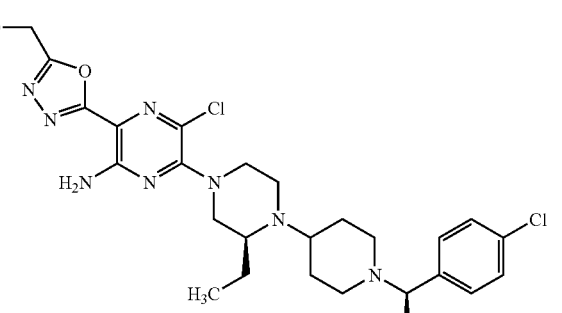 |

-continued

| Compound Number | STRUCTURE |
|---|---|
| 86 | 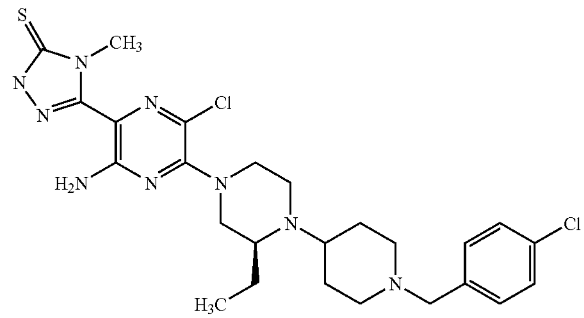 |
| 87 | 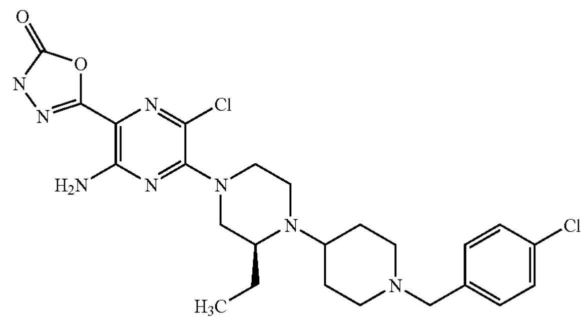 |
| 88 | 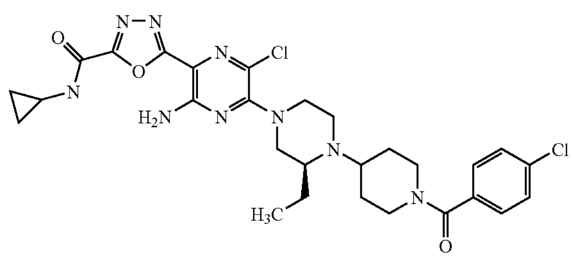 |
| 90 | 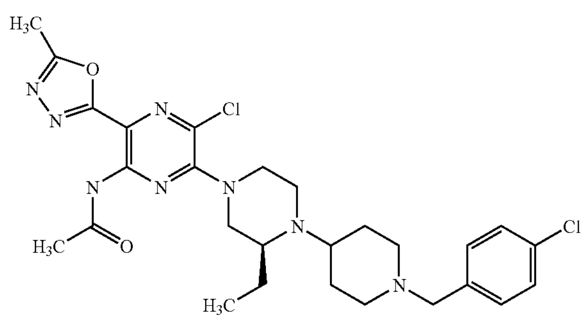 |
| 91 | 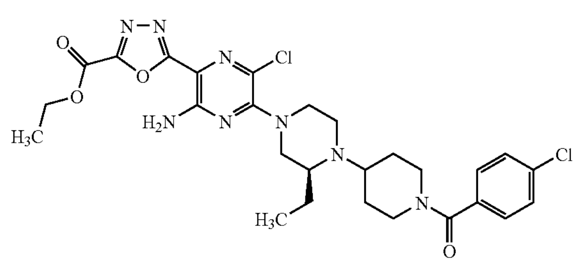 |

-continued
| Compound Number | STRUCTURE |
|---|---|
| 92 | 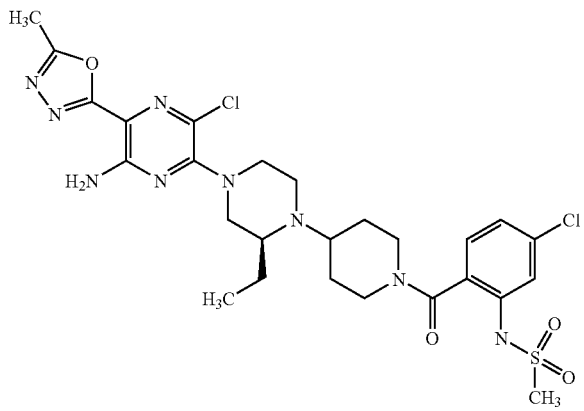 |
| 93 | 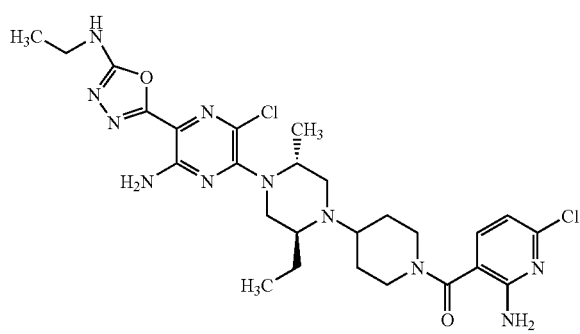 |
| 95 | 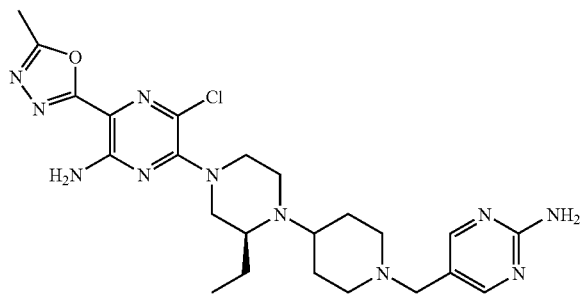 |
| 96 | 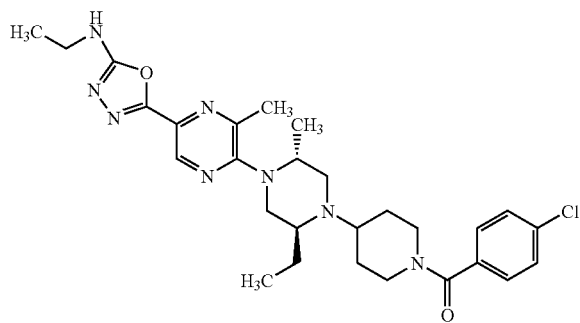 |

-continued
| Compound Number | STRUCTURE |
|---|---|
| 97 | 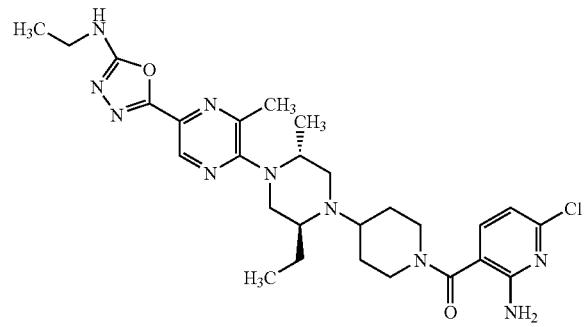 |
| 98 | 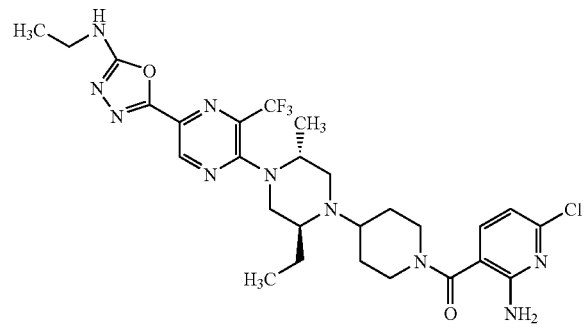 |
| 100 | 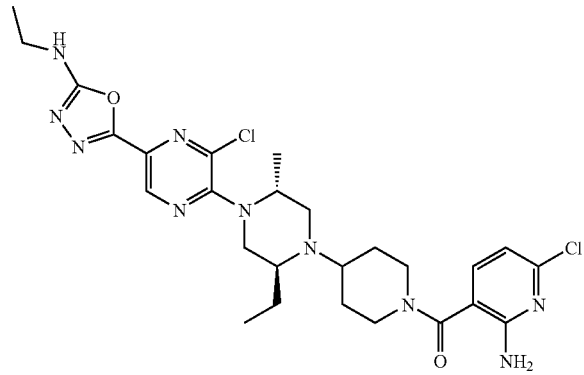 |
| 101 | 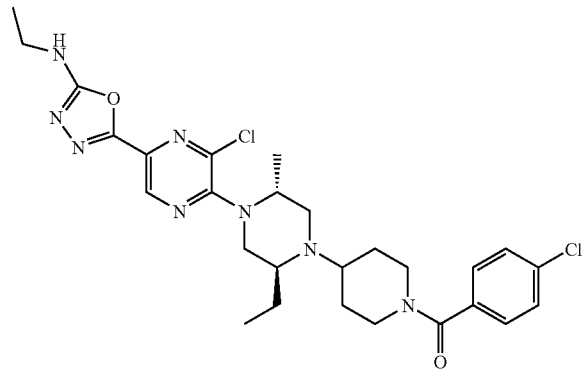 |

-continued
| Compound Number | STRUCTURE |
|---|---|
| 102 | 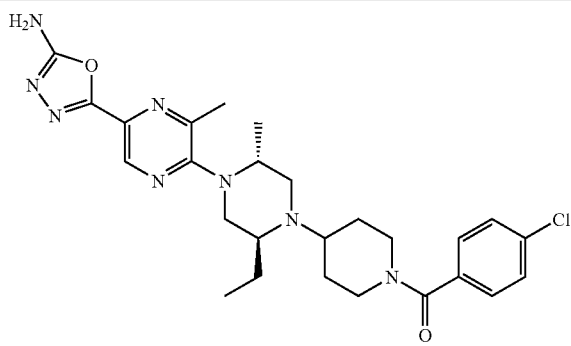 |
| 103 | 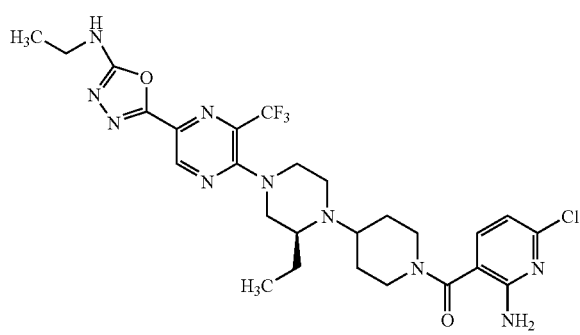 |
| 104 | 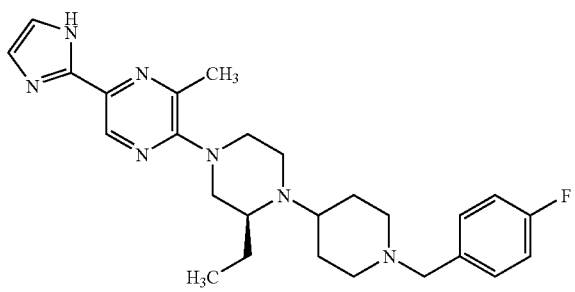 |
| 105 | 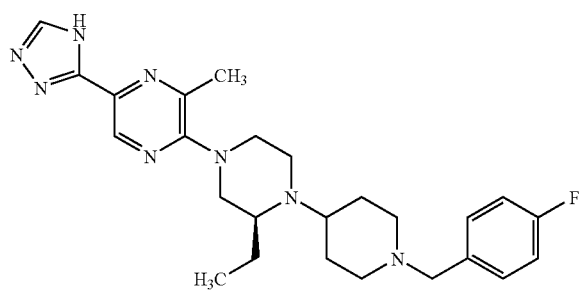 |
| 106 | 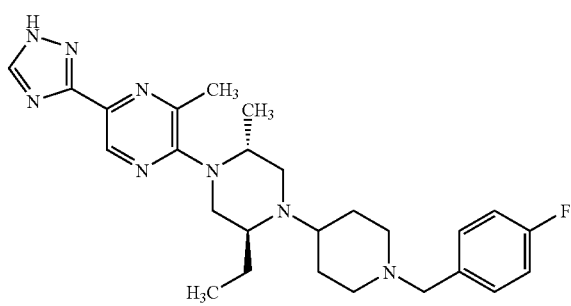 |

-continued
| Compound Number | STRUCTURE |
|---|---|
| 107 | 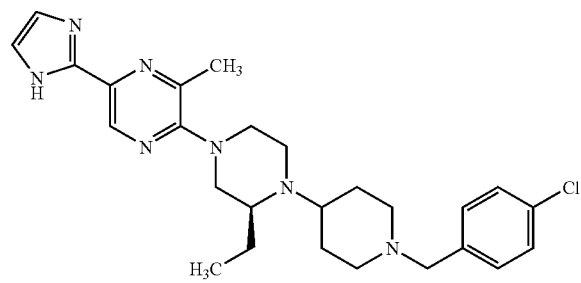 |
| 108 | 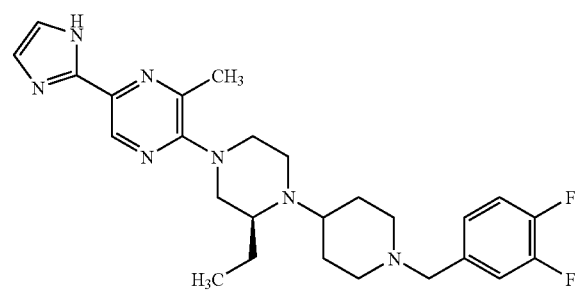 |
| 109 | 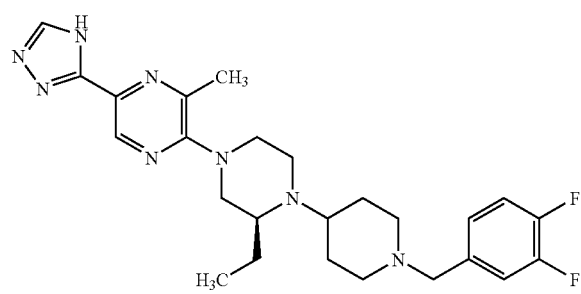 |
| 110 | 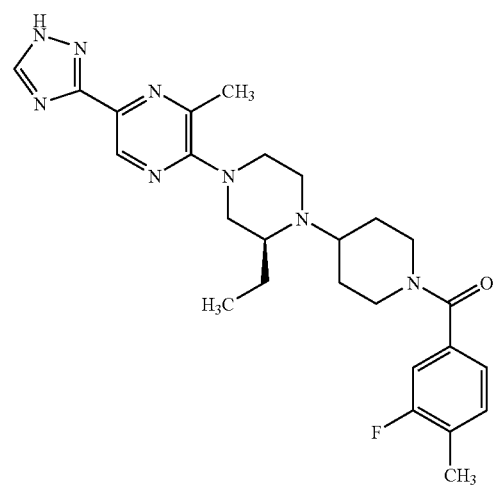 |

-continued
| Compound Number | STRUCTURE |
|---|---|
| 111 | 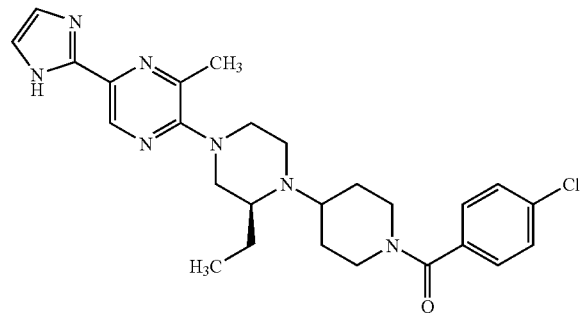 |
| 112 | 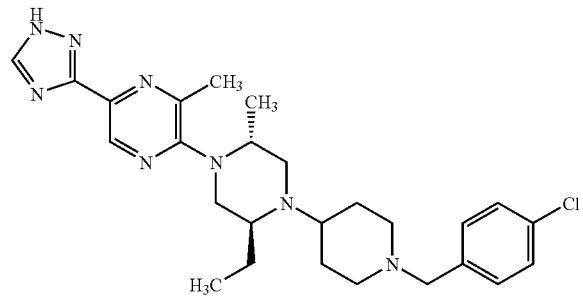 |
| 113 | 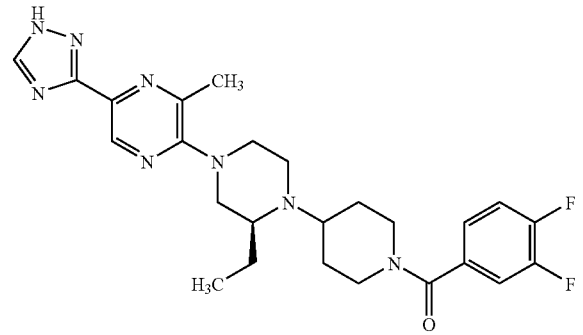 |
| 114 | 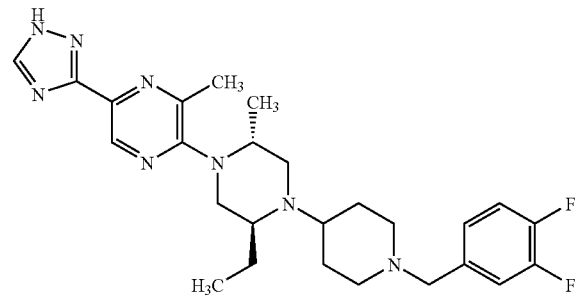 |

-continued
| Compound Number | STRUCTURE |
|---|---|
| 115 | 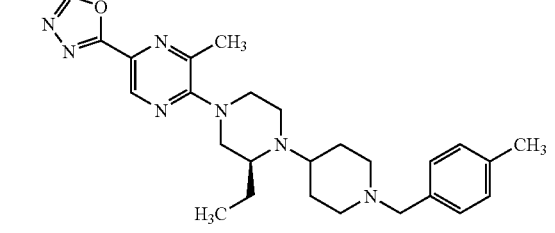 |
| 116 | 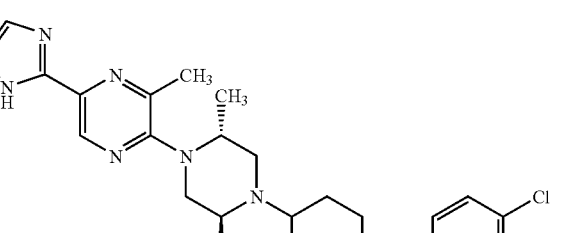 |
| 117 | 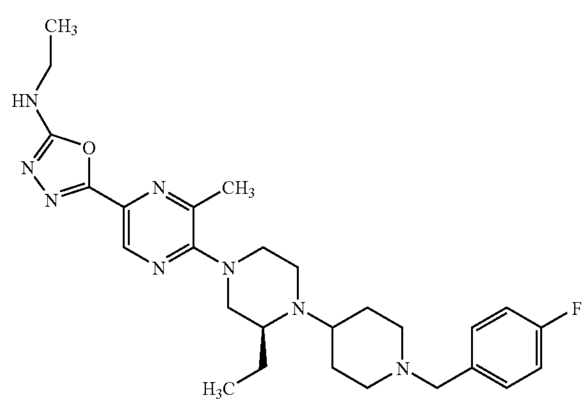 |
| 118 | 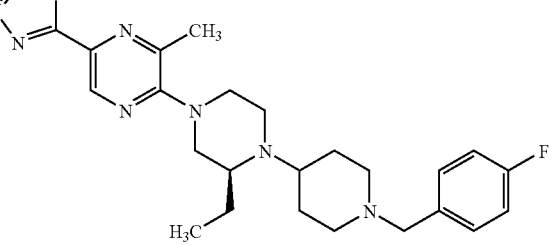 |

-continued
| Compound Number | STRUCTURE |
|---|---|
| 119 | 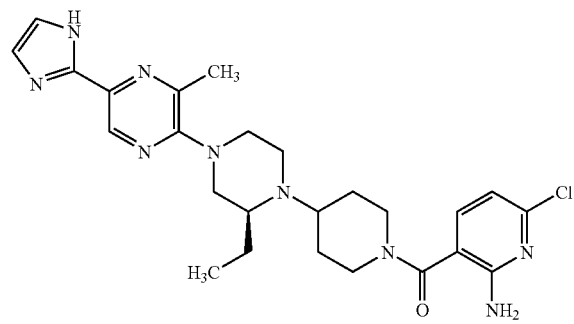 |
| 120 | 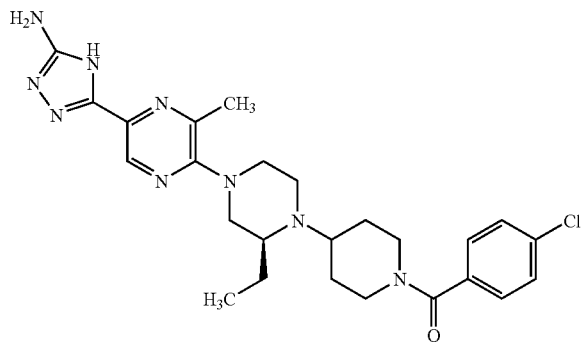 |
| 121 | 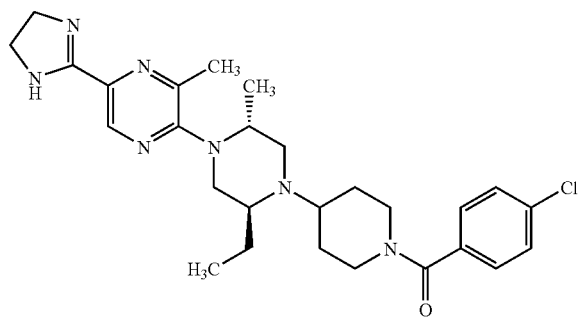 |
| 122 | 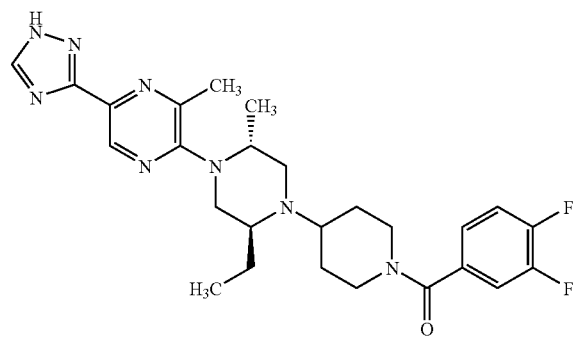 |

-continued
| Compound Number | STRUCTURE |
|---|---|
| 123 | 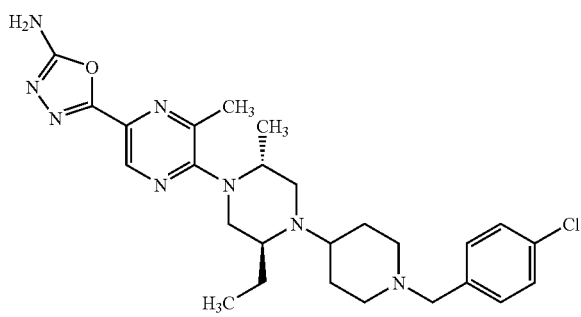 |
| 124 | 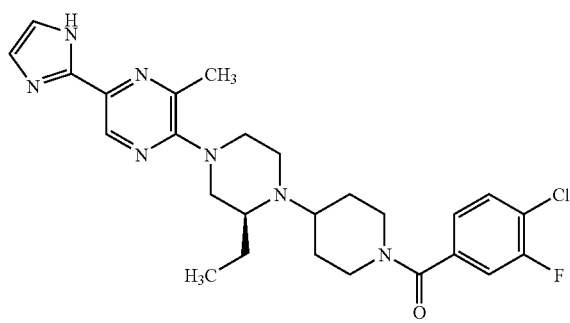 |
| 125 | 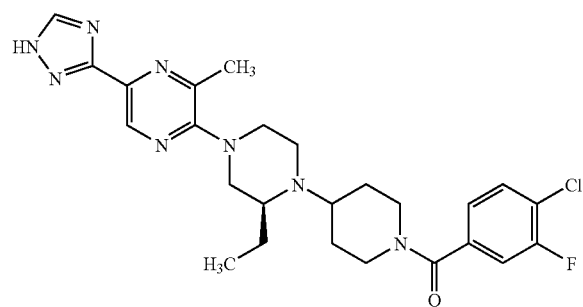 |
| 126 | 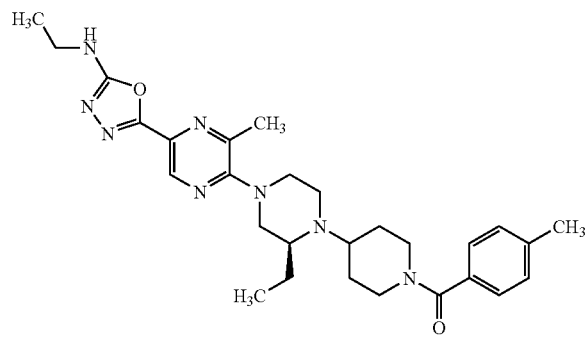 |

-continued
| Compound Number | STRUCTURE |
|---|---|
| 127 | 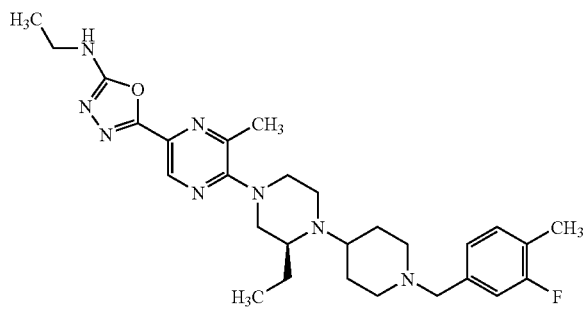 |
| 128 | 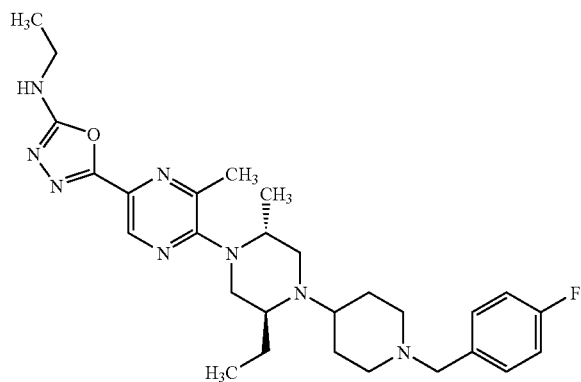 |
| 129 | 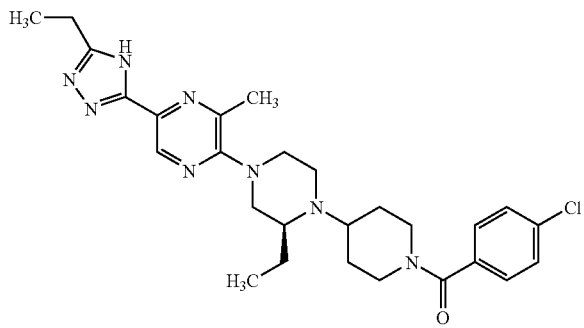 |
| 130 | 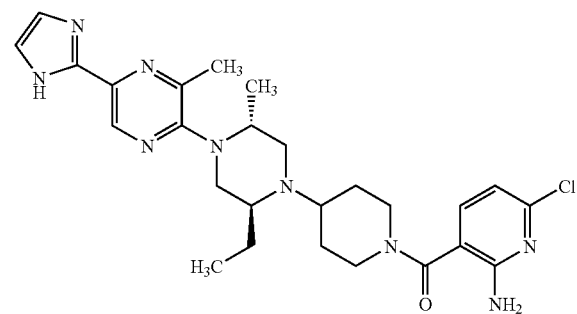 |

| Compound Number | STRUCTURE |
|---|---|
| 131 | 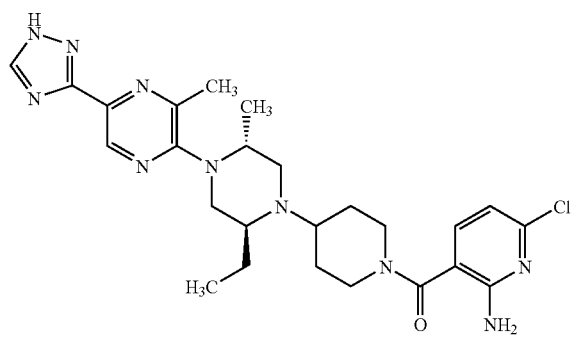 |
| 132 | 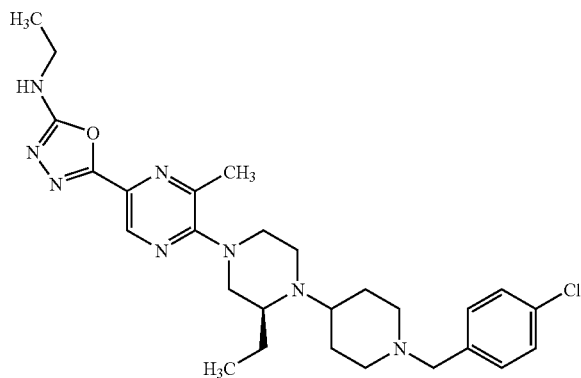 |
| 133 | 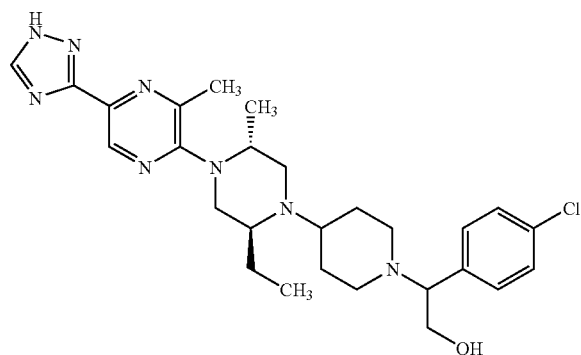 |
| 134 | 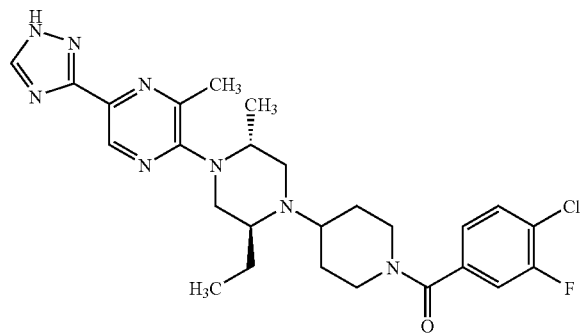 |

| Compound Number | STRUCTURE |
|---|---|
| 135 | 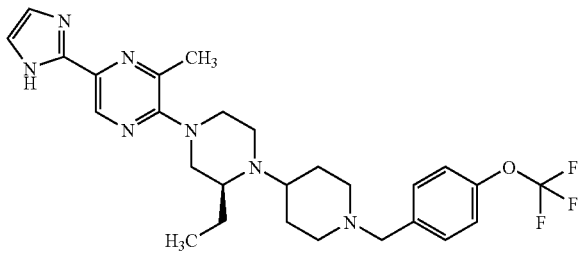 |
| 136 | 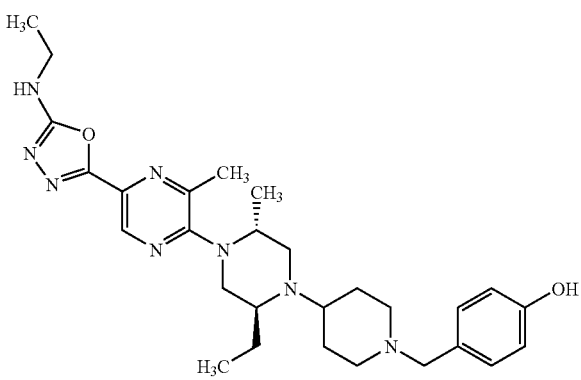 |
| 137 | 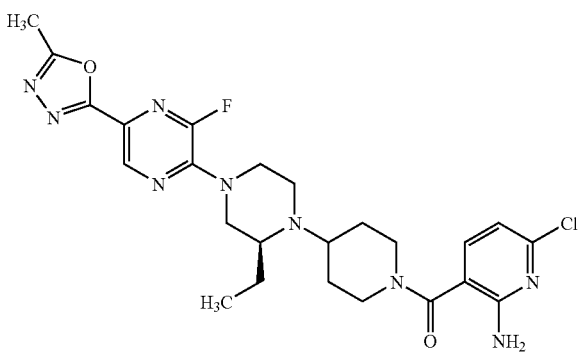 |
| 138 | 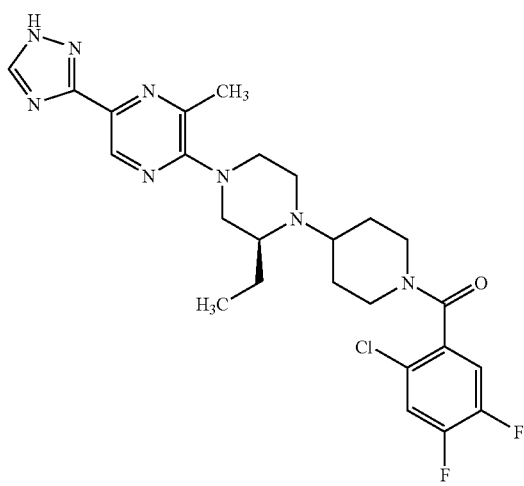 |

| Compound Number | STRUCTURE |
|---|---|
| 139 | 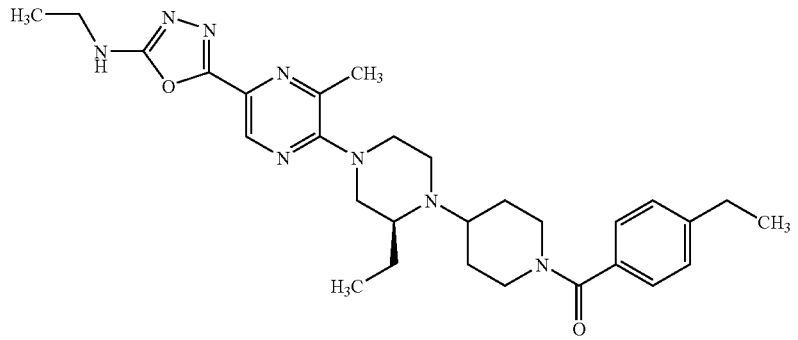 |
| 140 | 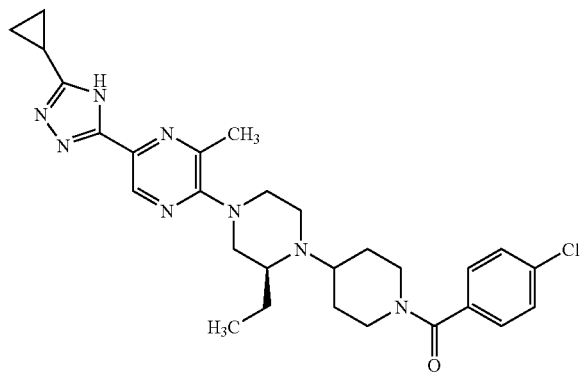 |
| 141 | 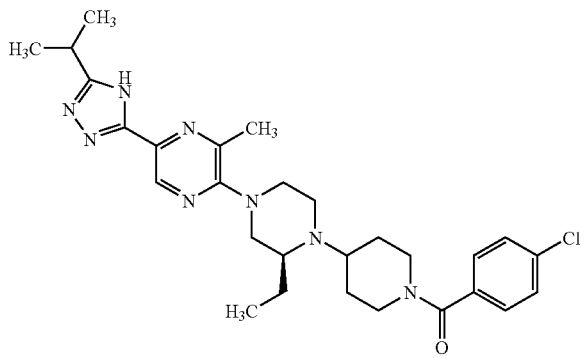 |
| 142 | 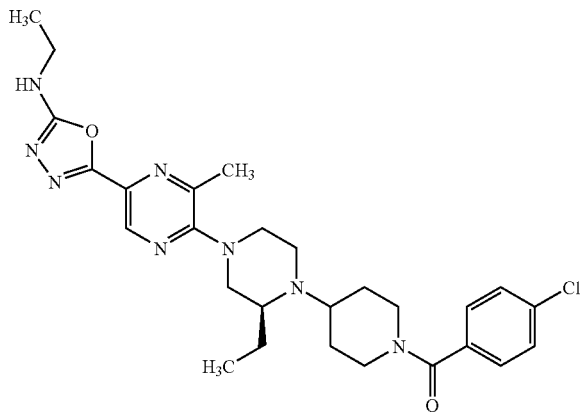 |

-continued
| Compound Number | STRUCTURE |
|---|---|
| 143 | 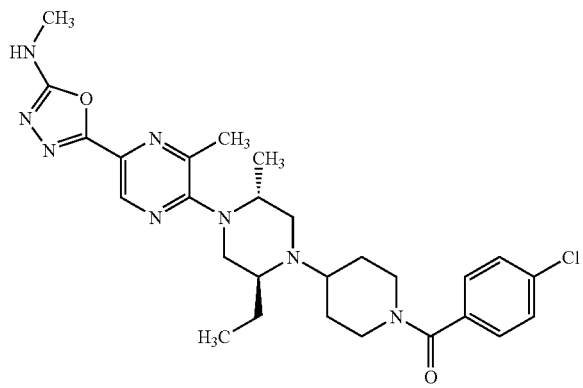 |
| 144 | 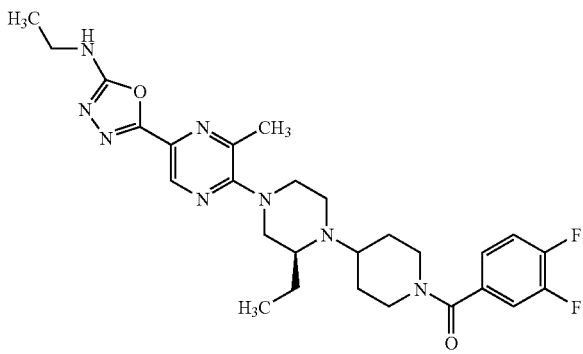 |
| 145 | 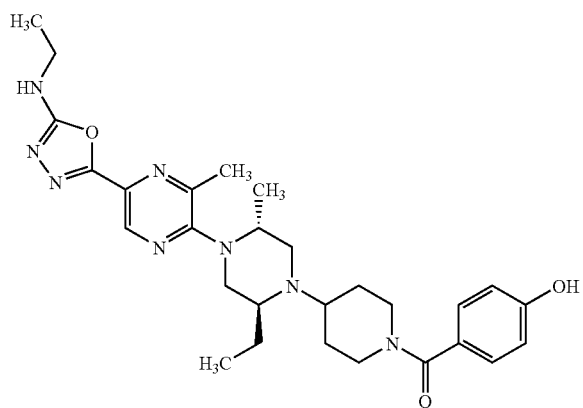 |
| 147 | 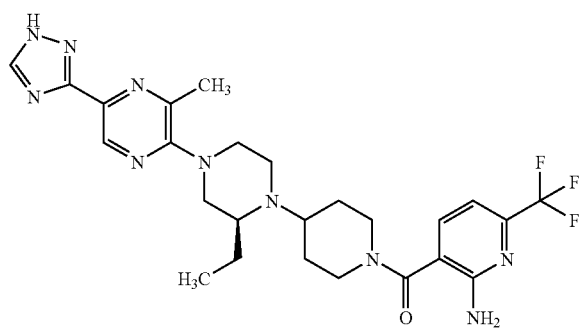 |

| Compound Number | STRUCTURE |
|---|---|
| 148 | 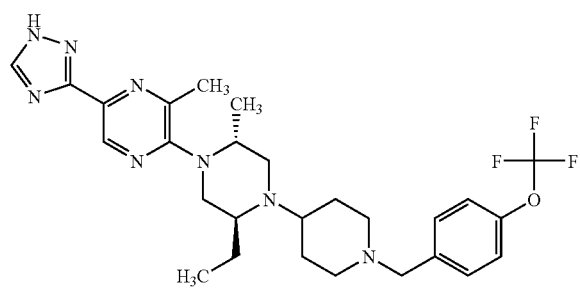 |
| 149 | 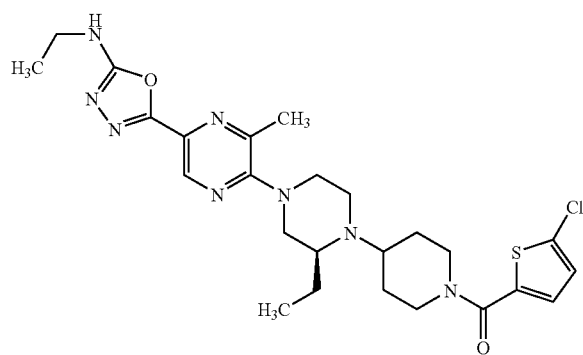 |
| 150 | 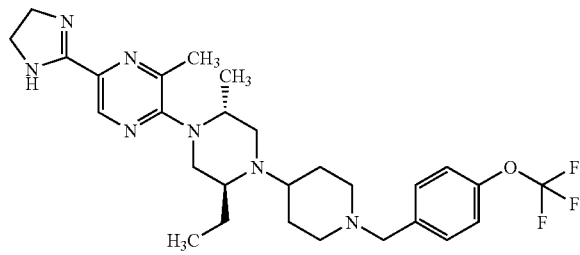 |
| 151 | 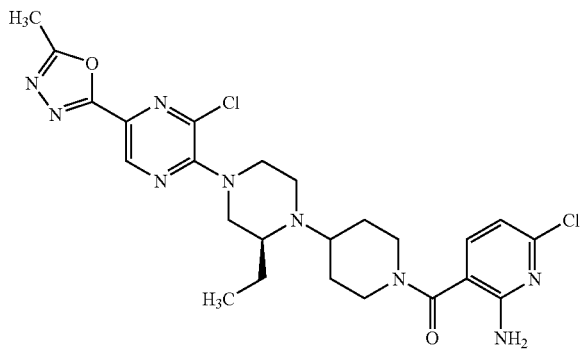 |

-continued
| Compound Number | STRUCTURE |
|---|---|
| 152 | 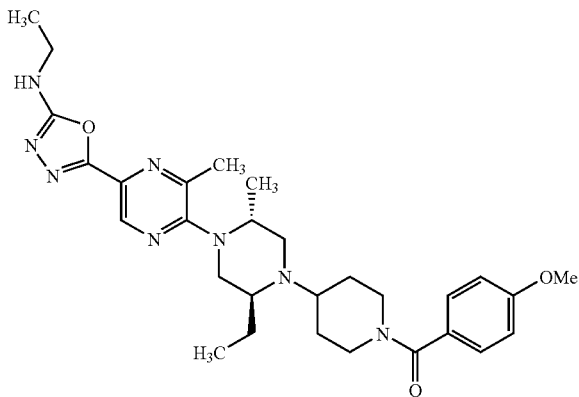 |
| 153 | 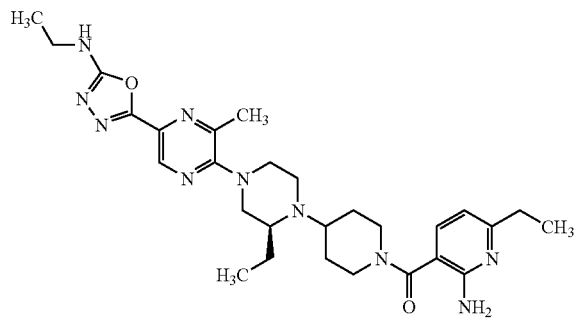 |
| 154 | 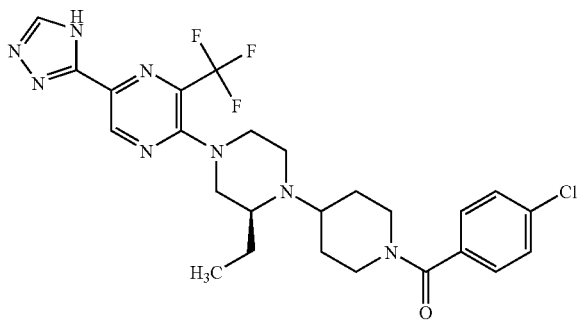 |
| 155 | 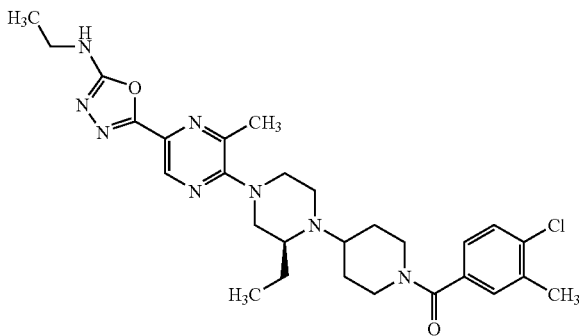 |

-continued
| Compound Number | STRUCTURE |
|---|---|
| 156 | 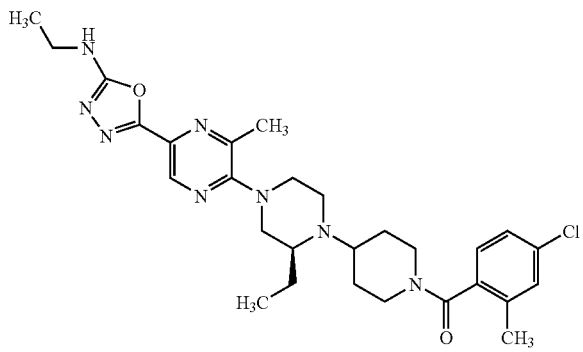 |
| 157 | 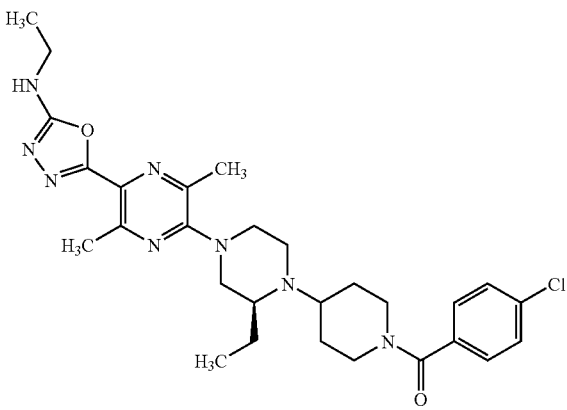 |
| 158 | 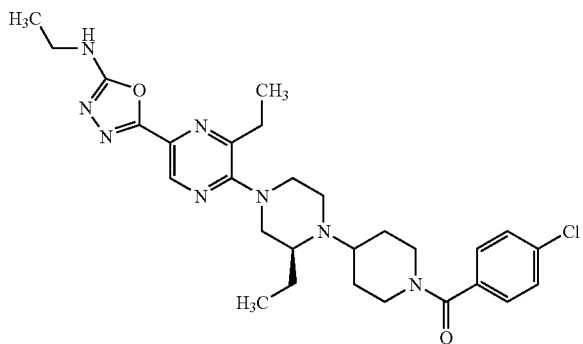 |
| 159 | 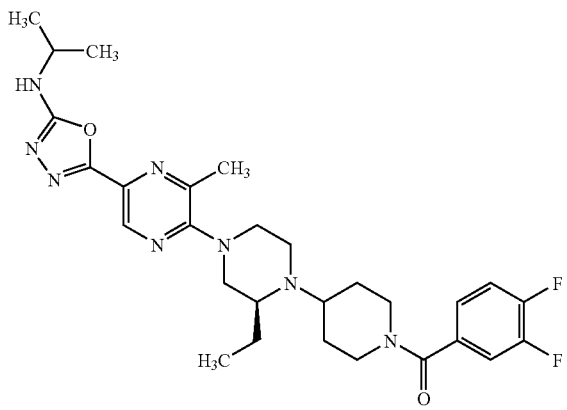 |

| Compound Number | STRUCTURE |
|---|---|
| 160 | 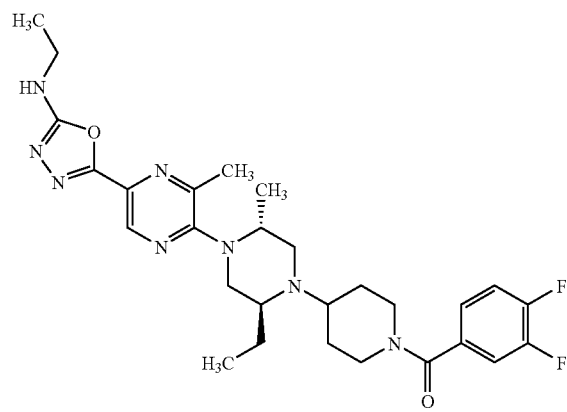 |
| 161 | 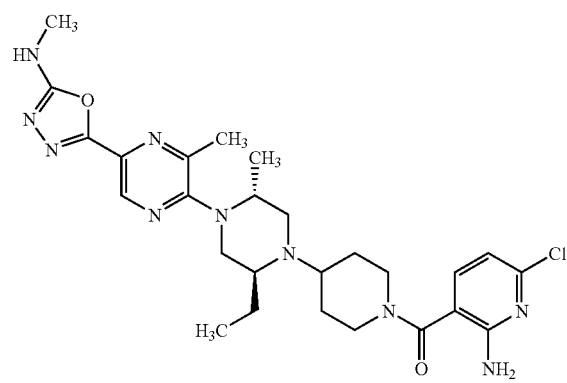 |
| 162 | 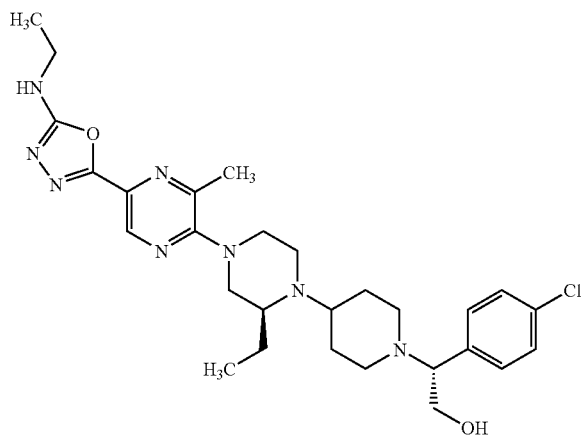 |

-continued
| Compound Number | STRUCTURE |
|---|---|
| 163 | 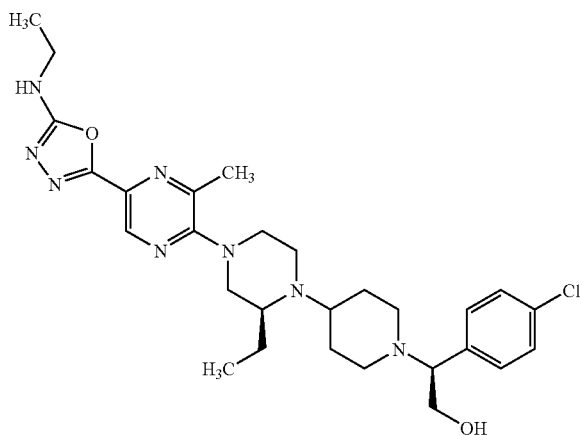 |
| 164 | 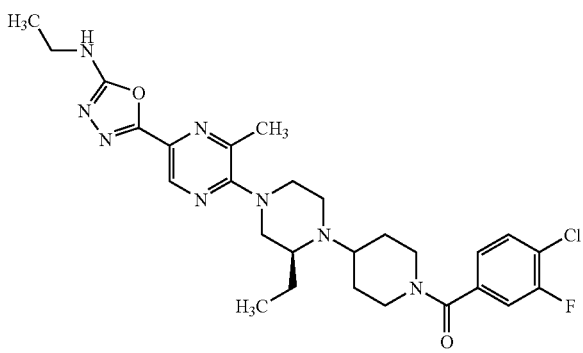 |
| 165 | 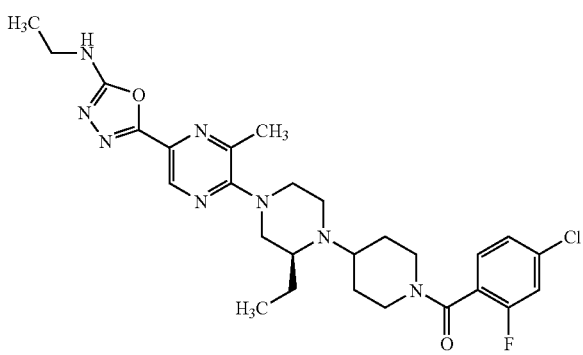 |
| 166 | 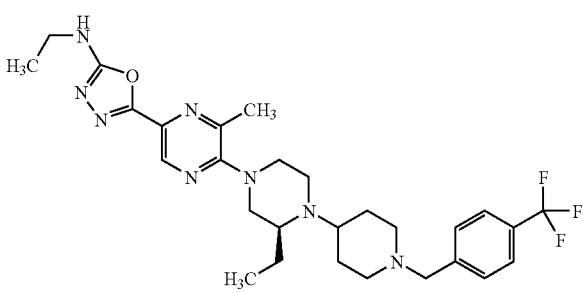 |

-continued
| Compound Number | STRUCTURE |
|---|---|
| 167 | 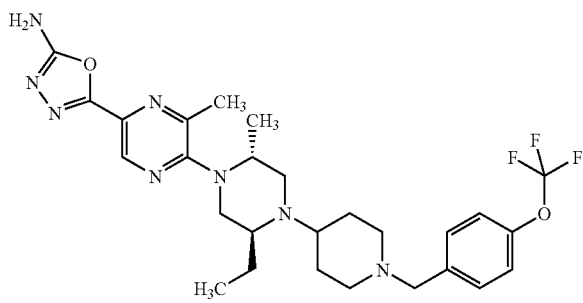 |
| 168 | 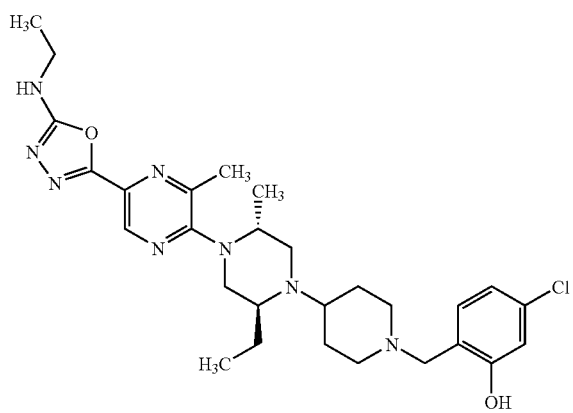 |
| 169 | 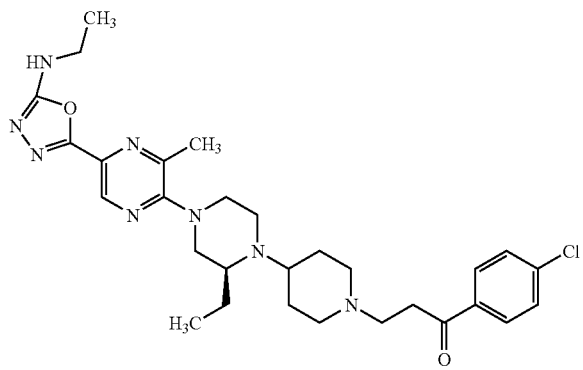 |
| 170 | 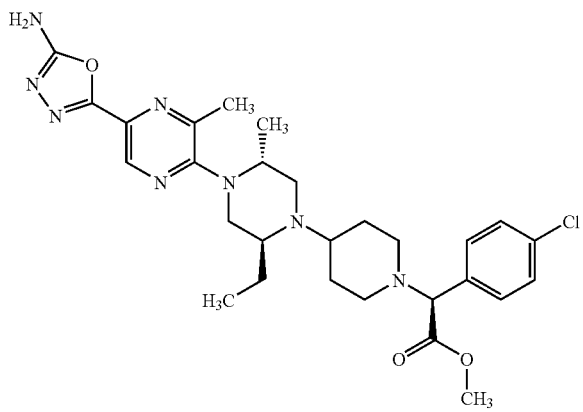 |

-continued
| Compound Number | STRUCTURE |
|---|---|
| 171 | 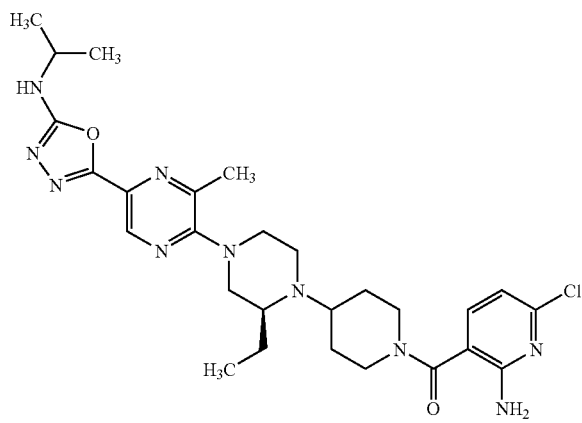 |
| 172 | 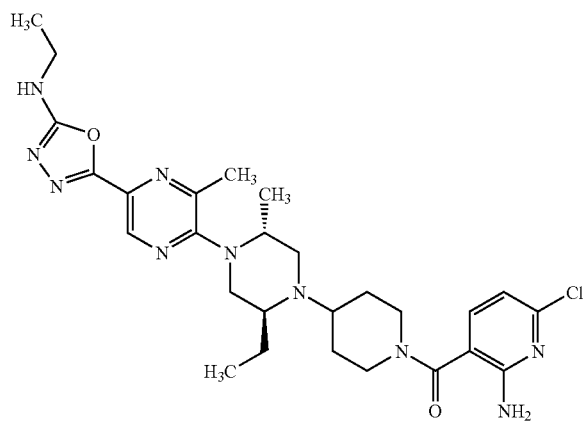 |
| 173 | 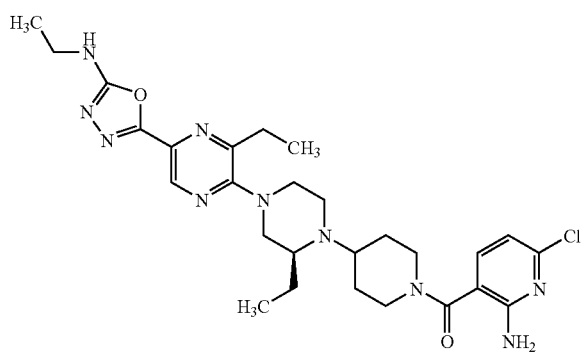 |
| 174 | 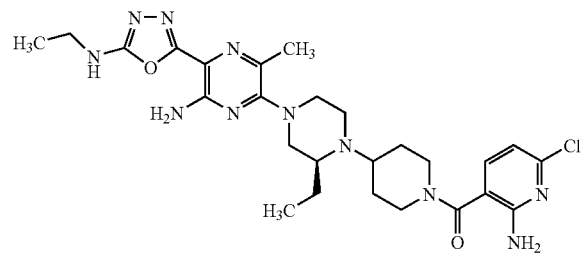 |

| Compound Number | STRUCTURE |
|---|---|
| 175 | 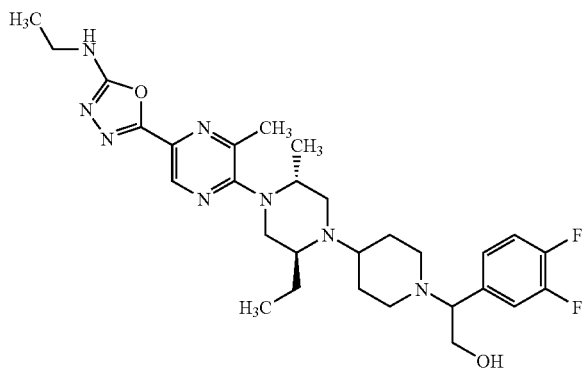 |
| 176 | 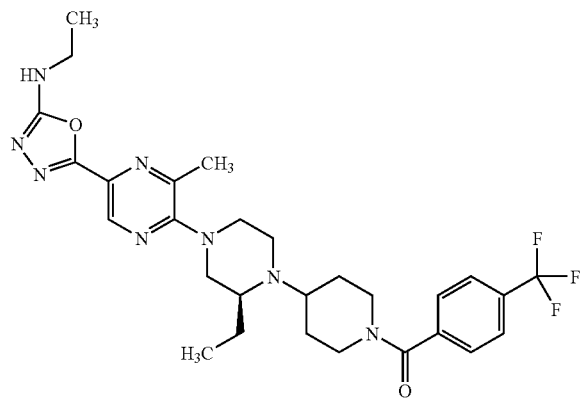 |
| 177 | 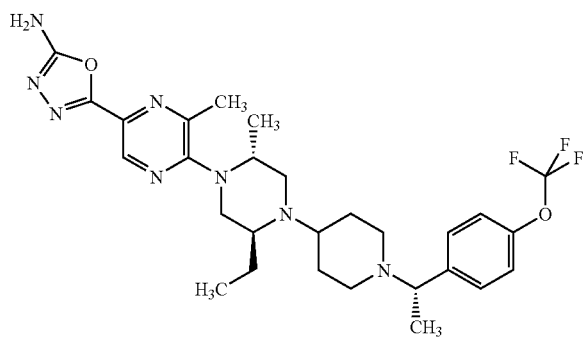 |
| 178 | 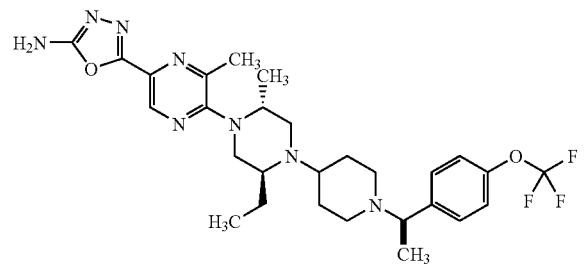 |

| Compound Number | STRUCTURE |
|---|---|
| 179 | 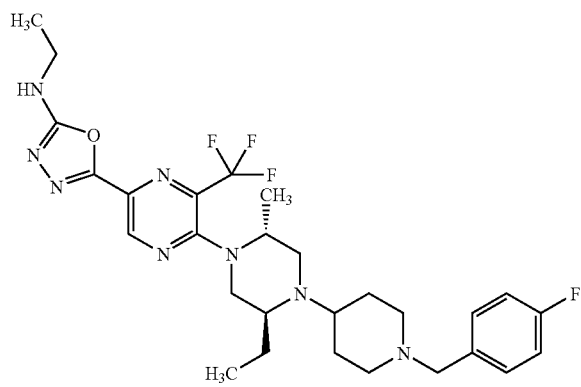 |
| 180 | 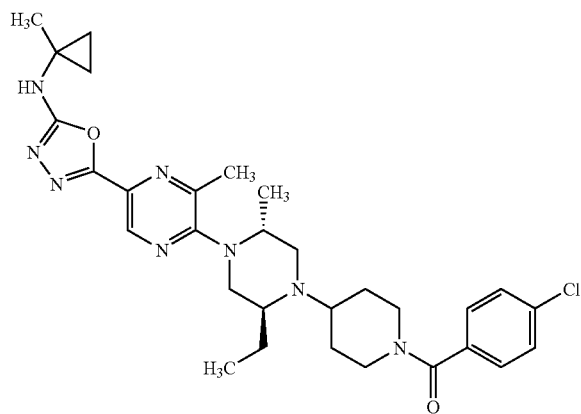 |
| 181 | 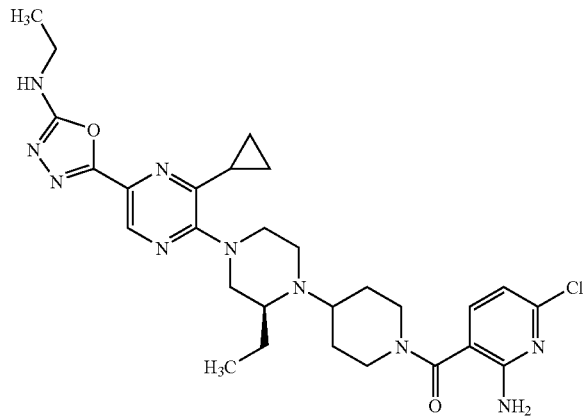 |

-continued

| Compound Number | STRUCTURE |
|---|---|
| 182 | 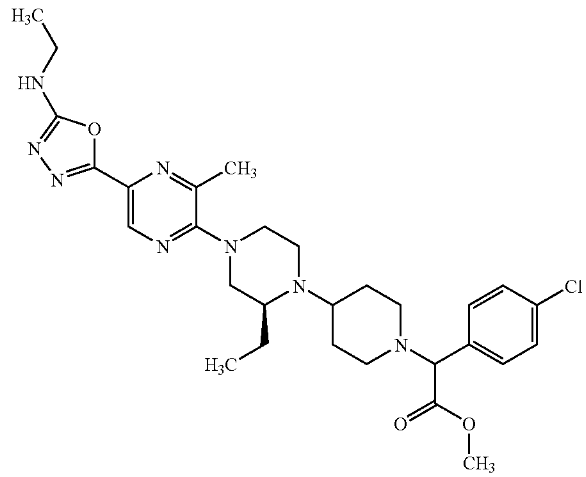 |
| 183 | 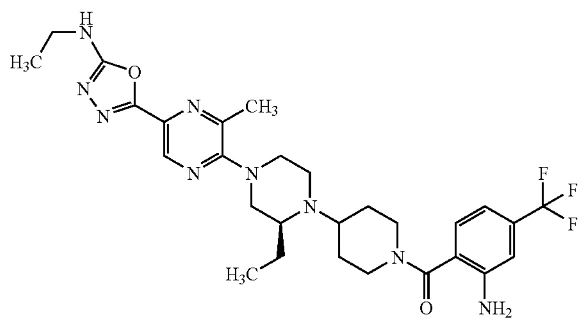 |
| 184 | 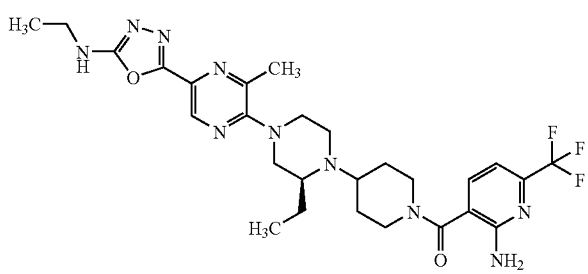 |
| 185 | 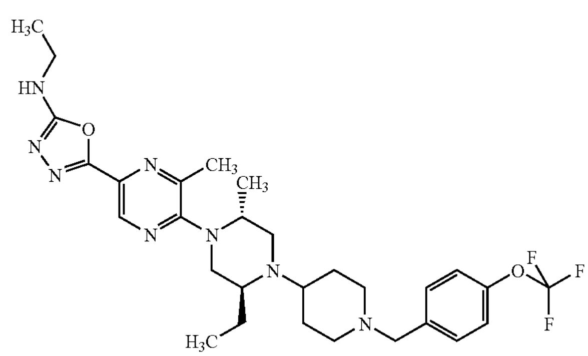 |

-continued
| Compound Number | STRUCTURE |
|---|---|
| 186 | 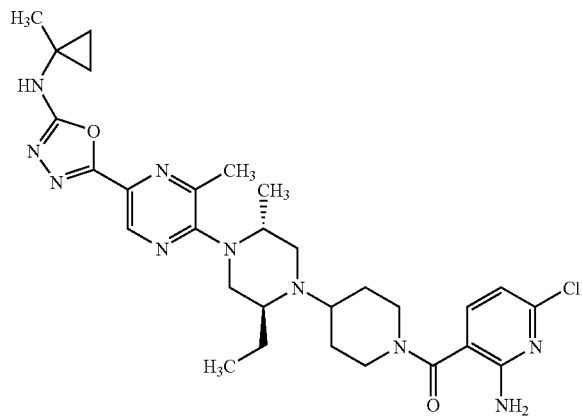 |
| 187 | 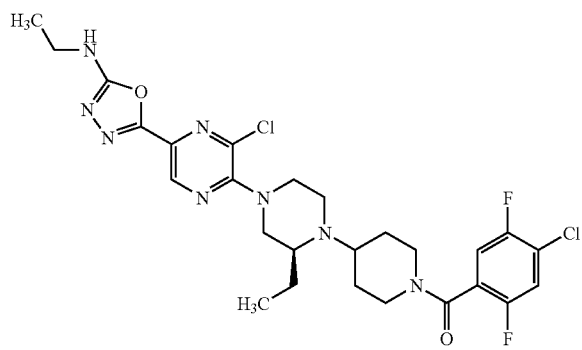 |
| 188 | 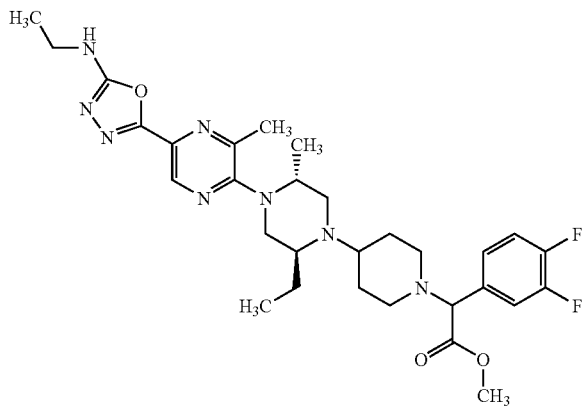 |
| 189 | 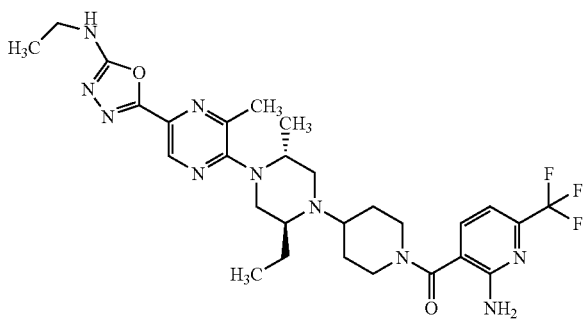 |

-continued
| Compound Number | STRUCTURE |
|---|---|
| 190 | 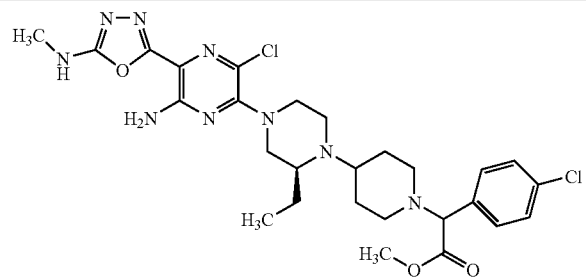 |
| 191 | 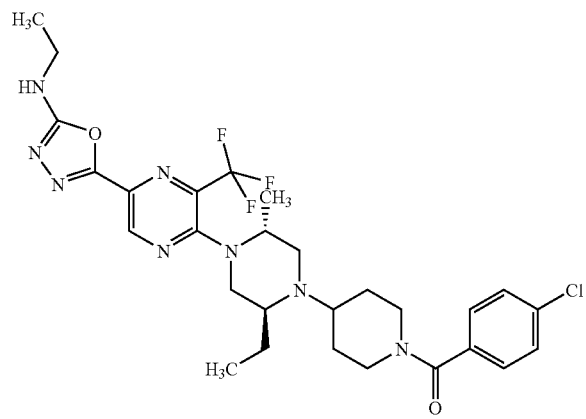 |
| 192 | 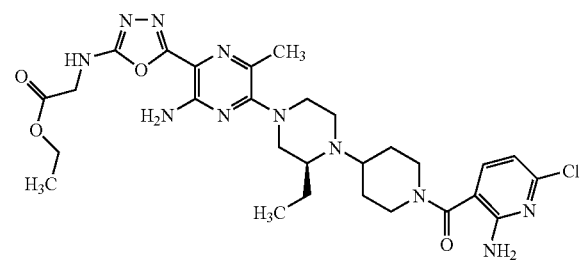 |
| 193 | 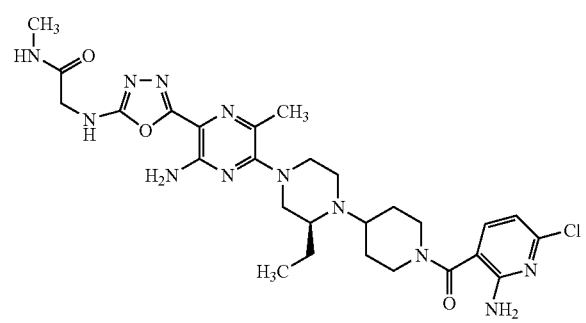 |
| 194 | 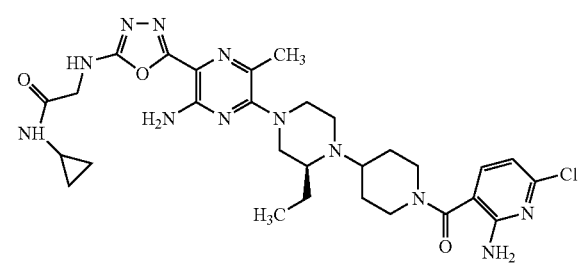 |

-continued
| Compound Number | STRUCTURE |
|---|---|
| 195 | 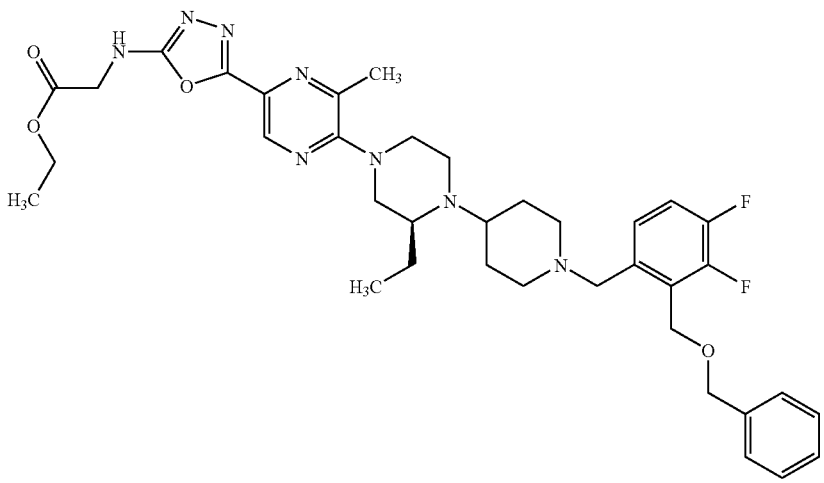 |
| 196 | 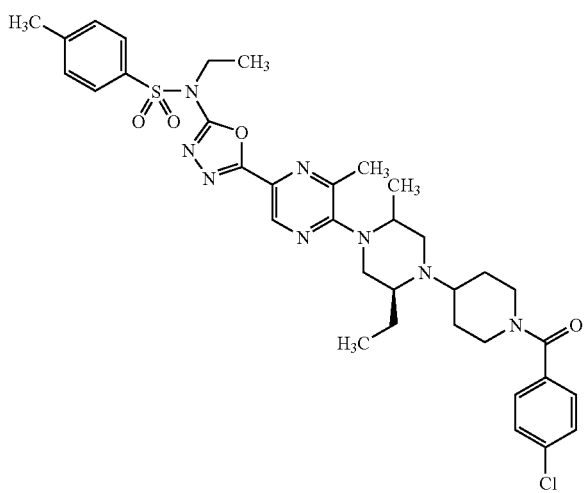 |
or a pharmaceutically acceptable salt thereof.
37. The compound according to claim 36, selected from the group consisting of
1
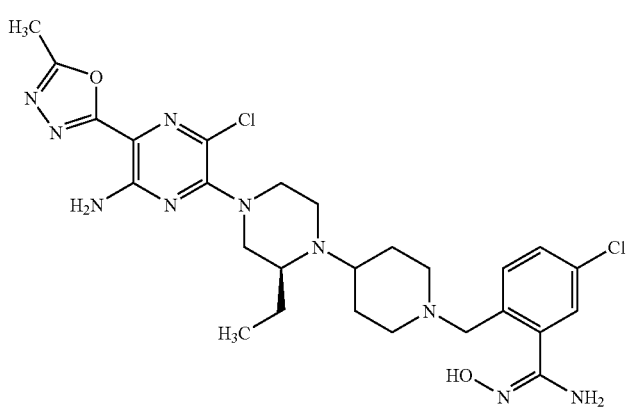

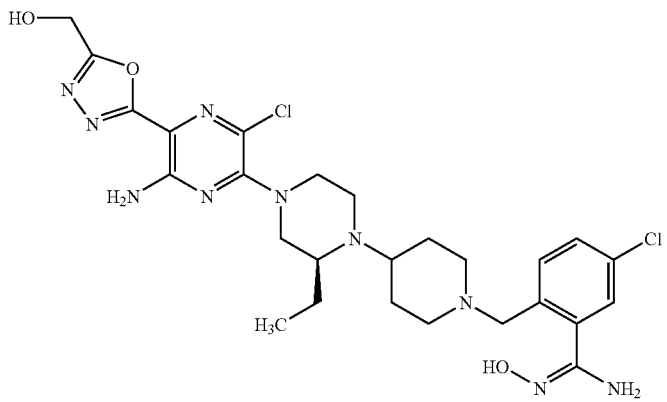
2
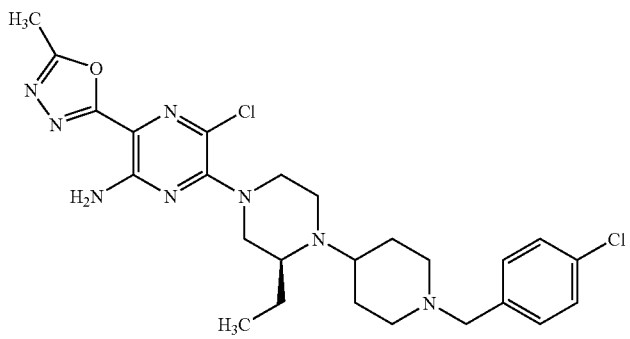
4
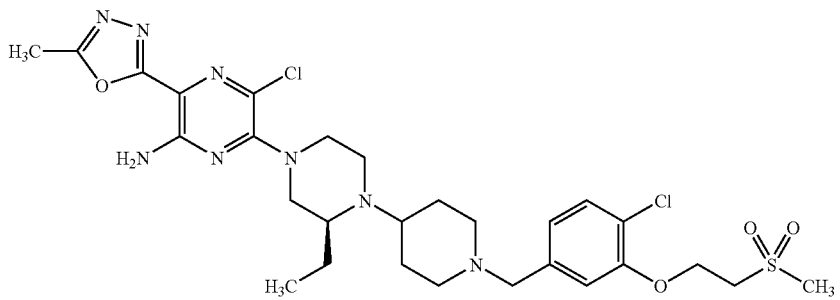
7
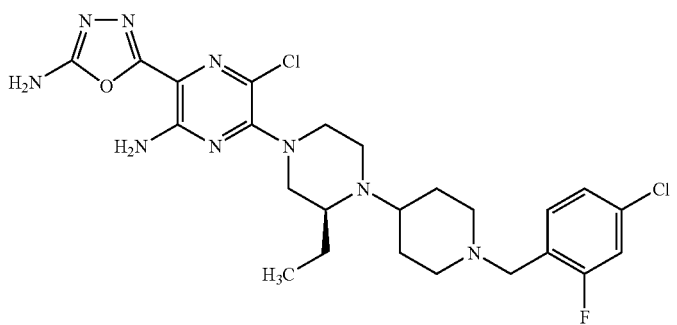
3

-continued
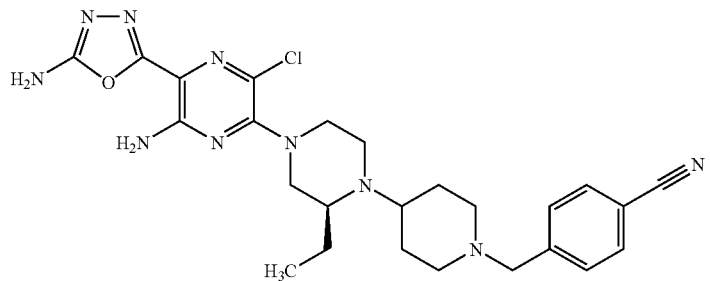
9
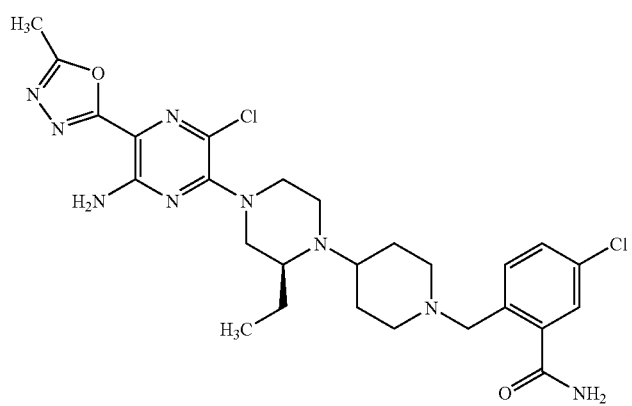
8
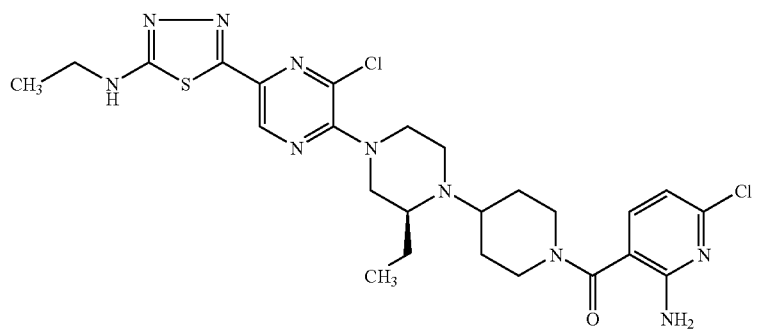
18
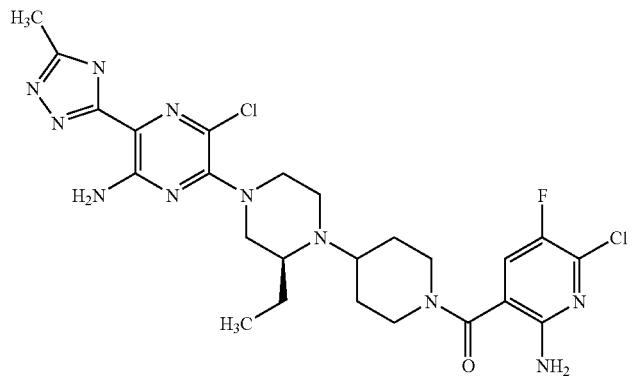
19

-continued
37
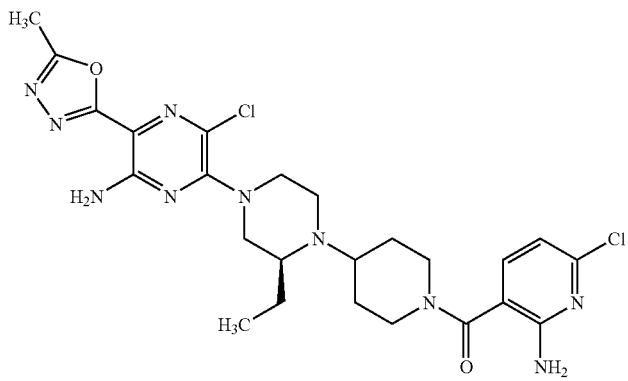
12
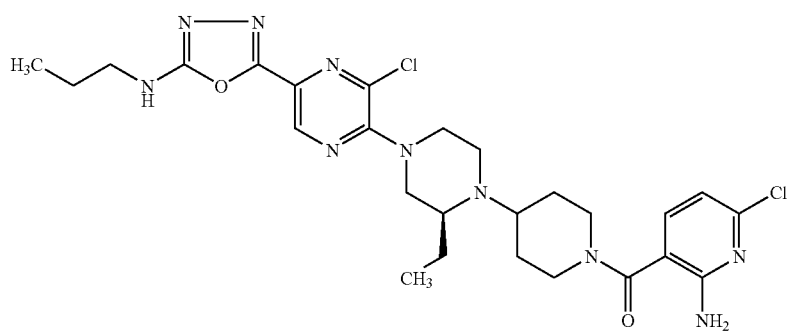
17
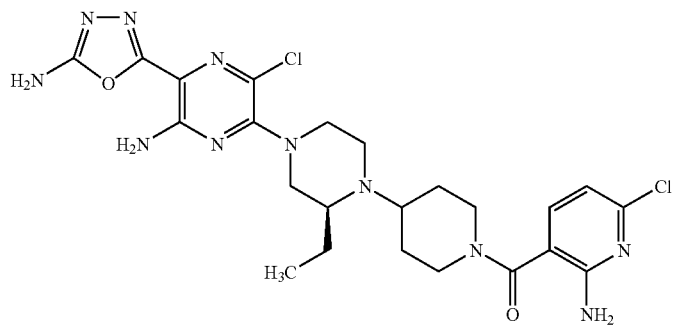
103
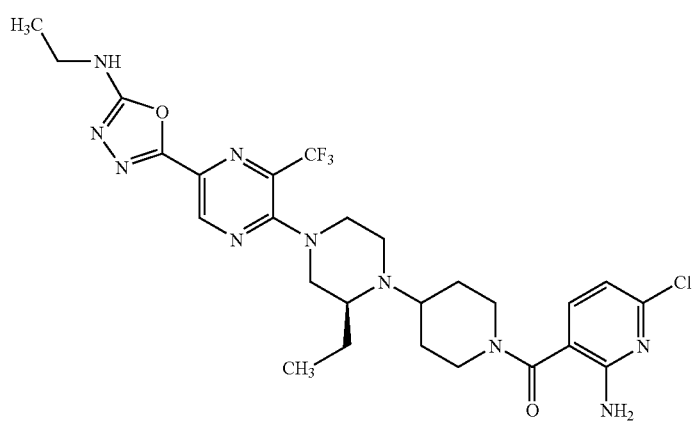

-continued
98
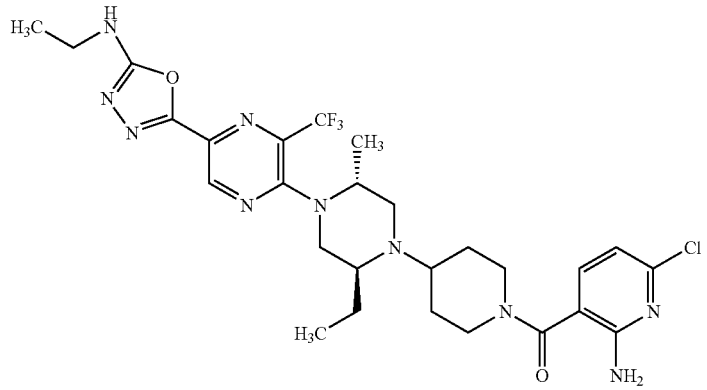
93
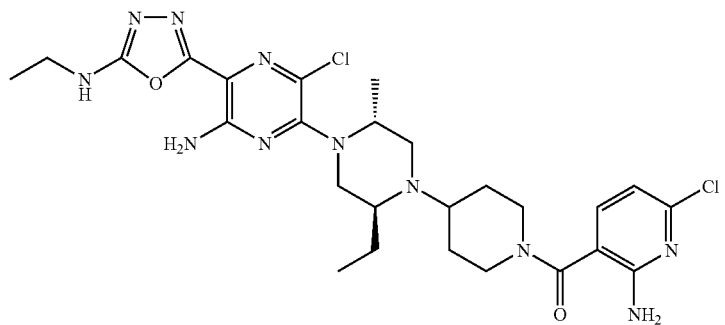
13
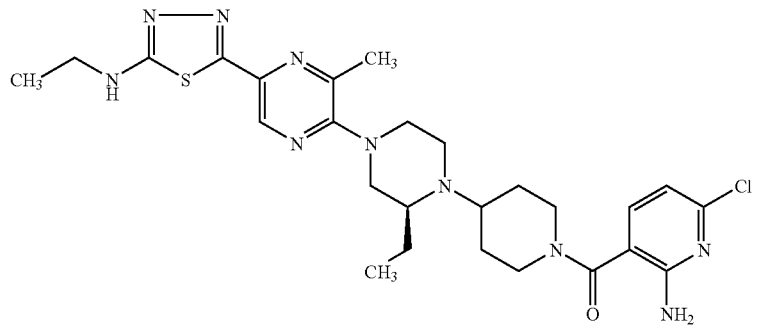
14
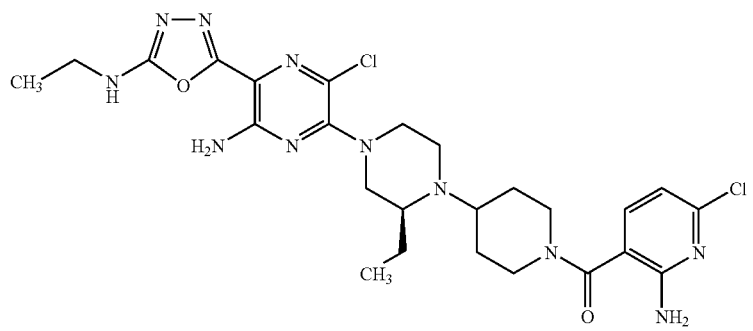

-continued
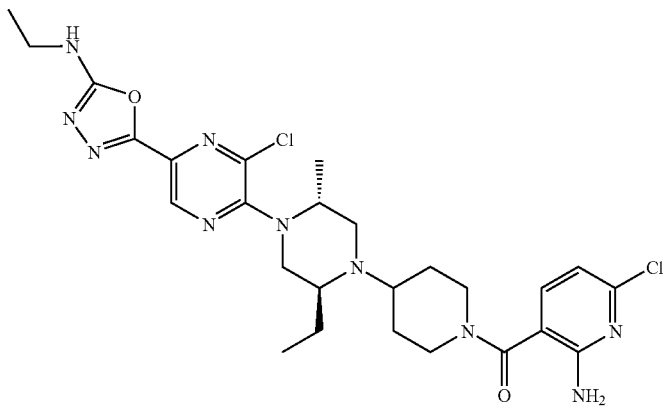
100
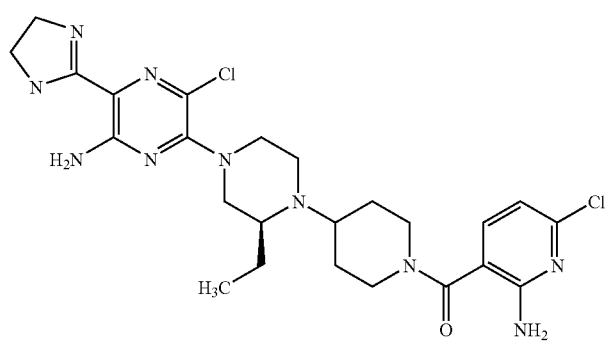
24
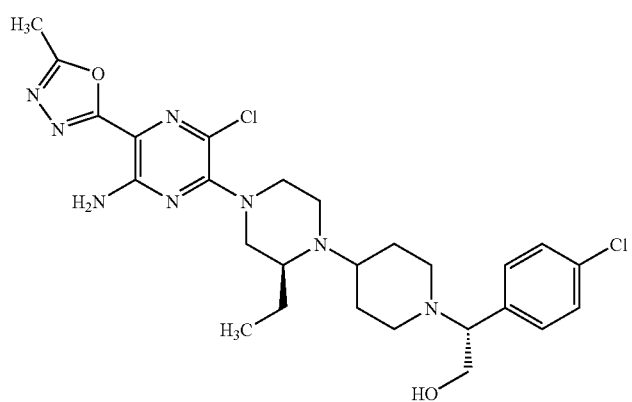
5
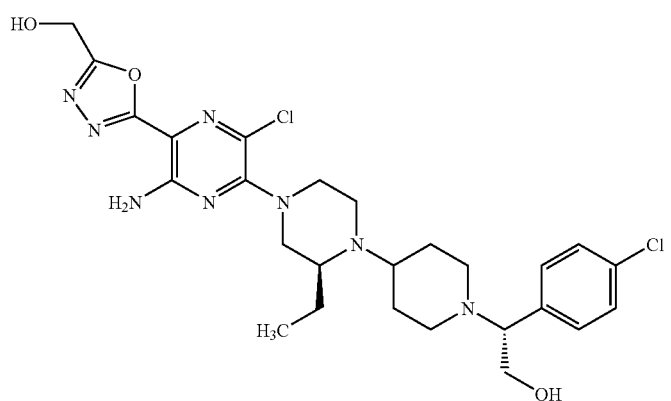
6

-continued
21
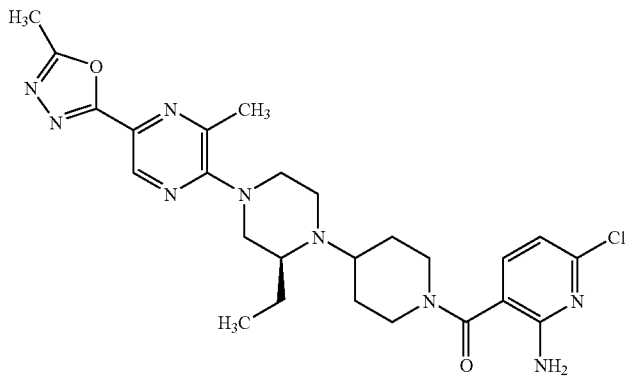
20
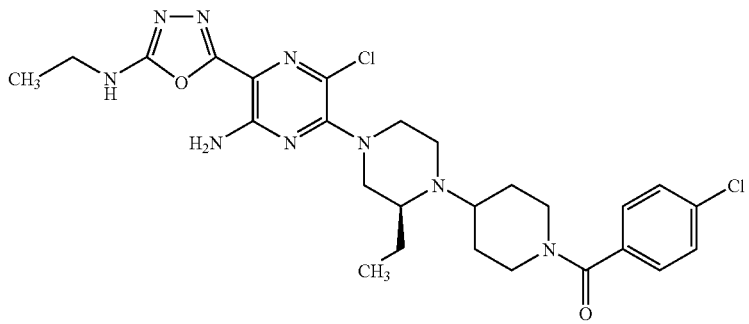
96
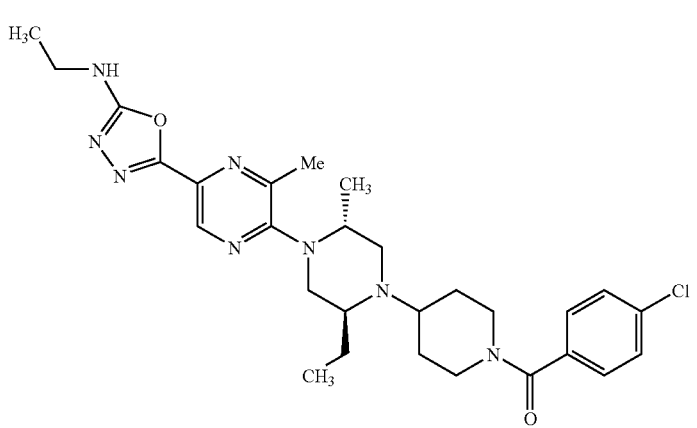
102
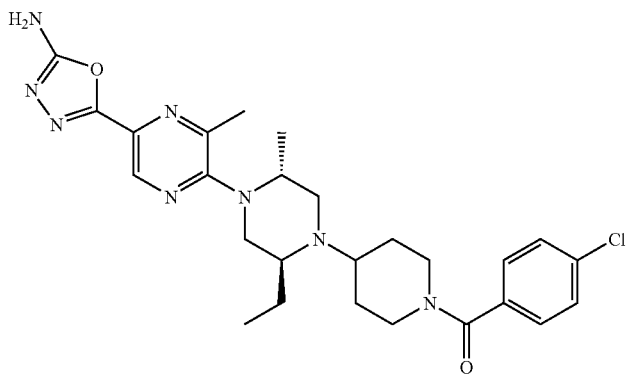

-continued
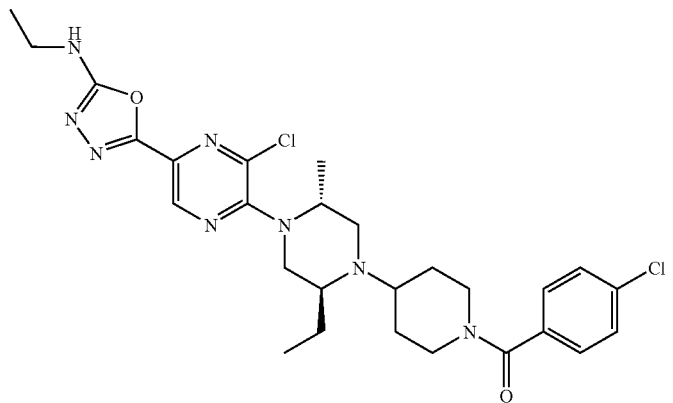
101
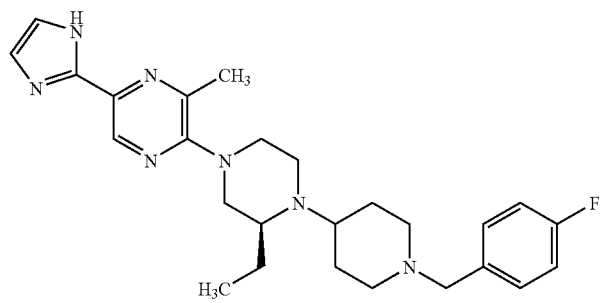
104
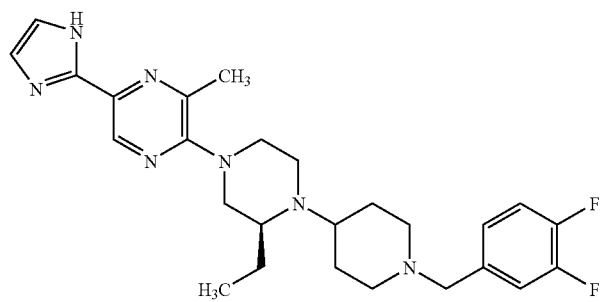
108

-continued

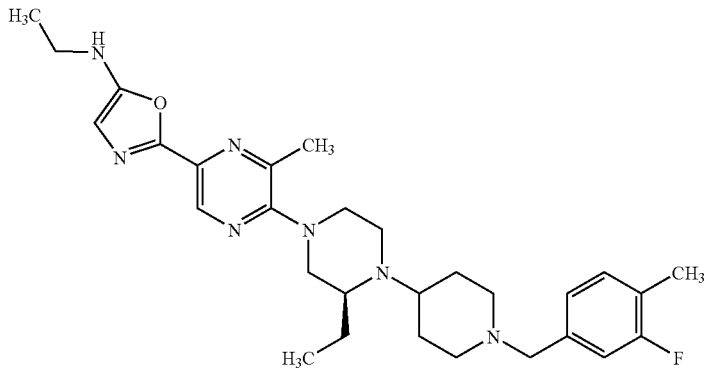

127

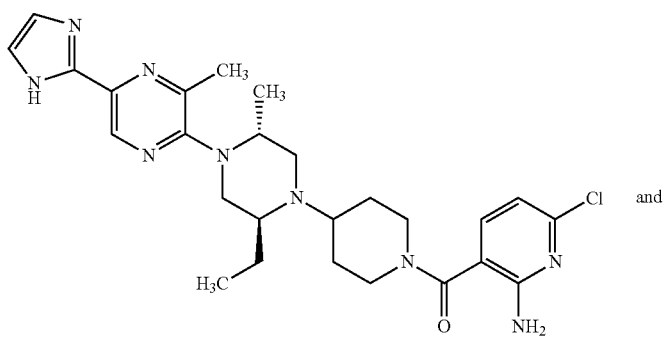

130 or a pharmaceutically acceptable salt thereof.

38. A compound of the formula

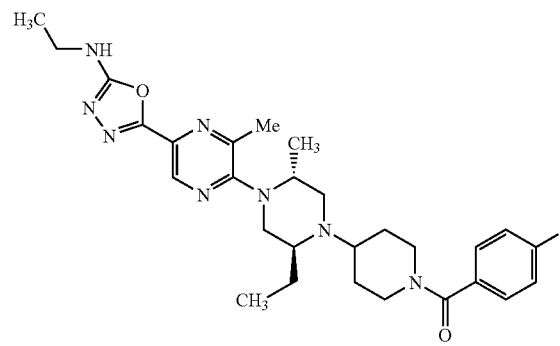

or a pharmaceutically acceptable salt thereof.

39. The compound according to claim 38, wherein said salt is a mesylate salt.

40. A pharmaceutical composition comprising at least one compound of claim 1, or a pharmaceutically acceptable salt thereof, in combination with at least one pharmaceutically acceptable carrier.

41. The pharmaceutical composition of claim 40, further comprising at least one additional agent, drug, medicament, antibody and/or inhibitor for treating a CXCR3 chemokine receptor mediated disease.

42. A pharmaceutical composition comprising at least one compound of claim 36, or a pharmaceutically acceptable salt thereof, in combination with at least one pharmaceutically acceptable carrier.

43. A pharmaceutical composition comprising at least one compound of claim 38, or a pharmaceutically acceptable salt thereof, in combination with at least one pharmaceutically acceptable carrier.

44. A compound selected from the group consisting of:

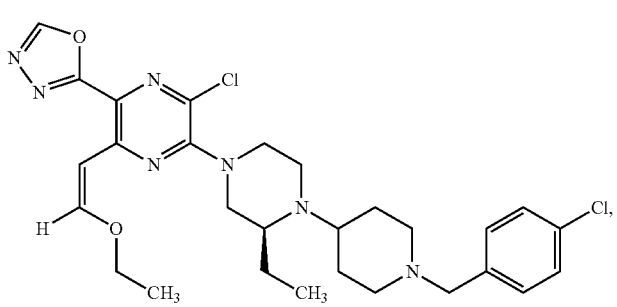

60

-continued
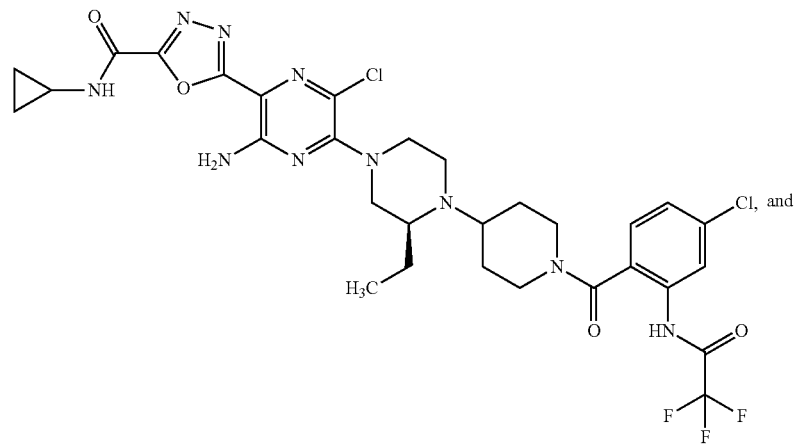
74
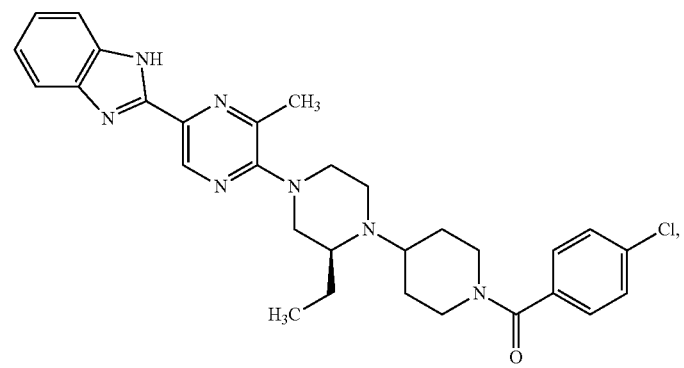
146
or a pharmaceutically acceptable salt thereof.
* * * * *